(12) United States Patent
Birnbaum et al.

(10) Patent No.: US 10,877,035 B2
(45) Date of Patent: Dec. 29, 2020

(54) ADVANCED DRUG DEVELOPMENT AND MANUFACTURING

(71) Applicant: ICAGEN, LLC, San Diego, CA (US)

(72) Inventors: Eva R. Birnbaum, Los Alamos, NM (US); Andrew T. Koppisch, Flagstaff, AZ (US); Sharon M. Baldwin, Santa Fe, NM (US); Benjamin P. Warner, Los Alamos, NM (US); T. Mark McCleskey, Los Alamos, NM (US); Jennifer A. Berger, Los Alamos, NM (US); Jeffrey J. Stewart, Cary, NC (US); Michael N. Harris, Los Alamos, NM (US); Anthony K. Burrell, Naperville, IL (US)

(73) Assignee: ICAGEN, LLC, San Diego, CA (US)

( * ) Notice: Subject to any disclaimer, the term of this patent is extended or adjusted under 35 U.S.C. 154(b) by 449 days.

(21) Appl. No.: 14/693,094

(22) Filed: Apr. 22, 2015

(65) Prior Publication Data

US 2015/0309021 A1 Oct. 29, 2015

Related U.S. Application Data

(62) Division of application No. 11/974,156, filed on Oct. 10, 2007, now abandoned.

(60) Provisional application No. 60/850,594, filed on Oct. 10, 2006.

(51) Int. Cl.
*G01N 33/566* (2006.01)
*G01N 23/223* (2006.01)
*G01N 23/2204* (2018.01)

(52) U.S. Cl.
CPC ......... *G01N 33/566* (2013.01); *G01N 23/223* (2013.01); *G01N 23/2204* (2013.01); *G01N 2223/076* (2013.01); *G01N 2500/04* (2013.01)

(58) Field of Classification Search
None
See application file for complete search history.

(56) References Cited

U.S. PATENT DOCUMENTS

| | | | |
|---|---|---|---|
| 4,241,184 A * | 12/1980 | Hou | C12N 1/30 435/148 |
| 4,436,826 A | 3/1984 | Wang | |
| 4,577,337 A | 3/1986 | Light | |
| 4,663,277 A | 5/1987 | Wang | |
| 5,143,854 A | 9/1992 | Pirrung et al. | |
| 5,216,126 A | 6/1993 | Cox et al. | |
| 5,902,723 A | 5/1999 | Dower et al. | |
| 5,958,345 A * | 9/1999 | Turner | B01L 3/5085 422/561 |
| 6,027,536 A * | 2/2000 | Westerink | C08B 1/003 162/157.6 |
| 6,147,344 A | 11/2000 | Annis et al. | |
| 6,329,209 B1 | 12/2001 | Wagner et al. | |
| 6,391,590 B1 | 5/2002 | Sano et al. | |
| 6,395,169 B1 | 5/2002 | Hindsgaul et al. | |
| 6,432,696 B2 | 8/2002 | Custance et al. | |
| 6,719,147 B2 | 4/2004 | Strano et al. | |
| 7,101,677 B1 | 9/2006 | Milligan et al. | |
| 2003/0023562 A1 * | 1/2003 | Bailey | G06F 21/6245 705/51 |
| 2003/0027129 A1 | 2/2003 | Warner et al. | |
| 2004/0017884 A1 | 1/2004 | Havrilla et al. | |
| 2004/0093526 A1 | 5/2004 | Hirsch | |
| 2004/0128518 A1 * | 7/2004 | Cavers | G06F 21/6245 713/185 |
| 2004/0235059 A1 | 11/2004 | Burrell et al. | |
| 2005/0011818 A1 | 1/2005 | Warner et al. | |
| 2005/0015596 A1 * | 1/2005 | Bowers | G06F 21/32 713/170 |
| 2005/0214847 A1 * | 9/2005 | Havrilla | G01N 23/223 435/6.13 |

FOREIGN PATENT DOCUMENTS

| | | |
|---|---|---|
| EP | 2084519 | 10/2008 |
| JP | 2001-289802 | 10/2001 |
| JP | 2004028583 | 1/2004 |
| JP | 5143841 B2 | 2/2013 |

OTHER PUBLICATIONS

Johansson et al. "Structural, Kinetic, and Mutational Studies of the Zinc Ion Environment in Tetrameric Cytidine Deaminase" Biochemistry 2004, 43, 6020-6029.*

Raddec International "The Core-Scanning µXRF Table of the Elements", retrieved from http://www.raddec.com/datasheets/XRFCoreScannerPeriodicTable.pdf on Aug. 13, 2017, one page.*

Sano et al. "A streptavidin-metallothionein chimera that allows specific labeling of biological materials with many different heavy metal ions" Proc. Nat. Acad. Sci. USA vol. 89, pp. 1534-1538, Mar. 1992.*

Bruker AXS, "Introduction to X-ray Fluorescence Analysis (XRF)—User's Manual", DOC-M84-E06001 (Jul. 2004), 127 pages total.*

Colletti et al. "Specimen Preparation Limitations in Trace Element Analysis Quantification Using Micro-X-Ray Fluorescence" Copyright JCPDS—International Centre for Diffraction Data 2000, Advances in X-ray Analysis, vol. 42, pp. 64-73 (Year: 2000).*

Chemplex Industries, "XRF Thin-Film Window Technical Information Thin-Film Sample Support Window Materials", retrieved from https://www.chemplex.com/series-10p-preassembled-sample-cup.html on Aug. 23, 2019, 4 pages.*

(Continued)

*Primary Examiner* — Christine Foster
(74) *Attorney, Agent, or Firm* — Knobbe, Martens, Olson & Bear LLP

(57) ABSTRACT

X-ray fluorescence (XRF) spectrometry has been used for detecting binding events and measuring binding selectivities between chemicals and receptors. XRF may also be used for estimating the therapeutic index of a chemical. For estimating the binding selectivities of a chemical versus chemical analogs, for measuring post translational modification of proteins, and for drug manufacturing.

18 Claims, No Drawings

(56) References Cited

OTHER PUBLICATIONS

Miller et al. "A new sample substrate for imaging and correlating organic and trace metal composition in biological cells and tissues", Anal Bioanal Chem (2007) 387:1705-1715, DOI 10.1007/s00216-006-0879-2.*
English translation of Japanese Office Action for related Japanese Application No. 2009-532446, dated Jan. 31, 2012 (2 pages).
English translation of Japanese Office Action for related Japanese Application No. 2012-122988, dated Dec. 17, 2013 (3 pages).
English translation of Japanese Office Action for related Japanese Application No. 2012-122988, dated Apr. 23, 2013 (8 pages).
English translation of Japanese Office Action for related Japanese Application No. 2009-532446, dated Aug. 7, 2012 (2 pages).
Lankosz et al., Spectrochemica Acta Part B vol. 59 (2004) pp. 1517-1521 (5 pages) Sep. 13, 2004.
Rindby et al., J. Synchroton Radiation, Jul. 1, 1997, vol. 4, No. 4, pp. 228-235 Abstract only (1 page).
Nagata et al., X-Ray Spectrometry Epub Oct. 24, 2005, vol. 35, No. 1, pp. 79-84 Abstract only (4 pages).
Supplemental European Search Report for EP07874491, dated Jan. 26, 2010 (6 pages).
European Search Report Written Opinion for EP07874491, dated Jan. 26, 2010 (6 pages).
International Preliminary Report on Patentability for PCT/US07/21888, dated May 30, 2010 (13 pages).
Communication from Examining Division regarding EP07874491, dated Nov. 26, 2010 (6 pages).
Communication from Examining Division regarding EP07874491, dated Jun. 24, 2011 (4 pages).
Communication from Examining Division regarding Intention to Grant EP07874491, dated Mar. 5, 2012 (4 pages).
Potts et al., J. Analyt. Atomic Spectrom., Issue, Oct. 2006 Abstract only (2 pages).
Eurpean Search Report for EP12164870 (2 pages), dated Feb. 21, 2013.
European Search Report Opinion for EP12164870 (4 pages), dated Feb. 21, 2013.
Communication from Examining Division regarding EP12164870, dated May 11, 2013 (4 pages).
Communication from Examining Division regarding EP12164870, dated Apr. 15, 2014 (4 pages).
Goldin et al., Biochem e Biophys Acta, 552 (1979) 120-128 Abstact only (2 pages).
Curnis et al., Cancer Research 62, pp. 867-874, Feb. 1, 2002 (8 pages).
Beveridge et al.J. Bacteriology, 149 (1982) pp. 1120-1123 (4 pages).
Miller et al., J. Comb. Chem., vol. 5 (2003) pp. 245-52 epub Feb. 28, 2003, Abstract only (2 pages).
Zhu et al., Current Opinion in Chemical Biology, vol. 7, pp. 55-63, (2003). (9 pages).
MacBeath et al., Schreiber, Science, vol. 289, pp. 1760-1763, (2000) (4 pages).
Fung et al., "Protein Biochips for Differential Profiling," Analytical Biotechnology, vol. 12, pp. 65-69, (2001) (5 pages).
Kukar et al., Analytical Biochemistry, vol. 306, pp. 50-54, (2002) (5 pages).
Chen et al., ChemBioChem, pp. 336-339, (2003) (4 pages).
Martin et al., Proteomics, vol. 3, pp. 1244-1255, (2003) (12 pages).
Burbaum etal., Current Opinion in Chemical Biology, vol. 6, pp. 427-433, (2002) (7 pages).
Hemmila et al., Drug Discovery Today, vol. 7, pp. S150-S156, pp. S150-S156, (2002) (7 pages).
Ulrich e al., Nature Reviews Drug Discovery, vol. 1, pp. 84-88 (2002) (6 pages).
Sherman, Spectrochimica Acta, incorporated by reference herein, vol. 7, pp. 283-306 (1955) (24 pages).
Barrow, "Rates and Mechanisms of Chemical Reactions," Physical Chemistry, 5th Ed., McGraw-Hill, NY, pp. 710-712, pp. 756-757, chapter7, chapter 18 (1988) (94 pages).
Jones, Practical COX-1 and COX-2 Pharmacology: What's it All About? 5 pages, which can be found at the website http://www.vetmedpub.com/cp/pdf/symposium/nov 1.pdf, (2004).
Perkins et al., Environmental Toxicology and Chemistry, vol. 22, pp. 1666-1679 (2003) (14 pages).
Schultz et al., THEOCHEM, vol. 622, pp. 1-22 (2003) (22 pages).
"Oianzapine (Zyprexa .." Clinical Toxicology Review, vol. 18, No. 2, Mar. 1997 (2 pages).
Lipinski et al., Advanced Drug Delivery Reviews, vol. 23, pp. 3-25, (1997) (23 pages).
Wallace, The Scientist, 15[12]:10, Jun. 11, 2001 (3 pages).
Ricci et al., X-Ray Spectrometry, Heyden & Sons Ltd., epub Apr. 11, 2005 Abstract only (3 pages).
Mertens et al. Spectra Acta Part BL Atomic Spectroscopy, vol. 56, Isue 11, Nov. 30, 2001, pp. 2157-2164, Abstract only (2 pages).
International Search Report for PCT/US07/21888, dated Mar. 5, 2009, (4 pages).
Machine translation of claims for Japanese patent application No. 2000-113225, filed Apr. 10, 2000 (1 page).
Machine translation of Detailed Description for Japanese patent application No. 2000-113225, filed Apr. 10, 2000 (13 pages).
Machine translation for Claims for Japanese patent No. 5143841 (48 pages), Published Feb. 13, 2013.
Machine translation for Detailed Description for Japanese patent No. 5143841 (129 pages), published Feb. 13, 2013.
Machine translation for Claims for Japanese patent publication 2004028583 (2 pages), published Jan. 29, 2004.
Machine translation for Detailed Description for Japanese patent publication 2004028583 (8 pages), published Feb. 13, 2013.

* cited by examiner

ADVANCED DRUG DEVELOPMENT AND MANUFACTURING

RELATED APPLICATIONS

This application is a Continuation of U.S. patent application Ser. No. 11/974,156, filed Oct. 10, 2007, which is a continuation-in-part of U.S. patent application Ser. No. 09/859,701, filed May 16, 2001, now U.S. Pat. No. 7,858,385 issued Dec. 28, 2010, and a continuation-in-part of U.S. patent application Ser. No. 10/206,524, filed Jul. 25, 2002, and a continuation-in-part of U.S. patent application Ser. No. 10/621,825 filed Jul. 16, 2003, now U.S. Pat. No. 6,858,148 issued Feb. 22, 2005, all hereby incorporated by reference herein. This application also claims the benefit of U.S. Provisional Application Ser. No. 60/850,594 filed Oct. 10, 2006, hereby incorporated by reference herein.

STATEMENT REGARDING FEDERAL RIGHTS

This invention was made with government support under Contract No. DE-AC52-06NA25396 awarded by the U.S. Department of Energy. The government has certain rights in the invention.

FIELD OF THE INVENTION

The present invention relates generally to detecting binding events and more particularly to estimating binding selectivities for chemicals, analogs, and drugs being tested with receptors and then manufacturing those having a high binding selectivity to the receptors.

BACKGROUND OF THE INVENTION

The desire to hasten the identification of potentially important drugs, catalysts, chemicals and biological sensors, medical diagnostics, and other materials is a constant challenge that has prompted the use of combinatorial synthetic screening strategies for synthesizing these materials and screening them for desirable properties. Combinatorial synthesis involves assembling a "library", i.e. a very large number of chemically related compounds and mixtures, usually in the form of an array on a substrate surface. High throughput screening of an array involves identifying which members of the array, if any, have the desirable property or properties. The array form facilitates the identification of a particular material on the substrate. Combinatorial arrays and high-throughput screening techniques have been used to solve a variety of problems related to the development of biological materials such as proteins and DNA because the screening techniques can be used to rapidly assay many biological materials.

The binding properties of a protein largely depend on the exposed surface amino acid residues of its polypeptide chain (see, for example, Bruce Alberts et al., "Molecular Biology of the Cell", $2^{nd}$ edition, Garland Publishing, Inc., New York, 1989; and H. Lodish et al., "Molecular Cell Biology", $4^{th}$ edition, W. H. Freeman and Company, 2000). These amino acid residues can form weak noncovalent bonds with ions and molecules. Effective binding generally requires the formation of many weak bonds at a "binding site," which is usually a cavity in the protein formed by a specific arrangement of amino acids. There should be a precise fit with the binding site for effective binding to occur.

The chemical properties and in particular, the binding properties of a protein depend almost entirely on the exposed surface amino acid residues of the polypeptide chain. These residues can form weak noncovalent bonds with other molecules. An effective binding between the protein, one example of a group of materials herein referred to as "receptors", and the material that binds to the receptor, referred to herein as "chemical", generally requires that many weak bonds form between the protein receptor and the chemical. Chemicals include organic molecules, inorganic molecules, salts, metal ions, and the like. The bonds between the protein and the chemical form at the "binding site" of the protein. The binding site is usually a cavity in the protein that is formed by a specific arrangement of amino acids that often belong to widely separated regions of the polypeptide chain and represent only a minor fraction of the total number of amino acids present in the chain. Chemicals should fit precisely into the binding site for effective binding to occur. The shape of these binding sites can differ greatly among different proteins, and even among different conformations of the same protein. Even slightly different conformations of the same protein may differ greatly in their binding abilities. For further discussion of the structure and function of proteins, see: Bruce Alberts et al., "Molecular Biology of the Cell", $2^{nd}$ edition, Garland Publishing, Inc., New York, 1989; and H. Lodish et al., "Molecular Cell Biology", $4^{th}$ edition, W. H. Freeman and Company, 2000.

After a receptor array is prepared, it is screened to determine which members have the desirable property or properties. U.S. Pat. No. 5,143,854 to M. C. Pirrung et al. entitled "Large Scale Photolithographic Solid Phase Synthesis of Polypeptides and Receptor Binding Screening Thereof", which issued Sep. 1, 1992, hereby incorporated by reference, describes one such screening method. A polypeptide array is exposed to a ligand (an example of a chemical) to determine which members of the array bind to the ligand. The ligands described are radioactive, or are "tagged", i.e. attached via one or more chemical bonds to a chemical portion that fluoresces when exposed to non-ionizing, ultraviolet radiation. Thus, the attached portion, i.e. the tag, makes the chemical visible by interrogation with ultraviolet radiation. Tagged molecules have also been used to aid in sequencing immobilized polypeptides as described, for example, in U.S. Pat. No. 5,902,723 to W. J. Dower et al. entitled "Analysis of Surface Immobilized Polymers Utilizing Microfluorescence Detection," which issued May 11, 1999. Immobilized polypeptides are exposed to molecules labeled with fluorescent tags. The tagged molecules bind to the terminal monomer of a polypeptide, which is then cleaved and its identity determined. The process is repeated to determine the complete sequence of the polypeptide.

It is generally assumed that the attachment of a fluorescent tag to a chemical only serves to make visible the otherwise invisible chemical, and does not alter its binding properties. Since it is well known that even small changes to the structure of a molecule could affect its function, this assumption that a tagged chemical, i.e. a "surrogate", has the same binding affinity as the untagged chemical may not be a valid one. Small structural changes that accompany even a conformational change of a receptor have been known to affect the binding affinity of the receptor. The tagged surrogates are structurally different from their untagged counterparts, and these structural differences could affect their binding affinities. Since binding affinities derived using tagged surrogates are suspect, the binding properties of receptors and chemicals should be evaluated using the untagged chemical or receptor and not with a tagged surrogate.

Pharmaceutical chemicals are the active ingredients in drugs, and it is believed that their therapeutic properties are linked to their ability to bind to one or more binding sites. The shapes of these binding sites may differ greatly among different proteins, and even among different conformations of the same protein. Even slightly different conformations of the same protein may differ greatly in their binding abilities. For these reasons, it is extremely difficult to predict which chemicals will bind effectively to proteins.

Development and manufacturing for a new pharmaceutical chemical for a drug, i.e. drug development, generally involves determining the binding affinities between a potential pharmaceutical chemical (preferably a water soluble organic chemical that can dissolve into the blood stream) and a receptor (generally a biological material such as an enzyme or non-enzyme protein, DNA, RNA, human cell, plant cell, animal cell, and the like) at many stages of the drug development process. The receptor may also be a microorganism (e.g. prion, virus, bacterium, spores, and the like) in whole or in part. The drug development process typically involves procedures for combining potential pharmaceutical chemicals with receptors, detecting chemical binding between the potential pharmaceutical chemicals and the receptors and determining the binding affinity and kinetics of binding of a receptor to a chemical to form a complex or the kinetics of release of a bound chemical from a complex. The binding affinity is defined herein as the associative equilibrium constant Ka for the following equilibrium expression:

$m$(chemical)+receptor  chemical-receptor complex

The binding affinity, Ka, is defined by equation (1) below.

$$Ka = [\text{chemical-receptor complex}]/[\text{receptor}][\text{chemical}]^m \quad (1)$$

In equation (1), [chemical-receptor complex] is the concentration in moles per liter of the chemical-receptor complex, [receptor] is the concentration in moles per liter of the receptor, 'm' is the number of molecules of chemical that bind to each molecule of receptor, and [chemical] is the concentration in moles per liter of the chemical. Any effects due to concentration can be simplified if the concentration of chemical used were the same for all receptors.

Nowadays, the drug development process may involve the rapid screening of hundreds or thousands of chemicals in order to identify a "lead compound," which is one of the many tested that binds very strongly, i.e. has a high binding affinity, with a particular receptor. After such a lead compound has been identified, then other potential pharmaceutical chemicals similar in structure to the lead compound, which are referred to herein as "analogs" of the lead compound, are synthesized and tested in order to determine which of these chemicals, if any, exhibits an even higher binding affinity.

The preparation and high-throughput screening of biological arrays is exemplified by the following papers: H. Zhu and M. Snyder, "Protein Chip Technology (Review)," *Current Opinion in Chemical Biology*, vol. 7, pp. 55-63, (2003); G. MacBeath and S. L. Schreiber, "Printing Proteins As Microarrays For High-Throughput Function Determination," *Science*, vol. 289, pp. 1760-1763, (2000); E. T. Fung et al., "Protein biochips for differential profiling," *Analytical Biotechnology*, Vol. 12, pp. 65-69, (2001); T. Kukar et al., "Protein Microarrays to Detect Protein-Protein Interactions Using Red and Green Fluorescent Proteins," *Analytical Biochemistry*, vol. 306, pp. 50-54, (2002); G. Y. J. Chen et al., "Developing a Strategy for Activity-Based Detection of Enzymes in a Protein Microarray," *ChemBioChem*, pp. 336-339, (2003); K. Martin et al., "Quantitative analysis of protein phosphorylation status and protein kinase activity on microarrays using a novel fluorescent phosphorylation sensor dye," *Proteomics*, Vol. 3, pp. 1244-1255, (2003); J. Burbaum and G. M. Tobal, "Proteomics in drug discovery," *Current Opinion in Chemical Biology*, Vol. 6, pp. 427-433, (2002); I. A. Hemmilä and P. Hurskainen, "Novel detection strategies for drug discovery," *Drug Discovery Today*, Vol. 7, pp. S150-S156, (2002), Pages S150-S156; all incorporated herein by reference.

Some screening methods are described in the following patents, all of which are hereby incorporated by reference.

U.S. Pat. No. 6,147,344 to D. Allen Annis et al. entitled "Method for Identifying Compounds in a Chemical Mixture", which issued Nov. 14, 2000, describes a method for automatically analyzing mass spectrographic data from mixtures of chemical compounds.

U.S. Pat. No. 6,344,334 to Jonathan A. Ellman et al. entitled "Pharmacophore Recombination for the Identification of Small Molecule Drug Lead Compounds," which issued Feb. 5, 2002, describes a method for identifying a drug lead compound by contacting target biological molecules with cross-linked binding fragments.

U.S. Pat. No. 6,395,169 to Ole Hindsgaul et al. entitled "Apparatus for Screening Compound Libraries," which issued May 28, 2002, describes an apparatus that employs frontal chromatography combined with mass spectrometry to identify and rank members of a library that bind to a target receptor.

Other current high-throughput screening methods, along with their associated drawbacks, are listed in TABLE 1 below, which is taken from the following paper: H. Zhu and M. Snyder, "Protein Chip Technology (Review)," *Current Opinion in Chemical Biology*, vol. 7, pp. 55-63, (2003).

TABLE 1

| Detection Technique | Probe Labeling | Data Acquirement |
|---|---|---|
| ELISA (Enzyme-Linked Immunosorbent Assay) | Enzyme-Linked Antibodies | CCD Imaging |
| Isotopic Labeling | Radioisotope Labeled Analyte | X-Ray Film Or Phospoimager |
| Sandwich Immunoassay | Fluorescently Labeled Antibodies | Laser Scanning |
| Surface Plasmon Resonance | Receptor must be attached to a surface | Refractive Index Change |
| Non-Contact Atomic Force Microscopy | None | Surface Topological Change |
| Planar Waveguide | Fluorescently Labeled Antibodies | CCD Imaging |
| SELDI (Surface Enhanced Laser Desorption Ionization Mass Spectrometry) | None | Mass Spectrometry |
| Electrochemical | Metal-Coupled Analyte | Conductivity Measurement |

TABLE 1 shows that most of the listed screening methods have the same drawback: they require either radiolabeled chemicals, chemicals that have been altered with a fluorescent tag, or chemicals that have been altered with a metal tag.

X-ray fluorescence (XRF) spectrometry is a powerful spectroscopic technique that has been used to determine the elements that are present in a chemical sample, and to determine the quantity of those elements in the sample. The underlying physical principle of the method is that when an atom of a particular element is irradiated with X-ray radiation, the atom ejects a core electron such as a K shell electron. The resulting atom is in then an excited state, and it can return to the ground state by replacing the ejected electron with an electron from a higher energy orbital. This is accompanied by the emission of a photon, i.e. X-ray fluorescence, and the photon energy is equal to the difference in the energies of the two electrons. Each element has a characteristic set of orbital energies and therefore, a characteristic X-ray fluorescence (XRF) spectrum.

An XRF spectrometer is an apparatus capable of irradiating a sample with an X-ray beam, detecting the X-ray fluorescence from an element included in the sample, and using the X-ray fluorescence to determine which elements are present in the sample and providing the quantity of these elements. A typical, commercially available X-ray fluorescence spectrometer is the EDAX Eagle XPL energy dispersive X-ray fluorescence spectrometer, equipped with a microfocus X-ray tube, lithium drifted silicon solid-state detector, processing electronics, and vendor supplied operating software. In principle, any element may be detected and quantified with XRF.

U. S. Patent Application 20030027129 entitled "Method for Detecting Binding Events Using Micro-X-ray Fluorescence Spectrometry," incorporated by reference herein, describes a method for detecting binding events using micro-x-ray fluorescence spectrometry. According to the '129 patent application, receptors are exposed to at least one potential chemical and arrayed on a substrate support. Each member of the array is exposed to X-ray radiation. The magnitude of a detectable x-ray fluorescence signal for at least one element can be used to determine whether a binding event between a chemical and a receptor has occurred, and can provide information related to the extent of binding between the chemical and receptor.

U. S. Patent Application 20040017884 entitled "Flow Method And Apparatus For Screening Chemicals Using Micro X-Ray Fluorescence," which was published on Jan. 29, 2004, incorporated by reference herein, describes a method for identifying binding events between potential pharmaceutical chemicals and receptors (e.g. proteins). The method involves modifying a mixture of potential pharmaceutical chemicals by adding at least one receptor to the mixture. After allowing sufficient time for any bound complex between any of the potential pharmaceutical chemicals and any of the receptors to form, if such a complex can form, the resulting solution is flow separated into at least two components. Each component is exposed to an x-ray excitation beam. If the exposed component emits a detectable x-ray fluorescence signal, that component is isolated. The identity of any isolated component can be determined using one or more standard analytical techniques, such as gas chromatography, liquid chromatography, mass spectrometry, nuclear magnetic resonance spectroscopy, infrared spectroscopy, ultraviolet spectroscopy, visible spectroscopy, elemental analysis, cell culturing, immunoassaying, and the like.

Effective drugs are selective drugs; they bind to a specific desired receptor, bypassing other receptors, to produce a desired therapeutic effect. This way, they target a specific disease in the body with minimal side effects; selectivity provides efficacy without undesirable side effects.

The therapeutic index is a measure of drug selectivity that is ordinarily calculated from data obtained from experiments with animals. The therapeutic index of the drug is typically defined as the ratio of two numbers, LD50/ED50, where LD50 is the dose of a drug that is found to be lethal (i.e. toxic) for 50 percent of the population of animals used for testing the drug, and ED50 is the dose of the drug that is found to have a therapeutic effect for 50 percent of that population. More broadly, it is a measure of the how much of the drug is needed to produce a harmful effect relative to the amount needed to produce a beneficial effect. The ratio LD50/ED50 is therefore, a measure of the approximate "safety factor" for a drug; a drug with a high therapeutic index can presumably be administered with greater safety than one with a low index.

Estimating the therapeutic index of a chemical involves measuring the binding affinity of a chemical to a first receptor, and measuring the binding affinity of the same chemical to a second receptor. After measuring these binding affinities, the ratio of the binding affinity of the chemical divided by the amount of first receptor versus the binding affinity of the chemical divided by the amount of the second receptor is determined. This ratio is provides an estimate of the "therapeutic index". For an example of using DNA arrays with optical fluorescence high-throughput screening to estimate a therapeutic index, see for example, R. Ulrich and S. H. Friend, "Toxicogenomics and Drug Discovery: Will New Technologies Help Us Produce Better Drugs?," *Nature Reviews Drug Discovery*, v. 1, pp. 84-88 (2002), incorporated herein by reference.

There remains a need for simpler methods for measuring binding affinities and selectivities, estimating the therapeutic index of a chemical, and for expediting drug manufacturing, Therefore, an object of the present invention is to provide a method for measuring binding affinities of chemicals.

Another object of the present invention is to provide a method for measuring selectivity of chemicals binding to receptors.

Yet another object of the invention is to provide a method for estimating the therapeutic index of a chemical.

Still another object of the invention is to provide a method that employs x-ray fluorescence for drug manufacture.

Additional objects, advantages and novel features of the invention will be set forth in part in the description which follows, and in part will become apparent to those skilled in the art upon examination of the following or may be learned by practice of the invention. The objects and advantages of the invention may be realized and attained by means of the instrumentalities and combinations particularly pointed out in the appended claims.

SUMMARY OF THE INVENTION

In accordance with the purposes of the present invention, as embodied and broadly described herein, the present invention includes a method for estimating the binding selectivity of a chemical having at least one heavy element (i.e. an element having an atomic number of nine or higher) to at least two receptors. The method includes establishing a baseline X-ray fluorescence signal for a heavy element in a portion of a first receptor and in a portion of at least one more receptor that may be the same or different from the first receptor, the heavy element being present in a chemical to be tested for binding to the receptors; exposing the receptors to the chemical and allowing the chemical to bind to them to form a first chemical-receptor complex and at least one more chemical-receptor complex; measuring the x-ray fluorescence signals due to the heavy element in the first chemical-receptor complex and in the at least one more chemical-receptor complex; subtracting the baseline x-ray fluorescence signal of the first receptor from the measured x-ray fluorescence signal of the of the first chemical-receptor complex to obtain a first net x-ray fluorescence signal; subtracting the baseline x-ray fluorescence signal of the at least one more receptor from the measured x-ray fluorescence signal of the of the at least one more chemical-receptor complex to obtain at least one more net x-ray fluorescence signal; and then estimating the selectivity of the chemical by dividing the first net x-ray fluorescence signal by the amount of receptor in the portion of the first receptor to obtain a first quotient, dividing the at least one more net x-ray fluorescence signal by the amount of receptor in the portion of the at least one more receptor to obtain at least one more quotient, and then comparing the first quotient to the at least one more quotient.

The invention also includes a method for estimating the binding selectivity of a chemical versus at least one analog of the chemical to at least two receptors, the chemical and the at least one analog each having at least one heavy element. The method includes establishing a baseline x-ray fluorescence signal for a first heavy element in a first portion of a first receptor and in a first portion of a second receptor, the first heavy element being present in a chemical to be tested for binding to the receptors; establishing a baseline x-ray fluorescence signal for a second heavy element in a second portion of the first receptor and in a second portion of a second receptor, the second heavy element being present in an analog of the chemical to be tested for binding to the receptors; exposing the first portions of the receptors to the chemical and allowing the chemical to bind to them to form a first chemical-receptor complex and a second chemical-receptor complex; measuring the x-ray fluorescence signal due to the first heavy element present in the first chemical-receptor complex and in the second chemical-receptor complex; exposing the second portions of the receptors to the analog and allowing the analog to bind to them to form a first analog-receptor complex and a second analog-receptor complex; measuring the x-ray fluorescence signal due to the second heavy element present in the first analog-receptor complex and in the second analog-receptor complex; calculating the net x-ray fluorescence signal due to the first heavy element in the first chemical-receptor complex by subtracting the baseline x-ray fluorescence signal of the first portion of the first receptor from the measured x-ray fluorescence signal of the of the first chemical-receptor complex; calculating the net x-ray fluorescence signal due to the first heavy element present in the second chemical-receptor complex by subtracting the baseline x-ray fluorescence signal of the first portion of the second receptor from the measured x-ray fluorescence signal of the second chemical-receptor complex; calculating the net x-ray fluorescence signal due to the second heavy element in the first analog-receptor complex by subtracting the baseline x-ray fluorescence signal of the second portion of the first receptor from the measured x-ray fluorescence signal of the of the first analog-receptor complex; calculating the net x-ray fluorescence signal due to the second heavy element present in the second analog-receptor complex by subtracting the baseline x-ray fluorescence signal of the second portion of the second receptor from the measured x-ray fluorescence signal of the second analog-receptor complex; estimating the selectivity of the chemical to binding to the receptors by dividing the net x-ray fluorescence of the first chemical-receptor complex by the amount of receptor in the first portion of the first receptor to obtain a first quotient, dividing the net x-ray fluorescence of the second chemical-receptor complex by the amount of receptor in the first portion of the second receptor to obtain a second quotient; estimating the selectivity of the analog to binding to the receptors by dividing the net x-ray fluorescence of the first analog-receptor complex by the amount of receptor in the second portion of the first receptor to obtain a third quotient, dividing the net x-ray fluorescence of the second analog-receptor complex by the amount of receptor in the second portion of the second receptor to obtain a fourth quotient; and comparing first quotient to the second quotient to the third quotient to the fourth quotient.

The invention also includes a method for manufacturing a drug. The method includes establishing a baseline X-ray fluorescence signal for a heavy element in a portion of a first receptor and in a portion of at least one more receptor that may be the same or different from the first receptor, the heavy element being present in a chemical to be tested for binding to the receptors; exposing the receptors to the chemical and allowing the chemical to bind to them to form a first chemical-receptor complex and at least one more chemical-receptor complex; measuring the x-ray fluorescence signals due to the heavy element in the first chemical-receptor complex and in the at least one more chemical-receptor complex; subtracting the baseline x-ray fluorescence signal of the first receptor from the measured x-ray fluorescence signal of the of the first chemical-receptor complex to obtain a first net x-ray fluorescence signal; subtracting the baseline x-ray fluorescence signal of the at least one more receptor from the measured x-ray fluorescence signal of the of the at least one more chemical-receptor complex to obtain at least one more net x-ray fluorescence signal; estimating the selectivity of the chemical by dividing the first net x-ray fluorescence signal by the amount of receptor in the portion of the first receptor to obtain a first quotient, dividing the at least one more net x-ray fluorescence signal by the amount of receptor in the portion of the at least one more receptor to obtain at least one more quotient, and then comparing the first quotient to the at least one more quotient; and manufacturing the chemical in sufficient quantity for use as a drug if the first quotient and the at least one more quotient are different by at least one percent.

The invention also includes a method for manufacturing a drug. The method includes establishing a baseline X-ray fluorescence signal for a first heavy element in a first portion of a first receptor and in a first portion of a second receptor, the first heavy element being present in a chemical to be tested for binding to the receptors; establishing a baseline X-ray fluorescence signal for a second heavy element in a second portion of the first receptor and in a second portion of a second receptor, the second heavy element being present in an analog of the chemical to be tested for binding to the receptors; exposing the first portions of the receptors to the chemical and allowing the chemical to bind to them to form a first chemical-receptor complex and a second chemical-receptor complex; measuring the x-ray fluorescence signal due to the first heavy element present in the first chemical-receptor complex and in the second chemical-receptor complex; exposing the second portions of the receptors to the analog and allowing the analog to bind to them to form a first analog-receptor complex and a second analog-receptor complex; measuring the x-ray fluorescence signal due to the second heavy element present in the first analog-receptor complex and in the second analog-receptor complex; calculating the net x-ray fluorescence signal due to the first heavy element in the first chemical-receptor complex by subtracting the baseline x-ray fluorescence signal of the first portion of the first receptor from the measured x-ray fluorescence signal of the of the first chemical-receptor complex; calculating the net x-ray fluorescence signal due to the first heavy element present in the second chemical-receptor complex by subtracting the baseline x-ray fluorescence signal of the first portion of the second receptor from the measured x-ray fluorescence signal of the second chemical-receptor complex; calculating the net x-ray fluorescence signal due to the second heavy element in the first analog-receptor complex by subtracting the baseline x-ray fluorescence signal of the second portion of the first receptor from the measured x-ray fluorescence signal of the of the first analog-receptor complex; calculating the net x-ray fluorescence signal due to the second heavy element present in the second analog-receptor complex by subtracting the baseline x-ray fluorescence signal of the second portion of the second receptor from the measured x-ray fluorescence signal of the second analog-receptor complex; estimating the selectivity of the chemical to binding to the receptors by dividing the net x-ray fluorescence of the first chemical-receptor complex by the amount of receptor in the first portion of the first receptor to obtain a first quotient, dividing the net x-ray fluorescence of the second chemical-receptor complex by the amount of receptor in the first portion of the second receptor to obtain a second quotient; estimating the selectivity of the analog to binding to the receptors by dividing the net x-ray fluorescence of the first analog-receptor complex by the amount of receptor in the second portion of the first receptor to obtain a third quotient, dividing the net x-ray fluorescence of the second analog-receptor complex by the amount of receptor in the second portion of the second receptor to obtain a fourth quotient; and comparing first, second, third, and fourth quotients to determine if the chemical or analog is the more selective and manufacturing the more selective one in sufficient quantity for use as a drug.

The invention also includes a method for comparing the ability of at least one chemical in a first solution to bind to a portion of at least one receptor versus the ability of that chemical in a second solution to bind to a separate portion of the same at least one receptor. The method includes establishing a baseline X-ray fluorescence signal for a heavy element in a first portion of a receptor and for the heavy element in a separate portion of the receptor, the heavy element being present in a chemical that is being tested for binding to the receptor; exposing the first portion of the receptor to a first solution that includes the chemical, and allowing the chemical to bind to the receptor to form a first chemical-receptor complex; exposing the separate portion of the receptor to a second solution also includes the chemical, and allowing the chemical to bind to the receptor to form a second chemical-receptor complex; measuring the x-ray fluorescence signals due to the heavy element in the first chemical-receptor complex and in the second chemical-receptor complex; calculating the net x-ray fluorescence signal due to the heavy element in the first chemical-receptor complex by subtracting the baseline x-ray fluorescence signal of the first portion of receptor from the measured x-ray fluorescence signal of the first chemical-receptor complex; calculating the net x-ray fluorescence signal due to the heavy element in the second chemical-receptor complex by subtracting the baseline x-ray fluorescence signal of the separate portion of receptor from the measured x-ray fluorescence signal of the second chemical-receptor complex; and estimating the binding selectivity of the chemical in the first solution versus the second solution by dividing the net x-ray fluorescence signal of the first chemical-receptor complex by the amount of receptor in the first portion of the receptor to obtain a first quotient, dividing the net x-ray fluorescence of the second chemical-receptor complex by the amount of receptor in the separate portion of the receptor to obtain a second quotient, and then comparing the first quotient to the second quotient.

The invention also includes a method for estimating the relative effectiveness of at least two drugs, each drug having at least one heavy element. The method includes providing a sample from a medical patient, the sample comprising at least a first portion and a second portion of a first receptor and a first portion and a second portion of a second receptor; establishing a baseline X-ray fluorescence signal for a first heavy element in the first portion of the first receptor and in the first portion of the second receptor, the first heavy element being present in a first drug to be tested for binding to the first and second receptors; establishing a baseline X-ray fluorescence signal for a second heavy element in the second portion of the first receptor and in the second portion of the second receptor, the second heavy element being present in a second drug to be tested for binding to first and second receptors; exposing the first portion of the first receptor and the first portion of the second receptor to the first drug and allowing the drug to bind to the first receptor to form a first drug-receptor complex, and to bind to the second receptor to form a second drug-receptor complex; measuring the x-ray fluorescence signal due to the first heavy element present in the first drug-receptor complex and in the second drug-receptor complex; exposing the second portion of the first receptor and the second portion of the second receptor to the second drug and allowing the second drug to bind to the first receptor to form a third drug-receptor complex, and to bind to the second receptor to form a fourth drug-receptor complex; measuring the x-ray fluorescence signal due to the second heavy element present in the third drug-receptor complex and in the fourth drug-receptor complex; calculating a first net x-ray fluorescence signal due to the first heavy element present in the first drug-receptor complex by subtracting the baseline x-ray fluorescence signal of the first portion of the first receptor from the measured x-ray fluorescence signal of the of the first drug-receptor complex; calculating a second net x-ray fluorescence signal due to the first heavy element present in the second drug-receptor complex by subtracting the baseline x-ray fluorescence signal of the first portion of the second receptor from the measured x-ray fluorescence signal of the second drug-receptor complex; calculating a third net x-ray fluorescence signal due to the second heavy element in the third drug-receptor complex by subtracting the baseline x-ray fluorescence signal of the second portion of the first receptor from the measured x-ray fluorescence signal of the of the third drug-receptor complex; calculating a fourth net x-ray fluorescence signal due to the second heavy element present in the fourth drug-receptor complex by subtracting the baseline x-ray fluorescence signal of the second portion of the second receptor from the measured x-ray fluorescence signal of the fourth drug-receptor complex; calculating binding quotients for the first drug by dividing the first net x-ray fluorescence signal by the amount of receptor in the first portion of the first receptor to obtain a first quotient, dividing the second net x-ray fluorescence signal by the amount of receptor in the first portion of the second receptor to obtain a second quotient; calculating binding quotients for the second drug by dividing the third net x-ray fluorescence signal by the amount of receptor in the second portion of the first receptor to obtain a third quotient, dividing the fourth net x-ray fluorescence signal by the amount of receptor in the second portion of the second receptor to obtain a fourth quotient; and comparing the first, second, third, and fourth quotients to estimate the relative effectiveness of the first drug versus the second drug.

The invention also includes a method for estimating binding affinity. The method involves depositing a portion of a receptor on a substrate; establishing a baseline X-ray fluorescence signal for a heavy element in the portion of the receptor, the heavy element being present in a chemical being testing for binding to the receptor; exposing the receptor to a solution comprising the chemical at a first temperature, and allowing the chemical to bind to the receptor to form a chemical-receptor complex; measuring the x-ray fluorescence signal due to the heavy element in the chemical-receptor complex using excitation photons having an energy of at least 300 electron-volts to electronically excite the heavy element, and detecting emission photons using an x-ray detector having a dead time, the emission photons being generated from an excited state of the heavy element, the excited state of the heavy element having a fluorescence lifetime that is less than the dead time of the x-ray detector; calculating the net x-ray fluorescence signal due to the heavy element in the chemical-receptor complex by subtracting the baseline x-ray fluorescence signal of the portion of receptor from the measured x-ray fluorescence signal of the chemical-receptor complex; and estimating the binding affinity of the chemical for the receptor by dividing the net x-ray fluorescence signal of the chemical-receptor complex by the amount of the receptor in the portion of the receptor.

The invention also includes a method for detecting protein modification. The method includes establishing a baseline X-ray fluorescence signal for a heavy element in a portion of a protein; exposing the portion of protein to conditions that may alter the amount of the heavy element present in the portion of the protein and then measuring the x-ray fluorescence signal due to the heavy element; and subtracting the baseline x-ray fluorescence signal from the measured x-ray fluorescence signal.

DETAILED DESCRIPTION

Overview

The present invention consists of improvements to the invention described in published US Patent Application 20040235059 "Drug Development and Manufacturing" to Benjamin P. Warner, T. Mark McCleskey, and Anthony K. Burrell, filed Jun. 29, 2004. These improvements consist of the following additional steps to be used in the process that improve the signal or signal to noise ratios obtained from the measurement, and specific requirements for preparation of samples that provide improved signals or signal to noise ratios. All of these methods may be used with multiple samples to provide comparisons between samples, or with single samples to obtain information about the sample.

Substrates

A key improvement to US Patent Application 20040235059 is the use of sample substrates which minimize noise. Characteristics to be optimized include the thickness of the substrate; the chemical and elemental composition of the substrate; and the variability in the chemical composition of the surface of the substrate.

Substrates are preferably thin enough to minimize the scattering of incident x-rays. Thick substrates cause scattering in the X-ray portion of the electromagnetic spectrum. Preferably, the substrates are less than 500 microns thick, and more preferably the substrates are less than about 50 microns thick. Most preferably, the substrates are between twenty (20) nanometers thick and twenty-five (25) microns thick. Examples of materials which may be conveniently used include 0.02 micron thick, 99.99% pure gold foil, available from Lebow Company, 5960 Mandarin Ave., Goleta, Calif. 93117 U.S.A.; 0.07 micron thick, 99.95% pure aluminum foil, available from Lebow Company, 5960 Mandarin Ave., Goleta, Calif. 93117 U.S.A.; 0.1 micron through 20 micron thick PARYLENE N®, available from Lebow Company, 5960 Mandarin Ave., Goleta, Calif. 93117 U.S.A.; and 0.5 micron thick to 25.0 micron thick, 99.99% pure titanium foil, available from Lebow Company, 5960 Mandarin Ave., Goleta, Calif. 93117 U.S.A.; and 4 micron thick to 8 micron thick polypropylene, available from Lebow Company, 5960 Mandarin Ave., Goleta, Calif. 93117 U.S.A. Other substrates that are conveniently used are AP1, AP3, ProLINE Series 10, ProLINE Series 20, DuraBeryllium substrates from Moxtek, 452 West 1260 North, Orem, Utah 84057. Other substrates that are conveniently used are ULTRALENE®, Mylar, polycarbonate, Prolene, and Kapton, available from SPEX CertiPrep Ltd, 2 Dalston Gardens, Stanmore, Middx HA7 1BQ, ENGLAND. Other substrates that may be conveniently used are HOSTAPHAN®, polyester, and ETNOM® available from Chemplex Industries, Inc., 2820 SW 42nd Avenue, Palm City, Fla. 34990-5573 USA. The substrate is preferably a polymer, and more preferably is a polymer that contains carbon. Radiation produced by radioactive materials will produce noise in the measurement. The substrate is preferably substantially free of the elements technetium, thorium, and uranium. Most of the chemicals to be studied using the present invention will contain one or more of the following elements: oxygen, fluorine, phosphorus, sulfur, and chlorine. Therefore, to minimize unwanted signal from these elements in the focusing chip, the focusing chip should consist of less than 50% by mass of at least one of these elements (fluorine, oxygen, phosphorus, sulfur, and chlorine). The substrate preferably comprises less than about 50% of at least one of the elements selected from the group comprising oxygen, fluorine, phosphorus, sulfur, and chlorine. Based on their structural and spectroscopic properties, elements that are useful in the window include beryllium, carbon, silicon, aluminum, iron, cobalt, and gold. The substrate therefore preferably contains at least 10% of at least one of the following elements: beryllium, carbon, silicon, aluminum, iron, cobalt, and gold. The substrate preferably comprises greater than about 10% of at least one of the elements selected from the group comprising beryllium, carbon, silicon, aluminum, iron, cobalt, and gold.

Substrates may absorb scattered x-rays that may contribute to noise in the measurement. Substrates that absorb scattered x-rays preferably have an x-ray emission peak between about 2.984 KeV (e.g. silver) and about 6.947 KeV (e.g. erbium) to avoid overlap with signals of interest. X-ray emission peaks that are at higher energies than about 6.947 KeV are generally non-productive for exciting the sample if it contains sulfur, phosphorus, or chlorine; although in cases where the sample contains elements such as selenium, x-rays of higher energy may be useful. X-ray emission peaks from the substrate that have energies between about 1.978 KeV (e.g. iridium) and about 2.984 KeV (e.g. silver) are generally counter-productive if the sample contains sulfur, chlorine, or phosphorus; this is the typical case for biological or pharmaceutically-important samples. If the sample to be measured contains phosphorus, then the substrate should not contain zirconium, phosphorus, platinum, gold, niobium, mercury, or thallium. If the sample to be measured contains sulfur, then the substrate should not contain thallium, molybdenum, sulfur, lead, bismuth, technetium, or ruthenium. If the sample to be measured contains chlorine, then the substrate should not contain technetium, ruthenium, chlorine, rhodium, or palladium. X-ray emission peaks from substrates that are less than 1.978 KeV are believed to be unproductive for exciting biological samples. The substrate should be substantially free of the elements that are not intended to be measured in the sample if energy dispersive x-ray fluorescence (EDXRF) is to be used for analysis. Wavelength dispersive x-ray fluorescence (WDXRF) have been shown to differentiate different chemical forms of elements, such as the sulfur compounds sulfate and sulfite; if WDXRF is used, then the substrate should be substantially free of the same chemical form of the element to be measured in the sample. In this paragraph, substantially free is defined as a substrate which produces less than 10% of the signal produced by the sample, which when measured using the same x-ray fluorescence conditions.

Substrates: Focusing Chips

The invention also consists of preparing a protein sample on a focusing chip. Focusing chips typically consist of a substrate having a pattern of hydrophobic and hydrophilic regions. Preferably, each hydrophilic region is circumscribed by a hydrophobic region. When a sample of an aqueous solution is placed on a hydrophilic region of the chip, the surrounding hydrophobic region repels the solvent and causes the sample to dry preferentially over the hydrophilic region. The drying may be accomplished through any means, including simple ambient air drying or heating. In this way, larger droplet may be dried into a predefined region using a focusing chip instead of a non-focusing slide. Focusing chips have been developed for depositing proteins for Matrix Assisted Laser Desorption Ionization Mass Spectrometry (MALDI-MS). Some of these focusing chips were described at the 54th ASMS Conference on Mass Spectrometry, May 28-Jun. 1, 2006, Washington State Convention & Trade Center, Seattle, Wash., described on the internet at: www.asms.org/Desktopmodules/inmergeab stractsearch/programprintview-.as px?sess=WP13, and quoted below in the bulleted list:

"Applications of a SAM-IMAC Biochip for the Purification and Concentration of Bioengineered or Phosphorylated Proteins with Detection by MALDI-MS" by Christopher M. Belisle; Irene Y. Chen; Julie K. Mirshad; Udo Roth; Kerstin Steinert; and John A. Walker, II; who stated that: "Immobilized metal affinity chromatography (IMAC) is a powerful technique which is routinely used in the purification of biomolecules containing a hexa-histidine tag, as well as phosphorylated peptides/proteins. This wide range of affinities is afforded by the chelation of specific metal ions by an immobilized poly-valent ligand (i.e. IDA-Ni(II) for hexa-His tags and IDA-Fe(III) for phosphorylated species). The utility of IMAC surfaces formed from SAMs has been demonstrated with SPR. In this work, chelated metals allows for high affinity capture and optimal orientation of tagged proteins for subsequent protein/protein interaction studies. We have developed a SAM-based biochip that takes full advantage of these properties and allows for volume containment, sample concentration and direct interface to and detection by MALDI-MS. Three distinct SAM regions were patterned on a gold-coated biochip in a 96 well format. Each site was comprised of a circular capture zone containing either NTA-Ni(II) or NTA-Fe(III) chemistry. Each site is surrounded by a non-wettable, protein-resistant SAM region and is capable of retaining sample volumes in excess of 25 µl. Centered in the capture zone was a 0.6 mm analysis zone consisting of a protein-resistant SAM. After chelating the metal, samples containing either His tags or phosphorylated amino acid residues were applied and purified on-chip. Subsequent release, concentration and detection of the captured analytes was facilitated by focusing and the addition of matrix."

"Effects of Nanoporous Silica Thin Film Parameters on LDI-MS Performance" by Srinivas Iyer; Raea Hicks; Steven Madrid; and Andrew Dattelbaum; who stated that "The use of MALDI-TOF MS in small molecule analysis has been limited due to matrix interference. We have shown that ordered nanoporous silica thin films on silicon substrates allow for the analysis of small organic molecules without the addition of a matrix. Patterned nanoporous films are prepared by an evaporation self-assembly method, followed by selective UV exposure, to prepare surfaces that may be spotted with many different analytes. The patterned films have been shown to remain active for over a year under atmospheric conditions. Here we report the effect of several variables, including film thickness, film porosity, instrumental settings and spotting technique, to optimize the mass spec analysis of small peptides and other biomolecular samples on nanoporous silica thin films. Mesoporous thin films are made by withdrawing an ozonated silicon crystal at a steady rate from a solution of TEOS, water, ethanol, HCl, and templating surfactant, then UV-patterning the film to remove the template and expose analyte-absorbing pores. Film thickness and pore size can be controlled by withdrawal speed and choice of surfactant, respectively. These films are mounted directly onto a standard MALDI plate. Fims of varying thickness and pore size were examined. Spotting conditions were also examined using a solution of FITC labeled angiotensin. Before MS, the spots were examined by fluorescent microscopy to determine spot spreading and coverage. MS analysis was conducted on a Voyager DE-STR in positive ion, reflector mode. Our data indicates that these films require no special storage conditions to remain stable for over a year. Preliminary studies show that mesoporous silica thin films yield acceptable results in terms of intensity and resolution for small molecules such as peptides and C60 and its derivatives. Reliable data was obtained for acid hydrolysates of bacterial siderophores. Optimizing spotting methods improved signal intensity by two orders of magnitude while retaining resolution. Fluorescence microscopy data shows that spotting small amounts of analyte, followed by removing excess solution after a minute gives a uniform spread of sample, this is further substantiated by MS data. With peptides and small molecules, we observe that thinner films perform better. Small changes in pore size do not appear to affect desorption-ionization significantly. However, when compared with MALDI, higher laser fluences are needed with these thin films. Future work will be directed towards improving sensitivity of this approach."

"Functionalized monolithic surfaces for single droplet sample handling" by Mohammed Kajjout; Xiayang Wang; Christian Rolando; Séverine Le Gac; who stated that "We describe here functionalized monolithic surfaces for single droplet handling. In many cases mass spectrometry analysts must face to single droplet handling either as the initial sample input of the analysis or for sample preparation before nano-ESI or MALDI.

The conventional strategy consists of dissolving the droplet in more solvent so as to perform sample preparation on devices working with continuous liquid flow. At the final stage liquid must be concentrated to go back to a the droplet state. Therefore the development of surface chemistry for the purification of single liquid droplets has a strong interest in order to minimize sample handling, contamination and loss. At the routine sensitivity level of mass spectrometry, monolayer surface chemistry does not provide enough interaction sites for real world analysis. Subsequently we decided to use monolithic polymer chemistry that we had previously developed for capillary columns dedicated to proteomics applications and that affords 1 micron-thick film. Methacrylate-based monoliths were anchored on a gold surface using a linker bearing at its two extremities a disulfide moiety and a methacrylate group respectively, and polymerisation was done according to an original living method. Non reactive and hydrophobic butylmethacrylate (BMA) or reactive glycidylmethacrylate (GMA) may be used and mixed together in any proportions. Either silicon wafer coated with gold or low-cost printed board circuit coated with copper or gold may be used as the starting surface. Using printed board enables rapid prototyping of patterned surfaces. Most of the experiments described were done either on plain gold surface or 400 µm gold spots. We first tested the desalting efficiency using a laurylmethacrylate phase. One microliter droplets of a salted (20%) solution containing various peptides (1 picomolar) were placed on the surface, and interactions were forced by several aspiration/ejection cycles. Spots were washed with water, extracted with acetonitrile/water and analyzed off line either by ESI or MALDI. In both cases, no adducts were detected on the mass spectra. The second test involved a functionalized glycidylmethacrylate on which was first linked trypsin. After washing of the surface, one microliter of Cytochrom C (1 picomolar) was deposited and let on the surface for a quarter of an hour. More water was added and the sample desalted. Resulting mass spectra showed a clean digestion, affording a high score identification on proteomics search engine!. Analysis on crude biological samples like human plasma will be also presented. The different parameters, monolith porosity and thickness, nature of monomers, droplet handling, are currently under investigation. We are also testing other monolithic phases we also developed for nano-LC capillary column for phopshopeptide (IMAC) and glycopeptide (phenylboronic acid) isolation."

"The Use of Reactive Surfaces for On-Chip Immobilization of Biomolecules and Subsequent Purification/Concentration of Analytes for MALDI-MS," by Julie K Mirshad; Christopher M Belisle; Irene Y Chen; Udo Roth; Kerstin Steinert; and John A Walker who stated that Currently in proteomics there is an increasing demand for high affinity purification of small amounts of analytes from complex samples. This requires methods that minimize sample handling and analyte loss while being amenable to high-throughput processing. Typically, highly selective purifications have been achieved by immobilized biomolecules such as mAb, steptavidin/biotin or nucleic acids. The most frequently used chemistry reported in literature for such immobilizations are active esters (i.e. N-Hydroxysuccinimide-NHS). We have developed a novel biochip platform used in MALDI-MS that consists of multiple sites with differing zones of wettability which enable immobilization of these biomolecules with subsequent concentration of the captured analytes. Three distinct SAM regions were patterned on a gold-coated biochip in a 96 well format. Each site was comprised of a circular capture zone containing the active NHS chemistry. These sites are capable of retaining sample volumes in excess of 25 µl and are surrounded by a non-wettable, protein-resistant background SAM region. Centered in the capture zone was a 0.6 mm analysis zone consisting of a highly wettable, protein-resistant SAM that facilitates MALDI performance. After protein immobilization, samples containing complementary antigens in complex mixtures were applied and purified on-chip. Subsequent release, concentration and detection of the captured analytes were facilitated by focusing and the addition of matrix. In initial experiments, analytes were used in spike/recovery experiments with various protein digests to test for specificity and the limits of detection (LOD) for the biochip. In subsequent experiments, mAb were immobilized and proteins were purified on-chip and then digested in situ with trypsin. Sample clean-up was performed by either transferring to a reverse-phase 3 zone biochip or by SPE. Results comparing the advantages of this technique are discussed."

"Enhanced MALDI ionization efficiency at the metal-matrix interface: practical and mechanistic consequences of sample thickness and preparation method," by Gregor McCombie; and Richard Knochenmuss, who stated that "Electrosprayed spots of varying thickness were evaluated for use as homogenous, high efficiency MALDI samples. The layer at the metal/matrix interface was found to give exceptionally strong signals. Ion yields and intensity ratios can be understood in the context of the previously described quantitative MALDI model including the matrix-metal interfacial ionization potential reduction effect (Knochenmuss, R. Anal. Chem. 2004, 76, 3179-3184). The absolute and relative stabilities of ion signals were found to be at least a factor of 2 better for the thin electrosprayed spots, compared to spots prepared by dried droplet methods. The sample preparation method was used for the analysis of yeast lipid composition. In order to detect differences in lipid content a stable sample preparation is necessary. Experiments were performed on a commercial MALDI TOF instrument (Voyager-DE STR, Applied Biosystems Framingham, Mass.). The mass range was from m/z 100 to 1500. The electrospray sample deposition was done on a home built electrospray device using a CTC Pal autosampler for the sample injection. The spray voltage was 5 kV and the distance of the needle to the sample plate 6 mm. Lipid extracts from yeast were done using the Bligh and Dyer method. Electrospary deposition of matrix (DHB) and analyte (Substance P or reserpine) on a MALDI target plate of varying spray times allowed us to control the thickness of the sample. Spray times between 2 and 30 seconds were used to demonstrate that the MALDI ion yield is 10 to 100 times higher at the metal/matrix interface. The results were consistent with, and could be explained by a previously described MALDI ionization model (Knochenmuss, R. Anal. Chem. 2004, 76, 3179-3184). The formation of more primary matrix ions was demonstrated by quantifying the suppression of the matrix signals (MSE score; McCombie, G.; Knochenmuss, R. Anal. Chem. 2004, 76, 4990-4997) and comparing a thin versus a thick sample. While the MSI score for the thick sample was 0.94 (0.06)—which is almost complete matrix suppression—the same conditions only gave a MSE score of 0.57 (0.08) for a thin sample. The homogeneity of the sample preparation method was demonstrated for phospholipids samples and crude lipid extracts. It was possible to separate groups of mouse serum based on their lipid spectra."

"MALDI on Silicon" by Jae-Kuk Kim; and Kermit K. Murray who stated that Porous silicon substrates have been used in the past for small molecule analyses with the matrix-free soft ionization method known as desorption/ionization on silicon (DIOS). Non-porous silicon targets have been used with infrared lasers for ionization that is similar DIOS in that a matrix is not required and ionization occurs without interference from low mass background ions. In this study, we demonstrate the benefits of using untreated silicon targets for matrix-assisted laser desorption ionization (MALDI). Samples and matrix are deposited along with matrix on a silicon wafer and were irradiated with a UV laser. The resulting ions are mass separated in a time-of-flight mass spectrometer. Riboflavin (MW: 376.4 Da, Formula: $C_{17}H_{20}N_4O_6$), bovine serum albumin (BSA, MW: 66,430.3 Da), lyophilized *Escherichia coli* strain W (ATCC 9637), and phosphorylase b from rabbit muscle (MW: 97 kDa) were ionized by MALDI on both non-porous silicon substrate and stainless steel substrate. The dried droplet method was used to sample preparation for both substrates. The Bruker Omniflex mass spectrometer can be operated in linear and reflectron mode and uses a 337 nm nitrogen laser (Pulse width: 3 ns, Pulse energy: 200 μJ max.) at a repetition rate of 2 Hz for ionization. An accelerating voltage of 19 kV was employed with delayed ion extraction. The typical heterogeneous MALDI sample deposit requires searching for "sweet spot" to obtain the optimum mass spectrum with a stainless steel substrate. One of the greatest advantages of the untreated silicon substrate is that it leads to a homogeneous sample spot so that a search for a sweet spot is not necessary. Comparison of small molecule LDI analysis of riboflavin showed significant difference between silicon and stainless steel substrates. The stainless steel target gave small analyte peaks only at high laser energy that also produced extensive background due to ablation of material on the metal target. In contrast, the untreated silicon substrate showed intense analyte peaks without background noise even at full laser energy. It was difficult to obtain signal from the stainless steel target, but highly reproducible mass spectra could be obtained for non-porous silicon substrate. BSA, *Escherichia coli* and phosphorylase b MALDI mass spectra could also be obtained easily on the silicon substrate with high spot-to-spot reproducibility. The silicon target required somewhat higher threshold energy compared to the metal target, but showed somewhat better signal-to-noise ratio and resolution than stainless steel substrate for small molecule as well as high molecule analyses. A surface characteristic of non-porous silicon substrate is hydrophobic which makes a smaller and more concentrated sample spot after solvent evaporation. It is possible that this produces homogeneous analyte and matrix crystals and efficient ion formation. An alternate explanation is that the lower number of electrons produced by irradiation of the silicon results in less charge recombination and therefore greater signal. Different target materials and surface imaging techniques are being used to explore, ion formation from silicon targets."

"Matrix-free Laser Desorption Ionization Mass Spectrometry using Porous Alumina Thin Film Structures," by Ranu Nayak; and Daniel R Knapp who stated that "Matrix-assisted laser desorption ionization (MALDI) mass spectrometry (MS) has been established as one of the key methods for proteomic analysis. MALDI is complicated by the need to have good co-crystallization of sample and matrix. Matrix-free methods of laser desorption ionization (LDI) offer the potential to eliminate this complication. MS from porous alumina surfaces has been reported (R1-Anal. Chem., 77, 5364-69, 2005), however, few details were provided and the report did not describe a systematic study of the experimental parameters. We report here the LDI MS analysis of some peptides using anodized aluminum (Al) surface on glass substrates and an investigation of the experimental factors controlling the MS signal intensity. Al thin films were grown on cleaned Pyrex glass substrates using a thermal evaporation technique. The as grown films were subjected to anodization using a dc regulated power supply at 50V, 60V, and 90V in a 10 vol. % phosphoric acid solution (at room temperature). The resulting porous oxide layer was confirmed by scanning electron microscopy. The anodized samples were coated with gold film by magnetron sputtering. Subsequently, different peptides (mass range-500 to 10,000 Da; concentration-0.1 to 1.0 mg/ml) were spotted on the conductive anodized aluminum surface and air dried. Spots were analyzed by a Voyager-DE-STR-MALDI-TOF mass spectrometer. For comparison, the same peptides were subjected to conventional MALDI analysis using α-cyano-4-hydroxycinnamic acid as a matrix. A porous structure is necessary for ionization of analytes in matrix-free LDI-MS (R1). In the present work we have grown some hexagonal porous alumina structures using thin films of Al on glass substrates. The as grown Al film thickness were 0.3, 0.5 and 0.7 μm. Utilizing Al film made the anodization process trivial by not being concerned on the tedious process of mechanical and electrochemical polishing which is an essential pretreatment step for anodizing directly on bulk Al substrates. In other (non-MS) work on nanostructured alumina films, multi-step anodization processes are often used on Al substrates to obtain more uniform porous structures. However, we have shown some promising results using a single step anodization process on the smooth surfaces of Al film with no pretreatment step. Thickness variation and anodization at different voltages have been examined to see the effect of pore depth and diameter on MS signal intensity. Samples anodized at 50V gave no peptide signals. Films anodized at 60V and 90V gave peak intensities comparable to those with conventional MALDI, however, higher laser intensity was required. Both 60V and 90V anodized samples showed similar results indicating less effect of pore diameter within a range of 75 to 120 nm. Thickness (depth of pores) comparison suggested that a 0.3 μm film is not suitable for MS analysis, as the laser flux tends to burn out the surface with each shot and subsequently decreasing the signal intensity. Degradation of signal intensity with time was also studied. A 15 days old alumina film did not show any change in signal intensity and further investigations are ongoing with older samples. These results suggest that porous alumina on glass can be a potential matrix-less approach for LDI-MS proteomic analysis."

"An statistical analysis of factors related to ion suppression in MALDI-TOF mass spectrometry" by Dongmei Yang; Michael S. Wisz; Kevin Ramkissoon; Morgan C. Giddings who stated that "Protein identification relies heavily on the measurement of peptides by a mass spectrometer, yet ion suppression impedes peptide measurement by causing a differential in their spectral intensities that can result in some peptide peaks being undetectable. The differing chemical properties of peptides are thought responsible for this phenomenon. We examined the correlations between observed peptide intensities and their amino acid sequence content for MALDI-TOF spectra in order to provide a predictive measure for the likelihood that a given peptide might be observed, given its sequence. These statistics may be used as an additional measure that can be factored into the search engines to increase the accuracy of protein identification, particularly for peptide mass fingerprint (PMF) data. We obtained TOF spectra on an ABI 4700 mass spectrometer, corresponding to trypsin-digested spots taken from coumassie stained gels of E. coli cytosolic extract. Proteins were identified by PMF analysis using Mascot and GFS searching tools, resulting in 350 matched proteins with significance $p<0.05$. We also generated 30,000 control spectra by picking random sets of peaks (mass, intensity) from the entire set of real spectra, selecting 350 whose match scores were at a significance level of $p<0.05$. We compared peptides and their matching sequences from the real spectra to randomly matched peptides from control spectra to analyze properties of peptides that correlate with peak intensity, including composition and N or C-terminal residues. Since there is a bias in the spectra where smaller peptides have higher average intensities, we divided the peptide masses into four distinct mass ranges for independent analysis. In each mass range, we divided peaks into three intensity categories (high, medium and low) based on thresholds picked to create an equal distribution of intensities in each category for each mass range. Comparing the amino acid, distribution in real peptides versus randomly-matched peptides revealed a strong negative correlation between peak intensity and the presence of both cysteine (C) and tryptophan (W). On the other hand, valine (V) and methionine (M) tend to be favored in high intensity peaks. Though we expected to see the acidic residues aspartic acid (D) and glutamic acid (E) corresponding with high peak intensity due to their negative charge, no such trend was observed. At the N-terminal position, some of the same trends held as for composition, though with significant differences. Methionine showed an opposite, negative correlation with peak intensity when at the N-terminus. Proline (P), tryptophan (W), and cysteine (C) were also disfavored, whereas valine (V), threonine (T), histidine (H), phenylalanine (F), isoleucine (I), and alanine (A) all favored peaks of high intensity when at the N-terminus. Of the two residues found at the C terminus of tryptic peptides, arginine (R) was correlated with high intensity peaks whereas lysine (K) was found more commonly in low intensity peaks. Our data indicate that composition of peptides plays a significant role in peak intensity and hence the likelihood of peptide observation in MALDI-TOF MS. These data can be used as an additional feature to improve protein identification methods."

"Advances in MALDI of small molecules using surfactants as matrix co-additives", by David C. Grant; and Robert J. Helleur, who stated that "Matrix-assisted laser desorption/ionization time-of-flight mass spectrometry has been innovative in the analysis of macromolecules. However, it is still developing as a technique for small molecule analysis. The main reason for this is the abundance of matrix-related ions in the low mass range of the spectra. The surfactant cetyltrimethylammonium bromide (CTAB) has previously been used by another group as a matrix suppressor. When added to the matrix α-cyano-4-hydroxycinnamic acid (CHCA) at an appropriate molar ratio it has been shown to selectively suppress matrix ions. Our research expands on this effect by examining a wider variety of surfactants for the analysis of peptides, cyclodextrins, and small phenolic compounds such as flavonoids and flavones. Experiments were performed on a Voyager DE-PRO MALDI-TOF. Analytes were dissolved in 4:1 MeOH:$H_2O$ (v/v) and pre-mixed with CHCA matrix. Each analyte was tested separately with seven surfactants: hexyltrimethylammonium bromide, dodecyltriethylammonium bromide, cetyltrimethylammonium bromide (CTAB), tetrabutylammonium bromide, decamethonium bromide, Triton X-100 and sodium dodecyl sulfate (SDS). Each surfactant was mixed with the analyte-matrix solution at varying mole ratios to examine the effect of surfactant concentration of analyte signal. The parameters monitored including analyte resolution, signal-to-noise, peak area and intensity. Mixtures of analytes were then tested with each surfactant. Finally, analysis of phenolic compounds in wine, green tea, and blueberry extracts were undertaken to illustrate real sample applications. Mass spectra of standard peptides, phenolic acids and other low mass molecules (m/z<500) demonstrate improved mass resolution by 15-45% using appropriate surfactants. Surfactant-mediated MALDI-TOF-MS has also been evaluated for small molecule quantitative analysis using a second analyte as an internal standard. In one experiment, p-coumaric acid (m/z 147.30) was analyzed using quercetin (m/z 303.45) as an internal standard and the resulting calibration curve displayed good linearity ($R^2=0.9872$). Surfactants tested showed promising results as matrix-ion suppressors, as spectra were mostly free of all matrix ions, and displayed low background noise at the appropriate molar ratio. It was found that a matrix:analyte:surfactant ratio of approximately 1000:20:1 gave the best spectra in most cases. In some cases, ion suppression was observed by using even lower amounts of surfactant (10000:20:1). Surfactant-mediated MALDI showed promise in analysis of analyte mixtures as well as real samples containing phenolic compounds. Several were identified and some quantitatively measured by MALDI. Their identity was confirmed by LC-MS. These results indicate that surfactant-mediated MALDI may be a good technique for analysis of small molecules."

"Sublayer Assisted MALDI (SA-MALDI): Practical Applications and Fundamental Studies," by Zaneer M. Segu; and Gary R. Kinsel, who stated that "MALDI analyses of complex proteomic mixtures suggest that desorption/ionization of high mass proteins is much less efficient than for lower mass peptides. The equilibrium model of the MALDI process suggests that analyte ionization proceeds via thermodynamically driven gas-phase ion-molecule reactions within the plume of laser desorbed material and, hence, that the primary limitation to obtaining MALDI ion signals from high MW proteins is likely related to inefficient desorption of these compounds. If true, alternate approaches that lead to improved desorption of these species within the MALDI plume should yield enhanced high molecular weight protein MALDI ion signals. We have explored this hypothesis through the use of various desorbable sublayers onto which conventional protein MALDI samples are deposited. Sublayers for SA-MALDI were chosen from a group of hydrophobic polyaromatic hydrocarbons. The sublayers were chosen a) to be insoluble in the matrix and analyte solvents, b) to absorb at 337 nm, c) to have no easily donatable protons and d) to have a range of IEs above and below those of typical MALDI matrices. MALDI MS and SA-MALDI MS analyses were performed using various peptides and proteins ranging in MW from 1,200 to 150,000 Da. Conventional dried droplet sample preparation was employed, either directly on the stainless steel MALDI target or on the sublayer coated MALDI target. Similar experiments were performed using peptide/protein mixtures and, finally, using a crude protein extract from cyanobacteria. The preliminary studies performed clearly demonstrate that a significant enhancement in the peptide/protein MALDI ion signal is achieved for SA-MALDI as compared with the conventional dried droplet sample preparation. For every peptide/protein tested between the MW's 1,200 to 150,000 Da a signal enhancement of 1-2 orders of magnitude was achieved when using selected sublayer compounds. The most significant enhancements were observed for the higher MW proteins. Furthermore, consistent with predictions of the equilibrium model of MALDI, the preliminary experiments also showed a strong dependence of the sublayer enhancement on the IE of the sublayer being greater than that of the MALDI matrix. This effect is consistent with the possibility of the sublayer acting as a "charge sink" and inhibiting protonation of the analyte i.e. if the IE of the sublayer is lower than that of the MALDI matrix then an electron transfer between the photoionized matrix molecules and the sublayer will occur leading to loss of the matrix ions necessary for analyte protonation. Finally, preliminary experiments suggest that SA-MALDI will be particulary useful for complex mixture analysis. Enhancements of both low MW and high MW signals of up to an order of magnitude are observed for both control mixtures of peptides/proteins and for the complex protein mixture derived from the cyanobacteria source."

"Sensitive and reproducible detection of peptides by Maldi-TOF MS using self-assembled monolayer (SAM)-based chips—specifications and applications," by Udo Roth; Holger Röhl; Matthias Gluckmann; Thorsten Jaskolla; Michael Karas; Kerstin Steinert; and Karsten Reihs, who stated that "Sensitivity, mass accuracy, and reproducibility are prerequisites for efficient MALDI-MS analyses used in current quantitative proteomic work-flows. Our approach consists of a novel technology for peptide sample preparation using plates with pre-deposited matrix spots of extra-fine sub-micron size CHCA crystals prepared by vacuum sublimation on an ultraphobic surface. Such a design enables the reliable application of nanoliter volumes of analyte solutions and facilitates highly reproducible signal detection in the low attomole range. To provide a platform for high-resolution LC-MALDI-TOF, a high-density array chip accommodating up to 1600 spots is supplied. We present the results of our investigation on the effect of the properties of the CHCA matrix crystals on the initial velocity of the peptide ions and their fragmentation in MS/MS experiments. Sensitivity, mass accuracy, and reproducibility were assessed using different volumes and concentrations of a peptide mixture spotted onto a Mass•Spec•Turbo Chip with 192 spots. Special attention was paid to the flatness of the target and its proper electrical ground connection. For LC-MALDI analysis, tryptic digests were separated using a reversed phase (C18) HPLC-column. Samples were spotted (Probot, LC Packings) on a high-density Mass•Spec•Turbo Chip (1600 spots). Prior to MS analysis, the air-dried spots were treated with 15 mM ammonium dihydrogen phosphate to efficiently reduce the formation of matrix cluster ions. The initial velocity was determined by the delayed extraction method in a linear two-stage acceleration TOF system. Experiments were carried out using MALDI-TOF instruments from Bruker (Reflex III) and Applied Biosystems (DE-Pro, 4700, 4800). In the sensitivity trial, detection of peptide amounts, which were applied from a standard dilution series, was achieved down to the attomole/spot range. A mass accuracy of an average mass deviation of less than 10 ppm for each spot was routinely obtained by external mass calibration using the four corner spots of the array. MS/MS experiments analyzing attomole amounts of peptides delivered fragment spectra that provided sufficient information for the unambiguous identification of peptides. Reproducibility of sample preparation yielded RSD values of typically less than 10-20% depending on the peptide. The benefits of sensitivity, mass accuracy, and reproducibility provide an optimal combination for high throughput LC-MALDI experiments. We show that peptide identification can be significantly increased compared to standard procedures using stainless steel substrates. Due to the sublimation deposition technique used for matrix spot preparation, we obtain very small CHCA crystals of a typical crystal size of less than 1 micron. We found that these spots yield significantly higher initial velocities of the emitted peptide ions in the range of 650 m/s compared to about 300 m/s for standard dried droplet preparations. Higher initial velocities may significantly influence fragmentation processes by more effective expansional cooling during ion formation. Results concerning the relationship between the initial velocity and the peptide fragmentation process will be presented and discussed."

"Predicting matrix conditions for drug analysis in tissue by MALDI MS/MS" by Sara L. Frappier; Sheerin K. Shahidi; and Richard M. Caprioli who stated that "It has been previously found that various drug classes have preferential matrix/solvent conditions when analyzing dosed tissue by MALDI MS/MS. Since there are no established trends known for matrix/solvent preference for such analyses, time consuming optimization procedures are needed before a study can commence. The goal of this study was to determine the trends of matrix/solvent preference for drugs within a class. A model has been developed that provides a method for analyzing a large number of drugs within a class and across classes. Using the identified trends, sample preparation of dosed tissue will have a guideline of matrix/solvent preference for analysis by MALDI MS/MS, saving time and resources. Liver tissue was excised from control (non-dosed) and Olanzapine (OLZ; 8 mg/kg), Spiperone (SPN; 5 mg/kg) or Propranolol (PPL; 10 mg/kg) dosed Fischer 344 mice. Using a cryostat, tissue was sectioned (20 µm) and thaw-mounted onto gold-coated MALDI target plates. For the prediction model, 1 µl of 1.5 µg/ml of a drug standard was spotted on to a MALDI plate, allowed to dry, and then covered with control liver tissue. Sinapinic Acid (SA), 2,5-dihydroxybenzoic acid (DHB) and α-cyano-4-hydroxycinnamic acid (CHCA) matrices were prepared at 25 mg/ml into various binary combinations of acetonitrile, methanol, isopropanol and water. Matrix combinations were spotted onto control and dosed tissue sections for MS/MS analysis by an oMALDI-Qq-TOF-MS. Purportedly, matrix/solvent preferences rely on extraction of drug from tissue and the drug's ability to co-crystallize with matrix. Our model mimics extraction of drug from dosed tissue. In order for drug signal to be detected, the solvent must extract the drug through the tissue so that it may co-crystallize with the matrix. Dosed tissue sections were spotted with each matrix/solvent combination to determine the optimal conditions for analysis. For each drug analyzed, transitions from parent to major fragment ions were monitored to avoid matrix signal interference. Results from the OLZ (m/z 313→256) dosed tissue showed that signal was seen with both CHCA and DHB matrices; however, optimal sensitivity by an order of magnitude was achieved using CHCA in 50% acetonitrile. The model predicted the same optimal matrix/solvent as for OLZ dosed tissue, but demonstrated a two-fold increase in sensitivity not seen in the dosed tissue. Similar drugs within the benzoazepine class, such as carbamazepine (m/z 237→194) and clozapine (m/z 328→272), preferred CHCA. Drugs in the β-andrenergic blocker class, such as PPL (m/z 260→116) and metaprolol (m/z 268→116), exhibited preference for CHCA based on the model; however, no clear difference in sensitivity was observed for various solvent conditions. This was also seen in the PPL dosed tissue. Dosed SPN tissue (m/z 396→165), indicated an affinity for DHB independent of solvent. This preference was also predicted by the model. Preliminary data indicates that matrix/solvent trends do exist within a drug class. The advantage of the model allows us to effectively mimic the behavior of dosed tissue, while avoiding the need to dose and sacrifice animals for each determination of optimal matrix/solvent combination. The model is being extended to butyrophenone (SPN) and β-andrenergic blocker (PPL) classes in addition to other drug classes, as well as, other tissues such as kidney and brain."

Focusing chips for MALDI-MS have different requirements than focusing chips for X-ray fluorescence. Focusing chips for X-ray fluorescence should preferably not interfere with XRF measurement. For example, the chips should have a limited amount of chemical elements that may interfere with the sample being measured. Preferably the focusing chip for use with X-ray fluorescence should have an amount of a chemical element that produces less than 25% of the signal of the sample being measured, when measured for at least one of the elements that are present in both the focusing chip and the sample. More preferably, the focusing chip for X-ray fluorescence is free of elements that may interfere with the sample being measured. Typical elements to be measured include sulfur, fluorine, phosphorus, chlorine, bromine, iron, zinc, magnesium, calcium, titanium, scandium, and platinum. The metal substrate that the focusing chip is supported on should not contain elements that have x-ray emission spectral peaks in the region of interest, and preferably do not have x-ray emission spectral peaks between 2 KeV and 3 KeV.

Focusing chips for X-ray fluorescence should preferably be thin. Thick chips or slides cause scattering in the X-ray portion of the electromagnetic spectrum. Preferably, the chips are less than 500 microns thick, and more preferably the chips are less than about 50 microns thick. Focusing chips as described in the MALDI-MS literature, for example from the list of presentations at the 54th ASMS Conference on Mass Spectrometry, May 28-Jun. 1, 2006, Washington State Convention & Trade Center, Seattle, Wash., should be re-manufactured on thin supports to facilitate their use with X-ray fluorescence.

The size of each hydrophilic region is important. Preferably, each hydrophilic region has an area between 75 square picometers (equivalent to a spot with a diameter of about 10 microns) and 3.6 square microns (equivalent to a spot with a diameter of about 4 millimeters).

One convenient method for preparing focusing chips uses polymer assisted deposition (PAD), described in: Published Patent Application 20050043184, "Polymer-assisted deposition of films," published Feb. 24, 2005, to Thomas M. McCleskey et al.; Published Patent Application 20050008777, "Polymer-assisted deposition of films," published Jan. 13, 2005, to Thomas M. McCleskey et al.; "Polymer-assisted deposition of metal-oxide films." Jia, Q. X.; McCleskey, T. M.; Burrell, A. K.; Lin, Y.; Collis, G. E.; Wang, H.; Li, A. D. Q.; Foltyn, S. R. Nature Materials 2004, 3(8), 529-532.; "Epitaxial growth of Eu2O3 thin films on LaAlO3 substrates by polymer-assisted deposition" Lin, Y.; Wang, H.; Hawley, H. E.; Foltyn, S. R.; Jia, Q. X.; Collis, G. E.; Burrell, A. K.; McCleskey, T. M. Appl. Phys. Lett., 2004, 85(16), 3426-3428; "Structural and dielectric properties of epitaxial Ba1-xSrxTiO3 films grown on LaAlO3 substrates by polymer-assisted deposition" Lin, Y.; Lee, J-H.; Wang, H.; Li, Y.; Foltyn, S. R.; Jia, Q. X.; Collis, G. E.; Burrell, A. K.; McCleskey, T. M.; Appl. Phys. Lett., 2004, 85(21), 5007-5009; "Green luminescent zinc oxide films prepared by polymer-assisted deposition with rapid thermal process" Lin, Y.; Xie, J.; Wang, H.; Li, Y.; Lee, S. Y.; Foltyn, S. R.; Crooker, S. A.; Jia, Q. X.; Burrell, A. K.; McCleskey, T. M. Thin Solid Films, 2005, 492(1-2), 101-104.; "Conformal coating of nanoscale features of microporous Anodisc™ membranes with zirconium and titanium oxides." Shukla, P.; Minogue, E. M.; McCleskey, T. M.; Jia, Q. X.; Lin, Y.; Lu, P.; Burrell, A. K.; Chemical Communications, 2006, (8), 847-849.; "Polymer assisted deposition (PAD) of thin metal films: a new technique to the preparation of metal oxides and reduced metal films." Shukla, P.; Lin, Y.; Minogue, E. M.; Burrell, A. K.; McCleskey, T. M.; Jia, Q.; Lu, Pi. Materials Research Society Symposium Proceedings 2006, 893, 183-188; all incorporated herein by reference. The PAD process may be used to deposit patterns of different materials, including metallic phase metals, metal oxides, and metal nitrides. Using PAD, different regions of hydrophilic materials and hydrophobic regions on a substrate, typically a silicon or aluminum substrate.

Another convenient method for preparing focusing chips uses the formation of hydrophilic and hydrophilic regions on a substrate using supported mesoporous silica. This method is described in A. M. Dattelbaum and S. Iyer, "Surface-assisted laser desorption ionization mass spectrometry," Expt. Rev. Proteomics. 2006, 3(1): 153-61; and in U.S. Pat. No. 6,958,480, "Sample desorption/ionization from mesoporous silica", published Oct. 25, 2005 to Srinivas Iyer and Andrew Dattelbaum; and Nancy H. Finkel et al, "Ordered Silicon Nanocavity Arrays in Surface-Assisted Desorption/Ionization Mass Spectrometry" Analytical Chemistry, 77 (4), 1088-1095, 2005 incorporated herein by reference.

In each of the cases described above, the MALDI focusing chips is preferably modified such that it is formed on a thin substrate, preferably less than 500 microns thick and more preferably less than 50 microns thick.

The XRF focusing chip is used by depositing a sample, which typically consists of an aqueous sample of a protein or nucleic acid, which has been optionally modified by addition of an inhibitor, co-factor, metal, protein, sugar, or other chemical. The sample is allowed to dry, and then the focusing chip with the deposited sample is irradiated with X-rays and any fluorescence of X-rays are measured.

The sample on the X-ray focusing chip may be conveniently measured using an X-ray fluorescence instrument with a monocapillary focusing optic, polycapillary focusing optic, a collimator, a microfocus X-ray tube, a synchrotron X-ray source, a linear accelerator X-ray source, a rhodium X-ray tube, a molybdenum X-ray tube, a chromium X-ray tube, a silver X-ray tube, a palladium X-ray tube, a monochromatic X-ray source, a polychromatic X-ray source, a polarized X-ray source, a confocal X-ray fluorescence spectrometer, a PIN diode detector, a semiconductor X-ray detector, a germanium or doped germanium X-ray detector, a silicon or doped silicon X-ray detector, a wavelength dispersive X-ray fluorescence spectrometer, an energy dispersive X-ray fluorescence spectrometer, total reflectance X-ray fluorescence spectrometer, and the like.

If total reflectance x-ray fluorescence (TXRF) is employed with the present invention, the preferred substrates are quartz, lucite, mylar, silica, silicon with a smooth surface for sample deposition.

Beam Size

In X-ray fluorescence microscopy, we have found that the most efficient (strongest signal with lowest noise) X-ray beam size, ceteris paribus, is one that is essentially matched to the sample size. This situation has not arisen previously because the samples used in the past have been larger than the beam size, so many systems use a small beam size and rastering or scanning across the sample. Also, many samples are not homogenous, so having a beam size matched to the sample size has not previously made much sense.

For the biomedical samples we have analyzed, the samples are generally circular and tend to have diameters between 40 μm and 2 mm (i.e., areas of about between 1 square nanometer and 3 square microns). These samples are also homogenous or otherwise have no need to be sampled in subregions. In such cases, we have found that matching the beam size to the spot size provides the strongest signal to noise ratio. Thus, a preferred X-ray fluorescence source for measuring a sample comprises an X-ray source, where the transmitted X-ray beam has a cross-sectional area essentially the same surface area as the sample. Thus the beam preferably has a cross-sectional area of between about 1 square nanometer and 3 square microns. "Matching" would preferentially be as close a match as practical, but an imperfect match where the beam has a cross-sectional area of between 25% and 250% of the surface area of the sample is also acceptable.

This area matching may be accomplished in rare cases by having an X-ray source whose transmitted beam cross-sectional area matches the sample area without any modification of the beam. More typically, the beam size will have to be modified to match the sample size. Modification is typically carried out by means of focusing optics or by a collimator. Thus, the source further comprises a focusing means or collimator disposed between the source and the sample.

Sample Composition

Many samples, such as proteins, require a buffer to maintain the pH within a particular range (i.e. a pH buffer), or to maintain the redox state of a chemical (i.e. a redox buffer). Many buffers contain elements which might interfere with the measurement of the chemical. The buffer should preferably be free of at least one chemical element having an atomic number of greater than four, where that chemical element is present in the chemical. The buffer should also preferably be free of at least one chemical element having an atomic number of greater than four, where that chemical element is present in the receptor. The buffer should more preferably be free of at least one chemical element having an atomic number of greater than eight, where that chemical element is present in the chemical. The buffer should also more preferably be free of at least one chemical element having an atomic number of greater than eight, where that chemical element is present in the receptor. The buffer should be free of surfactants or detergents that contain sulfur or phosphorus. The buffer should preferably be free of at least one of the following chemicals or functional groups: dimethylsulfoxide, thiols, sulfate anion, sulfonate anions, chloride anion, bromide anion, fluoride anion, iodide anion, perchlorate anion, phosphate anion, and phosphonate anions. The buffer preferably does contain one or more of the following chemical or functional groups: amine, imine, nitrate anion, nitrite anion, ammonium cation, and iminium cation; these chemicals offer the correct buffering properties with minimal x-ray fluorescence interference. Most preferably, the buffer consists of an ammonium nitrate salt such as tris(ethanol)amine nitrate, also known as tris nitrate.

The proteins to be used with the present invention are preferably purified to remove chemicals which are not chemically bound or which are loosely bound to the protein. Loosely bound is defined in this paragraph as meaning having a binding affinity that is weaker than about one (1) millimolar. This desalting step may be conducted conveniently using gel filtration chromatography or size exclusion chromatography, such as using a SEPHADEX G25 or SEPHADEX G50 column. Desalting may also be accomplished using dialysis, including Vibratory Shear Enhanced Process dialysis described in www.vsep.com/pdf/PolymerDiafiltration.pdf. This process is amenable to multiplexing using a well plate format, such as a 96-well, 384-well, or 1536-well plate format. Separations systems such as Zeba 96-well plates available from Pierce Biotechnology Inc., PO Box 117, Rockford, Ill., 61105, are particularly convenient. As can be seen in the following table, Zeba well-plates function across a wide range of concentrations of Bovine Serum Albumin, where the units for the numbers in the table are percent mass recovered, unless otherwise noted:

|              | 5 micromolar | 10 micromolar | 25 micromolar | 50 micromolar |
|--------------|--------------|---------------|---------------|---------------|
| 10 microliters | 39 +/− 21% | 48 +/− 2% | 63 +/− 5% | 62 +/− 3% |
| 20 microliters | 79 +/− 11% | 70 +/− 2% | 78 +/− 2% | 83 +/− 2% |
| 30 microliters | 87 +/− 3% | 79 +/− 4% | 80 +/− 2% | 90 +/− 4% |
| 40 microliters | 103 +/− 3% | 95 +/− 1% | 89 +/− 8% | 98 +/− 5% |

The single-plexed or multiplexed gel filtration chromatography process may be expedited using a centrifuge, such as a the IEC Multi and Multi RF Centrifuges with a Microplate Rotor Available through Fisher Scientific, catalog #05-375-77, Liberty Lane, Hampton, N.H. 03842, manufactured by International Equipment Company; or a vacuum manifold, such as a Vacuum apparatus such as the MultiScreen Vacuum manifold with Direct Stack from Millipore, 290 Concord Road, Billerica, Mass. 01821, attached to a standard vacuum pump (Catalog # WP61 115 60) also available from Millipore. Separation may be performed using ZIPPLATE®. micro-SPE Plate and MALDISPOT™. Accessories also available from Millipore, as well as similar protein desalting well plates and DNA detaining well plates. Separations are preferably carried out in less than 30 seconds at 4 degrees Celsius, as described in Annis D A et al, An affinity selection-mass spectrometry method for the identification of small molecule ligands from self-encoded combinatorial libraries: Discovery of a novel antagonist of *E. coli* dihydrofolate reductase. International Journal of Mass Spectrometry. 2004, 238:77-83. An alternative method of separation is ultrafiltration, such as is described in the following examples:

First Example

We measured the interaction between biotin and avidin to demonstrate that RPM could quantify the sulfur-containing small molecule (biotin, $C_{10}H_{16}N_2O_3S$) over the sulfur content of a protein (tetrameric avidin, Sigma-Aldrich, 16 sulfur atoms, see Korpela J. Avidin, a high affinity biotin-binding protein, as a tool and subject of biological research. *Medical Biol.* 1984, 62:5-26). Previous studies have shown that the ratio of sulfur in avidin-biotin:avidin is 19.5:16, or 1.22, see Green N. Mex. Purification of Avidin. *Meth Enzymol.* 1970, XVIII(A):414-417. We incubated 500 micrograms of avidin in 1.0 ml of 0.20 millimolar biotin at pH 8.0 for 5 minutes and then centrifuged the sample for 3 hours at 7000 g using a Centricon YM-3 resulting in a concentrated avidin-biotin sample of 25-50 μl. We diluted the sample to 0.75 ml in TRIS buffer (pH 8.0), centrifuged for 2 hours at 7000 g, and repeated this process twice. We treated an avidin control sample identically. We used RPM to measure the sulfur content of the avidin-biotin complex and the avidin. We confirmed that the amount of avidin in each sample was identical using bicinchoninic acid protein assay kit (Pierce). As predicted, the avidin-biotin complex contained 1.2 times the sulfur than the avidin alone as measured by RPM. This set of experiments demonstrated that RPM can measure strong non-covalent interactions and use fluorescence ratios to determine binding even when m the protein and analyte have only a shared RPM atom (in this case, sulfur).

Second Example

Our preliminary data show that RPM measures non-covalent protein-inhibitor complexes. We used di-zinc aminopeptidase (aAP) and its competitive inhibitor leucine phosphonic acid (LPA). LPA binds to aAP with a Ki of 6.6 μM at pH 8.0, see Stamper C et al. Inhibition of the aminopeptidase from *Aeromonas proteolytica* by L-leucine-phosphonic acid. Spectroscopic and crystallographic characterization of the transition state of peptide hydrolysis. *Biochemistry,* 2001, 40:7035-7046. We incubated 500 micrograms of aAP in 1.0 mls of 0.20 millimolar LPA (>10×Ki) at pH 8.0 for 5 minutes. We centrifuged the aAP-LPA sample for 3 hours at 7000 g using a Centricon YM-3 resulting in a concentrated sample of 25-50 μl. We diluted this sample to 0.75 ml in TRIS buffer (pH 8.0), centrifuged for 2 hours at 7000 g, and repeated this process twice. We subjected two negative control samples to the same filtering conditions described above: The first control was 1.0 ml of 0.20 millimolar LPA, and the second control was 200 micrograms of avidin and 1.0 ml of 0.20 millimolar LPA to test the possibility of electrostatic and hydrophobic interactions between LPA and non-specific protein. We measured phosphorus was measured in the aAP-LPA complex in a 1:2 ratio; no phosphorus was observed in the control samples. This set of experiments demonstrated that RPM can measure weak non-covalent interactions (6.6 micromolar) and use fluorescence ratios to determine binding when the protein and analyte have different RPM atoms (in this case, zinc and phosphorus).

Sample Deposition

Samples may be conveniently deposited on substrates in several ways. One very convenient manner for sample deposition is deposition of a volume of solution containing the sample using a pipette or syringe. Pipettes are especially preferred because they may be multiplexed, such as an EPPENDORF®. Research Multichannel Pipette catalog number 022452002, available from EPPENDORF North America Inc, One Cantiague Road, P.O. Box 1019, Westbury, N.Y. 11590-0207. The amount of sample to be deposited is important. Large sample solution volumes tend to dry slowly and unevenly. Small sample volumes contain only small amounts of sample. Preferably, the sample solution is deposited in a volume of between 1 nanoliter and 50 microliters, and more preferably the sample solution is deposited in volumes of between 10 nanoliters and 10 microliters. Most preferably, the sample solution is deposited in volumes of between about 25 nanoliters and about 8 microliters. The sample concentration is also important. The sample solution that is deposited preferably contains between 100 picograms of protein and 1 gram of protein. More preferably, the sample solution that is deposited contains between about 1 nanogram of protein and 1 milligram of protein. The reason for this sample mass requirement is to balance the cost of protein and the measurement requirements of the technique. The measurement technique can measure samples containing as little as about 100 femtograms of the chemical elements to be measured. More conveniently, measurements are obtained on samples containing between ten nanograms and one microgram of the element to be measured. Robotic pipettes or automated biological printers may be used, such as a BioDot BJQ3000 BioJet Quanti 3000 or BJP3000 BioJet Plus 3000, available from BioDot, Inc, 17781 Sky Park Circle, Irvine, Calif. 92614. Acoustic printers may be conveniently used, such as the Echo 555 Liquid Handler, the Echo 550 Liquid Handler, and the PORTRAIT™. 630 MALDI Reagent Multi-Spotter, available from Labcyte Inc., 1190 Borregas Avenue, Sunnyvale, Calif. 94089.

Samples should be dried in a manner that promotes formation of an evenly distributed spot. Drying a sample of protein into an evenly distributed spot is extremely challenging. Proteins affect the surface tension of water, especially at high protein concentrations and small solvent volumes, i.e. the exact conditions for drying. This problem is well known in the art, and has prompted the development of highly expensive solutions such as the Labcyte acoustic equipment mentioned above, and described in "The Echo 550tm Delivering Results in Screening," by Jennifer Zewinski, available at www.labcyte.com/aboutus/publications/Zewinski(BMS)EchoPresentation-.pdf;

and in "Acoustic Non-Contact Dispensing—The Right Choice for UHTS," By Timothy P. Spicer, available at www.labcyte.com/news/events/Spicer %20Presentation %20for %20SBS %202 004%20revised %208.sub.-19.sub.-041.ppt; and by "Pharmacological Evaluation of Different Compound Dilution and Transfer Paradigms on an Enzyme Assay in Low Volume 384-well Format," by Tim Spicer, Yvonne Fitzgerald, Neil Burford, Sandra Matson, Moneesh Chatterjee, Mark Gilchrist, Jim Myslik and Jonathan O'Connell, available at www.labcyte.com/aboutus/publications/BMSposterDDT2005-2.ppt. While no ideal solution has been found, preferable solutions include the following. One preferable approach to protein deposition uses focusing chips (described above), which promote even drying of protein solutions. Another convenient approach to protein deposition is to digest the protein using pepsin or trypsin or other proteases; this approach changes the surfactant properties of the protein and promotes more even drying of samples. Other matrix modifying chemicals, such as acetic acid, trifluoracetic acid, detergents, salts (especially salts that do not contain some or all of the chemical elements being measured in the chemical or the protein) or surfactants, promote the even drying of samples; these matrix modifiers are thought to cause proteins to denature or to adopt a molten globular state by disrupting protein folding through the disruption of hydrogen bonds, salt bridges, disulfide bonds, and other covalent and non-covalent interactions that affect protein folding. This molten globular state must be achieved without precipitation of the protein, which leads to inhomogeneity in the sample. Proteins may also be denatured or rendered into their molten globular state by heating the solutions of the sample, preferably above 90 degrees Celsius, but at least above about 40 degrees Celsius, depending on the protein and its thermal stability. High quality protein spots may be generated by heating under an infrared lamp, or a sun lamp, or a halogen lamp, or any lamp with a wattage above about 55 watts. High quality protein spots may also be obtained when the sample is dried while being centrifuged, preferably also under reduced pressure. Centrifugation under at least a partial vacuum is particularly convenient for samples that are multiplexed, because the whole set of multiplexed samples may be dried under identical conditions.

X-Ray Sources

Many x-ray sources will function with the present invention. Rhodium and molybdenum x-ray sources are commonly employed. Biological samples and pharmaceutical samples frequently contain the elements phosphorus, sulfur, and chlorine. It is preferable that the x-ray sources do not generate noise or excessive scattered x-rays in the region of the spectrum that is of most importance. Therefore, it is preferable to use a chromium, palladium or silver x-ray source. If the sample is known or believed not to contain chlorine, or if the chlorine spectrum is not needed for the analysis, then a rhodium source may be used. Molybdenum x-ray sources are less efficient than other x-ray tubes at exciting phosphorus, sulfur, and chlorine, and are less preferred. Most preferably, the x-ray tube has a characteristic K-alpha or L-alpha line at or above about 2.838 KeV and less than about 9.441 KeV. X-ray M lines are frequently broad and less efficient. The x-ray source preferably does not have an M line above 2.120 KeV. X-rays that impinge on the sample may be generated by x-ray tubes directly, or indirectly by the excitation of a target by x-rays.

Chemicals

While this process may be used for many chemicals, it is preferable that the chemical to be measured comprises at least one of the following chemical elements chemically bound to the majority of the chemical: fluorine, phosphorus, sulfur, chlorine, bromine, iodine, platinum, copper, iron, zinc, gallium, or gadolinium; in this context, chemically bound is defined as covalent bonds or metal-ligand bonds having a bond strength of at least 30 kCal/mole.

Chemicals which may be used with the present invention include the following, along with any salts and free bases: Chlorpheniramine; Methimazole; Nelfinavir; Zonisamide; Naltrexone; Carmustine; Ifosfamide; Rizatriptan; Ramipril; Milrinone; Tenoxicam; Apraclonidine; Neomycin; Gabapentin; Anastrozole; Alitretinoin; Oxytetracycline; Prazosin; Amifostine; Desipramine; Hydroxyurea; Naloxone; Kanamycin; Candoxatril; Tramadol; Chlorpropamide; Oxaprozin; Trichlormethiazide; Sulpiride; Cyproheptadine; Brimonidine; Tamsulosin; Misoprostol; Pentolinium; Donepezil; Itraconazole; Penciclovir; Bicalutamide; Epinastine; Trimethaphan; R-mephobarbital; Clavulanate; Nitrofurazone; Bethanechol; Losartan; Gemifloxacin; Clonazepam; Atorvastatin; Heparin; Methohexital; Efavirenz; Duloxetine; Cyclizine; Methoxamine; Benazepril; Amsacrine; Fluticasone Propionate; Divalproex; Etodolac; Enoxaparin; Indinavir; Trihexyphenidyl; Tadalafil; Progabide; Pantoprazole; Meperidine; Guanfacine; Sulfamethoxazole; Lansoprazole; Porfimer; Triamterene; Cocaine; Ribavirin; Theophylline; Vitamin C; Dopamine; Minoxidil; Nicardipine; Phenacemide; Dexrazoxane; Carvedilol; Hydrochlorothiazide; Phentermine; Rifabutin; Zolpidem; Tegaserod; Orphenadrine; Digoxin; Phenelzine; Aprepitant; Vinorelbine; Cerivastatin; Trimethoprim; Simvastatin; Argatroban; Norgestrel; Perhexiline; Pefloxacin; Indomethacin; Levobupivacaine; Rescinnamine; Dicyclomine; Bexarotene; Chlorambucil; Lorazepam; Hesperetin; Melphalan; Acetazolamide; Codeine; Pentoxifylline; Dobutamine; Tamoxifen; Dactinomycin; Venlafaxine; Idarubicin; Chlorthalidone; Tizanidine; Flecainide; Uracil Mustard; Dichlorphenamide; Adenosine; Valsartan; Nandrolone Phenpropionate; Ouabain; Quinidine; Methacycline; Olanzapine; Isotretinoin; Balsalazide; Amoxapine; Vitamin D4 (Dihydrotachysterol); Exemestane; Riluzole; Tolterodine; Citalopram; Cidofovir; Delavirdine; Nilutamide; Rofecoxib; Sulfasalazine; Nitroglycerin; Thiamylal; Cilostazol; Pramipexole; Methoxsalen; Oxymorphone; Succinylcholine; Carbidopa; Mupirocin; Remikiren; Captopril; Levobunolol; Phenindione; Probenecid; Solifenacin succinate; Almotriptan; Tolazoline; Arsenic Trioxide; Atenolol; Trifluoperazine; Clonidine; Sertraline; Tubocurarine; Propantheline; Sirolimus; Prilocaine; Clarithromycin; Isoproterenol; Valdecoxib; Phenobarbitone; Doxorubicin; Oxaliplatin; Risperidone; Proguanil; Oxyphenonium; Sulfadiazine; Nitrofurantoin; Lercanidipine; Propranolol; Carteolol; Cefadroxil; Prednisolone; Reboxetine; Caspofungin; Nicotine; Gemcitabine; Pentostatin; Capecitabine; Vitamin B6 (Pyridoxine); Leflunomide; Galantamine; Rifampin; Metoprolol; Streptozocin; Metaproterenol; Crotamiton; Isoflurane; Cyclobenzaprine; Gentamicin; Morphine; Abacavir; Torasemide; Pimozide; Sevoflurane; Naratriptan; Memantine; Buspirone; Olmesartan Medoxomil; Cevimeline; Piperazine; Emtricitabine; Amitriptyline;

Phenprocoumon; Timolol; Suprofen; Ibandronate; Netilmicin; Glyburide; Enflurane; Levothyroxine; Paramethadione; Topiramate; Etoposide; Didanosine; Phenytoin; Mexiletine; Cefaclor; Clotrimazole; Betaxolol; Calcitriol; Bupivacaine; Amoxicillin; Mechlorethamine; Cephalexin; Ethacrynic acid; Acetaminophen; Clomipramine; Ranitidine; Orlistat; Valproic Acid; Bisoprolol; Trimeprazine; Paclitaxel; Cladribine; Propafenone; Phenmetrazine; Ganciclovir; Aspirin; Zileuton; Butalbital; Tolbutamide; Trimetrexate; Picrotoxin; Frovatriptan; Ridogrel; Demeclocycline; Enprofylline; Loperamide; Tacrolimus; Salmeterol; Clofazimine; Alprazolam; Moxifloxacin; Vigabatrin; Mitomycin; Cefuroxime; Tridihexethyl; Tropicamide; Amiodarone; Mometasone; Thioguanine; Lomustine; Gemfibrozil; Bumetanide; Torsemide; Famotidine; Propylthiouracil; Isradipine; Flucytosine; Mefloquine; Nadolol; Ropinirole; Pentamidine; Tirofiban; Sertaconazole; Triprolidine; Clobazam; Chlorzoxazone; Levodopa; Olopatadine; Estradiol; Ritonavir; Triazolam; Methscopolamine; Trimethadione; Remoxipride; Quinacrine; Ethosuximide; Fenfluramine; Ampicillin; Rivastigmine; Thiethylperazine; Desloratadine; Piperacillin; Vitamin B12; Fluconazole; Pravastatin; Aminophylline; Dacarbazine; Cinnarizine; Vidarabine; Verapamil; Cromolyn; Carbamazepine; Propiomazine; Prednisone; Warfarin; Methylprednisolone; Clomocycline; Tiagabine; Dapsone; Fluvastatin; Fentanyl; Fexofenadine; Palonosetron; Methotrexate; Meclizine; Zopiclone; Promazine; Cisplatin; Dipyridamole; Epirubicin; Tretinoin; Esomeprazole; Paroxetine; Phenylephrine; Diphenoxylate; Dofetilide; Acrosoxacin; Lovastatin; Mitoxantrone; Ibuprofen; Celecoxib; Felodipine; Zolmitriptan; Zafirlukast; Zanamivir; Sumatriptan; Pyridostigmine; Glimepiride; Pilocarpine; Procyclidine; Loratadine; Dutasteride; Mequitazine; Oxycodone; Flupenthixol; Toremifene; Vindesine; Trospium; Pemirolast; Ceftriaxone; Conjugated Estrogens; Azithromycin; Doxepin; Oxyphencyclimine; Raloxifene; Ketoconazole; Nefazodone; Rosiglitazone; Chloroprocaine; Fenofibrate; Physostigmine; Cyclophosphamide; Phenylbutazone; Risedronate; Zaleplon; Streptomycin; Irbesartan; Entacapone; Carisoprodol; Domperidone; Halofantrine; Candesartan; Nitrendipine; Triamcinolone; Penicillin V; Ciprofloxacin; Fluvoxamine; Vitamin D2 (Ergocalciferol); Oxybutynin; Calcidiol; Perphenazine; Raltitrexed; Eszopiclone; Mifepristone; Testosterone; Montelukast; Allopurinol; Glipizide; Sulfanilamide; Repaglinide; Stavudine; Protriptyline; Budesonide; Omapatrilat; Clopidogrel; Tolcapone; Omeprazole; Zidovudine; Epinephrine; Sulfacetamide; Bleomycin; Cisapride; Isosorbide Dinitrate; Sibutramine; Phenylpropanolamine; Mecamylamine; Gliclazide; Cefprozil; Acetophenazine; Methysergide; Phytonadione; Triflupromazine; Carboplatin; Chloroquine; Norfloxacin; Clozapine; Reserpine; Diltiazem; Doxazosin; Brinzolamide; Dihydroergotamine; Levofloxacin; Lidocaine; Amphetamine; Ondansetron; Chlorpromazine; Telithromycin; Methadone; Vitamin A; Guanabenz; Troglitazone; Alfuzosin; Sulfapyridine; Ropivacaine; Ketamine; Mitotane; Vincristine; Phensuximide; Secobarbital; Trimipramine; Cytarabine; Fondaparinux; Ofloxacin; Carbimazole; Idoxuridine; Felbamate; Vitamin D3 (Cholecalciferol); Disopyramide; Terbinafine; Procainamide; Enalapril; Phenformin; Mephenytoin; Betamethasone; Metaxalone; Pirenzepine; Fluorouracil; Sulfametopyrazine; Dolasetron; Amlodipine; Daunorubicin; Proparacaine; Quinapril; Selegiline; Fosinopril; Diclofenac; Isosorbide Mononitrate; Meloxicam; Fluoxetine; Apomorphine; Trazodone; Modafinil; Proflavine; Vitamin B3 (Niacin); Ipratropium; Haloperidol; Benzocaine; Ziprasidone; Ritodrine; Voriconazole; Chlorhexidine; Rosuvastatin; Minocycline; Propoxyphene; Primidone; Amikacin; Baclofen; Vitamin B1 (Thiamine); Albuterol; Metaraminol; Sildenafil; Temozolomide; Nitazoxanide; Marimastat; Lisinopril; Alendronate; Zalcitabine; Quinine; Beclomethasone; Lymecycline; Clindamycin; Acyclovir; Cimetidine; Norgestimate; Lamotrigine; Marinol; Tetracycline; Pemetrexed; Loxapine; Sotradecol; Dorzolamide; Dexmedetomidine; Irinotecan; Alosetron; Tobramycin; Cefixime; Astemizole; Diphenhydramine; Estrone; Terbutaline; Nifedipine; Hydrocodone; Aminoglutethimide; Nateglinide; Fludarabine; Sulfisoxazole; Thioridazine; Doxycycline; Halothane; Pyrimethamine; Famciclovir; Promethazine; Nortriptyline; Moclobemide; Primaquine; Amprenavir; Terfenadine; Hyoscyamine; Furosemide; Flucloxacillin; Mesoridazine; Nimodipine; Encainide; Atomoxetine; Phentolamine; Scopolamine; Nicergoline; Framycetin; Ezetimibe; Sulfinpyrazone; Bupropion; Bromocriptine; Saquinavir; Prochlorperazine; Estramustine; Vitamin B2 (Riboflavin); Medroxyprogesterone; Papaverine; Benzonatate; Cetirizine; Metronidazole; Finasteride; Fluphenazine; Pseudoephedrine; Nisoldipine; Lisuride; Cinalukast; Aripiprazole; Clodronate; Testolactone; Formoterol; Diazepam; Cefdinir; Tranylcypromine; Penicillin G; Mimosine; Dexfenfluramine; Teniposide; Procaine; Phenoxybenzamine; Altretamine; Pioglitazone; Fulvestrant; Dextromethorphan; Acarbose; Methylphenidate; Terconazole; Thiopental; Acamprosate; Valrubicin; Pergolide; Busulfan; Metoclopramide; Bendroflumethiazide; Terazosin; Metipranolol; Foscarnet; Buprenorphine; Sufentanil; Imipramine; Caffeine; Dexamethasone; Quetiapine; Temazepam; Ergotamine; Pindolol; Norethindrone; Midazolam; Lamivudine; Chlordiazepoxide; Escitalopram; Sulfamethizole; Mirtazapine; Cetrorelix; Topotecan; Hydroxyzine; Tripelennamine; Tacrine; Ethinyl Estradiol; Floxuridine; Pipobroman; Novobiocin; Procarbazine; Decamethonium; Valacyclovir; Leucovorin; Vardenafil; Progesterone; Isocarboxazid; Cerulenin; Sulfoxone; Nevirapine; Nizatidine; Eplerenone; Vinblastine; Desoxycorticosterone Pivalate; Bromodiphenhydramine; Ergoloid Mesylate; Gallamine Triethiodide; Methdilazine; Betazole; Chlorotrianisene; Chlorprothixene; Diphenylpyraline; Chlorothiazide; Hexachlorophene; Buclizine; Adinazolam; Biperiden; Alfentanil; Bepridil; Benzthiazide; Ethopropazine; Mefenamic acid; Cycrimine; Ethoxzolamide; Levallorphan; Methyprylon; Minaprine; Alprenolol; Clidinium; Ethanol; Methylergonovine; Methazolamide; Anileridine; Melatonin; Methoxyflurane; Levomethadyl Acetate; Maprotiline; Benztropine; Aminosalicylic Acid; Isoetharine; Methantheline; Butabarbital; Flurbiprofen; L-Norgestrel; Fludrocortisone; Metharbital; Benzphetamine; Ethynodiol Diacetate; Dicumarol; Desogestrel; Isoflurophate; Levorphanol; Carbinoxamine; Etonogestrel; Disulfiram; Dyphylline; Dexbrompheniramine; Ambenonium; Acebutolol; Acetohexamide; Acetohydroxamic Acid; Acitretin; Adapalene; Adefovir Dipivoxil; Albendazole; Alclometasone; Alprostadil; Alseroxylon; Amantadine; Amcinonide; Amdinocillin; Amiloride; Aminocaproic Acid; Aminohippurate; Aminolevulinic Acid; Amlexanox; Amodiaquine; Amphotericin B; Anagrelide; Anisindione; Anisotropine Methylbromide; Arbutamine; Ardeparin; Atazanavir; Atovaquone; Atracurium; Atropine; Auranofin; Azacitidine; Azatadine; Azathioprine; Azelaic Acid; Azelastine; Azlocillin; Aztreonam; Bacitracin; Oxybuprocaine; Bentiromide; Bentoquatam; Benzquinamide; Benzyl Benzoate; Benzylpenicilloyl Polylysine; Betanidine; Bimatoprost; Bitolterol Mesylate; Bortezomib; Bosentan; Bretylium; Bromfenac; Brompheniramine; Butenafine; Butoconazole; Butorphanol Tartrate; Cabergoline; Calcium Acetate; Calcium Chloride; Calcium Gluceptate; Candicidin; Capreomycin; Carbachol; Carbenicillin; Carboprost Tromethamine; Carphenazine; Carprofen; Cefditoren Pivoxil; Cefmenoxime; Cefmetazole; Ceforanide; Cefotaxime; Cefotiam; Cefpiramide; Ceftazidime; Cephaloglycin; Cephalothin; Cephapirin; Ceruletide; Chloramphenicol; Chlormerodrin; Chlormezanone; Chloroxine; Chlorphenesin; Ciclopirox; Cinacalcet; Cinoxacin; Cisatracurium Besylate; Clemastine; Clobetasol; Clocortolone; Clofarabine; Clofibrate; Clomifene; Clorazepate; Cloxacillin; Colesevelam; Colestipol; Colistimethate; Colistin; Cryptenamine; Cyclacillin; Cyclopentolate; Cycloserine; Cyclothiazide; Cysteamine Bitartrate; Dantrolene; Dapiprazole; Darifenacin; Deferoxamine; Demecarium bromide; Deserpidine; Desflurane; Deslanoside; Desoximetasone; Dextrothyroxine; Dezocine; Diatrizoate; Diazoxide; Dibucaine; Dicloxacillin; Dienestrol; Diethylcarbamazine; Diethyipropion; Diethylstilbestrol; Diflorasone; Diflunisal; Dimenhydrinate; Dimethyl Sulfoxide; Dinoprost Tromethamine; Dinoprostone; Diphemanil Methylsulfate; Diphenidol; Dipivefrin; Dirithromycin; Docetaxel; Docosanol; Doxacurium Chloride; Doxapram; Doxylamine; Dromostanolone; Droperidol; Dyclonine; Dydrogesterone; Echothiophate Iodide; Econazole; Edrophonium; Eletriptan; Emedastine; Enoxacin; Entecavir; Epoprostenol; Eprosartan; Erlotinib; Ertapenem; Erythromycin; Esmolol; Estazolam; Ethambutol; Ethchlorvynol; Ethinamate; Ethiodol; Ethionamide; Ethotoin; Etidronate; Etomidate; Etretinate; Fenoldopam; Fenoprofen; Flavoxate; Flumazenil; Flumethasone Pivalate; Flunisolide; Fluocinolone Acetonide; Fluocinonide; Fluorescein; Fluorometholone; Fluoxymesterone; Flurandrenolide; Flurazepam; Flutamide; Fomepizole; Fomivirsen; Fosfomycin; Furazolidone; Gadobenate dimeglumine; Gadodiamide; Gadopentetate dimeglumine; Gadoteridol; Gadoversetamide; Galsulfase; Ganirelix; Gatifloxacin; Gefitinib; Gentian Violet; Glatiramer Acetate; Glycopyrrolate; Gonadorelin; Granisetron; Grepafloxacin; Griseofulvin; Guaifenesin; Guanadrel Sulfate; Guanethidine; Guanidine; Halazepam; Halobetasol Propionate; Haloprogin; Hetacillin; Hexafluorenium Bromide; Hexylcaine; Histamine Phosphate; Homatropine Methylbromide; Hydrocortamate; Hydrocortisone; Hydroflumethiazide; Hydromorphone; Hydroxocobalamin; Hydroxypropyl Cellulose; Hydroxystilbamidine Isethionate; Ibutilide Fumarate; Icodextrin; Iloprost; Imatinib; Imiquimod; Indapamide; Indecainide; Inulin; Iron Dextran; Isoniazid; Ivermectin; Ketoprofen; Ketorolac; Ketotifen Fumarate; Labetalol; Lactulose; Latanoprost; Letrozole; Levamisole; Levetiracetam; Levocabastine; Levocarnitine; Lindane; Linezolid; Liothyronine; Lomefloxacin; Loracarbef; Loteprednol Etabonate; Magnesium Sulfate; Malathion; Mannitol; Masoprocol; Mazindol; Mebendazole; Meclofenamate; Medrysone; Megestrol; Mepivacaine; Meprobamate; Mercaptopurine; Meropenem; Mesalamine; Metformin; Metixene; Methocarbamol; Methyclothiazide; Methyl aminolevulinate; Methyldopa; Metolazone; Metyrapone; Metyrosine; Mezlocillin; Micafungin; Miconazole; Midodrine; Miglitol; Miglustat; Mivacurium; Moexipril; Monobenzone; Moricizine; Nabilone; Nabumetone; Nafarelin; Nafcillin; Naftifine; Nalbuphine; Nalidixic Acid; Naproxen; Natamycin; Nedocromil; Nitisinone; Nitric Oxide; Nitroprusside; Nystatin; Oseltamivir Phosphate; Oxacillin; Oxamniquine; Oxandrolone; Oxazepam; Oxiconazole Nitrate; Oxymetazoline; Pamidronate; Paricalcitol; Pemoline; Penicillamine; Pentagastrin; Pentazocine; Pentobarbital; Pentosan Polysulfate; Perflutren; Perindopril Erbumine; Pimecrolimus; Piroxicam; Podofilox; Polymyxin B Sulfate; Pralidoxime; Praziquantel; Prednicarbate; Pregabalin; Propofol; Pyrazinamide; Rabeprazole; Ramelteon; Remifentanil; Rifapentine; Rifaximin; Rimantadine; Rimexolone; Rocuronium; Sevelamer; Sotalol; Sparfloxacin; Spectinomycin; Spironolactone; Succimer; Sucralfate; Sulindac; Tazarotene; Telmisartan; Tenofovir; Thalidomide; Thiabendazole; Ticlopidine; Tiludronate; Tinidazole; Tioconazole; Tocainide; Tolazamide; Tolmetin; Trandolapril; Tranexamic Acid; Travoprost; Treprostinil; Trifluridine; Trilostane; Trimethobenzamide; Trovafloxacin; Vancomycin; Verteporfin; Zoledronate; Levosimendan; Tetrahydrobiopterin; Lubiprostone; Dornase alfa (Dnase); Alpha-1-proteinase inhibitor; Cyclosporine; Infliximab; Muromonab; Coagulation factor VIIa; Daclizumab; Laronidase; Leuprolide; Collagenase; Asparaginase; Oral interferon alfa; Reteplase; Rituximab; Ribavirin and Alfa Interferon (Intron A); Oxytocin; Interferon gamma-1b; Menotropins; Tenecteplase; Thyrotropin Alfa; Oprelvekin; Hyaluronidase; Interferon alfa-n3; Lepirudin; Calcitonin, salmon; Imiglucerase; Digibind; Streptokinase; Antihemophilic Factor; Urokinase; Insulin, porcine; Darbepoetin alfa; Sermorelin; Choriogonadotropin alfa; Sargramostim; Gramicidin D; Alglucerase; Factor IX; Secretin, synthetic; Antithymocyte globulin; Abciximab; Palifermin; Peginterferon alfa-2a; Pegvisomant; Insulin Glargine recombinant; Digoxin Immune Fab; Peginterferon alfa-2b; Adalimumab; Alteplase; Abarelix; Etanercept; Becaplermin; OspA lipoprotein; Alefacept; Lutropin alfa; Glucagon recombinant; Human Serum Albumin; Anakinra; Desmopressin acetate; Interferon alfacon-1; Eptifibatide; Follitropin beta; Insulin Lyspro recombinant; Interferon alfa-2b; Pancrelipase; Drotrecogin alfa; Ibritumomab; Botulinum toxin type B; Cetuximab; Filgrastim; Basiliximab; Efalizumab; Agalsidase beta; Bivalirudin; Gemtuzumab ozogamicin; Interferon beta-1b; Pegaspargase; Capromab; Omalizumab; Aldesleukin; Natalizumab; Denileukin diftitox; Tositumomab; Somatropin recombinant; Bevacizumab; Octreotide acetate; Serum albumin iodonated; Rasburicase; Immune globulin; Botulinum Toxin; Interferon beta-1a; Pegfilgrastim; Interferon alfa-2a; Interferon alfa-n1; Palivizumab; Trastuzumab; Follitropin alfa/beta; Pegademase bovine; Serum albumin; Anistreplase; Epoetin alfa; Urofollitropin; Insulin recombinant; Enfuvirtide; Arcitumomab; Satumomab Pendetide; Alemtuzumab; Vasopressin; Daptomycin; Desmopressin; Goserelin; Felypressin; Cetrorelix; fkb-001; tmc114; uic-94017; ca-074; [n-(1-3-trans-propyl-carbamoyl-oxirane-2-carbonyl)-1-isoleucyl-1-proline]; 4-[5-[2-(1-phenyl-ethylamino)-pyrimidin-4-yl]-1-methyl-4-(3-trifluoromethylphenyl)-1h-imidazol-2-yl]-piperidine; 1-(5-chloroindol-3-yl)-3-hydroxy-3-(2h-tetrazol-5-yl)-propenone; 2'-deoxy-adenosine 3'-monophosphate; 4-(5-bromo-2-oxo-2h-indol-3-ylazo)-benzenesulfonamide; didecyl-dimethyl-ammonium; (1n)-4-n-butoxyphenylsulfonyl-(2r)-n-hydroxycarboxamido-(4s)-methanesulfo-nylamino-pyrrolidine; 7,8-dihydroxy-1-methoxy-3-methyl-10-oxo-4,10-dihydro-1h,3h-pyrano[4,3-b]chromene-9-carboxylic acid; mevastatin; 2-(2-oxo-1,2-dihydro-pyridin-3-yl)-1h-benzoimidazole-5-carboxamidine; 2-(2-hydroxy-phenyl)-3h-benzoimidazole-5-carboxamidine; 2-(2-hydroxy-5-methoxy-phenyl)-1h-benzoimidazole-5-carboxamidine; 2-(2-hydroxy-phenyl)-1h-indole-5-carboxamidine; spiro(2,4,6-trinitrobenzene[1,2a]-2o',3o'-methylene-adenine-triphosphate; [2(formyl-hydroxy-amino)-ethyl]-phosphonic acid; 12-hydroxydodecanoic acid; 6-chloro-2-(2-hydroxy-biphenyl-3-yl)-1h-indole-5-carboxamidine; 1-(o-carboxy-phenylamino)-1-deoxy-d-ribulose-5-phosphate; n-[5'-o-phosphono-ribofuranosyl]-2-[2-hydroxy-2-[4-[glutamic acid]-n-carbonylphenyl]-3-[2- amino-4-hydroxy-quinazolin-6-yl]-propanylamino]-acetamide; 1,3-dihydroxyacetonephosphate; n-hexadecanoylglycine; 2-amino-3-[5-(amino-carboxy-methyl)-2,3-dihydro-isoxazol-3-ylsulfanyl]-propionic acid; tris-hydroxymethyl-methyl-ammonium; 1-o[o-nitrophenyl]-beta-d-galactopyranose; sd146; 1-o[p-nitrophenyl]-beta-d-galactopyranose; d-galctopyranosyl-1-on; n-(3-(aminomethyl)benzyl)acetamidine; 4,5-dimethyl-1,2-phenylenediamine; (3-carboxy-2-(r)-hydroxy-propyl)-trimethyl-ammonium; (2s)-2-[(2,4-dichloro-benzoyl)-(3-trifluoromethyl-benzyl)-amino]-3-phenyl-propionic acid; (2s)-2-[(5-benzofuran-2-yl-thiophen-2-ylmethyl)-(2,4-dichloro-benzoyl)-amino]-3-phenyl-propionic acid; 6-[n-(1-isopropyl-3,4-dihydro-7-isoquinolinyl)carbamyl]-2-naphthalenecarboxamidine; 4-[3-oxo-3-(5,5,8,8-tetramethyl-5,6,7,8-tetrahydro-naphthalen-2-yl)-propenyl]-benzoic acid; n-{3-[4-(3-amino-propyl)-piperazin-1-yl]-propyl}-3-nitro-5-(galactopyranosyl)-beta-benzamide; 5-[4-(1-carboxymethyl-2-oxo-propylcarbamoyl)-benzylsulfamoyl]-2-hydroxy-benzoic acid; pantothenyl-aminoethanol-acetate pivalic acid; 1-(4-tert-butylcarbamoyl-piperazine-1-carbonyl)-3-(3-guanidino-propyl)-4-oxo-azetidine-2-carboxylic acid; cetyl-trimethyl-ammonium; 1,6-diaminohexane; 16 g; 2-phenylamino-ethanesulfonic acid; 2-amino-5-hydroxy-benzimidazole; benzoylformic acid; 4-chlorobenzoic acid; 3,5-dihydro-5-methylidene-4h-imidazol-4-on; 4-(4-hydroxy-3-isopropylphenylthio)-2-isopropylphenol; bms184394; [1-(1-methyl-4,5-dioxo-pent-2-enylcarbamoyl)-2-phenyl-ethyl]-carbamic acid benzyl ester; propionyl coenzyme a; (2s)-4-(beta-alanylamino)-2-aminobutanoic acid; 4-{2-[(3-nitrobenzoyl)amino]phenoxy}phthalic acid; 4-{2,4-bis[(3-nitrobenzoyl)amino]phenoxy}phthalic acid; ru82197; (2r)-n-[4-cyano-3-(trifluoromethyl)phenyl]-3-[(4-fluorophenyl)sulfonyl]-2-hydroxy-2-methylpropanamide; 1-aminocyclopropanecarboxylic acid; diureido-acetate; 2-fluoroaniline; butan-1-ol; 1-bromopropane-2-ol; coproporphyrin i; 1-deazaadenosine; n-(2-morpholin-4-yl-1-morpholin-4-ylmethyl-ethyl)-3-nitro-5-(3,4,5-trihydroxy-6-hydroxymethyl-tetrahydro-pyran-2-yloxy)-benzamide; 12-phenylheme; 2-deoxy-2-aminogalactose; 6-hydro-1-methyladenosine-5'-monophosphate; 1-methylcytosine; 1-methylimidazole; 1 na; (3r)-1-acetyl-3-methylpiperidine; [(1e)-4-phenylbut-1-enyl]benzene; 2-(2-{2-[2-(2-methoxy-ethoxy)-ethoxy]-ethoxy}-ethoxy)-ethanol; n'-(pyrrolidino [2,1-b]isoindolin-4-on-8-yl)-n-(pyridin-2-yl)urea; alpha-ribazole-5'-phosphate derivative; tribenuron methyl; 1-amino-6-cyclohex-3-enylmethyloxypurine; 8-amino-1,3-dimethyl-3,7-dihydropurine-2,6-dione; pas219; bmsc-0013; compound 9; 6-[n-(4-(aminomethyl)phenyl)carbamyl]-2-naphthalenecarboxamidine; (s)-2-amino-3-(6h-selenolo[2,3-b]-pyrrol-4-yl)-propionic acid; 2,4-difluorobenzyl alcohol 2,4-difluoro-1-(hydroxymethyl)benzene; sr11254; ru79256; ru78262; zk-800270; 5-chloro-.1h-indole-2-carboxylic acid{[cyclopentyl-(2-hydroxy-ethyl)-carbamoyl]-methyl}-amide; ru78299; 2-amino-p-cresol; 2-amino-adenosine; 2-aminophenol; 1-anilino-8-naphthalene sulfonate; beta-methyl-aspartic acid; alpha-benzyl-aminobenzyl-phosphonic acid; (1 r,4s)-2-azabornane; benzofuran-2-carboxylic acid {(s)-3-methyl-1-[3-oxo-1-(pyridin-2-ylsulfonyl)azepan-4-ylcarbamoyl]butyl}amide; 2-chlorophenol; 2-chloro-6-methyl-aniline; 2-carboxypropyl-coenzyme a; 2-deoxy-beta-d-galactose; 2'3'-dideoxyinosine; 2',3'-dideoxythymidine-5'-monophosphate; 2-fluoroadenosine; 2-fluoro-2'-deoxyadenosine; 2-fluoro-2-deoxy-beta-d-galactopyranose; 2-phenylheme; 2-fluoro-2-deoxy-beta-d-galactopyranosyl-beta-d-glucopyranose; difluoromethionine; 1,6-fructose diphosphate (linear form); guanosine-2'-monophosphate; dihydroxyacetone; trans-2-hydroxycinnamic acid; o-coumaric acid; dihydrogenphosphate ion; d-myo-inositol-1,4-bisphosphate; 2-oxobutanoic acid; 2-allylphenol; leucine-reduced carbonyl; methacrylyl-coenzyme a; 2-methylleucine; 3,4-dimethylphenol; n3, n4-dimethylarginine; 2,2-dimethylthiazolidine-4-carboxylic acid; (dmt)thiazolidine; 2'-deoxyinosine; l-2-amino-6-methylene-pimelic acid; 2-oxo-glutaric acid; (2s)-2-hydroxypropanal; 3'-o-n-octanoyl-a-d-glucopyranosyl-b-d-fructofuranoside; 2-[(dioxidophosphino)oxy]benzoate; 3,4-dihydro-2h-pyrrolium-5-carboxylate; nonaethylene glycol; 2-phosphoglyceric acid; 2-amino-pentanoic acid; phosphoglycolic acid; adenylosuccinic acid; ru78300; 6-[n-(1-isopropyl-1,2,3,4-tetrahydro-7-isoquinolinyl)carbamyl]-2-naphthalenecarboxamidine; cra_17312; 2-[5-hydroxy-3-methyl-1-(2-methyl-4-sulfo-phenyl)-1 h-pyrazol-4-ylazo]-4-sulfo-benzoic acid; (s)-2-amino-3-(4h-selenolo[3,2-b]-pyrrol-6-yl)-propionic acid; cra_9334; {3-[(3-hydroxy-2-methyl-5-phosphonooxymethyl-pyridin-4-ylmethyl)-amino]-2-methyl-propyl}-phosphonic acid; 5-methoxy-1,2-dimethyl-3-(phenoxymethyl)indole-4,7-dione; 3,4-dimethylaniline; (3-chloro-4-propoxy-phenyl)-acetic acid; 1-(2,6-dichlorophenyl)-5-(2,4-difluorophenyl)-7-piperidin-4-yl-3,4-dihydroquinolin-2(1h)-one; guanosine-3',5'-monophosphate; 3,9-dimethyladenine; 3-aza-2,3-dihydrogeranyl diphosphate; 3'-deoxy 3'-amino adenosine-5'-diphosphate; n-omega-propyl-l-arginine; cordycepin triphosphate; s,s'-(1, 3-phenylene-bis(1,2-ethanediyl))bis-isothiourea; 3-chlorophenol; 2'-deoxyadenosine; 3-deoxyguanosine; gamma-glutamylcysteine; guanosine-3'-monophosphate; (2r)-2,3-dihydroxypropanal; 2-amino-3-hydroxybenzoic acid; 3-hydroxybutyryl-coenzyme a; 3-indolebutyric acid; 3h-indole-5,6-diol; n-[2(s)-cyclopentyl-1(r)-hydroxy-3(r) methyl]-5-[(2(s)-tertiary-butylamino-carbonyl)-4-(n1-(2)-(n-methylpiperazinyl)-3-chloro-pyrazinyl-5-carbonyl)-piperazino]-4(s)-hydroxy-2(r)-phenylmethyl-pentanamide; 3-(benzyloxy)pyridin-2-amine; 3-methoxybenzamide; 3-methylcytosine; 2s,3s-3-methylaspartic acid; 3-o-methyl-fructose in linear form; 3-methylpyridine; (3s)-tetrahydrofuran-3-yl(1r,2s)-3-[4-((1r)-2-{[(s)-amino(hydroxy)methyl] oxy}-2,3-dihydro-1h-inden-1-yl)-2-benzyl-3-oxopyrrolidin-2-yl]-1-benzyl-2-hydroxypropylcarbamate; 3-hydroxypropanoic acid; 1-octen-3-ol; (1r)-4-[(1e,3e,5e,7z,9e,11z, 13e,15e)-17-hydroxy-3,7,12,16-tetramethylheptadeca-1,3, 5,7,9,11,13,15-octaen-1-yl]-3,5,5-trimethylcyclohex-3-en-1-ol; (3s)-3,4-di-n-hexanoyloxybutyl-1-phosphocholine; 3-phosphoglyceric acid; triphospate; 2-carboxyethylphosphonic acid; 3-hydroxypyruvic acid; 4-o-(4,6-dideoxy-4-{[4,5,6-trihydroxy-3-(hydroxymethyl)cyclohex-2-en-1-yl] amino}-beta-d-lyxo-hexopyranosyl)-alpha-d-erythro-hexopyranose; (r)-2-hydroxy-3-sulfopropanoic acid; compound 6; n-(allyloxycarbonyl)-4-[n-(carboxy-formyl)-2-(benzoic acid)-amino]-1-phenylalaninyl-amino-butyloxy-(6-hydroxy-benzoic acid methyl ester); bilh 434; 4-(1h-imidazol-4-yl)-3-(5-ethyl-2,4-dihydroxy-phenyl)-1h-pyrazole; [3,5-dibromo-4-(4-hydroxy-3-phenethylcarbamoyl-phenoxy)-phenyl]-acetic acid; dmp450; 3-(5-amino-7-hydroxy-[1,2,3]triazolo[4,5-d]pyrimidin-2-yl)-n-(3,5-dichlorobenzyl)-benzamide; naphthyridine inhibitor; ru85493; 6-[n-(4-ethyl-1,2,3,4-tetrahydro-6-isoquinolinyl)carbamyl]-2-naphthalenecarboxamidine; 4-amino-2-deoxy-2,3-dehydro-n-neuraminic acid; (r)-4-amino-isoxazolidin-3-one; 4-(1,3-benzodioxol-5-yl)-5-(5-ethyl-2,4-dihydroxyphenyl)-2h-pyrazole-3-carboxylic acid; s,s'-(1,4-phenylene-bis(1,2-ethanediyl))bis-isothiourea; 4-(hydroxymethyl)benzamidine; 4-hydroxybenzyl coenzyme a; 4-carboxyphenylboronic acid; 4-hydroxyphenacyl coenzyme a; 1-(4-methoxyphenyl)-3,5-dimethyl-1h-pyrazole-4-carboxylic acid ethyl ester; [2-(1-amino-2-hydroxypropyl)-4-(4-fluoro-1h-indol-3-ylmethyl)-5-hydroxy-imidazol-1-yl]-acetic acid; 4-fluorophenethyl alcohol; 4-fluorotryptophane; 4-hydroxybutan-1-aminium; 4-hydroxy-1-benzopyran-2-one; 4-hydroxycoumarin; 4-hydroperoxy-2-methoxy-phenol; [4-(4-hydroxy-3-iodo-phenoxy)-3,5-diiodo-phenyl]-acetic acid; 2-amino-3-(4-amino-1h-indol-3-yl)propanoic acid; inositol-(1,3,4,5)-tetrakisphosphate; 4-methyl valeric acid; 4-methylimidazole; 4-nitrocatechol; 4-nitrophenyl phosphate; 4-oxosebacic acid; propyl acetate; n-hydroxy-4-phosphono-butanamide; 4-piperidino-piperidine; (r)-rolipram; (s)-rolipram; 4-(2-thienyl)butyric acid; 4-hydroxy-l-threonine-5-monophosphate; 2,6-dihydroanthra/1,9-cd/pyrazol-6-one; cd564; cp-166572, 2-hydroxymethyl-4-(4-n, n-dimethylaminosulfonyl-1-piperazino)-pyrimidine; 3-(4-fluorophenyl)-2-(6-methylpyridin-2-yl)-5,6-dihydro-4h-pyrrolo[1,2-b]pyrazole; l-709,587; 3,5-difluoroaniline; 5-(aminomethyl)-6-(2,4-dichlorophenyl)-2-(3,5-dimethoxyphenyl)pyrimidin-4-amine; 5'-o-(n-ethyl-sulfamoyl)adenosine; 5'-o-(n-(1-cysteinyl)-sulfamoyl)adenosine; 2-amino-3-(cystein-s-yl)-isoxazolidin-5-yl-acetic acid; 1-(4-aminophenyl)-3,5-dimethyl-1h-pyrazole-4-carboxylic acid ethyl ester; adenosine-5'-pentaphosphate; 5'-fluoro-5'-deoxyadenosine; guanosine-5'-monophosphate; pyroglutamic acid; 5-hydroxymethyluridine-2'-deoxy-5'-monophosphate; 5-iodo-2'-deoxyuridine-5'-monophosphate; 5-methylbenzimidazole; 5-methylcytidine-5'-monophosphate; 5-methyl-2'-deoxypseudouridine; 5-methylpyrrole; 5-methyluridine 5'-monophosphate; 5-nitroindazole; 5-methoxybenzimidazole; n-pyridoxyl-1-aminocyclopropanecarboxylic acid-5-monophosphate; 5-phenylvaleric acid; (r)-mesopram; ribulose-5-phosphate; 5alpha-androstan-3,17-dione; 5-fluorouridine; (5z)-2-[(1s,2r)-1-amino-2-hydroxypropyl]-5-[(4-amino-1 h-indol-3-yl)methylene]-3-(2-hydroxyethyl)-3,5-dihydro-4h-imidazol-4-one; n-[2-(1-formyl-2-methylpropyl)-1-(4-piperidin-1-yl-but-2-enoyl)-pyrrolidin-3-yl]-methanesulfonamide; zk-805623; xv638; cra_23653; 4-(2-thienyl)-1-(4-methylbenzyl)-1h-imidazole; cra_10655; cra_10656; (5r)-6-(4-{[2-(3-iodobenzyl)-3-oxocyclohex-1-en-1-yl]amino}phenyl)-5-methyl-4,5-dihydropyridazin-3 (2h)-one; 6-oxo-8,9,10,11-tetrahydro-7h-cyclohepta[c][1]benzopyran-3-o-sulfamate; 1-(5-carboxypentyl)-5-[(2,6-dichlorobenzyl)oxy]-1 h-indole-2-carboxylic acid; 6-(n-phenylcarbamyl)-2-naphthalenecarboxamidine; cra_9678; i-5; 6-methylamino-5-nitroisocytosine; ono-6818; ru84687; cra_17693; cra_8696; 6-aminobenzoic acid; 1-(2-chlorophenyl)-3,5-dimethyl-1h-pyrazole-4-carboxylic acid ethyl ester; 6-hydroxy-flavin-adenine dinucleotide; 4-(1-benzyl-3-carbamoylmethyl-2-methyl-1h-indol-5-yloxy)-butyric acid; 6-methylpurine; 6-nitroindazole; 6((s)-3-benzylpiperazin-1-yl)-3-(naphthalen-2-yl)-4-(pyridin-4-yl)pyrazine; 6-phosphogluconic acid; acarbose derived hexasaccharide; cp403700, (s)-1-{2-[(5-chloro-1h-indole-2-carbonyl)-amino]-3-phenyl-propionyl}-azetidine-3-carboxylate; 6-[3-(4-morpholinyl)propyl]-2-(3-nitrophenyl)-5-thioxo-5,6,-dihydro-7h-thienol[2',3':4,5]pyrrolo[1,2-c]imidazol-7-one; zk-806711; trans-6-(2-phenylcyclopropyl)-naphthalene-2-carboxamidine; 9-n-phenylmethylamino-tacrine; 3-(oxalyl-amino)-naphthalene-2-carboxylic acid; cra_10762; ru79072; cra_7806; cra_9785; ru78783; ru79073; ru78191; compound 5,2-(naphthalen-1-yl-oxalyl-amino)-benzoicacid; (4r)-7aza-7,8-dihydrolimonene; 9-amino-n-[3-(dimethylamino)propyl]acridine-4-carboxamide; 3,5-dimethyl-1-(3-nitrophenyl)-1h-pyrazole-4-carboxylic acid ethyl ester; 7-deazaguanine; 7-hydroxy-pyrazolo[4,3-d]pyrimidine; 7-nitroindazole-2-carboxamidine; 7n-methyl-8-hydroguanosine-5'-monophosphate; 7-nitroindazole; 7-alpha-d-ribofuranosyl-2-aminopurine-5'-phosphate; 7-alpha-d-ribofuranosyl-purine-5'-phosphate; cra_1801; cra_1802; zk-806450; ru82129; ru82209; 1,3,4,9-tetrahydro-2-(hydroxybenzoyl)-9-[(4-hydroxyphenyl)methyl]-6-methoxy-2h-pyrido[3,4-b]indole; ru81843; cra_16847; ru85053; (1-tert-butyl-5-hydroxy-1h-pyrazol-4-yl)-(6-methanesulfonyl-4'-methoxy-2-methyl-biphenyl-3-yl)-methanone; ru83876; novo nordisk a/s compound; cyclohexyl-{4-[5-(3, 4-dichlorophenyl)-2-piperidin-4-yl-3-propyl-3h-imidazol-4-yl]-pyrimidin-2-yl}amine; 3-(3,5-dibromo-4-hydroxybenzoyl)-2-ethyl-benzofuran-6-sulfonic acid (4-sulfamoyl-phenyl)-amide; 8-bromoadenosine-5'-monophosphate; 8-hydroxy-2'-deoxyguanosine; 8-iodo-guanine; [3-(1-benzyl-3-carbamoylmethyl-2-methyl-1h-indol-5-yloxy)-propyl-]-phosphonic acid; 2-[(2e,6e,10e,14e,18e,22e,26e)-3,7, 11,15,19,23,27,31-octamethyldotriaconta-2,6,10,14,18,22, 26,30-octaenyl]phenol; compound 19; ru90395; cra_9076; 5-methoxy-1,2-dimethyl-3-(4-nitrophenoxymethyl)indole-4,7-dione; compound 15; cra_10950; sp7343-sp7964; (3-{3-[[2-chloro-3-(trifluoromethyl)benzyl](2,2-diphenylethyl) amino]propoxy}phenyl)acetic acid; cra_10972; 2-amino-5-bromo-6-phenylpyrimidin-4-ol; cyclopropyl-{4-[5-(3,4-dichlorophenyl)-2-[(1-methyl)-piperidin]-4-yl-3-propyl-3h-imidazol-4-yl]-pyrimidin-2-yl}amine; compound 12, n-acetyl-4-[(carboxycarbonyl)(2-carboxyphenyl)amino]-n-pentyl-1-napthylalaniamide; cra_10991; 1-[3,3-dimethyl-2-(2-methylamino-propionylamino)-butyryl]-pyrrolidine-2-carboxylic acid(1,2,3,4-tetrahydro-naphthalen-1-yl)-amide; 9-amino-2-deoxy-2,3-dehydro-n-acetyl-neuraminic acid; 9-aminophenanthrene; 9-hydroxy-8-methoxy-6-nitrophenanthrol[3,4-d][1,3]dioxole-5-carboxylic acid; 9-deazaadenine; 9-deazaguanine; 9-deazainosine; 9-(4-hydroxyphenyl)-2,7-phenanthroline; 9-deazahypoxanthine; 9-methylguanine; 2,6-diamino-(s)-9-[2-(phosphonomethoxy)propyl]purine; phosphomethylphosphonic acid adenosyl ester; antiproliferative agent a771726; n-acetyl-2-deoxy-2-amino-galactose; adenosine-2'-5'-diphosphate; 2-ammoniobut-3-enoate, 2-amino-3-butenoate; 3-acetylpyridine adenine dinucleotide; 2-amino-3-methyl-1-pyrrolidin-1-yl-butan-1-one; adenosine-3'-5'-diphosphate; n'-l-seryl-3'-amino-(3'-deoxy)-adenosine; 3-(5-amino-7-hydroxy-[1,2,3]triazolo[4,5-d]pyrimidin-2-yl)-benzoic acid; 6-(adenosine tetraphosphate-methyl)-7,8-dihydropterin; '5'-o-(n-(l-alanyl)-sulfamoyl)adenosine; arabinose-5-phosphate; n-(5,5,8,8-tetramethyl-5,8-dihydro-naphthalen-2-yl)-terephthalamic acid; a-98881; 4-[4-(1-amino-1-methylethyl) phenyl]-5-chloro-n-[4-(2-morpholin-4-ylethyl)phenyl] pyrimidin-2-amine; acetylamino-acetic acid; 5'-[[2-(aminooxy)ethyl]methylsulfonio]-5'-deoxy-adenosine; [2-(amino-oxy)ethyl](5'-deoxyadenosin-5'-yl)(methyl) sulfonium; acetoacetic acid; n-alpha-l-acetyl-arginine; alpha-adenosine monophosphate; arginineamide; s-adenosyl-1,8-diamino-3-thiooctane; lfa703; abt-378, lopinavir; 3-(4-amino-1-tert-butyl-1h-pyrazolo[3,4-d]pyrimidin-3-yl) phenol; alpha-aminobutyric acid; (2s,4(r)-1-acetyl-n-[(1s)-4-[(aminoiminomethyl)amino]-1-(2-benzothiazolylcarbonyl)butyl]-4-hydroxy-2-pyrrolidinecarboxamide; modified acarbose hexasaccharide; abequose; beta-d-arabinofuranose-5'-phosphate; 2(s)-amino-6-boronohexanoic acid; 5-amidino-benzimidazole; 5-amino-5-deoxy-cellobiono-1, 5-lactam; alpha-methylene adenosine monophosphate; benzylamine; 8-bromoadenosine-5'-diphosphate; gamma (amino)-butyric acid; 5-[1-(acetylamino)-3-methylbutyl]-2, 5-anhydro-3,4-dideoxy-4-(methoxycarbonyl)pentonic acid; n-(4-aminobutanoyl)-s-(4-methoxybenzyl)-l-cysteinylglycine; n44-hydroxymethyl-cyclohexan-6-yl-1,2,3-trioq-4,6-dideoxy-4-aminoglucopyranoside; 9-hyroxyethoxymethylguanine; aicar; aminocaproic acid; arachidonic acid; modified acarbose pentasaccharide; acetylcholine; 6-amino-4-hydroxymethyl-cyclohex-4-ene-1,2,3-triol; acetamide; adenosine-5'-[beta, gamma-methylene]triphosphate; adenosine-5'-[beta, gamma-methylene]tetraphosphate; 1-[(1s)-carboxy-2-(methylsulfinyl)ethyl]-(3r)-[(5s)-5-amino-5-carboxypentanamido]-(4r)-sulfanylazetidin-2-one; acetate ion; l-d-(a-aminoadipoyl)-l-cysteinyl-d-valine; alpha-cyclodextrin (cyclohexa-amylose); acetic acid; 2-amino-4-(4-amino-cyclohexa-2,5-dienyl)-butyric acid; 3-deazaadenosine; alpha d-galacturonic acid; (1'r,2's)-9-(2-hydroxy-3'-keto-cyclopenten-1-yl)adenine; 2,6,8-trimethyl-3-amino-9-benzyl-9-methoxynonanoic acid; 1-amino-2,3-dihydroxy-5-hydroxymethyl cyclohex-5-ene; 3-methyladenine; acetyl dithranol; adamantane; adamantanone; adenosine-5'-diphosphate; adenosine-5'-monophosphate glucopyranosyl-monophosphate ester; adenosine-5'-(dithio)phosphate; ampcpr; {[5-(6-amino-purin-9-yl)-3,4-dihydroxy-tetrahydro-furan-2-ylmethoxy]-hydroxy-phosphorylmethyl}-phosphonic acid mono-(3,4,5-trihydroxy-tetrahydro-furan-2-ylmethyl) ester; adenosine-5'-ditungstate; adenosine-5'-phosphosulfate; 3'-oxo-adenosine; aetiocholanolone; aeruginosin 98-b; threonine-aspartic ester; 1-[4-(octahydro-pyrido[1,2-a]pyrazin-2-yl)-phenyl]-2-phenyl-1,2,3,4-tetrahydro-isoquinolin-6-ol; 2-aminoethanimidic acid; 3-[(1-amino-2-carboxy-ethyl)-hydroxy-phosphinoyl]-2-methyl-propionic acid; 4-deoxy-4-((5-hydroxymethyl-2,3,4-trihydroxycyclohex-5,6-enyl) amino)fructose; 2-[4-(4-chlorophenyl)cyclohexylidene]-3,4-dihydroxy-1(2h)-naphthalenone; alpha-l-fucose; 4-{2-(4-fluoro-benzyl)-6-methyl-5-[(5-methyl-isoxazole-3-carbonyl)-amino]-4-oxo-heptanoylamino}-5-(2-oxo-pyrrolidin-3-yl)-pentanoic acid ethyl ester; n-(1-adamantyl)-n'-(4-guanidinobenzyl)urea; alpha-d-glucose; 4,6-dideoxy-4-amino-alpha-d-glucose; 2-deoxy-2-amino glucitol-6-phosphate; phosphothiophosphoric acid-adenylate ester; aminoguanidine; (4r,5s, 6s, 7r)-1,3-dibenzyl-4,7-bis(phenoxymethyl)-5,6-dihydroxy-1,3 diazepan-2-one; 6-amino hexanoic acid; beta-hydroxyasparagine; 4-aminohydrocinnamic acid; s-hydroxymethyl glutathione; 2-[4-(hydroxymethoxy-methyl)-benzyl]-7-(4-hydroxymethyl-benzyl)-1,1-dioxo-3,6-bis phenoxymethyl-1lambda6-[1,2,7] thiadiazepane-4,5-diol; 2,5-anhydroglucitol-1,6-biphosphate; descarboxy-nor-n(omega)-hydroxy-l-arginine; alpha-l-arabinofuranose; adenosine diphosphate 5-(beta-ethyl)-4-methyl-thiazole-2-carboxylic acid; n-benzyl-3-(3,4,5-trihydroxy-6-hydroxymethyl-tetrahydro-pyran-2-yloxy)-benzamide; bmsc001; 3-benzylaminocarbonylphenyl-alpha-d-galactoside; bapg; alpha-aminoisobutyric acid; compound 15; compound 18; n-[3-(dimethylamino)propyl]-2-({[4-({[4-(formylamino)-1-methyl-1h-pyrrol-2-yl] carbonyl}amino)-1-methyl-1h-pyrrol-2-yl] carbonyl}amino)-5-isopropyl-1,3-thiazole-4-carboxamide; acetylsalicylic acid, aspirin; 2,6-diamino-8-(1h-imidazol-2-ylsulfanylmethyl)-3h-quinazoline-4-one; 5-aminoimidazole ribonucleoside; compound 19; compound 16; 3-(prop-2-ene-1-sulfinyl)-propene-1-thiol; 10-{4-dimethylamino-5-[4-hydroxy-6-methyl-5-(6-methyl-5-oxo-tetrahydro-pyran-2-yloxy)-tetrahydro-pyrane-2-yloxy]-6-methyl-tetrahydro-pyran-2-yloxy}-8-ethyl-1,8,11-trihydroxy-7,8,9,10-tetrahydro-naphthacene-5,12-dione; 2-amino-3-ketobutyric acid; 2-oxyglutaric acid; acrylic acid; 10-(4-dimethylamino-5-hydroxy-6-methyl-tetrahydro-pyran-2-yloxy)-8-ethyl-1,8,11-trihydroxy-7,8,9,10-tetrahydro-naphthacene-5,12-dione; a17182; a15424; a15300; a14623; a16528; a17099a; a17089a; a15927; delta-2-albomycin a1; adr adrenaline; tetrafluoroaluminate ion; n''-{3-[(3s,8ar)-1,4-dioxooctahydropyrrolo[1,2-a]pyrazin-3-yl]propyl}guanidine; d-allopyranose; 2-methyl-propionic acid; alrestatin; 2-amino-3-oxo-4-sulfo-butyric acid; 1-2-amino-4-methoxy-cis-but-3-enoic acid; aminomethylcyclohexane; n-acetylmethionine; alpha-methyl-d-galactoside; trans-4-aminomethylcyclohexane-1-carboxylic acid; allosamizoline; amylamine; aspartyl-adenosine-5'-monophosphate; adenosine monophosphate; ampa; 3-mercuri-4-aminobenzenesulfonamide; adenosine monotungstate; aminoanthracene; 3-beta-hydroxy-5-androsten-17-one; adenine; nalpha-(2-naphthylsulfonylglycyl)-3-amidino-d,l-phenylalanine-isopropylester; p-anisic acid; phosphoaminophosphonic acid-adenylate ester; (6e)-6-[(2e, 4e,6e)-3,7-dimethylnona-2,4,6,8-tetraenylidene]-1,5,5-trimethylcyclohexene; (2s,3r)-3-amino-2-hydroxy-5-(ethylsulfanyl)pentanoyl-((s)-(-)-(1-naphthyl)ethyl)amide; n'-(2s, 3r)-3-amino-4-cyclohexyl-2-hydroxy-butano-n-(4-methylphenyl)hydrazide; (aminooxy)acetic acid; n-butyl-11-[(7r,8r,9s,13s,14s,17s)-3,17-dihydroxy-13-methyl-7,8,9,11,12,13,14,15,16,17-decahydro-6h-cyclopenta[a] phenanthren-7-yl]-n-methylundecanamide; 5-alpha-androstane-3-beta,17beta-diol; 5-alpha-androstane-3-beta, 17-alpha-diol; {3-[3-(3,4-dimethoxy-phenyl)-1-(1-{1-[2-(3, 4,5-trimethoxy-phenyl)-butyryl]-piperidin-2yl}-vinyloxy)-propyl]-phenoxy}-acetic acid; phosphomethylphosphonic acid adenosyl ester; 5,6-cyclic-tetrahydropteridine; bis(adenosine)-5'-pentaphosphate; 2,4-diamino-6-phenyl-5,6,7,8,-tetrahydropteridine; amido phenyl pyruvic acid; m-aminophenylboronic acid; alpha,beta-methyleneadenosine-5'-triphosphate; 3-methylphenylalanine; 2,6-diaminopimelic acid; d-2-amino-3-phosphono-propionic acid; 2,6-diamino-8-propylsulfanylmethyl-3h-quinazoline-4-one; adenosine-5-diphosphoribose; 9-hydroxypropyladenine, s-isomer; pteric acid; adenylyl-3'-5'-phospho-uridine-3'-monophosphate; 2'-monophosphoadenosine-5'-diphosphoribose; 4-aminophthalhydrazide; erlotinib; 2-aminoquinazolin-4(3h)-one; modified ribosylated glutamyl ester; alpha-l-arabinose; beta-l-arabinose; 3,7,11,15-tetramethyl-hexadecan-1-ol; 4-o-(4,6-dideoxy-4-{[4-[(4-o-hexopyranosylhexopyranosyl)oxy]-5,6-dihydroxy-3-(hydroxymethyl)cyclohex-2-en-1-yl]amino}hexopyranosyl) hexopyranose; 9-hydroxypropyladenine, r-isomer; n-(4-(2-((3-chlorophenylmethyl)amino)ethyl)phenyl)-2-thiophecarboxamidine; 5-n-allyl-arginine; n-methyl-n-(10-methylundecanoyl)-d-seryl-l-alanyl-n~1~-[(7s,10s,13s)-13-carboxy-3,18-dihydroxy-10-methyl-8,11-dioxo-9,12-diazatricyclo[13.3.1.1~2,6~]icosa-1(19),2(20),3,5,15,17-hexaen-7-yl]-n~1~-methylglycinamide; argininosuccinate; aspartate semialdehyde; aspartic acid-4-carboxymethyl ester; ascorbic acid; 4-androstene-3-17-dione; n-acetyl serotonin; 1-iso-aspartate; phosphoaspartate; 4-aminophenylarsonic acid; delta-(l-alpha-aminoadipoyl)-l-cysteinyl-d-vinylglycine; 2-amino-3-(5-tert-butyl-3-(phosphonomethoxy)-4-isoxazolyl)propionic acid; atrazine glutathione conjugate; 16,17-androstene-3-ol; 4-hydroxyaconitate ion; 3'-azido-3'-deoxythymidine-5'-monophosphate; apstatin; chloroacetone; 2-aminothiazoline; 2'-monophosphoadenosine-5'-diphosphate; gamma-arsono-beta, gamma-methyleneadenosine-5'-diphosphate; alsterpaullone; 3'-o-acetylthymidine-5'-diphosphate; adenosine-5'-diphosphate-2',3'-vanadate; 2-amino-4-(2-amino-ethoxy)-butyric acid; 2-{1-[2-amino-2-(4-hydroxy-phenyl)-acetylamino]-2-oxo-ethyl}-5,5-dimethyl-thiazolidine-4-carboxylic acid; 4-acetamido-2,4-didexoy-d-glycero-beta-d-galacto-octopyranosylphosphonic acid (an axial phosphonate); n-acetylalanine; 3-(6-aminopyridin-3-yl)-n-methyl-n-[(1-methyl-1h- indol-2-yl)methyl]acrylamide; azelaic acid; 8-azaxanthine; n-acetyl-n'-beta-d-glucopyranosyl urea; 3'-azido-3'-deoxythymidine-5'-diphosphate; all-trans axerophthene; 8-azaguanine; 5-acetamido-1,3,4-thiadiazole-2-sulfonamide; aztreonam; cobalamin; balanol analog 1; factor iiim; 2-[(2-oxo-2-piperidin-1-ylethyl)thio]-6-(trifluoromethyl)pyrimidin-4 (1h)-one; beta-1,4-galactobioside; 4-dimethylamino-n-(6-hydroxycarbamoyethyl)benzamide-n-hydroxy-7-(4-dimethyla minobenzoyl)aminoheptanamide; 2-[3-(2-hydroxy-1,1-dihydroxymethyl-ethylamino)-propylamino]-2-hydroxymethyl-propane-1,3-diol; beta-1,4-galactotrioside; heptyl-beta-d-glucopyranoside; balanol analog 8; 1-(5-tert-butyl-2-p-tolyl-2h-pyrazol-3-yl)-3-[4-(2-morpholin-4-yl-ethoxy)-naphthalen-1-yl]-urea; balanol; bis(adenosine)-5'-triphosphate; (tert-butyloxycarbonyl)-alanyl-alanyl-amine; bis(5-amidino-benzimidazolyl)methane; bis(5-amidino-2-benzimidazolyl)methane ketone hydrate; hemi-babim; bis(5-amidino-2-benzimidazolyl)methane ketone; beta-alanine; bis(5-amidino-2-benzimidazolyl) methanone; batimastat; bb94; bis(5-amidino-benzimidazolyl)methane zinc; bb-3497; 2-[(formyl-hydroxy-amino)-methyl]-heptanoic acid [1-(2-hydroxymethyl-pyrrolidine-1-carbonyl)-2-methyl-propyl]-amide; 3-(3,5-dibromo-4-hydroxy-benzoyl)-2-ethyl-benzofuran-6-sulfonic acid dimethylamide; bis-benzamidine; 1-benzyl-3-(4-methoxy-benzenesulfonyl)-6-oxo-hexahydro-pyrimidine-4-carboxylic acid hydroxyamide; 5-bromo-n-(2,3-dihydroxy-propoxy)-3,4-difluoro-2-[(2-fluoro-4-iodophenyl)amino] benzamide; 2-hydroxy-5-[4-(2-hydroxy-ethyl)-piperidin-1-yl]-5-phenyl-1h-pyrimidine-4,6-dione; 2'-(4-dimethylaminophenyl)-5-(4-methyl-1-piperazinyl)-2,5'-bi-benzimidazole; 4-hydroxybenzoyl coenzyme a; cyclohepta-amylose; butyrylthiocholine; bacteriochlorophyll a; bicine; 2-bromo-6-chloro-purine; benzylcysteine; beta-3-cysteine; bcx-1812; balanol analog 2; 4,4'-biphenyldiboronic acid; bromo-dodecanol; beta-d-fructopyranose; 2-butyl-5,6-dihydro-1h-imidazo[4,5-d]pyridazine-4,7-dione; brodimoprim-4,6-dicarboxylate; 2,3-bis-benzo[1,3]dioxol-5-ylmethyl-succinic acid; n-bromoacetyl-aminoethyl phosphate; 2-aminobenzoic acid; inhibitor bea403; tricyclazole; inhibitor bea369; inhibitor bea388; inhibitor bea403; inhibitor bea409; inhibitor bea425; inhibitor bea322; inhibitor bea428; 2,3,5,6-tetrafluoro-4-methoxy-benzamide; 2,4-dinitro,5-[bis(2-bromoethyl)amino]-n-(2',3'-dioxopropyl) benzamide; benzamidine; butenoic acid; berberine; bestatin; trimethyl glycine; benzoic acid; aspartate beryllium trifluoride; 2-(1,1'-biphenyl-4-yl)propanoic acid; n-[1-(4-bromophenyl)ethyl]-5-fluoro salicylamide; 3-methyl-5-sulfo-pyrrolidine-2-carboxylic acid; 5-(hydroxy-methyl-amino)-3-methyl-pyrrolidine-2-carboxylic acid; 5-hydroxyamino-3-methyl-pyrrolidine-2-carboxylic acid; beta-d-glucose-6-phosphate; beta-d-glucose; 4-benzoylamino-4-{1-{1-carbamoyl-2-[4-(difluoro-phosphono-methyl)-phenyl]-ethylcarbamoyl}-2-[4-(difluoro-phosphono-methyl)-phenyl]-ethylcarbamoyl}-butyric acid; b-2-octylglucoside; beta-galactose-6-phosphate; 4-methyl-pyrroline-5-carboxylic acid; 3-({5-benzyl-6-hydroxy-2,4-bis-(4-hydroxy-benzyl)-3-oxo-[1,2,4]-triazepane-1-sulfonyl)-benzonitrile; (6r,1'r,2's)-5,6,7,8 tetrahydrobiopterin; 6-[5-(2-oxo-hexahydrothieno[3,4-d]imidazol-4-yl)-pentanoylamino]-hexanoic acid; 2-hydroxy-4-aminobenzoic acid; 2,6-diamino-8-(2-dimethylaminoethylsulfanylmethyl)-3h-quinazolin-4-one; benzene hexacarboxylic acid; beta-hydroxyaspartic acid; 2-hexyloxy-6-hydroxymethyl-tetrahydro-pyran-3,4,5-triol; n-butyl-n'-hydroxyguanidine; 4-bromo-3-hydroxy-3-methyl butyl diphosphate; benzhydroxamic acid; (s)-5-(4-benzyloxy-phenyl)-4-(7-phenyl-heptanoylamino)-pentanoic acid; 6s-5,6,7,8-tetrahydrobiopterin; rbt205 inhibitor; 3-[1-(3-aminopropyl)-1 h-indol-3-yl]-4-(1-methyl-1 h-indol-3-yl)-1 h-pyrrole-2,5-dione; 3-335; beta-amino isobutyrate; 2,3-dicarboxy-4-(2-chloro-phenyl)-1-ethyl-5-isopropoxycarbonyl-6-methyl-pyridinium; biopterin; 2-benzyl-3-iodopropanoic acid; n-[3-[((1-aminoethyl)(hydroxy)phosphoryl]-2-(1,1-biphenyl-4-ylmethyl)propanoyl]alanine; (s)-blebbistatin, (3as)-3a-hydroxy-6-methyl-1-phenyl-3,3a-dihydro-1h-pyrrolo[2,3-b]quinolin-4(2h)-one; 1(r)-1-acetamido-2-(3-carboxyphenyl)ethyl boronic acid; 2-{n'-[2-(5-amino-1-phenylcarbamoyl-pentylcarbamoyl)-hexyl]-hydrazinomethyl}-hexanoic acid(5-amino-1-phenylcarbamoyl-pentyl)-amide; biliverdine ix alpha; bulgecin a; 4-oxo-2-phenylmethanesulfonyl-octahydro-pyrrolo[1,2-a]pyrazine-6-carboxylic acid [1-(n-hydroxycarbamimidoyl)-piperidin-4-ylmethyl]-amide; (2r,3r,4r,5r)-3,4-dihydroxy-n,n'-bis[(1 s,2r)-2-hydroxy-2,3-dihydro-1 h-inden-1-yl]-2,5-bis(2-phenylethyl)hexanediamide; n1-[3-(dimethylsulfonio)-propyl]bleomycinamide; morpholine-4-carboxylic acid [1s-(2-benzyloxy-1r-cyano-ethylcarbamoyl)-3-methyl-butyl]amide; biliverdin ix gamma chromophore; beta-d-mannose; butyramide; beta-mercaptoethanol; 6-hydroxyuridine-5'-phosphate; 1-(5'-phospho-beta-d-ribofuranosyl)barbituric acid; 1-(5-tert-butyl-2-methyl-2h-pyrazol-3-yl)-3-(4-chloro-phenyl)-urea; balhimycin; 2-(2-hydroxy-phenyl)-1h-benzoimidazole-5-carboxamidine; n-benzylformamide; b-nonylglucoside; biotinyl p-nitroaniline; benzenesulfonyl; 2-bromo-6-hydroxy-purine; tert-butyloxycarbonyl group; b-octylglucoside; bombykol; bis(5-amidino-benzimidazolyl)methanone zinc; bromopurine; 2'-chloro-biphenyl-2,3-diol; 2',6'-dichloro-biphenyl-2,6-diol; n-(m-trifluoromethylphenyl) phenoxazine-4,6-dicarboxylic acid; 9-(4-hydroxybutyl)-n2-phenylguanine; biphenyl-2,3-diol; 6-phenyl-4(r)-(7-phenyl-heptanoylamino)-hexanoic acid; para-bromobenzyl alcohol; 12-bromododecanoic acid; 1-beta-ribofuranosyl-1,3-diazepinone; brequinar analog; 6-fluoro-2-(2'-fluoro-1,1'-biphenyl-4-yl)-3-methylquinoline-4-carboxylic acid; 2-bromoacetyl group; diminazine aceturate; 1,3-tris-(4'amidinophenyl)triazine; 2-bromo-2-propene-1-ol; (2r)-2-{[formyl(hydroxy)amino]methyl}hexanoic acid; 5-bromonicotinamide; 5-bromo-2'-deoxyuridine-5'-monophosphate; (3e)-6'-bromo-2,3'-biindole-2',3(1 h,1'h)-dione 3-oxime; 6-(1,1-dimethylallyl)-2-(1-hydroxy-1-methyl-ethyl)-2,3-dihydro-7h-furo[3,2-g]chromen-7-one; n-benzyl-4-sulfamoyl-benzamide; beta-3-serine; 2-(biphenyl-4-sulfonyl)-1,2,3,4-tetrahydro-isoquinoline-3-carboxylic acid; bistris buffer; 5-bromothienyldeoxyuridine; [formylmethyl] trimethyl-ammonium, n,n,n-trimethylammonium acetaldehyde; 2-thiomethyl-3-phenylpropanoic acid; 3-(2-benzothiazolylthio)-1-propanesulfonic acid; 1,4-butanediol; 1,3-butanediol; (r,r)-2,3-butanediol; butanoic acid; 1-butane boronic acid; 2-amino-n,3,3-trimethylbutanamide; 4-hydroxy-2-butanone; butyl group; [3-(4-{3-[3-nitro-5-(galactopyranosyloxy)-benzoylamino]-propyl}-piperazin-1-yl)-propylamino]-2-(3-{4-[3-(3-nitro-5-[galactopyranosyloxy]-benzoylamino)-propyl]-piperazin-1-yl}; bv2; bv3; bv4; 5-bromovinyldeoxyuridine; bvdu-mp; bromo-willardiine; 2-benzo[1,3]dioxol-5-ylmethyl-3-benzyl-succinic acid; benzo[b]thiophene-2-boronic acid; 2-(3'-methoxyphenyl) benzimidazole-4-carboxamide; n-benzoyl-n'-beta-d-glucopyranosyl urea; benzofuran; benzimidazole; benzoic acid phenylmethylester; benzene, benzoyl-; benzophenone (8ci); benzoylbenzene; diphenyl ketone; ketone, diphenyl; methanone, diphenyl-(9ci); phenyl ketone; win: rvr; cytidine-5'-monophosphate; undecyl-phosphinic acid butyl ester; tetradecane; n-dodecyl-n,n-dimethyl-3-ammonio-1- propanesulfonate; morpholine-4-carboxylic acid (1-(3-benzenesulfonyl-1-phenethylallylcarbamoyl)-3-methylbutylyamide; 5-methyl-5,6,7,8-tetrahydrofolic acid; cytidine 5'-diphosphoglycerol; 3-chloroalaninate; cytidine-2'-monophosphate; cytidine-3'-monophosphate; cholesterol-sulfate; n1-(1-dimethylcarbamoyl-2-phenyl-ethyl)-2-oxo-n4-(2-pyridin-2-yl-ethyl)-succinamide; morpholine-4-carboxylic acid [1-(2-benzylsulfanyl-1-formykethylcarbamoyl)-2-phenyl-ethyl]-amide; (hydroxyethyloxy)tri(ethyloxy)octane; coa-s-trimethylene-acetyl-tryptamine; coa-s-acetyl 5-bromotryptamine; acetoacetyl-coenzyme a; 4-carboxy-4-aminobutanal; cacodylate ion; hydroxydimethylarsine oxide; camphane; cystein-s-yl cacodylate; 5-exo-hydroxycamphor; camphor; canaline; oxidized coenzyme a; 1,2-dihydroxybenzene; cytosine arabinose-5'-phosphate; s-(dimethylarsenic)cysteine; dodecane-trimethylamine; (2s,4s)-alpha-campholinic acid; carboxymethylenecysteine; acylated ceftazidime; cb1954; phosphoric acid mono-[5-(4-amino-5-bromo-2-oxo-2h-pyrimidin-1-yl)-3,4-dihydroxy-tetrahydro-furan-2-ylmethyl]; 10-propargyl-5,8-dideazafolic acid; pinacol[[2-amino-alpha-(1-carboxy-1-methylethoxyimino)-4-thiazoleacetyl]amino]methaneboronate; cibacron blue; c-(1-hydrogyl-beta-d-glucopyranosyl) formamide; s-(d-carboxybutyl)-1-homocysteine; cellobiose; clorobiocin; carbenoxolone; 2-{4-[4-(4-chloro-phenoxy)-benzenesulfonyl]-tetrahydro-pyran-4-yl}-n-hydroxy-acetamide; [{(5-chloro-2-pyridinyl)amino}0 methylene]-1,1-bisphosphonate; di(n-acetyl-d-glucosamine); n,n-bis(4-chlorobenzyl)-1h-1,2,3,4-tetraazol-5-amine; (4-{2-acetylamino-2-[1-(3-carbamoyl-4-cyclohexylmethoxy-phenyl)-ethylcarbamoylyethyl}-2-phosphono-phenoxy)-acetic acid; {4-[2-acetylamino-2-(3-carbamoyl-2-cyclohexylmethoxy-6,7,8,9-tetrahydro-5h-benzocyclohepten-5ylcarbamoyl)-ethyl]-2-phosphono-phenyl}-phosphonic acid; n-cyclopentyl-n-cyclobutylformamide; carbamyl-choline; clorocruoro hem; carboxymethylthio-3-(3-chlorophenyl)-1,2,4-oxadiazol; butylphosphonate; o5'-(4-(3-{2-[2-((r)-3-hydroxy-4-(trimethylammonio)-1-oxo-butyl)sulfanyl-ethylcarbamoyl]-ethylcarbamoyl}4)-3-hydroxy-2,2-dimethyl-propyl)-1-hydroxy-3-oxido-1,3-dioxo-2,4-dioxa-1,3-diphosphabut-1-yl) 3'-phospho-adenosine; crc200 (chiron-behring); carboxymethylated cysteine; 6-(dihydroxy-isobutyl)-thymine; [2-cytidylate-o'-phosphonyloxyl]-ethyl-trimethyl-ammonium; cytidine-5'-diphosphate; methyl 4,6-o-[(1r)-1-carboxyethylidene]-beta-d-galactopyranoside; d-(l-a-aminoadipoyl)-l-cysteinyl-d-isodehydrovaline; 2c-methyl-d-erythritol 2,4-cyclodiphosphate; 4-diphosphocytidyl-2-c-methyl-d-erythritol; cardiolipin; 2,3-dideoxyfucose; n-carbamyl-d-methionine; n-cyclohexyl-n'-decylurea; n-carbamyl-d-valine; icrf-187; 2-chlorodideoxyadenosine; (s)-atpa, (s)-2-amino-3-(3-hydroxy-5-tert-butyl-isoxazol-4-yl) propionic acid; cysteine sulfenic acid; degraded cephaloridine; cefotaxime group; 4,6-o-(1-carboxyethyl-idene)-beta-d-glucose; cephalosporin analog; coelenteramide; hydrolyzed cephalothin; cephalothin group; ethyl-trimethyl-silane; chloro diiron-oxo moiety; 6-chloro-2-fluoropurine; cefoxitin; cytidyl-2'-5'-phospho-guanosine; c-(1-azido-alpha-d-glucopyranosyl) formamide; 5-oxo-pyrrolidine-2-carbaldehyde; 2'-deoxycytidine-2'-deoxyguanosine-3',5'-monophosphate; gamma-carboxy-glutamic acid; chromophore (met-tyr-gly); 1-hydroxy-2-amino-3-cyclohexylpropane; cholic acid; 5-chloro-1h-indole-2-carboxylic acid [1-(4-fluorobenzyl)-2-(4-hydroxypiperidin-1yl)-2-oxoethyl]amide; chlorophyll b; glycochenodeoxycholic acid; 3-chloro-4-hydroxyphenylglycine; (3s,8ar)-3-(1h-imidazol-5-ylmethyl)hexahydropyrrolo[1,2-a]pyrazine-1,4-dione, ncs-chromophore; cyclohexane; chymostatin; 2-amino-6-chloropyrazine; cilastatin; 4-carboxycinnamic acid; cis-4-cyano-4-[3-(cyclopentyloxy)-4-methoxyphenyl]cyclohexanecarboxylic acid; citric acid; n-cyclohexyl-n'-(4-iodophenyl)urea; 4-(2,5-dichloro-thiophen-3-yl)-pyrimidin-2-ylamine; 4-(2,4-dimethyl-thiazol-5-yl)-pyrimidin-2-ylamine; n-[4-(2,4-dimethyl-1,3-thiazol-5-yl)pyrimidin-2-yl]-n'-hydroxyimidoformamide; 4-(2,4-dimethyl-thiazol-5-yl)-pyrimidin-2-yl]-(4-trifluoromethyl-phenyl)-amine; 3-[4-(2,4-dimethyl-thiazol-5-yl)-pyrimidin-2-ylamino]-phenol; 4-[4-(4-methyl-2-methylamino-thiazol-5-yl)-pyrimidin-2-ylamino]-phenol; [4-(2-amino-4-methyl-thiazol-5-yl)-pyrimidin-2-yl]-(3-nitro-phenyl)-amine; n-(2-aminoethyl)-5-chloroisoquinoline-8-sulfonamide; alpha chlorophyll a; n-methyl-n-[3-(6-phenyl[1,2,4]triazolo[4,3-b]pyridazin-3-yl)phenyl]acetamide; n-{3-[5-(6-amino-purin-9-yl)-3,4-dihydroxy-tetrahydro-furan-2-yl]-allyl}-2,3-dihydroxy-5-nitro-benzamide; chlorophyll a; d-para-chlorophenyl-1-acetamidoboronic acid alanine; n-acetyl-p-nitrophenylserinol; d-para-chlorophenyl-1-acteamidoboronic acid alanine; mdl-29951; alpha-n-dichloroacetyl-p-aminophenylserinol; cholesteryl linoleate; chloramphenicol; cholesterol; 3-acetoxymethyl-8-oxo-7-(2-thiophen-2-yl-acetylamino)-5-thia-1-aza-bicyclo[4.2.0]oct-2-ene-2-carboxylic acid; gamma-phenyl-butyric acid; trichloro-acetaldehyde; 5-chloryl-2,4,6-quinazolinetriamine; carboxymycobactin s; carboxymycobactin t; n2-(carboxyethyl)-l-arginine; s,s-(2-hydroxyethyl)thiocysteine; 6-o-cyclohexylmethyl guanine; s-(methylmercury)-l-cysteine; cmp-2-keto-3-deoxy-octulosonic acid; cyclic amp; camp; 5-chloro-6-[(2-iminopyrrolidin-1-yl)methyl]pyrimidine-2,4 (1h,3h)-dione; carba-nicotinamide-adenine-dinucleotide; co-cyanocobalamin; 5-beta-d-ribofuranosylnicotinamide adenine dinucleotide; acetone cyanohydrin; 1,8-cineole; cyanamide; 2-propenyl-n-acetyl-neuramic acid; 2-(4-chlorophenyl)-5-quinoxalinecarboxamide; hexadecyl octanoate; 2,4-diamino-5-methyl-6-[(3,4,5-trimethoxy-n-methyl-anilino)methyl]pyrido[2,3-d]pyrimidine; octanoyl-coenzyme a; co-methylcobalamin; dephospho coenzyme a; furo[2,3-d]pyrimidine antifolate; trifluoroacetonyl coenzyme a; 2,4-diamino-6-[n-(2',5'-dimethoxybenzyl)-n-methylamino] quinazoline; protoporphyrin ix containing co; 2-oxo-4-methylpentanoic acid; hydrogenobyrinic acid; 2-(oxalyl-amino)-4,7-dihydro-5h-thieno[2,3-c]thiopyran-3-carboxylic acid; 2,4-diamino-6-[n-(3',5'-dimethoxybenzyl)-n-methylamino]pyrido[2,3-d]pyrimidine; coenzyme a persulfide; coa-s-acetyl tryptamine; coenzyme a; 1,2-dichloro-propane; coproporphyrin iii; cp-526423; 1,2-bis(2-(5-chloroindole-2-carbonylamino)ethoxy)ethane; (2z)-3-{[oxido(oxo)phosphino]oxy}-2-phenylacrylate; cp-271485; (6r)-4-benzyl-6-(1-methyl-2,2-dioxido-1,3-dihydro-2,1-benzisothiazol-5-yl) morpholin-3-one; 2'-deoxycytidine-2'-deoxyadenosine-3',5'-monophosphate; flavopiridol; 1-cyclopropyl-6-fluoro-4-oxo-7-piperazin-1-yl-1,4-dihydroquinoline-3-carboxylic acid; palmitoyl-linoleoyl phosphatidylcholine; coprogen; 2-cyclopropylmethylenepropanal; deoxy-bigchap; 6-chloropurine riboside, 5'-monophosphate; n-cyclohexyl-n'-(propyl)phenyl urea; (s)-2-amino-3-(1,3,5,7-pentahydro-2,4-dioxo-cyclopenta[e]pyrimidin-1-yl) proionic acid; 4-(4-chlorophenyl)imidazole; 1-(2-ethanone)-2-hydroxy-2-(1-amino-2-methyl-2-ethanol)-4-(2-dimethyl)ethane-imidazoline-5-one; chromophore (thr-leu-gly); 1-deoxy-1-methoxycarbamido-beta-d-glucopyranose; [2-(methyleneamine)-4-(4-hydroxy-benzylidine)-5-oxo-4,5-dihydro-imidazol-1-yl]-acetaldehyde; cra_10433; cra_1144; (2r)-2-(aminomethyl)-2,4-dihydroxy-5-oxo-3-(2-oxoethyl)-2,5-dihydro-1 h-imidazol-3-ium; 1-deoxy-1-acetylaminobeta-d-gluco-2-heptulopyranosonamide; cra_11092; 1-deoxy-1-methoxycarbamido-beta-d-gluco-2-heptulopyranosonamide; carbaphosphonate; capric acid; crotonaldehyde; [2-(1-amino-2-hydroxy-propyl)-4-(1h-indol-3-ylmethylene)-5-oxo-4,5-dihydro-imidazol-1-yl]-acetaldehyde; 4-{(z)-[2-[3-(methylsulfanyl)propanoyl]-5-oxo-1-(2-oxoethyl)-1,5-dihydro-4h-imidazol-4-ylidene]methyl}benzenolate; carboxyethyllumazine; chromophore (gly-tyr-gly); m-cresol; glycerol; carbazole butanoic acid; 3-thiaoctanoyl-coenzyme a; s-acetonylcysteine; cephalosporin c; 3-sulfinoalanine; selenocysteine; n,4-dihydroxy-n-oxo-3-(sulfooxy)benzenaminium; s-hydroxycysteine; s-phosphocysteine; s-arsonocysteine; s-mercaptocysteine; cysteine-s-sulfonic acid; double oxidized cysteine; s-oxy cysteine; [4-(4-hydroxy-benzyl)-2-(2-hydroxy-1-methyl-ethyl)-5-oxo-imidazolidin-1-yl]-acetic acid; s-selanyl cysteine; (5-chloropyrazolo[1,5-a]pyrimidin-7-yl)-(4-methanesulfonylphenyl)amine; 4-[5-(trans-4-aminocyclohexylamino)-3-isopropylpyrazolo[1,5-a]pyrimidin-7-ylamino]-n,n-dimethylbenzenesulfonamide; cyclotheonamide a; n-2-thiophen-2-yl-acetamide boronic acid; 7-chlorotetracycline; 3-deazacytidine; cytidine; chitotriose; cytidine-5'-triphosphate; cellotriose; (1s,6s,7r,8r,8ar)-1,6,7,8-tetrahydroxyindolizidine; cellotetraose; 8-benzyl-2-hydroxy-2-(4-hydroxy-benzyl)-6-(4-hydroxyphenyl)-2h-imidazo[1,2-a]pyrazin-3-one; (mu-4-sulfido)-tetra-nuclear copper ion; 4-(carboxyvin-2-yl)phenylboronic acid; crystal violet; phenylalanine-n-sulfonamide; pentaethylene glycol monodecyl ether; cyclohexylformamide; cyclohexanol; n-carboxymethionine; [3-(o-chlorophenyl)-5-methyl-4-isoxazolyl]penicillin; cyclohexane propionic acid; 3-cyclohexyl-1-propylsulfonic acid; carboxyatractyloside; cytidine-5'-diphospho-beta-d-xylose; 2-amino-3-mercapto-propionamide; s-butyryl-cystein; cyclohexanone; s-methyl phosphocysteine; calyculin a; (3-formyl-but-3-enyl)-phosphonic acid; 3-bicyclo[2.2.1]hept-5-en-2-yl-6-chloro-3,4-dihydro-2h-1,2,4-benzothiadiazine-7-sulfonamide 1,1 dioxide; thiarsa dihydroxy cysteine; br-coeleneterazine; 8-benzyl-2-hydroperoxy-2-(4-hydroxy-benzyl)-6-(4-hydroxy-phenyl)-2h-imidazo[1,2-a]pyrazin-3-one; i-coeleneterazine; n-coeleneterazine; cp-coeleneterazine; thiarsahydroxy-cysteine; decane; dodecane; zd 1694; (4s,5s)-1,2-dithiane-4,5-diol; 2-[4-(2,4-dichlorophenoxyl)phenoxy] propanoic acid; (2r)-amino(3,5-dihydroxyphenyl)acetic acid; 2',3'-dehydro-2',3'-deoxy-thymidine 5'-diphosphate; (2s)-amino(4-hydroxyphenyl)acetic acid; 2',3'-dehydro-2',3'-deoxy-thymidine 5'-triphosphate; 2-deoxy-glucose-6-phosphate; 2-deoxy-d-glucitol 6-(e)-vinylhomophosphonate; adma; 2,4-diaminobutyric acid; 2-decenoyl n-acetyl cysteamine; 2',3'-dideoxyadenosine-5'-triphosphate; 1,4-deoxy-4-((5-hydroxymethyl-2,3,4-trihydroxycyclohex-5-enyl)amino)fructose; 4,6-dideoxy-4-amino-beta-d-glucopyranoside; 3,4-dihydroxyphenylalanine; 4-(n,n-dimethylamino)cinnamoyl-d-alanine; n-methyl-alpha-beta-dehydroalanine; 2-deoxy-2,3-dehydro-n-acetyl-neuraminic acid; lauric acid; d-arginine; d-aspartic acid; 2deoxy-thymidine-5'-diphospho-alpha-d-glucose; delta-amino valeric acid; 5-bromo-n[2-(dimethylamino)ethyl]-9-aminoacridine-4-carboxamide; trencam-3,2-hopo; 7-(1,1-dioxo-1h-benzo[d]isothiazol-3-yloxymethyl)-2-(oxalyl-amino)-4,7-dihydro-5h-thieno[2,3-c]pyran-3-carboxylic acid; dibenzofuran-4,6-dicarboxylic acid; 2,3-dihydroxy-benzoic acid; deglucobalhimycin; 9-(6-deoxy-beta-d-allofuranosyl)-6-methylpurine; debromohymenialdisine; adamantane-1-carboxylic acid-5-dimethylamino-naphthalene-1-sulfonylamino-butyl-amide; 2,3,-dihydroxybenzoylserine; z-dehydrobutyrine; 3-(benzoylamino)-l-alanine; desulfo-coenzyme a; 2',4'-dinitrophenyl-2deoxy-2-fluro-b-d-cellobioside; dodecyl-coa; diethylcarbamodithioic acid; ethylene dichloride; 2'-deoxycytidine-5'-monophosphate; diclosan; 3,3-dichloro-2-phosphonomethyl-acrylic acid; 2'-deoxycytidine-5'-triphosphate, d-pyridoxyl-n,o-cycloserylamide-5-monophosphate; d-cysteine; 2'-deoxycytidine; 5,4'-dideoxyflavanone; diphthamide; 2-(3-carboxyamido-3-(trimethylammonio)propyl) histidine; 5,10-dideazatetrahydrofolic acid; diacetyldeuteroheme; 1,5-dideoxy-1,5-imino-d-mannitol; ((2r,3s,5r)-3-hydroxy-5-(4-hydroxy-2-oxo-3,4-dihydropyrimidin-1 (2h)-yl)-tetrahydrofuran-2-yl)methyldihydrogen phosphate; 6-hydroxy-d-norleucine; 2,4-diamino-4,6-dihydroxypyrimidine; decylamine-n,n-dimethyl-n-oxide; n,o-didansyl-l-tyrosine; 2'-5'dideoxyuridine; d-eritadenine; 6-deoxyerythronolide b; 2-dimethylamino-ethyl-diphosphate; 3,5-dimethyl-1 h-pyrazole-4-carboxylic acid ethyl ester; desferal; 4-deoxy-lactose; decyloxy-methanol; indene; 2-[2-(1,3-dioxo-1,3-dihydro-2h-isoindol-2-yl)ethyl]-4-(4'-ethoxy-1,1'-biphenyl-4-yl)-4-oxobutanoic acid; diethyiphosphono group; dequadin; d-4-phosphoerythronic acid; diethylstilbestrol; co(iii)-(deuteroporphyrin ix); 4-phospho-d-erythronate; diphenylacetic acid; 2,3-difluorobenzyl alcohol; 4'-hydroxyflavanone; 3-[3-(2,3-dihydroxy-propylamino)-phenyl]-4-(5-fluoro-1-methyl-1 h-indol-3-yl)-pyrrole-2,5-dione; diisopropylphosphono group; 5-deoxyflavanone; 2-deoxy-glucitol-6-phosphate; d-glucuronic acid; digalactosyl diacyl glycerol (dgdg); 1-[glycerolylphosphonyl]-2-[8-(2-hexyl-cyclopropyl)-octanal-1-yl]-3-[hexadecanal-1-yl]-glycerol; (2r)-amino(4-hydroxyphenyl)acetic acid; 2'-deoxyguanosine-5'-diphosphate; d-glutamic acid; d-glutamine; 2'-deoxyguanosine-5'-monophosphate; 3,6-anhydro-d-galactose-2-sulfate; 2'-deoxyguanosine-5'-triphosphate; (2s,3s)-trans-dihydroquercetin; 2,3-didehydroalanine; 3,4-dihydroxybenzoic acid; 3,4-dihydroxycinnamic acid; heme d; dihydrofolic acid; 3-dehydroshikimate; 2,6-dimethyl-7-octen-2-ol; 5-hydroxy norvaline; deoxycholic acid; 3-decyl-2,5-dioxo-4-hydroxy-3-pyrroline; 3,4-dihydro-5-methyl-isoquinolinone; (2s)-hydroxy(4-hydroxyphenyl)ethanenitrile; 3-amino-4,5-dihydroxy-cyclohex-1-enecarboxylate; dihydrotestosterone; 2-(3,4-dihydroxyphenyl)acetic acid; 1,8-diaminooctane; octamethylenediamine; 1,8-octanediamine; 3,4-dichioroisocoumarin; 4,4'[1,6-hexanediylbis(oxy)]bisbenzenecarboximidamide; 2,5-dideoxy-2,5-imino-d-glucitol; 4'-deaza-1'-aza-2'-deoxy-1'-(9-methylene)-immucillin-h, (3r,4r)-n-[9-deazahypoxanthin-9-yl)methyl]-4-hydroxymethyl-pyrrolidin-3-ol; methylphosphonic acid diisopropyl ester; 1,4-diethylene dioxide; dinor-n(omega)-hydroxy-l-arginine; disordered solvent; d-isovaline; dcka, 5,7-dichlorokynurenic acid; decanoic acid; 4-[2-(3-benzyloxycarbonylamino-4-cyclohexyl-1-hydroxy-2-oxo-butylamino)-5-guanidino-pentanoylamino]-4-(1-carboxy-2-cyclohexyl-ethylcarbamoyl)-butyric acid; d-lactic acid; d-leucine; 2-hexyloxy-6-hydroxymethyl-tetrahydro-pyran-3,5-diol; di-linoleoyl-3-sn-phosphatidylcholine; d-lysine; dimethylallyl diphosphate; 5,6-dimethylbenzimidazole; dimethylformamide; dimethylglycine; 2,3-dimethylimidazolium ion; 1-deoxymannojirimycin; terminal dimethyl; alpha-difluoromethylornithine; dmp450 (inhibitor of dupont merck); dimethyl sulfoxide; 2,3-dihydroxy-valerianic acid; 3,5-dinitrocatechol; deamido-nad+; 2,4-dinitrophenol; 1-deoxy-nojirimycin; 7,8-diamino-nonanoic acid; 3-amino-alanine; dnqx; 2-amino-6-oxo-hexanoic acid; 2,4-dihydroxybenzoic acid; 2',3'-dideoxycytidine-5'-monophosphate; 4-(3,12,14-trihydroxy-10,13-dimethyl-hexadecahydro-cyclopenta[a]phenanthren-17-yl)-5h-furan-2-one; beta-hydroxy aspartic acid; dalfopristin; 2'-deoxymaltose; domoic acid; dihydroorotic acid; delta-bis(2,2'-bipyridine)imidazole osmium (ii); 1-n(omega)-nitroarginine-2,4-l-diaminobutyric amide; n-{(4s)-4-amino-5-[(2-aminoethyl)amino]pentyl}-n'-nitroguanidine; 1-n(omega)-nitroarginine-(4r)-amino-l-proline amide; dpb-t; dipyrromethane cofactor; d-phenylalanine; diphosphate; d-proline; 3-(1h-indol-3-yl)-2-[4-(4-phenyl-piperidin-1-yl)-benzenesulfonylamino]-propionic acid; 4,7-dimethyl-[1,10]phenanthroline; mixed carbamic phosphoric acid anhydride of 7,8-diaminononanic acid; 3,5-diaminophthalhydrazide; 3-dehydroquinic acid; duroquinone; 1-(2,6-dichlorophenyl)-5-(2,4-difluorophenyl)-7-piperazin-1-yl-3,4-dihydroquinazolin-2(1h)-one; 2,6-diaminoquinazolin-4(3h)-one; 11-deoxy-beta-rhodomycin; delta-bis(2,2'-bipyridine)-(5-methyl-2-2'-bipyridine)-c9-adamantane ruthenium (ii); 5,6-dihydro-benzo[h]cinnolin-3-ylamine; delta-bis(2,2'-bipyridine)imidazole ruthenium (ii); 4,7-dioxosebacic acid; 7-(carboxyamino)-8-aminononanoic acid; d-asparagine; d-serine; adamantane-1-carboxylic acid-5-dimethylamino-naphthalene-1-sulfonylamino-octyl-amide; methyl methylsulfinylmethyl sulfide; dimethylallyl s-thiolodiphosphate; d-dethiobiotin; bishydroxy[2h-1-benzopyran-2-one,1,2-benzopyrone]; dithiane diol; 4-[(10s,14s,18s)-18-(2-amino-2-oxoethyl)-14-(1-naphthylmethyl)-8,17,20-trioxo-7,16,19-triazaspiro[5.14]icos-11-en-10-yl]benzylphosphonic acid; d-threonine; d-treitol; 2,4-diamino-6-[n-(3',4',5'-trimethoxybenzyl)-n-methylamino]pyrido[2,3-d]pyrimidine; 2'-deoxyadenosine 5'-triphosphate; 4-[3-hydroxyanilino]-6,7-dimethoxyquinazoline; d-tryptophan; 1,4-dithiothreitol; (2r,3s)-1,4-dimercaptobutane-2,3-diol; (2s,3s)-1,4-dimercaptobutane-2,3-diol; 4-(3,14-dihydroxy-10,13-dimethyl-hexadecahydro-cyclopenta[a]phenanthren-17-yl)-5h-furan-2-one; d-tyrosine; 3,4-dihydrouracil; deoxyuridine-5'-diphosphate; 2,4(1h,3h)-pyrimidinedione, 1-[2-deoxy-5-o-[hydroxy (phosphonoamino)phosphinyl]-beta-d-erythro-pentofuranosyl]-; 2'-deoxyuridine 5'-alpha,beta-imido-triphosphate; 2'-deoxyuridine; deoxyuridine-5'-triphosphate; d-valinexvigaxaxvxwxwxwxwx; 3-(4-carbamoyl-1-carboxy-2-methyl-sulfonyl-buta-1,3-dienylamino)-indolizine-2-carboxylic acid; desvancosaminyl vancomycin; 1,2-hydro-1-oxy-3,4-hydro-3-(1-methoxy-2-oxy-3,4-dihydroxypentyl)-8,9-dihydroxy-7-(sec-butyl)-anthracene; 1,2-dimethoxyethane; 4-deoxyglucarate; 1-deoxy-d-xylulose-5-phosphate; methylmalonic acid; 4-(1,3,2-dioxaborolan-2-yloxy)butan-1-aminium; 4',7-dihydroxyisoflavone; 7-o-b-d-glucopyranoside; 3-hydroxymethyl-5-aziridinyl-1methyl-2-[1h-indole-4,7-dione]-propanol; ethyl oxo(piperidin-1-yl)acetate; prostaglandin b2; compound 4-d; erythose-4-phosphate; n-[n-[1-hydroxycarboxyethyl-carbonyl]leucylamino-butyl]-guanidine; n[1-hydroxycarboxyethyl-carbonyl]leucylamino-2-methyl-butane; 1,n6-ethenoadenine; 2-amino-vinyl-phosphate; 5-{2-[1-(6-ethyl-6-hydroxy-1-methyl-octa-2,4-dienyl)-7a-methyl-octahydro-inden-4-ylidene]-ethylidene}-4-methylene-cyclohexane-1,3-diol; 22-24-diene-24a,26a,27a,trihomo-1alpha,25-dihydroxyvitamin d3; 3,4-epoxybutyl-alpha-d-glucopyranoside; diethyl 4-methyl-benzylphosphonate; ethylene glycol; {[-(bis-carboxymethyl-amino)-ethyl]-carboxymethyl-amino}-acetic acid; ethyl dihydrogen phosphate; aminodi(ethyloxy)ethylaminocarbonylbenzenesulfonamide; ethylene glycol; epigallocatechin; n-(1-benzyl-3-{[3-(1,3-dioxo-1,3-dihydro-isoindol-2-yl)-propionyl]-[2-(hexahydro-benzo[1,3]dioxol-5-yl)-ethyl]-amino}-2-hydroxy-propyl)-4-benzyloxy-3,5-dimethoxy-benzamide; 3-hydroxyphenylalanine; 4-hydroxy-3-methyl butyl diphosphate; 1,3-di(n-propyloxy-a-mannopyranosyl)-carbomyl 5-methyazido-benzene; elaidoylamide; methyl-carbamic acid ethyl ester; 5-[1-(3,4-dimethoxy-benzoyl)-1,2,3,4-tetrahydro-quinolin-6-yl]-6-methyl-3,6-dihydro-[1,3,4]thiadiazin-2-one; emodin; n-aminoethylmorpholine; 2-(ethylmercuri-thio)-benzoic acid; etheno-nad; ethyl isocyanide; hpp; etheno-nadp; epothilone b; epothilone d; l-alpha-phosphatidyl-beta-oleoyl-gamma-palmitoyl-phosphatidylethanolamine; heptanyl-p-phenol; 1-hydroxy-2-s-glutathionyl-3-para-nitrophenoxy-propane; equilin; equilenin; ergosterol; 4-methoxy-e-rhodomycin t; ethanesulfonic acid; 4-iodobenzo[b]thiophene-2-carboxamidine; 1,3,5(10)-estratriene-3,16,17-triol; 2-methoxyestradiol; thieno[2,3-b]pyridine-2-carboxamidine; benzo[b]thiophene-2-carboxamidine; ethanolamine; 2-{2-[2-2-(methoxy-ethoxy)-ethoxy]-ethoxy}-ethanol; trifluoroethanol; 2-(trimethylammonium) ethyl thiol; methylethylamine; 3-(4-benzenesulfonyl-thio-phene-2-sulfonylamino)-phenylboronic acid; n-ethyl retinamide; (4s-trans)-4-(ethylamino)-5,6-dihydro-6-methyl-4h-thieno(2,3-b)thiopyran-2-sulfonamide-7,7-dioxide; 2-ethoxyethanol; 2-methoxy-4-vinyl-phenol; nonan-1-ol; tricosanoic acid; 1,6-di-o-phosphono-d-allitol; coenzyme f420; n-(2,6-diflouro-benzyl)-4-sulfamoyl-benzamide; fructose-6-phosphate; fructose-6-phosphate; 2,3-anhydro-quinic acid; 5-(6-amino-9h-purin-9-yl)-4-hydroxytetrahydrofuran-3-yl dihydrogen phosphate; 2-anhydro-3-fluoro-quinic acid; 3-hydroxyimino quinic acid; flavin-adenine dinucleotide-n5-isobutyl ketone; hexafluoroacetone hydrate; flavin-adenine dinucleotide; flavin-n7 protonated-adenine dinucleotide; 1-hexyldecanoic acid; 4-fluorobenzylamine; fructose-1,6-diphosphate; 4-flourobenzenesulfonamide; 2,6-difluorobenzenesulfonamide; 3,5-difluorobenzenesulfonamide; thiocoumarin; alpha-d-fucose; beta-d-fucose; 5-(2-chlorophenyl)furan-2-carboxylic acid; ferricrocin-iron; 1,2-epoxypropylphosphonic acid; alpha,alpha,alpha-trifluoro-p-cresol; deoxy-2-fluoro-b-d-cellotrioside; alpha-fluoro-carboxymethyldethia coenzyme a complex; free cysteine; n-alpha-(2-naphthylsulfonyl)-n-(3-amidino-l-phenylalaninyl)-d-pipecolinic acid; n-alpha-(2-naphthylsulfonyl)-n(3-amidino-l-phenylalaninyl) isopipecolinic acid methyl ester; n-alpha-(2-naphthylsulfonyl)-n(3-amidino-l-phenylalaninyl)-4-acetyl-piperazine; phosphoric acid mono-[3-fluoro-5-(5-methyl-2,4-dioxo-3,4-dihydro-2h-pyrimidin-1-yl)-tetrahyro-furan-2-ylmethyl]ester; d-gluco-2,5-anhydro-1-deoxy-1-phosphonohexitol-6-phosphate; 7-(1-methyl-1,2,3-triazol-4-yl)-6-formyl-2,7-dihydro-[1,4]thiazepine-3-carboxylic acid, brl42715, c6-(n1-methyl-1,2,3-triazolylmethylene)penem; monoazido-mu-oxo-diiron; n-(2-ferrocenylethyl)maleimide; n-(4-hydroxyphenyl)all-trans retinamide; [(4-{4-[4-(difluoro-phosphono-methyl)-phenyl]-butyl}-phenyl)-difluoro-methyl]-phosphonic acid; fexaramine; n-(2,3,4,5,6-pentaflouro-benzyl)-4-sulfamoyl-benzamide; trifluorofurnesyl diphosphate; 5-formyl-6-hydrofolic acid; n-[4-(2-{2-[3-(2-bromo-acetylamino)-propionylamino]-3-hydroxy-propionylamino}-ethyl)-phenyl]-oxalamic acid; 2-aminopropanedioic acid; 2-amino-3-hydroxy-3-phosphonooxy-propionic acid; (e)-2-fluoro-p-hydroxycinnamate; fidarestat; filaminast; fidarestat(stereoisomer); fidarestat(stereoisomer); k506; flurbiprofen methyl ester; 6,4'-dihydroxy-3-methyl-3',5'-dibromoflavone; trifluoroalanine; furoyl-leucine; flufenamic acid; fluoresceinylthioureido; methanal, oxomethane, oxymethylene, methylene oxide, formic aldehyde, methyl aldehyde; 3-fluoro-2-methyl-aniline; fluorescein; 2,5,7-trihydroxynaphthoquinone; n-[(furan-2-yl)carbonyl]-(s)-leucyl-(r)-[1-amino-2(1h-indol-3-yl)ethyl]-phosphonic acid; n7-methyl-formycin a; 6-methyl-formycin a; formycin b; formycin; 4-((3r,4s,5r)-4-amino-3,5-dihydroxy-hex-1-ynyl)-5-fluoro-3-[1-(3-methoxy-1h-pyrrol-2- yl)-meth-(z)-ylidene]-1,3-dihydro-indol-2-one; n-formyl-methionine; 2-deoxy-2-fluoro-alpha-d-mannosyl fluoride; n-{3-chloro-4-[(3-fluorobenzyl)oxy]phenyl}-6-[5-({[2-(methylsulfonyl)ethyl]amino}methyl)-2-furyl]-4-quinazolinamine; riboflavin monophosphate; formycin-5'-monophosphate; fumarate; formic acid; 5-aminocarbonyl-3-nitrophenyl-alpha-d-galactopyranose; {[7-(difluoro-phosphono-methyl)-naphthalen-2-yl]-difluoro-methyl}-phosphonic acid; n-sulfo-flavin mononucleotide; fucitol; farnesol; forskolin; fosmidomycin; 5-formyl-5,6,7,8-tetrahydrofolate; f-loop of vitamin b12; [[n-(benzyloxycarbonyl)amino]methyl]phosphate; d-fructose-6-phosphate (open form); 3-fluoro-2-(phosphonooxy)propanoic acid; 3-(4-fluorophenyl)-1-hydroxy-2-(pyridin-4-yl)-1h-pyrrolo[3,2-b]pyridine; n-formylpiperidine; fluoro-phosphite ion; 5-fluoro-4-(s)-hydroxy-3,4-dihydropyrimidine; fr117016; 2-[4-[[(s)-1-[[(s)-2-[[(rs)-3,3,3-trifluoro-1-isopropyl-2-oxopropyl]aminocarbonyl]pyrrolidin-1-yl-]carbonyl]-2-methyl-propyl]aminocarbonyl]benzoylamino]acetic acid; fr221647; fr230513; fr233623; fr239087; fr236913; sp2456; feruloyl coenzyme a; (r)-n-[2-[1-(aminoiminomethyl)-3-piperidinyl]-1-oxoethyl]-4-(phenylethynyl)-1-phenylalanine methylester; 5-[2,3-dichloro-4-(5-{1-[2-(2-guanidino-4-methyl-pentanoylamino)-acetyl]-piperidin-4-yl}-1-methyl-1h-pyrazol-3-yl)-phenoxymethyl]-furan-2-carboxylic acid; sp4160; 3-(3,5-dibromo-4-hydroxy-benzoyl)-2-ethyl-benzofuran-6-sulfonic acid [4-(thiazol-2-ylsulfamoyl)-phenyl]-amide; 2-{3-[4-(4-fluorophenyl)-3,6-dihydro-1(2h)-pyridinyl]propyl}-8-methyl-4(3h)-quinazolinone; fructose; n-(2-flouro-benzyl)-4-sulfamoyl-benzamide; fusicoccin; 3-fluorosialic acid; [1-(4-fluorobenzyl)cyclobutyl]methyl (1s)-1-[oxo(1h-pyrazol-5-ylamino)acetyl]pentylcarbamate; 3-(4-phenylamino-phenylamino)-2-(1 h-tetrazol-5-yl)-acrylonitrile; 1-(2-fluorobenzyl)-3-butyl-8-(n-acetyl-4-aminobenzyl)-xanthine; trifluoro-thiamin phosphate; fluorotryptophane; 3-hydroxy-myristic acid; fusidic acid; fucose; fumagillin; 6-deoxy-beta-l-galactose; fumaric acid; fudp; fluoro-willardiine; fica; n-1-methylheptylformamide; 4-[5-pyridin-4-yl-1h-[1,2,4]triazol-3-yl]-pyridine-2-carbonitrile; alpha-d-glucose 1,6-bisphosphate; alpha-d-glucose-1-phosphate; 4-acetyl-4-guanidino-6-methyl(propyl)carboxamide-4,5-dihydro-2h-pyran-2-carboxylic acid; gc-24; 5-n-acetyl-4-amino-6-diethylcarboxamide-4,5-dihydro-2h-pyran-2-carboxylic acid; 2-deoxy-2fluoro-glucose; glycerate-2-phosphate; phosphomethylphosphonic acid guanylate ester; 5-n-acetyl-3-(1-ethylpropyl)-1-cyclohexene-1-carboxylic acid; guanosine-3'-monophosphate-5'-diphosphate; glyceraldehyde-3-phosphate; 3-phosphoglycerol; 8-oxo-2'-deoxyguanosine-5'-monophosphate; 4-deoxy-alpha-d-glucose; guanosine-5',3'-tetraphosphate; d-galactose-4-sulfate group; 6-deoxy-alpha-d-glucose; alpha-d-glucose-6-phosphate; glucose-6-phosphate; n7-methyl-guanosine-5'-monophosphate; 9-(1,3-dihydroxy-propoxymethane)guanine; metanitrophenyl-alpha-d-galactoside; gabaculine; dihydro-acarbose; 2,6-anhydro-3-deoxy-d-erythro-hex-2-enonic acid; 3-hydroxyisoxazole-4-carboxylic acid; guanidine; glycinamide ribonucleotide; p-aminophenyl-alpha-d-galactopyranoside; 4-hydroxy-1,2,5-thiadiazole-3-carboxylic acid; s-(3-iodobenzyl)glutathione; s-(n-hydroxy-n-bromophenylcarbamoyl)glutathione; 4-guanidinobenzoic acid; 4-deoxy-d-glucuronic acid; 1-guanidinium-7-amino-heptane; 4,5-dehydro-d-glucuronic acid; trypanothione; n-cholylglycine; 3-deoxy-d-glucosamine; gluconic acid; gallichrome; 2-amino-2-deoxy-d-glucose; 4,5-dihydroxy-tetrahydro-pyran-2-carboxylic acid; 4-o-methyl-alpha-d-glucuronic acid; 4-o-methyl-beta-d-glucuronic acid; 4-deoxy-4-amino-beta-d-glucose; 1-(s-glutathionyl)-2,4-dinitrobenzene; 2-acetamido-2-deoxy-d-glucono-1,5-lactone; geldanamycin; glutathione s-(2,4 dinitrobenzene); guanosine-5'-diphosphate; guanosine-5'-diphosphate-rhamnose; oxidized glutathione disulfide; udp-d-galactopyranose; guanosine 5'-(trihydrogen diphosphate), p'-d-mannopyranosyl ester; ge2270a; (4e)-4-aminohex-4-enoic acid; 1-o-octyl-2-heptylphosphonyl-sn-glycero-3-phosphoethanolamine; 2-guanidinoethylthio)succinic acid; guanidino-ethylmercaptosuccinic acid; gemsa; 5,7-dihydroxy-3-(4-hydroxyphenyl)-4h-1-benzopyran-4-one; 4',5,7-trihydroxyisoflavone; prunetol; genisteol; genz-10850; geran-8-yl geran; g418; l-2-amino-4-(guanidinooxy)butyric acid; 1-menaphthyl glutathione conjugate; beta-1,2,3,4,6-penta-o-galloyl-d-glucopyranose; ghavamiol; 4-hydroxyphenylglycine; (8ar)-hexahydropyrrolo[1,2-a]pyrazine-1,4-dione; s-(n-hydroxy-n-iodophenylcarbamoyl)glutathione; glucarate; alpha-d-galactose-1-phosphate; 3-amino-8,9,10-trihydroxy-7-hydroxymethyl-6-oxa-1,3-diaza-spiro[4.5]decane-2,4-dione; 8,9,10-trihydroxy-7-hydroxymethyl-2-thioxo-6-oxa-1,3-diaza-spiro[4.5]decan-4-one; 3,8,9,10-tetrahydroxy-7-hydroxymethyl-6-oxa-1,3-diaza-spiro[4.5]decane-2,4-dione; (3,4,5-trihydroxy-6-hydroxymethyl-tetrahydro-pyran-2-yl)-phosphoramidic acid dimethyl ester; 8,9,10-trihydroxy-7-hydroxymethyl-3-methyl-6-oxa-1,3-diaza-spiro[4.5]decane-2,4-dione; (4ar,6s,8ar)-11-[8-(1,3-dioxo-1,3-dihydro-2h-isoindol-2-yl)octyl]-6-hydroxy-3-methoxy-5,6,9,10-tetrahydro-4ah-[1]benzofuro[3a,3,2-ef][2]benzazepin-11-ium; n-(8,9,10-trihydroxy-7-hydroxymethyl-2,4-dioxo-6-oxa-1,3-diaza-spiro[4.5]dec-3-yl-acetamide; glucose; 4,6-dideoxyglucose; alpha-d-glucopyranosyl-2-carboxylic acid amide; skf 107457; glycoluril; d-glucose in linear form; glucosamine 6-phosphate; 2,3-dihydroxy-5-oxo-hexanedioate; beta-d-glucopyranose spirohydantoin; glyoxalate, glyoxylate; 6-deoxyglucose; glycinamid; gm6001; 4-amido-4-carbamoyl-butyric acid; l-glycero-d-manno-heptopyranose; gallamine; guanosine; 2,4-deoxy-4-guanidino-5-n-acetyl-neuraminic acid; s-p-nitrobenzyloxycarbonylglutathione; aminophosphonic acid-guanylate ester; 2-(3,4-dihydro-3-oxo-2h-benzo[b][1,4]thiazin-2-yl)-n-hydroxyacetamide; (−)-galanthamine; hydroxyacetic acid; hydroxyethanoic acid; d-gluconhydroximo-1,5-lactam; glucosamine 1-phosphate; phosphomethylphosphonic acid guanosyl ester; diguanosine-5'-triphosphate; glucosamine 4-phosphate; 1-(4-amidinophenyl)-3-(4-chlorophenyl)urea; 1-(2-amidinophenyl)-3-(phenoxyphenyl)urea; l-alpha-glycerophosphorylethanolamine; gpi-1046; glyphosate; geranyl diphosphate; (9r,10r)-9-(s-glutathionyl)-10-hydroxy-9,10-dihydrophenanthrene; (9s,10s)-9-(s-glutathionyl)-10-hydroxy-9,10-dihydrophenanthrene; guanosine 5'-diphosphate 2':3'-cyclic monophosphate; 1-thio-beta-d-glucopyranose; 4-thio-beta-d-glucopyranose; o4-sulfonyl-galactose; s-benzyl-glutathione; 4-thio-d-glucose; l-alpha-glycerophosphorylserine; gluthathione; 5'-guanosine-diphosphate-monothiophosphate; 7-methyl-gpppa; s-(p-nitrobenzyl)glutathione; mrna cap analog n7-methyl gpppg; d-galactohydroximo-1,5-lactam; o1-methyl-4-deoxy-4-thio-beta-d-glucose; phosphoaminophosphonic acid guanylate ester; phosphomethylphosphonic acid-guanylate ester; guanosine-5'-triphosphate; galacturonic acid; glutathione sulfonic acid; s-hexylglutathione; s-octylglutathione; (5r, 6s, 7s, 8s)-5-hydroxymethyl-6,7,8-trihydroxy-tetrazolo[1,5-a]piperidine; 2-amino-7-[2-(2-hydroxy-1-hydroxymethyl-ethylamino)-ethyl]-1,7-dihydro-purin-6-one; glutaric acid; glucose-uridine-c1,5'-diphosphate; 5-fluoro-beta-l-gulosyl fluoride; 4-methylumbelliferyl chitobiose; guanine; heparin disaccharide i-s; (6r,7r)-3-[(acetyloxy)methyl]-7-{[((6s)-6-

(glycylamino)-7-oxido-7-oxoheptanoyl]amino}-8-oxo-5-thia-1-azabicyclo[4.2.0]octane-2-carboxylate; quinonoid 7,8-tetrahydrobiopterin; heptulose-2-phosphate; heparin disaccharide iii-s; 5,10-dimethylene tetrahydromethanopterin; 1-deoxy-6-o-phosphono-1-[(phosphonomethyl)amino]-l-threo-hexitol; hydantocidin-5'-phosphate; 9-(5,5-difluoro-5-phosphonopentyl)guanine; beta-cyclohexylalanine; (carboxyhydroxyamino)ethanoic acid; acetohydroxamic acid; gshna; cyclohexylammonium ion; histidyl-adenosine monophosphate; n-omega-hydroxy-l-arginine; hydroxyaminovaline; p-hydroxybenzaldehyde; n-[2-hydroxy-2-(8-isopropyl-6,9-dioxo-2-oxa-7,10-diaza-bicyclo[11.2.2]heptadeca-1(16),13(17),14-trien-11-yl)-ethyl]-n-(3-methyl-butyl)-benzenesulfonamide, inhibitor 3; 2-(11-{2-[benzenesulfonyl-(3-methyl-butyl)-amino]-1-hydroxy-ethyl}-6,9-dioxo-2-oxa-7,10-diaza-bicyclo[11.2.2]heptadeca-1(16),13(17),14-trien-8-yl)-acetamide, inhibitor 2; 7,8-dihydrobiopterin; 7,8-dihydro-l-biopterin; 1-histidine beta naphthylamide; 2,4-dihydroxy-7-(methyloxy)-2h-1,4-benzoxazin-3(4h)-one; r,3-hydroxybutan-2-one; s,3-hydroxybutan-2-one; 4-[hydroxy[methyl-phosphinoyl]]-3-oxo-butanoic acid; para-coumaric acid; 2',4,4'-trihydroxychalcone; 3pp; 3-phenylpropionic acid; 2-acetyl-protoporphyrin ix; 2-amino-4-mercapto-butyric acid; hadacidin; 3r-hydroxydecanoyl-coa; heme; dimethyl propionate ester heme; methylhydrazine; 1-hexadecanosulfonic acid; 4-[(4-imidazo[1,2-a]pyridin-3-ylpyrimidin-2-yl)amino]benzenesulfonamide; n-[4-(2-methylimidazo[1,2-a]pyridin-3-yl)-2-pyrimidinyl]acetamide; 2-{(9as)-9a-[(1s)-1-hydroxyethyl]-2,7-dimethyl-9a,10-dihydro-5h-pyrimido[4,5-d][1,3]thiazolo[3,2-a]pyrimidin-8-yl}ethyl trihydrogen diphosphate; 6,7-dicarboxyl-1,2,3,4,5,8-hexamethylhemin; hybrid between b and c type hemes (protoporphyrin ixcontaining fe); heme c; 2-hydroxyethyl disulfide; n-hexylphosphonate ethyl ester; (2s,5r,6r)-6-{[(6r)-6-(glycylamino)-7-oxido-7-oxoheptanoyl]amino}-3,3-dimethyl-7-oxo-4-thia-1-azabicyclo[3.2.0]heptane-2-carboxylate; heme; 2-[(3-hydroxy-2-methyl-5-phosphonooxymethyl-pyridin-4-ylmethyl)-imino]-5-phosphono-pent-3-enoic acid; zinc substituted heme c; 1,3-dedimethyl-1,3-divinyl heme; hexane; hexane-1,6-diol; alpha-hydroxy-beta-phenyl-propionic acid; 5-(3,3-dihydroxypropeny)-3-methoxy-benzene-1,2-diol; 2-formyl-protoporphryn ix; hg9a-9, nonanoyl-n-hydroxyethylglucamide; glutamine hydroxamate; 4-(hydroxymercury)benzoic acid; methyl mercury ion; mercury diiodide; n-hydroxyguanidine; [pterin-6-ylmethanyl]-phosphonophosphate; (2s,3s)-trans-2,3-dihydro-3-hydroxy-anthranilic acid; 1-monohexanoyl-2-hydroxy-sn-glycero-3-phosphate; (2s)-2,8-diaminooctanoic acid; 6-hydroxymethyl-7,8-dihydropterin; 6-hydroxymethylpterin; 4-methyl-histidine; fe-mesopone; (8,12-diethyl-3,8,13,17-tetramethyl-7-oxo-porphyrinato-2,18-dipropionic acid)iron(iii); 2-methyl-3-(2-aminothiazolo)propanal; n-hydroxy-n-isopropyloxamic acid; nd1-phosphonohistidine; 2-bromo-2-chloro-1,1,1-trifluoroethane; beta-hydroxyleucine; 5-hydroxymethyl-chonduritol; hymenialdisine; (s)-hmg-coa; 4-amino-5-hydroxymethyl-2-methylpyrimidine; isoformononetin; 1-hydroxyamine-2-isobutylmalonic acid; 1,8-di-hydroxy-4-nitro-anthraquinone; hydantocidin-5'-monophosphate; 2,3-propandiol; hypoxanthine; 2-hydroxy-3-amino-4-phenyl butane; open form of 2'-deoxy-ribofuranose-5'-phosphate; n-(1-carboxy-3-phenylpropyl)phenylalanyl-alpha-asparagine; n-heptylformamide; heptanamide; hydroxyphenyl propionic acid; 6-hydroxy-7,8-dihydro purine nucleoside; phenyiphosphate; 6-hydroxypropyithymine; 4-hydroxy-3,4-dihydro-1h-pyrimidin-2-one; 5-methyl-5-(4-phenoxy-phenyl)-pyrimidine-2,4,6-trione; 1-homoarginine; 5-hydroxy-l-tryptophan; phosphoric acid mono-[2-amino-3-(3h-imidazol-4-yl)-propyl-]ester; 1-homoserine; 1-hexadecylsulfonyl fluoride; homoserine lactone; histamine; histidinol; 4-carboxy-5-(1-pentyl)hexylsulfanyl-1,2,3-triazole; heptyl 1-thiohexopyranoside; (4s)-4-{[(2s)-2-amino-3-oxopropyl]sulfanyl}-l-homoserinate; 2-acetyl-3-[(4-amino-2-methyl-5-pyrimidinyl)methyl]-4-methyl-5-(4,6,6-trihydroxy-3,5-dioxa-4,6-diphosphahex-1-yl)thiazolium inner salt p,p'-dioxide; heptane-1,2,3-triol; hydroxy-phenyl-acetic acid 8-methyl-8-aza-bicyclo[3.2.1]oct-3-yl ester; beta-hydroxytryptophane; huperzine b; huperaine a; 3-chloro-9-ethyl-6,7,8,9,10,11-hexahydro-7,11-methanocycloocta[b]quinolin-12-amine; willardiine; docosa-4,7,10,13,16,19-hexaenoic acid; hexanoyl-coenzyme a; 3,6-dihydroxy-xanthene-9-propionic acid; phenylacetaldehyde; em-1745; hyperforin; 2-phenethyl-2,3-dihydro-phthalazine-1,4-dione; 1-[2-(3-biphenyl)-4-methylvaleryl)]amino-3-(2-pyridylsulfonyl)amino-2-propanone; 2-[trans-(4-aminocyclohexyl)amino]-6-(benzyl-amino)-9-cyclopentylpurine; d-myo-inositol-2,4,5-trisphosphate; 1-benzyl-5-methoxy-2-methyl-1 h-indol-3-yl)-acetic acid; d-myo-inositol-1,4,5-triphosphate; (1s,3s,4s)-1,3,4-triphospho-myo-inositol; isobutylbenzene; (1s,3r,4r,6s)-1,3,4,6-tetrapkisphosphate; sc-74020; 4r-fluoro-n6-ethanimidoyl-1-lysine; dpi59; inositol-(1,3,4,5,6)-pentakisphosphate; inhibitor idd 384; 4,6-dideoxy-4-{[4,5,6-trihydroxy-3-(hydroxymethyl)cyclohex-2-en-1-yl]amino}-alpha-d-lyxo-hexopyranosyl-(1->4)-alpha-d-threo-hexopyranosyl-(1->6)-alpha-l-threo-hexopyranose; 4-[(isopropylamino)methyl]phenylalanine; 4-iodo-acetamido phenylboronic acid; beta-aspartyl residue; isoaspartyl group; ado-p-ch2-p-ps-ado; 2-amino-3-(3-hydroxy-7,8-dihydro-6h-cyclohepta[d]-4-isoxazolyl)propionic acid; gamma-glutamyl[s-(2-iodobenzyl)cysteinyl]glycine; l-alpha-glycerophospho-d-myo-inositol-4,5-bis-phosphate; 2-iodobenzylthio group; ic261; isocitrate calcium complex; 4-imino-5-methidyl-2-methylpyrimidine; isocitric acid; 5-iododeoxyuridine; idd552; imidazole-derived cellobiose; gluco-phenylimidazole; (5s)-5-iodohydro-2,4(1h,3h)-pyrimidinedione; 7-iodo-1,2,3,4-tetrahydro-isoquinoline; indole naphthyridinone; l-iduronic acid; o2-sulfo-glucuronic acid; 4,5-dehydro-l-iduronic acid; 1,4-dideoxy-o2-sulfo-glucuronic acid; (2r,3r,4s,5r)-2-acetamido-3,4-dihydroxy-5-hydroxymethyl-piperidinium; (3r,4r,5r)-5-(hydroxymethyl)piperidine-3,4-diol; 4-imino-5-methidyl-2-trifluoromethylpyrimidine; alpha-amino-2-indanacetic acid; indole-3-glycerol phosphate; n-(r-carboxy-ethyl)-alpha-(s)-(2-phenylethyl); 3,5-dichloro-4-[(4-hydroxy-3-isopropylphenoxy)phenylacetic acid; n-isopropyl-n'-hydroxyguanidine; d-myo-inositol-hexasulphate; 4-imidazolmethylene-5-imidazolone chromophore; allo-isoleucine; 4'-deoxy-4'-acetylyamino-pyridoxal-5'-phosphate; 3-(1-aminoethyl)nonanedioic acid; n-[isoleucinyl]-n'-[adenosyl]-diaminosufone; glutamyl group; n5-iminoethyl-l-ornithine; n-[o-phosphono-pyridoxyl]-isoleucine; [4-({[5-benzyloxy-1-(3-carbamimidoyl-benzyl)-1 h-indole-2-carbonyl]-amino}methyl)-phenyl]-trimethyl-ammonium; imidazole; tetra(imidazole)diaquacopper (ii); tetra(imidazole)diaquacopper (i); immucillin-g; 1,4-dideoxy-4-aza-1-(s)-(9-deaza-hypoxanthin-9-yl)-d-ribitol; 2-iminobiotin; 2-(beta-d-glucopyranosyl)-5-methyl-1,2,3-benzimidazole; 6-o-phosphoryl inosine monophosphate; inosinic acid; 2-hydroxymethyl-pyrrolidine-3,4-diol; phosphoric acid mono-[5-(2-amino-4-oxo-4,5-dihydro-3h-pyrrolo[3,2-d]pyrimidin-7-yl)-3,4-dihydroxy-pyrrolidin-2-ylmethyl]; cis-[4,5-bis-(4-chlorophenyl)-2-(2-isopropoxy-4-methoxyphenyl)-4,5-dihydroimidazol-1-yl]-piperazin-1-yl-methanone; cis-

[4,5-bis-(4-bromophenyl)-2-(2-ethoxy-4-methoxyphenyl)-4,5-dihydroimidazol-1-yl]-[4-(2-hydroxyethyl)piperazin-1-yl]methanone; {1-[(3-hydroxy-methyl-5-phosphonooxy-methylpyridin-4-ylmethyl)-amino]-ethyl}-phosphonic acid; 1,5-bis(n-benzyloxycarbonyl-1-leucinyl)carbohydrazide; 1-octadecyl-2-acetamido-2-deoxy-sn-glycerol-3-phosphoethylmethyl sulfide; indole; 3-bromo-7-nitroindazole; d-[(n-hydroxyamino)carbonyl]phenylalanine; d-[(amino)carbonyl]phenylalanine; n-(r-carboxy-ethyl)-alpha-(s)-(2-phenylethyl)glycyl-l-arginine-n-phenylamide; 5-nitro-6-ribityl-amino-2,4(1 h,3h)-pyrimidinedione; 5-(6-d-ribitylamino-2,4-dihydroxypyrimidin-5-yl)-1-pentyl-phosphonic acid; al-6629, [2h-thieno[3,2-e]-1,2-thiazine-6-sulfonamide,2-(3-methoxyphenyl)-3-(4-morpholinyl)-, 1,1-dioxide]; al-6619, [2h-thieno[3,2-e]-1,2-thiazine-6-sulfonamide,2-(3-hydroxyphenyl)-3-(4-morpholinyl)-, 1,1-dioxide]; indirubin-5-sulphonate; myo-inositol; tl-3-093; n-(3-cyclopropyl(5,6,7,8,9,10-hexahydro-2-oxo-2h-cycloocta[b]pyran-3-yl)methyl)phenylbenzensulfonamide; 4-(aminosulfonyl)-n-[(4-fluorophenyl)methyl]-benzamide; 4-(aminosulfonyl)-n-[(2,4-difluorophenyl)methyl]-benzamide; 2-(carboxymethoxy)-5-[(2s)-2-({(2s)-2-[(3-carboxypropanoyl)amino]-3-phenylpropanoyl}amino)-3-oxo-3-(pentylamino)propyl]benzoic acid; carpropamide; 2-{4-[(2s)-2-[({[(1s)-1-carboxy-2-phenylethyl]amino}carbonyl)amino]-3-oxo-3-(pentylamino)propyl]phenoxy}malonic acid; 4-(aminosulfonyl)-n-[(2,5-difluorophenyl)methyl]-benzamide; 3-iodo-benzyl alcohol; 4-(aminosulfonyl)-n-[(2,3,4-trifluorophenyl)methyl]-benzamide; 4-(aminosulfonyl)-n-[(2,4,6-trifluorophenyl)methyl]-benzamide; 4-(aminosulfonyl)-n-[(3,4,5-trifluorophenyl)methyl]-benzamide; 2-propanol, isopropanol; 4-iodophenol; (diaminomethyl-methyl-amino)-acetic acid; indolylpropionic acid; isopenicillin n; 1-hydroxy-3-methylbutane; 1-methyl-2-oxy-5,5-dimethyl pyrrolidine; isopropyl alcohol; 5-methyl-2-(1-methylethyl)phenol; 3-[isopropyl(4-methylbenzoyl)amino]-5-phenylthiophene-2-carboxylic acid; d-myo-inositol-l-phosphate; phenol; indole-3-propanol phosphate; 3-isopropylmalic acid; para-iodo-d-phenylalanine hydroxamic acid; (p-iodophenylacetylamino)methylphosphinic acid; isopentyl pyrophosphate; 1-(isopropylthio)-beta-galactopyranside; s-isopropyl-isothiourea; 2-methoxy-3-isopropylpyrazine; (5-oxo-5,6-dihydro-indolo[1,2-a]quinazolin-7-yl)-acetic acid; (7as,12ar,12bs)-1,2,3,4,7a,12,12a,12b-octahydroindolo[2,3-a]quinolizin-7(6h)-one; (1s)-1(9-deazahypoxanthin-9yl)1,4-dideoxy-1,4-imino-d-ribitol-5-phosphate; iso24; pd150606; isobutyric acid; isochorismic acid; p-(2'-iodo-5'-thenoyl)hydrotropic acid; isatin; para-isopropylaniline; phosphorylisopropane; isoquinoline; se-ethyl-isoselenourea; isoniazid; tubazid; rimitsid; isonicotinylhydrazine; lanizid; nydrazid; inositol 1,3-bisphosphate; imino-tryptophan; inositol 1,3,4,5-tetrakisphosphate; ethyl-isothiourea; iso-ursodeoxycholic acid; 5-iodouracil; isovaleric acid; iodo-willardiine; indirubin-3'-monoxime; n-alpha-acetyl-3,5-diiodotyrosylglycine; 3-iodo-tyrosine; threonine derivative; n-{3-[4-(3-amino-propyl)-piperazin-1-yl]-propyl}-3-(2-thiophen-2-yl-acetylamino)-5-(3,4,5-trihydroxy-6-hydroxymethyl-tetrahydro-pyran-2-yloxy)-benzamide; n-{3-[4-(3-amino-propyl)-piperazin-1-yl]-propyl}-3-nitro-5-(galactopyranosyl)-alpha-benzamide; jaspisamide a; je-2147, ag1776, kni-764; 3-[(2,4-dichlorobenzoyl)(isopropyl)amino]-5-phenylthiophene-2-carboxylic acid; k201; kabiramide c; n-pyridoxyl-7-keto-8-aminopelargonic acid-5'-monophosphate; kanamycin a; 7-keto-8-aminopelargonic acid; 3"-(beta-chloroethyl)-2",4"-dioxo-3,5"-spiro-oxazolidino-4-deacetoxy-vinblastine; hydrolyzed cephalothin; lysine nz-carboxylic acid; 2-keto-3-deoxygluconate; 3-deoxy-d-manno-oct-2-ulosonic acid; 10-cf3c(oh)2-ddacthf, hydrolyzed form of 10-trifluoroacetyl-5,10-dideaza-acyclic-5,6,7,8-tetrahydrofolic acid; 1alpha,25-dihydroxyl-20-epi-22-oxa-24,26,27-trihomovitamin d3; ara-alpha(1,3)-xyl; 4-nitrophenyl-ara; kifunensine; alpha-ketoisovaleric acid; ketovaline; 2-amino-6-aminomethyl-8-phenylsulfanylmethyl-3h-quinazolin-4-one; kaempherol; 4-(methylsulfanyl)-2-oxobutanoic acid; 5-hydroxy-2-(hydroxymethyl)-4h-pyran-4-one; 17-dmag; (2-[2-ketopropylthio]ethanesulfonate; 2-dehydropantoate; (s)-2-amino-4-[(2s,3r)-2,3,5-trihydroxy-4-oxo-pentyl]mercapto-butyric acid; k-252a; bis-napthyl beta-ketophosphonic acid; l-2-amino-4-[2-aminophenyl]-4-oxobutanoic acid; 1-acetyl-4-(4-{4-[(2-ethoxyphenyl)thio]-3-nitrophenyl}pyridin-2-yl)piperazine; n-[(3z)-5-tert-butyl-2-phenyl-1,2-dihydro-3h-pyrazol-3-ylidene]-n'-(4-chlorophenyl)urea; inhibitor of p38 kinase; 1,2-di-1-(3,7,11,15-tetramethyl-hexadecane)-sn-glycero-3-phosphate; ly249543; 1,2-di-1-(3,7,11,15-tetramethyl-hexadecane)-sn-glycerol; ly374571; 2,3-di-o-phytanyl-3-sn-glycero-1-phosphoryl-3'-sn-glycerol-l'-phosphate; 3-[(5s)-1-acetyl-3-(2-chlorophenyl)-4,5-dihydro-1h-pyrazol-5-yl]phenol; l-756,423; lactic acid; 5-fluorolevulinic acid; maltosyl-alpha (1,4)-d-gluconhydroximo-1,5-lactam; allo-lactose; n,n-dimethyl-l-alanine; 4'-nitrophenyl-3i-thiolaminaritrioside; lanosterol; 1-alfa-lysophosphatidylcholine, lauroyl; 4-(17-hydroxy-5,12-dimethyl-3-oxo-2,16-dioxabicyclo[13.3.1]nonadeca-4,8,10-trien-17-yl)-2-thiazolidinone; lactose; dodecanoic acid; perchlorate ion; l-pyridoxyl-n,o-cycloserylamide-5-monophosphate; (5r)-5-amino-6-hydroxyhexylcarbamic acid; lauryl dimethylamine-n-oxide; [3-(dodecanoylamino)propyl](hydroxy)dimethylammonium; 6-hydroxy-l-norleucine; levulinic acid; (4s)-5-fluoro-1-leucine; d-limonene 1,2-epoxide; 6-[1-(3,5,5,8,8-pentamethyl-5,6,7,8-tetrahydronaphthalen-2-yl)cyclopropyl]pyridine-3-carboxylic acid; l-guluronic acid 6-phosphate; gluconolactone; 1-glucuronic acid; 1,2-dipalmitoyl-phosphatidyl-glycerole; l-[(n-hydroxyamino)carbonyl]phenylalanine; lipid fragment; 3,4-dihydroxy-1-methylquinolin-2(1h)-one; (3e)-3-[(4-hydroxyphenyl)imino]-1h-indol-2(3h)-one; 3-pyridin-4-yl-2,4-dihydro-indeno[1,2-c]pyrazole; sri-9439; sri-9662; 2-tridecanoyloxy-pentadecanoic acid; 3-oxo-pentadecanoic acid; 3a-oxo-butyric acid; l-myo-inositol-1-phosphate; 3-oxiran-2ylalanine; 5-thio-a/b-d-mannopyranosylamine; 4-amino-1-[(1s,3r,4r,7s)-7-hydroxy-1-(hydroxymethyl)-2,5-dioxabicyclo[2.2.1]hept-3-yl]-5-methylpyrimidin-2(1h)-one; n'-pyridoxyl-lysine-5'-monophosphate; nz-(dicarboxymethyl)lysine; (3r)-3-methyl-l-glutamic acid; [(2r,3s,4r,5r)-5-(6-amino-9h-purin-9-yl)-3,4-dihydroxytetrahydro-2-furanyl]methyl sulfamate; dodecyl-alpha-d-maltoside; 5-nitroso-6-ribityl-amino-2,4(1h,3h)-pyrimidinedione; pentane; 1-leucyl-hydroxylamine; 3-amino-4-{3-[2-(2-propoxy-ethoxy)-ethoxy]-propylamino}-cyclobut-3-ene-1,2-dione; noradrenaline; [[4-(aminomethyl)phenyl]amino]oxo-acetic acid; 7-(2-amino-2-phenyl-acetylamino)-3-chloro-8-oxo-1-aza-bicyclo[4.2.0]oct-2-ene-2-carboxylic acid; lambda-bis(2,2'-bipyridine)imidazole osmium (ii); xylose-derived lactam oxime; lpc-ether; 2-amino-but-3-ynoic acid; lysophosphotidylserine; lambda-bis(2,2'-bipyridine)-(5-methyl-2-2'-bipyridine)-c9-adamantane ruthenium (ii); lambda-bis(2,2'-bipyridine)imidazole ruthenium (ii); 6-hydroxy-6-methyl-heptan-3-one; 1-tryptophanamide; 1-tryptophan; 7,8-dimethylalloxazine; 6,7-dimethyl-alloxazine; (3r,5r)-7-((1 r,2r,6s,8r,8as)-2,6-dimethyl-8-{[(2r)-2-methylbutanoyl]oxy}-1,2,6,7,8,8a-hexahydronaphthalen-1-yl)-3,5-dihydroxyheptanoic acid; (2s)-2-amino-3-butenoic acid, (2s)-2-aminobut-3-enoicacid; l-xylulose 5-phosphate; l-xylose (cyclic form); l-xylitol 5-phosphate; 8,9-dichloro-2,3,4,5-tetrahydro-1h-benzo[c]azepine; 2-(4-morpholinyl)-8-phenyl-4h-1-benzopyran-4-one; ly341770; ly231514; ly231514 tetra glu; 2-allyl-6-methyl-phenol; 2,6-diamino-hexanoic acid amide; butylamine; 1-amino-1-carbonyl pentane; 6-amino-1-methylpurine; (3s)-3-amino-1-(cyclopropylamino)heptane-2,2-diol; d-mannose 1-phosphate; (2s)-2-amino-4-(methylsulfanyl)-1-pyridin-2-ylbutane-1,1-diol; 1-methoxy-2-(2-methoxyethoxy)ethane; n-trimethyllysine; alpha-d-mannose-6-phosphate; 6'-methyl-thiamin diphosphate; 7n-methyl-8-hydroguanosine-5'-diphosphate; d-glycero-d-mannopyranose-7-phosphate; 1,4-dithio-alpha-d-mannose; 4-methylthio-alpha-d-mannose; o1-methyl-4-deoxy-4-thio-alpha-d-glucose; cyclohexyl-hexyl-beta-d-maltoside; mannobiose; mercury acetate ion; maleic acid; 2-deoxy-2-fluoro-alpha-d-mannose; alpha-methyl-n-acetyl-d-glucosamine; 3-hydroxy-3-methyl-glutaric acid; alpha-ketomalonic acid; maltose; 1-o-methyl-alpha-d-mannose; alpha-d-mannose; 2-amino-8-methylquinazolin-4(3h)-one; aurodox; 1-methylmocimycin; antibiotic x-5108; goldinodox; goldinomycin; d-mannuronic acid; 4-deoxy-d-mannuronic acid; artigenin congener; dibenzylbutyrolactone lignanolide; mafp; 3-methyl-benzene-1,2-diol; 2-deoxy-2-fluoro-beta-d-mannose; methyl-beta-d-galactose; toluene; mercuribenzoic acid; 1-[(2-amino-6,9-dihydro-1h-purin-6-yl)oxy]-3-methyl-2-butanol; 2-hydroxy-5-({1-[(4-methylphenoxy)methyl]-3-oxoprop-1-enyl}amino)-1-tyrosine; tribromomethane; r-2-{[4'-methoxy-(1,1'-biphenyl)-4-yl]-sulfonyl}-amino-6-methoxy-hex-4-ynoic acid; mesobiliverdin iv alpha; methicillin acyl-serine; (1s,5z,7z,17alpha,22e)-24-cyclopropyl-9,10-secochola-5,7,10,22-tetraene-1,3,24-triol; 1-alpha,24s-(oh) 2-22-ene-26,27-dehydrovitamin d3; methylmalonyl-coenzyme a; 4-(1-amino-1-carboxy-ethyl)-benzoic acid; mercaptocarboxylate inhibitor; nz-(1-carboxyethyl)-lysine; pterin cytosine dinucleotide; 1-(3-mercapto-2-methyl-propionyl)-pyrrolidine-2-carboxylic acid; 4-methyl-1,2-benzenediol; mdl72527; n-[2-(1-maleimidyl)ethyl]-7-diethyl-aminocoumarin-3-carboxamide; malonaldehyde; 5-mercaptoethanol-2-decenoyl-coenzyme a; 7n-methyl-8-hydroguanosine-5'-diphosphate; n-methyldehydrobutyrine; methyl-o3-(alpha-d-mannose)-alpha-d-mannose; 4-methylidene-5-one; 9-(2-deoxy-beta-d-ribofuranosyl)-6-methylpurine; 1-ethoxy-2-(2-methoxyethoxy)ethane; ethyl-carbamic acid methyl ester; d-methionine; 2s,3r-2-amino-3-methyl-pentanedioic acid; n5-methylglutamine; meropenem; merrem; meronem; 2-(n-morpholino)-ethanesulfonic acid; (r)-mevalonate; mf268; trifluoromethionine; alpha-l-1-methyl-fucose; beta-l-methyl-fucose; (2s,3s,8s,9s)-3-amino-9-methoxy-2,6,8-trimethyl-10-phenyldeca-4,6-dienoic acid; alpha-l-methyl-fucose; 7-methylguanosine; beta-methyl-d-galactoside; o1-methyl-glucose; 7-methyl-guanosine-5'-triphosphate; malachite green; 7n-methyl-8-hydroguanosine-5'-triphosphate; n-(2-acetamido)iminodiacetic acid; 3-mercapto-1-(1,3,4,9-tetrahydro-b-carbolin-2-yl)-propan-1-one; mesoheme; s-oxymethionine; alpha-methylisocitric acid; [cyclohexylethyl]-[[[[4-[2-methyl-1-imidazolyl-butyl]phenyl]acetyl]-seryl]-lysinyl]-amine; monoisopropyl ester phosphonic acid group; monoisopropylphosphorylserine; dicarboxylic acid c3; propanediolic acid; metahnedicarboxylic acid; malonyl-coenzyme a; n-methylleucine; n-methyl-n-propargyl-3-(2,4-dichlorophenoxyl)propylamine; malonate ion; 3-amino-3-oxopropanoic acid; (s)-2-(phosphonoxy)caproyl-l-leucyl-p-nitroanilide; 1-aminocyclopropylphosphonate; amylotriose; malate ion; n-dimethyl-lysine; n-methyl-lysine; cu-cyclam; cu-bicyclam; n-hydroxy-4-[(4-methoxylphenyl)sulfonyl]-2,2-dimethyl-hexahydro-1,4-thiazepine-3(s)-carboxamide; o1-methyl-mannose; mmi-175; n-acetylmannosaminitol; n-methylmesoporphyrin; mercaptomethyl phosphonate; 1-carboxyethylaminomethyl-4-aminomethylbenzene; 5-mercapto-2-nitro-benzoic acid; methyl isocyanide; dansylamide; mant-adp; 1,8-di-hydroxy-4-nitro-xanthen-9-one; 5,8-di-amino-1,4-dihydroxy-anthraquinone; heptamolybdate; 6-(1,3-dihydro-7-hydroxy-5-methoxy-4-methyl-1-oxoisobenzofuran-6-yl)-4-methyl-4-hexanoic acid; mometasone furoate; 8-methyl-9-oxoguanine; 4-(2-{[4-{[3-(4-chlorophenyl)propyl]sulfanyl}-6-(1-piperazinyl)-1,3,5-triazin-2-yl]amino}ethyl)phenol; dioxothiomolybdenum(vi) ion; moxalactam derivative; n-methylmesoporphyrin containing copper; 2-methyl-2,4-pentanediol; (1h-indol-3-yl)-(2-mercapto-ethoxyimino)-acetic acid; 1-monooleoyl-rac-glycerol; methionine phosphonate; methionine phosphinate; n-methyl-pyridoxal-5'-phosphate; 3[n-morpholino]propane sulfonic acid; 3-(3,4-dimethoxyphenyl)propionic acid; methylphosphinic acid; cyanocinnoline; 5-(4-methoxyphenoxy)-2,4-quinazolinediamine; 2-methylpentane-1,2,4-triol; (4r)-2-methylpentane-2,4-diol; meso-erythritol; beta-dadf, msa, multisubstrate adduct inhibitor; 2,2-dichloro-1-methanesulfinyl-3-methyl-cyclopropanecarboxylic acid [1-(4-bromo-phenyl)-ethyl]-amide; inhibitor msa367; methyl-oxy-4-sulfone-benzene; [methylseleno]acetate; selenomethionine selenoxide; 5'-o-[(I-methionyl)-sulphamoyl]adenosine; 4-[3-methylsulfanylanilino]-6,7-dimethoxyquinazoline; 5'-deoxy-5'-methylthioadenosine; [methylteluro]acetate; [methylthio]acetate; 5'-deoxy-5'-(methylthio)-tubercidin; (1s)-1-(0-deazahypoxanthin-9-yl)-1,4-dideoxy-1,4-imino-5-methylthio-d-ribitol, mt-immucillin-h, mt-immh; d-mannitol; (1s)-1-(9-deazaadenin-9-yl)-1,4,5-trideoxy-1,4-imino-5-methylthio-d-ribitol; 9-beta-d-ribofuranosyl-6-methylthiopurine; (molybdopterin-s,s)-dioxo-thio-molybdenum(v); (5-methyl-6-oxo-1,6-dihydro-pyridin-3-yl)-1,2-dideoxy-ribofuranose-5-monophosphate; (4s-trans)-4-(methylamino)-5,6-dihydro-6-methyl-4h-thieno(2,3-b)thiopyran-2-sulfonamide-7,7-dioxide; maltotetraose; meta-tyrosine; 9-methyl uric acid; 4-methylumbelliferyl-alpha-d-glucose; methylumbelliferyl sialic acid; 6-(2,5-dimethoxy-benzyl)-5-methyl-pyrido[2,3-d]pyrimidine-2,4-diamine; 2-methoxyethanol; 7-((carboxy (4-hydroxyphenyl)acetyl)amino)-7-methoxy-(3-((1-methyl-1 h-tetrazol-5-yl)thio)methyl)-8-oxo-5-oxa-1-azabicyclo[4.2.0]oct-2-ene-2-carboxylic acid; 2-o methyl fucose; 6-deoxy-2-o-methyl-alpha-l-galactopyranose; myristoyl-coa; 2-(3,4,5-trihydroxyphenyl)-3,5,7-trihydroxy-4h-1-benzopyran-4-one; 3,3',4',5,5',7-hexahydroxy-flavone; myricetin; cannabiscetin; {[5-(6-amino-purin-7-yl)-3,4-dihydroxy-tetrahydro-furan-2-ylmethoxy]-hydroxy-phosphorylmethyl}-phosphonic acid; n2-({[(4-bromophenyl)methyl]oxy}carbonyl)-n1-[(1s)-1-formylpentyl]-l-leucinamide; glucosaminyl-(alpha-6)-d-myo-inositol; 4-morpholin-4-yl-piperidine-1-carboxylic acid [1-(3-benzenesulfonyl-1-propyl-allylcarbamoyl)-2-phenylethyl]-amide; pentadecane; metyrapone; 4-carbamoyl-1-beta-d-ribofuranosyl-imidazolium-5-olate-5'-phosphate; 1-deazo-thiamin diphosphate; ethylbenzene; pentane-1,5-diamine; 3'-deazo-thiamin diphosphate; n-butylbenzene; n-(5-cyclopropyl-1h-pyrazol-3-yl)benzamide; n-acetylproline; 2-(acetylamino)-2-deoxy-6-o-methyl-alpha-d-allopyranose; n-acetyl-d-allosamine; 3-acetyl pyridine adenine dinucleotide; nicotinamide adenine dinucleotide acetone adduct; m-(n,n,n-trimethylammonio)-2,2,2-trifluoro-1,1-dihydroxyethylbenzene; nicotinamide-adenine-dinucleotide; nicotinamide-adenine-dinucleotide (acidic form); 2-iminiopropanoate; beta-(2-naphthyl)-alanine; 5-n-acetyl-alpha-d- neuraminic acid; 2'-monophoshoadenosine 5'-diphosphoribose; nicotinamide adenine dinucleotide 3-pentanone adduct; naringenin; monastrol; n-butyl-benzenesulfonamide; s-4-nitrobutyryl-coa; [(2-ethoxy-1-naphthoyl)amino] methylboronic acid; 1-n-acetyl-beta-d-glucosamine; n2-[(benzyloxy)carbonyl]-n1-[(3s)-1-cyanopyrrolidin-3-yl]-l-leucinamide; n-butyl isocyanide; nicotinamide 8-bromoadenine dinucleotide phosphate; 2-hydroxy-5-({1-[(2-naphthyloxy)methyl]-3-oxoprop-1-enyl}amino)tyrosine; n6-benzyl adenosine-5'-diphosphate; nitrocefin acyl-serine; nicotinamide; n-carbamoyl-alanine; cytidine-5'-monophosphate-5-n-acetylneuraminic acid; n-carbamoyl-l-aspartate; norcamphor; namn; cobalt hexammine ion; 2-nitro-p-cresol; (s)-(−)-nicotine, 3-[(2s)-1-methyl-2-pyrrolidinyl]pyridine; 3-aminomethyl-pyridinium-adenine-dinucleotide; nicotinamide adenine dinucleotide cyclohexanone; 2-(acetylamino)-2-deoxy-a-d-glucopyranose; 7,9-dimethylguanine; nadph dihydro-nicotinamide-adenine-dinucleotidephosphate; ethyl dimethyl ammonio propane sulfonate; n-ethyl-5'-carboxamido adenosine; 1-ethyl-pyrrolidine-2,5-dione; neopterin; n-ethylmaleimide; 2-(2-hydroxy-1,1-dihydroxymethyl-ethylamino)-ethanesulfonic acid; phenylalanine amide; 2,4-dinitrophenyl 2-deoxy-2-fluoro-beta-d-allopyranoside; 2-[(3-trifluoromethyl)phenyl]amino-3-pyridine-carboxylic acid; 3-amino-5-phenylpentane; n-acetyl-d-galactosamine 6-sulfate; 2-(acetylamino)-2-deoxy-4-o-sulfo-alpha-d-galactopyranose; acetylgalactosamine-4-sulfate; 3ar,5r,6s,7r, 7ar-5-hydroxymethyl-2-methyl-5,6,7,7a-tetrahydro-3ah-pyrano[3,2-d]thiazole-6,7-diol; nogalaviketone; 3-(4-amino-2-tert-butyl-5-methyl-phenylsulfanyl)-6-cyclopentyl-4-hydroxy-6-[2-(4-hydroxy-phenyl)-ethyl]-5,6-dihydro-pyran-2-one; n-hydroxy-4-(methyl{[5-(2-pyridinyl)-2-thienyl]sulfonyl}amino)benzamide; n-cyclohexyltaurine; ches; s-(2-oxo)pentadecylcoa; nicotinamide-adenine-dinucleotide-5-hydroxy-4-oxonorvaline; (10r)-10-formyl-5,8,10-trideazafolic acid; 10-formyl-5,8, 10-trideazafolic acid; 4-nitro-inden-1-one; dinitrophenylene; meta-nitro-tyrosine; naphthalen-1-yl-acetic acid; 2-(acetylamino)-2-deoxy-4-o-beta-d-galactopyranosyl-alpha-d-glucopyranose; norleucine; n-acetyl-l-glutamate; norleucine phosphonate; n-acetyl-1-glutamine; n-methyl-naloxonium; aha047; n-pyridoxyl-2-methylalanine-5-phosphate; n-naphthalen-1-ylmethyl-2'-[3,5-dimethoxybenzamido]-2'-deoxy-adenosine; methylamine; n-[amino(imino)methyl]glycine; (r)-n-(1-methyl-hexyl)-formamide; nicotinamide mononucleotide; 2-[2-(2-cyclohexyl-2-guanidino-acetylamino)-acetylamino]-n-(3-mercapto-propyl)-propionamide; nitromethyldethia coenzyme a; nor-n-omega-hydroxy-l-arginine; nitrosoethane; 1-deoxynojirimycin; nanaomycin d; methyl nonanoate (ester); pyridoxal-5'-phosphate-n-oxide; inosine; 3-nitrophenylboronic acid; n-succinyl phenylglycine; cysteine-methylene-carbamoyl-1,10-phenanthroline; 2-aminopimelic acid; n-propyl isocyanide; p-nitrophenol; 7,8-dihydroneopterin; nna; n,n'-bis(4-amino-2-methylquinolin-6-yl)urea; 5-(aminomethyl)-2-methylpyrimidin-4-amine; nitrilotriacetic acid; quinolinic acid; heparin pentasaccharide; naphthalene trisulfonate; n1,n14-bis((s-methyl)isothioureido)tetradecane; nojirimycine tetrazole; nu1025; norvaline; dica; (5z)-5-(1h-indol-3-ylmethylene)-4h-imidazol-4-one; n-allyl-aniline; phosphoric acid mono-[3-amino-5-(5-methyl-2, 4-dioxo-3,4-dihydro-2h-pyrimidin-1-yl)-tetra hydro-furan-2-ylmethyl]ester; tetrazolyl histidine; 5,6-dihydroxy-nadp; 2-(2f-benzothiazolyl)-5-styryl-3-(4f-phthalhydrazidyl)tetrazolium chloride; oxaloacetate ion; trans-o-hydroxy-alpha-methyl cinnamate; 2'-o-acetyl adenosine-5-diphosphoribose; 6-(oxalyl-amino)-1h-indole-5-carboxylic acid; oxidized acetyl dithranol; o-acetylserine; 2-(oxalyl-amino)-benzoic acid; octanoic acid (caprylic acid); 3-carboxy-n,n, n-trimethyl-2-(octanoyloxy)propan-1-aminium; cysteine-sulfonic acid; n-octane; hydroxyethylcysteine; 4-oxo-nicotinamide-adenine dinucleotide phosphate; 4-methylpiperazin-1-yl carbonyl group; n-octyl-2-hydroxy-ethyl sulfoxide; o-trifluoromethylphenyl anthranilic acid; 2-[3-({methyl[1-(2-naphthoyl)piperidin-4-yl] amino}carbonyl)-2-naphthyl]-1-(1-naphthyl)-2-oxoethylphosphonic acid; 4-hydroxytamoxifen; octahydroindole-2-carboxylic acid; atropine; n-(3-phenyl-2-sulfanylpropanoyl)phenylalanylalanine; 9,10-deepithio-9, 10-didehydroacanthifolicin; oleic acid; n-acetyl-l-citrulline; olomoucine; 4-bromo-3-(5'-carboxy-4'-chloro-2'-fluorophenyl)-1-methyl-5-trifluoromethyl-pyrazol; mo(vi)(=o)(oh)2 cluster; orotidine-5'-monophosphate; s-dioxymethionine; 5-oxo-l-norleucine; 2-(oxalyl-amino)-4,7-dihydro-5h-thieno [2,3-c]pyran-3-carboxylic acid; oxyphenbutazone; 9r,13r-opda; colamine phosphoric acid; oxiranpseudoglucose; o1-pentyl-mannose; 1-[pyrrol-1-yl-2,5-dione-methoxymethyl]-pyrrole-2,5-dione; orotic acid; o-succinylbenzoate; o-sulfo-l-serine; 6-(hydroxyethyldithio)-8-(aminomethylthio)octanoic acid; n-octanoyl-b-d-fructofuranosyl-a-d-glucopyranoside,sucrose monocaproylate; 2-(oxalyl-amino)-4, 5,6,7-tetrahydro-thieno[2,3-c]pyridine-3-carboxylic acid; carbamic acid; ovalicin; 2-(beta-d-glucopyranosyl)-5-methyl-1,3,4-oxadiazole; oxonic acid; oxalic acid; ortho-xylene; oxalate ion; oxamic acid; 2-oxo-3-pentenoic acid; 4-hydroxy-1,2,5-oxadiazole-3-carboxylic acid; 4-oxoretinol; 2-oxalosuccinic acid; tetrahydrooxazine; [1-(3-hydroxy-2-oxo-1-phenethyl-propylcarbamoyl)2-phenyl-ethyl]-carbamic acid pyridin-4-ylmethyl ester; pd173955; deacetoxycephalosporin-c; ethyl dihydrogen diphosphate; propyl trihydrogen diphosphate; pentyl trihydrogen diphosphate; {[2-(1h-1,2,3-benzotriazol-1-yl)-2-(3,4-difluorophenyl)propane-1,3-diyl]bis[4,1-phenylene(difluoromethylene)]}bis(phosphonic acid); 3',5'-dinitro-n-acetyl-l-thyronine; phosphoric acid mono-[3,4-dihydroxy-5-(5-hydroxy-benzoimidazol-1-yl)tetrahydro-furan-2-ylmethyl] ester; (2s)-pyrrolidin-2-ylmethylamine; heptaethylene glycol, peg330; 3,6,9,12,15-pentaoxaheptadecane; 1-3 sugar ring of pentamannosyl 6-phosphate; tetraphenylphosphonium; '5'-o-(n-(l-prolyl)-sulfamoyl)adenosine; purine riboside-5'-monophosphate; {4-[(2s,4e)-2-(1,3-benzothiazol-2-yl)-2-(1h-1,2,3-benzotriazol-1-yl)-5-phenylpent-4-enyl] phenyl}(difluoro)methylphosphonic acid; 5-phosphoarabinonic acid; 4-aminobenzoic acid; cpad; phosphonoacetic acid; 2,4-dihydroxy-3,3-dimethyl-butyrate; 2-phospho-d-glyceric acid; phosphonoacetohydroxamic acid; {[(2,2-dihydroxy-ethyl)-(2,3,4,5-tetrahydroxy-6-phosphonooxy-hexyl)-amino]-methyl}-phosphonic acid; pantoyl adenylate; n-(phosphonacetyl)-l-aspartic acid; palmitoleic acid; 5-phospho-d-arabinohydroxamic acid; n-(phosphonoacetyl)-l-ornithine; 3'-phosphate-adenosine-5'-diphosphate; 2-oxy-4-hydroxy-5-(2-hydrazinopyridine) phenylalanine; phosphorylated aspartate; n-[(2r)-2,4-dihydroxy-3,3-dimethylbutanoyl]-beta-alanine; (2r,4s)-2-methyl-2,3,3,4-tetrahydroxytetrahydrofuran; 3-(2-aminoethyl)-4-(aminomethyl)heptanedioic acid; phenylethane boronic acid; phenyl boronic acid; proline betaine; 2-aminomethylpyrrol-3-acetic acid 4-propionic acid; porphobilinogen; 5-(aminomethyl)-4-(carboxymethyl)-1h-pyrrole-3-propanoic acid; [2-aminomethyl-5-oxo-4-(4-oxo-cyclohexa-2,5-dienylmethyl)-4,5-dihydro-imidazol-1-yl]-acetaldehyde; 4-phenylbutylamine; pentabromophenol; di-stearoyl-3-sn-phosphatidylcholine; coproporphyrin i containing co(iii); 1,2-di-n-pentanoyl-snglycero-3-dithiophosphocholine; molybdenum cofactor; moco; cyclic guanosine monophosphate; 1-[n[(phenylmethoxy)carbonyl]-l-leucyl-4-[[n/n-[(phenylmethoxy)carbonyl]-/nl-leucyl]amino]-3-pyrrolidinone/n; 2-{1-[2-(2-amino-thiazol-4-yl)-2-methoxyimino-acetylamino]-2-oxo-ethyl}-5,5-dimethyl-thiazolidine-4-carboxylic acid; pantothenoylaminoethenethiol; carboxylic prpp; cprpp; 3,5,3',5'-tetrachloro-biphenyl-4,4'-diol; p-cresol; (z,z)-4-hydroxy-n,n,n-trimethyl-10-oxo-7-[(1-oxo-9-octadecenyl)oxy]-3,5,9-trioxa-4-phosphaheptacos-18-en-1-aminium-4-oxide; deoxyguanidinoproclavaminic acid; phosphorylated dihydropteroate; pyridoxyl-alanine-5-phosphate; dipicolinic acid; n-(5'-phosphopyridoxyl)-d-alanine; n-(5'-phosphopyridoxyl)-l-alanine; 1,3-propandiol; 2,3-di-o-sulfo-alpha-d-glucopyranose; 9-(4-hydroxy-3-(hydroxymethyl)but-1-yl)guanine; 2-(2-{2-[2-(2-{2-[2-(2-ethoxy-ethoxy)-ethoxy]-ethoxy}-ethoxy)-ethoxy]-ethoxy}-ethoxy)-ethanol, polyethyleneglycol peg400; 1-deoxy-1-thio-heptaethylene glycol; 3,6,9,12,15,18,21-heptaoxatricosane-1,23-diol; 2-phenylethylamine; 3-[aminoethylphosphoryl]-[1,2-dipalmitoyl]sn-glycerol; di-stearoyl-3-sn-phosphatidylethanolamine; n-valeric acid; 2-phenyl-ethanol; phosphoenolpyruvate; 1-phospholactate; 2-(phosphonooxy)butanoic acid; pf-00356231; 3-phenyl-3-({[4-(4-pyridin-4-ylphenyl)thien-2-yl]carbonyl}amino)propanoic acid; 2-[4-(4-hydroxy-3-isopropyl-phenoxy)-3,5-dimethyl-phenyl]-2h-[1,2,4]triazine-3,5-dione; 2,3,4,5,6-pentafluorobenzyl alcohol; phenylferricrocin-iron; {4-[3-(6,7-diethoxy-quinazolin-4-ylamino)-phenyl]-thiazol-2-yl}-methanol; 2,6-diisopropylphenol; propofol; platelet activating factor; 1-(n-imidazolyl)-2-hydroxy-2-(2,3-dichlorophenyl)octane; penicillin g acyl-serine; (5e,13e)-9,15-dihydroxy-11-oxoprosta-5,13-dien-1-oicacid; guanidine-3-propanol; tetraethylene glycol; 1-methoxy-2-[2-(2-methoxy-ethoxy]-ethane; 1-(2-methoxy-ethoxy)-2-{2-[2-(2-methoxy-ethoxy]-ethoxy}-ethane; 2-phosphoglycolic acid; o-phosphoglycolohydroxamate; phosphoglycolohydroxamic acid; lysophosphatidylglycerol; 1,2-propanediol; s-1,2-propanediol; r-1,2-propanediol; 2-deazo-6-thiophosphate guanosine-5'-monophosphate; pyridoxyl-glutamic acid-5'-monophosphate; prostaglandin g2; n-(chlorophenyl)-n'-hydroxyguanidine; (2z)-2-(benzoylamino)-3-[4-(2-bromophenoxyl)phenyl]-2-propenoic acid; p-hydroxybenzoic acid; n-methyl-n-(methylbenzyl)formamide; aspartyl phosphate; phenylmercury; 4,5,6,7-tetrachloro-3h-isobenzofuran-1-one; iodo-phenylalanine; n-[(aminooxy)carbonyl]aniline; 3-amino-1-chloro-4-phenyl-butanol-2-yl; l-phenylalaninol; phenylalanylmethane; 1,10-phenanthroline; formic acid benzyl ester; phthalic acid; peridinin; 1,2-diacyl-sn-glycero-3-phosphoinositol; 2-[2-(2-hydroxy-ethoxy)-ethoxy]-ethanol; iodophenyl; piclamilast; 4-phenyl-1h-imidazole; thiopyrophosphate; carbobenzoxy-pro-lys-phe-y(po2)-ala-pro-ome; diundecyl phosphatidyl choline; n-pyridoxyl-glycine-5-monophosphate; palmitic acid; pregnenolone; leucine phosphonic acid; palmitoyl; [2-amino-6-(2,6-difluoro-benzoyl)-imidazo[1,2-a]pyridin-3-yl]-phenyl-methanone; pyromellitic acid; para-mercurybenzenesulfonic acid; 3-(phosphonomethyl)pyridine-2-carboxylic acid; pmp-hydroxyisoxazole, pyridoxamine-5-phosphate-hydroxyisoxazole; pimelic acid; pterin-6-yl-methyl-monophosphate; phosporic acid mono-[3,4-dihydroxy-5-(5-methoxy-benzoimidazol-1-yl)-tetrahydrofuran-2-ylmethyl]ester; pyridoxamine-5'-phosphate; benzylsulfonic acid; 4'-phosphopantetheine; 1,3-bis(4-aminophenoxy)pentane; 1-benzyl-(r)-propylamine; hypophosphite; phosphonoacetaldehyde; phosphocholine; 1-proponol; pyrophosphate 2-; porphyrin fe(iii); 1-ter-butyl-3-p-tolyl-1h-pyrazolo[3,4-d]pyrimidin-4-ylamine; 1-tert-butyl-3-(4-chloro-phenyl)-1h-pyrazolo[3,4-d]pyrimidin-4-ylamine; pyridoxyl-alanine-5-phosphate; vitamin b6 complexed with alanine; protoporphyrin ix; 5-phosphoribosyl-1-(beta-methylene) pyrophosphate; pyridoxyl-glutamic acid-5'-monophosphate; phosphonoformic acid; 4-(2-amino-ethoxy)-2-[(3-hydroxy-2-methyl-5-phosphonooxymethyl-pyridin-4-ylmethyl)-amino]-but-3-enoic acid; propanoic acid; (diphosphono)aminophosphonic acid; 3h-pyrazolo[4,3-d]pyrimidin-7-ol; 3-phenyl-1,2-propandiol; 2-amino-4-(hydroxymethyl-phosphinyl)butanoic acid; phosphonopyruvate; 3'-phosphate-adenosine-5'-phosphate sulfate; 3-(p-tolyl)propionic acid; 3-phenylpyruvic acid; 2-(pyrido[1,2-e]purin-4-yl)amino-ethanol; 7-deaza-7-cyano-guanine; pyrroloquinoline quinone; rpr131247; s,s-propyithiocysteine; 3-phenylpropylamine; 13-acetylphorbol; n-[4-methyl-3-[[4-(3-pyridinyl)-2-pyrimidinyl]amino]phenyl]-3-pyridinecarboxamide; n6-(2,5-dimethoxy-benzyl)-n6-methyl-pyrido[2,3-d]pyrimidine-2,4,6-triamine; 7-deaza-7-aminomethyl-guanine; 6-hydroxy-1,6-dihydro purine nucleoside; propidium; alpha-phosphoribosylpyrophosphoric acid; thioproline; phosphoribosyl atp; adenosine-5'-propylphosphate; 2-propyl-aniline; 2-isobutyl-3-methoxypyrazine; pentasulfide-sulfur; 3-(5-amino-7-hydroxy-[1,2,3]triazolo[4,5-d]pyrimidin-2-yl)-n-[2-(2-(hydroxymethyl-phenylsulfanyl)-benzyl]-benzamide; o-phosphoethanolamine; pasbn; ndelta-(n'-sulphodiaminophosphinyl)-l-ornithine; thiobutyric acid s-{2-[3-(2-hydroxy-3,3-dimethyl-4-phosphonooxy-butyrylamino)-propionylamino]-ethyl}; ethylaminobenzylmethylcarbonyl group; pseudouridine-5'-monophosphate; pteroic acid; n-propyl-tartramic acid; 2-prolyl-5-tert-butyl-[1,3,4]oxadiazole; pentanedial; tungstopterin cofactor; 2-phenyl-1-[4-(2-piperidin-1-yl-ethoxy)-phenyl]-1,2,3,4-tetrahydro-isoquinolin-6-ol; pentanal; pseudotropine; phosphonotyrosine; tungstopterin; s-ethyl-n-phenyl-isothiourea; phosphatidylethanolamine; 9-butyl-8-(2,5-dimethoxy-benzyl)-2-fluoro-9h-purin-6-ylamine; 8-(2-chloro-3,4,5-trimethoxy-benzyl)-2-fluoro-9-pent-4-ynyl-9h-purin-6-ylamine; 8-(2,5-dimethoxy-benzyl)-2-fluoro-9h-purin-6-ylamine; 9-butyl-8-(3,4,5-trimethoxybenzyl)-9h-purin-6-amine; 9-butyl-8-(4-methoxybenzyl)-9h-purin-6-amine; 9-butyl-8-(3-methoxybenzyl)-9h-purin-6-amine; 9-butyl-8-(2,5-dimethoxy-benzyl)-9h-purin-6-ylamine; 9-butyl-8-(2-chloro-3,4,5-trimethoxy-benzyl)-9h-purin-6-ylamine; 8-(2-chloro-3,4,5-trimethoxy-benzyl)-9-pent-4-ylnyl-9h-purin-6-ylamine; u-pi-a-pi; purine riboside; putrescine; 8-benzo[1,3]dioxol-,5-ylmethyl-9-butyl-2-fluoro-9h-purin-6-ylamine; 8-(2,5-dimethoxy-benzyl)-2-fluoro-9-pent-9h-purin-6-ylamine; purvalanol; pyoverdine-chromophore; pyruvoyl group; pyridoxamine; pyridoxine-5'-phosphate; para-xylene; 4-(3-pyridin-2-yl-1h-pyrazol-4-yl)quinoline; 3-(mercaptomethylene)pyridine; vitamin b6 complexed with 2-amino-pentanoic acid; vitamin b6 complexed with 2-amino-hexanoic acid; 3-(1,10-phenanthrol-2-yl)-1-alanine; pyrrole-2-carboxylate; tetrahydropyran; pyridin-3-ylmethanol; pyruvamide; 1,2,5,6-tetrahydro-4h-pyrrolo(3,2,1-ij)quinolin-4-one; 2-pyridinethiol; 2-aminoprop-2-enamide; 4-iodopyrazole; pyrazole; praziquantel; {(1s)-1-benzyl-4-[3-carbamoyl-1-(1-carbamoyl-2-phenyl-ethylcarbamoyl)-(s)-propylcarbamoyl]-2-oxo-5-phenyl-pentyl}-carbamic acid tert-butyl ester; quinaldic acid; 8-hydroxy-4-(1-hydroxyethyl)quinoline-2-carboxylic acid; 3,5,7,3',4'-pentahydroxyflavone; n-{(1s)-4-[bis(2-chloroethyl)amino]-1-methylbutyl}-n-(6-chloro-2-methoxy-9-acridinyl)amine; quisqualate; (4'-{[allyl(methyl)amino]methyl}-1,1'-biphenyl-4-yl)(4-bromophenyl)methanone; allyl-{6-[3-(4-bromophenyl)-1-methyl-1 h-indazol-6-yl]oxy}hexyl)-n-methylamine; (2e)-n-allyl-4-{[3-(4-bromophenyl)-5-fluoro-1-methyl-1h-indazol-6-yl]oxy}-n-methyl-2-buten-1-amine; 4-{[1-methyl-5-(2-methyl-benzoimidazol-1-ylmethyl)-1h-benzoimidazol-2-ylmethyl]-amino}-benzamidine; allyl-{4-[3-(4-bromo-phenyl)-benzofuran-6-yloxy]-but-2-enyl}-methyl-amine; methyltrienolone; 17beta-hydroxy-17methyl-19norandrosta-4,9,11-trien-3-one; r1881; allyl-{6-[3-(4-bromo-phenyl)-benzofuran-6-yloxy]-hexyl-}-methyl-amin; ribose-1-phosphate; methyl-[4-(4-piperidine-1-ylmethyl-phenyl)-cyclohexyl]-carbaminic acid-(4-chlorophenyl)-ester; 4-amino-n-{4-[2-(2,6-dimethyl-phenoxy)-acetylamino]-3-hydroxy-1-isobutyl-5-phenyl-pentyl}-benzamide; 3-amino-n-{4-[2-(2,6-dimethyl-phenoxy)-acetylamino]-3-hydroxy-1-isobutyl-5-phenyl-pentyl}-benzamide; ribose-5-phosphate; (1-methyl-1h-imidazol-2-yl)-(3-methyl-4-{3-[(pyridin-3-ylmethyl)-amino]-propoxy}-benzofuran-2-yl)-methanone; r048-8071; n-(6-{[3-(4-bromophenyl)-1,2-benzisothiazol-6-yl]oxy}hexyl)-n-methylprop-2-en-1-amine; wrr-99; 1-[4-carboxy-2-(3-pentylamino)phenyl]-5,5'-di(hydroxymethyl) pyrrolidin-2-one; 9-beta-d-arabinofuranosyl-adenine; argifin; rhamnose; rapamycin immunosuppressant drug; rasagiline; (4r)-7-azabisabolene; r-azabisabolene; riboflavin; vitamin b2; alpha-ribazole-5'-phosphate; ricinoleic acid; radicicol; phosphoramidon; 6,7-dioxo-5h-8-ribitylaminolumazine; glycyl-l-a-aminopimelyl-e-(d-2-aminoethyl)phosphonate, dihydrolipoic acid; (1,10 phenanthroline)-(tri-carbon monoxide) rhenium (i); 4-phospho-d-erythronohydroxamic acid; glycyl-l-alpha-amino-epsilon-pimelyl-d-alanyl-d-alanine; glycyl-l-alpha-amino-epsilon-pimelyl-d-alanine; delta-bis(2,2'-bipyridine)-(5-methyl-2-2'-bipyridine)-c2-adamantane ruthenium (ii); 8-demethyl-8-dimethylamino-flavin-adenine-dinucleotide; rifampicin; 2,5-diaziridin-1-yl-3-(hydroxymethyl)-6-methylcyclohexa-2,5-diene-1,4-dione; 5-(3-amino-4,4-dihyroxy-butylsulfanylmethyl)-tetrahydro-furan-2,3,4-triol; tmr; 5-hydroxy-n-propargyl-1(r)-aminoindan; rhodamine 6g; ribose; rifamycin cgp 4832; argadin; 5-amino-2-aminomethyl-6-[4,6-diamino-2-(3,4-dihydroxy-5-hydroxymethyl-tetrahydro-furan-2-yloxy)-3-hydroxy-cyclohexyloxy]-tetrahydro-pyran-3,4-diol; ribose(pyranose form); 1-hydroxy-2-(3-pyridinyl)ethylidene bis-phosphonic acid; wrr-112; 3-(7-hydroxy-8-ribityllumazine-6-yl) propionic acid; n-methyl-n-propargyl-1(r)-aminoindan; mono-[3,4-dihydroxy-5-(5-methyl-benzoimidazol-1-yl)-tetrahydor-furan-2-ylmethyl] ester; (r)-mandelic acid; 1-rhamnose; 1-rhamnitol; 1-deoxy-ribofuranose-5'-phosphate; roflumilast; 7,8-dihydro-7,7-dimethyl-6-hydroxypterin; 4-[3-(cyclopentyloxy)-4-methoxyphenyl]-2-pyrrolidinone; c-1027 aromatized chromophore; propionamide; [(2r,3s,4s,5r)-3,4,5-trihydroxytetrahydrofuran-2-yl]methyl dihydrogen phosphate; (c8-r)-hydantocidin 5'-phosphate; (c8-s)-hydantocidin 5'-phosphate; (r)-1-para-nitro-phenyl-2-azido-ethanol; 2-ribofuranosyl-3-iodo-2,3-dihydro-1h-pyrazolo[3,4-d]pyrimidin-4-ylamine; rpr128515; reactive red 1 dye; azo-dye hapten; 3-{[(1r)-1-benzyl-2-sulfanylethyl]amino}-3-oxopropanoic acid; n-propargyl-1(s)-aminoindan; d-2-keto-3-deoxygalactonate; r-styrene oxide; ribavirin triphosphate; 2-(3,4-dihydroxyphenyl)-5,7-dihydroxy-4-oxo-4h-chromen-3-yl 6-o-(6-deoxy-alpha-l-mannopyranosyl)-beta-d-glucopyranoside; ribavirin monophosphate; rwj-51084; 1-benzyloxycarbonylamino-2-phenyl-ethyl}{-[1-carbamoyl-2-(1h-indol-3-yl)-ethylcarbamoyl]-5-phenyl-pentyl}-phosphinic acid; (2e,3s)-3-hydroxy-5'-[(4-hydroxypiperidin-1-yl)sulfonyl]-3-methyl-1,3-dihydro-2,3'-biindol-2' (1'h)-one; soraphen a; 1-hexadecanosulfonyl-o-l-serine; s-2-(boronoethyl)-l-cysteine; shikimate-3-phosphate; 1-phenylsulfonamide-3-trifluoromethyl-5-parabromophenylpyrazole; 1-o-phosphono-d-glucitol, d-glucitol-6-phosphate; a disubstituted succinyl caprolactam hydroxymate mmp3inhibitor; 5'-[n-[(3s)-3-amino-3-carboxypropyl]-n-methylamino]-5'-deoxyadenosine; (s)-2-hydroxy-2-phenyl-propionic acid; (s)-alpha-methylmandelic acid; 4-sulfonamide-[1-(4-aminobutane)]benzamide; n-acetyl-serine; selenazole-4-carboxyamide-adenine dinucleotide; 3-[(1s)-1-(dimethylamino)ethyl]phenol; s-adenosyl-l-homocysteine; s-adenosyl-l-homoselenocysteine; salicylic acid; adenosine-5'-diphosphate monothiophosphate; (4s)-7-azabisabolene; s-azabisabolene; sb220025; 4-(fluorophenyl)-1-cyclopropylmethyl-5-(2-amino-4-pyrimidinyl)imidazole; n-[2-(1h-indol-5-yl)-butyl]-4-sulfamoyl-benzamide; d-naphthyl-1-acetamido boronic acid alanine; 1,3,2-dioxaborolan-2-ol; (s)-4-bromo-3-hydroxy-3-methylbutyl diphosphate; l-naphthyl-1-acetamido boronic acid alanine; trihydroxyantimonite(iii); [3-(1,3,2-dioxaborolan-2-yloxy)propyl]guanidine; (r)-n-(3-indol-1-yl-2-methyl-propyl)-4-sulfamoyl-benzamide; (s)-n-(3-indol-1-yl-2-methyl-propyl)-4-sulfamoyl-benzamide; 2-butanol; [4-(1,3,2-dioxaborolan-2-yloxy)methyl]benzamidine; succinyl-coenzyme a; s-methyl thiocysteine group; 1-thiocitrulline; acetic acid salicyloyl-amino-ester; succinamide-coa; pyridoxyl-n,o-cycloserylamide-5-monophosphate; sucrose octasulfate; (south)-methanocarba-thymidine; s-acetylcysteine; n-(sulfanylacetyl) tyrosylprolylmethioninamide; s-{2-[amino(dihydroxy)-lambda~4~-sulfanyl]ethyl}-d-cysteine; 2-amino-3-(diethoxy-phosphoryloxy)-propionic acid; dodecyl sulfate; o-benzylsulfonyl-serine; hydroxyalanine; mdl 101,146; 3-amino-4-oxybenzyl-2-butanone; 2-sulfhydryl-ethanol; phosphonoserine; 2-amino-4-butyl-5-propylselenazole; s-ethylisothiourea; (3s,6s,9r,10r,11s,12s,13e,15e,18s,21s)-18-{(1e,3e,7s,8s)-9-[(2s,3r,4s,5s,6r,9s,11s)-9-ethyl-4-hydroxy-3,5,11-trimethyl-8-oxo-1-oxa-7-azaspiro[5.5]undec-2-yl]-8-hydroxy-1,7-dimethylnona-1,3-dienyl}-10,12-dihydroxy-3-(3-hydroxybenzyl)-6-isopropyl-11-methyl-9-(3-oxobutyl)-19-oxa-1,4,7,25-tetraazabicyclo[19.3.1] pentacosa-13,15-diene-2,5,8,20-tetrone; adenosyl-ornithine; 5,10,15,20-tetrakis(4-sulpfonatophenyl)-21h,23h-porphine; 3-nitro-4-(2-oxo-pyrrolidin-1-yl)-benzenesulfonamide; 1-methyl-3-oxo-1,3-dihydro-benzo[c]isothiazole-5-sulfonic acid amide; o3-sulfonylgalactose; 4-deoxy-4-thio-beta-d-glucopyranose; 1-hydroxy-1-thio-glycerol; monothioglycerol; n,o6-disulfo-glucosamine; guanosine-2',3'-cyclophosphorothioate; salicylhydroxamic acid; laevulinic acid; saha; (s)-des-me-ampa; 6-(2-oxo-hexahydro-thieno[3,4-d]imidazol-4-yl)-hexanoic acid; (4-hydroxymaltosephenyl)glycine; n-(5-amino-5-carboxypentyl)glutamic acid; heptanoic acid; o-sialic acid (chair conformation); o-sialic acid; 3-trimethylsilylsuccinic acid; 1,2,3,4-tetrahydro-isoquinoline-7-sulfonic acid amide; 5-(1-carboxy-1-phosphonooxy-ethoxyl)-shikimate-3-phosphate; beta-sialic acid; 2-(thiomethylene)-4-methylpentanoic acid; lactose sialic acid; alpha(2,3) sialyl lactose; 2-methylbutanoic acid; s-methylcysteine; methyl-2-s-(alpha-d-mannopyranosyl)-2-thio-alpha-d-mannopyranoside; methionine sulfoxide; n-succinyl methionine; (s)-mandelic acid; sulfamic acid 2,3-o-(1-methylethylidene)-4,5-o-sulfonyl-beta-fructopyranose ester; 2,4-dihydroxy-trans cinnamic acid; 5-[bis-2 (chloro-ethyl)-amino]-2,4-dinitro-benzamide; n-{1-[5-(1-carbamoyl-2-mercapto-ethylcarbamoyl)-pentylcarbamoyl]-2-[4-(difluoro-phosphono-methyl)-phenyl]-ethyl}-3-{2-[4-(difluoro-phosphono-methyl)-phenyl]-acetylamino}-succinamic acid; thionicotinamide-adenine-dinucleotide; selenoinosine; 3-aminosuccinimide; 1-(isopropylamino)-3-(1-naphthyloxy)-2-propanol; 4-(2-oxo-hexahydro-thieno[3, 4-d]imidazol-4-yl)-butyricacid; isatoic anhydride; dioxyselenocysteine; methyl phosphinic acid; adenosine phosphonoacetic acid; d-sorbitol; sp-adenosine-3',5'-cyclic-monophosphorothioate; n-hydroxy 1n(4-methoxyphenyl) sulfonyl-4-(z,e-n-methoxyimino)pyrrolidine-2r-carboxamide; n-(2-amino-propyl)-1,4-diaminobutane; pa(34); sinapoyl coenzyme a; 2-deamino-6-deoxy-6thiophosphite-5'-phosphate guanosine; sphingosine; n-hydroxy-1-(4-methoxyphenyl)sulfonyl-4-benzyloxycarbonyl-piperazine-2-carboxamide; spermine (fully protonated form); sparsomycin; sulfopyruvate; (4e,8e,12z,16z)-n,n,4,8,13,17,21-heptamethyldocosa-4,8,12,16,20-pentaen-1-amine; lipid fragment; sr12813; siroheme; 5'-o-(n-(1-seryl)-sulfamoyl) adenosine; 3-butylthiolane 1-oxide; (2s,5s)-5-carboxymethylproline; 1,4-deoxy-1,4-dithio-beta-d-glucopyranose; d-2-keto-3-deoxygluconate; 4-(acetylamino)-3-amino benzoic acid; 4-(acetylamino)-3-guanidinobenzoic acid; 4-(acetylamino)-3-[(hydroxyacetyl)amino]benzoic acid; 4-(acetylamino)-3-[(aminoacetyl)amino]benzoic acid; 4-sulfonamide-[4-(thiomethylaminobutane)]benzamide; stearic acid; 2-amino-4h-1,3-benzoxathiin-4-ol; sti-571; resveratrol; 2-{[formyl(hydroxy)amino]methyl}-4-methylpentanoic acid; staurosporine; staurosporine; su4984; su9516; 16923; (3r)-4-(p-toluenesulfonyl)-1,4-thiazane-3-carboxylicacid-l-phenylalanine ethyl ester; sucrose; 4-diphosphocytidyl-2-c-methyl-d-erythritol 2-phosphate; n~2~succinylarginine; 2-[3,4-dihydroxy-2-hydroxymethyl-5-(2-hydroxy-nonyl)-tetrahydro-furan-2-yloxy]-6-hydroxymethyl-tetra hydropyran-3,4,5-triol; n~2~succinylornithine; serine vanadate; swainsonine; 4-hydroxy-3-[(1s)-3-oxo-1-phenylbutyl]-2h-chromen-2-one; 2s,4r-4-methylglutamate; thymidine-5'-monophosphate; [1-(1-benzyl-3-hydroxy-2-oxo-propylcarbamoyl)-2-phenyl-ethyl]-carbamic acid benzyl ester; 3-{2,6,8-trioxo-9-[(2r,3s,4r)-2,3,4,5-tetrahydroxypentyl]-1,2,3,6,8,9-hexahydro-7h-purin-7-yl}propyl dihydrogen phosphate; 2'-o-methyl-3'-methyl-3'-deoxy-arabinofuranosyl-thymine-5'-phosphate; 3-{2,6,8-trioxo-9-[(2s,3r,4r)-2,3,4,5-tetrahydroxypentyl]-1,2,3,6,8,9-hexahydro-7h-purin-7-yl}propyl dihydrogen phosphate; 3,5,3',5'-tetraiodo-l-thyronine; 3,3',5,5'-tetraiodothyroacetic acid; 3-{2,6,8-trioxo-9-[(2r,3r,4r)-2,3,4,5-tetrahydroxypentyl]-1,2,3,6,8,9-hexahydro-7h-purin-7-yl}propyl dihydrogen phosphate; p1-(5'-adenosyl)p5-(5'-thymidyl)pentaphosphate; 3-{2,6,8-trioxo-9-[(2s,3s,4r)-2,3,4,5-tetrahydroxypentyl]-1,2,3,6,8,9-hexahydro-7h-purin-7-yl}propyl dihydrogen phosphate; trehalose-6-phosphate; [(1-{2[(4-carbamimidoyl-phenylamino)-methyl]-1-methyl-1h-benzoimidazol-5-yl}-cyclopropyl)-pyridin-2-yl-methyleneaminooxy]-acetic acid ethyl ester; (s)-2-[4-(aminomethyl)-1h-1,2,3-triazol-1-yl]-4-methylpentanoic acid; acetic acid n-[2-chloro-5-[6-ethyl-2,4-diamino-pyrimid-5-yl]-phenyl]-[benzyl-triazen-3-yl] ethyl; 9-(6-deoxy-alpha-l-talofuranosyl)-6-methylpurine; tris(hydroxyethyl)aminomethane; tatp; 2,4,6-triaminoquinazoline; d(−)-tartaric acid; trihydroxyarsenite(iii); adenosine-5'-rp-alpha-thio-triphosphate; 2-aminoethanesulfonic acid; (s)-2-{methyl-[2-(naphthalene-2-sulfonylamino)-5-(naphthalene-2-sulfonyloxy)-benzoyl]-amino}-succinicacid; tazobactam; tetrabutylammonium ion; tazobactam intermediate; pnu177836; tazobactam trans-enamine intermediate; 7-deazaadenosine; 2,4,6-tribromophenol; hexantantalum dodecabromide; tetrabromo-2-benzotriazole; 2-methyl-2-propanol; thiocellobiose; taurocholic acid; triclosan; thiocamphor; tert-butyl(1s)-1-cyclohexyl-2-oxoethylcarbamate; 1,3,5-trichloro-benzene; n-tridecanoic acid; (e)-(2r,3r,4s,5r)-3,4,5-trihydroxy-2-methoxy-8,8-dimethyl-non-6-enoic acid ((3s,6r)-6-hydroxy-2-oxo-azepan-3-yl)-amide; thiodigalactoside; thiamin diphosphate; thymine; 1-azepan-1-yl-2-phenyl-2-(4-thioxo-1,4-dihydro-pyrazolo [3,4-d]pyrimidin-5-yl)ethanone adduct; thymidine-5'-diphospho-beta-d-xylose; 2-thioethenamine; 2-(3-cyano-4-isobutoxy-phenyl)-4-methyl-5-thiazole-carboxylic acid; triethyl phosphate; malate like intermediate; tetrahydrofuran-2-carboxylic acid; 2-[5-methanesulfonylamino-2-(4-aminophenyl)-6-oxo-1,6-dihydro-1-pyrimidinyl]-n-(3,3,3-trifluoro-1-isopropyl-2-oxopropyl)acetamide; s-ethyl-n-[4-(trifluoromethyl)phenyl]isothiourea; triglu-5-formyl-tetrahydrofolate; 2-(beta-d-glucopyranosyl)-5-methyl-1,3,4-benzothiazole; 5-hydroxymethylene-6-hydrofolic acid; (6s)-5,6,7,8-tetrahydrofolate; deoxythymidine; 2'-deoxythymidine; reduced threonine; thymidine-3',5'-diphosphate; thymidine-5'-(dithio)phosphate; c16-fatty-acyl-substrate-mimic; tetrahydrodeoxyuridine; [2(r,s)-2-sulfanyl-heptanoyl]-phe-ala; (2-sulfanyl-3-phenylpropanoyl)-phe-tyr; rb106; beta(2-thienyl)alanine; 4-hydroxy-3,5-dimethyl-5-(2-methyl-buta-1,3-dienyl)-5h-thiophen-2-one; n-pyridoxyl-threonine-5-monophosphate; thio-maltopentaose; thio-maltohexaose; tetramethylammonium ion; 5,10-methylene-6-hydrofolic acid; tris(hydroxymethyl)aminomethane; thymidine-5'-phosphate; n-(4-methoxybenzyl)-n'-(5-nitro-1,3-thiazol-2-yl)urea; n-1,2,3,4-tetrahydronaphth-1-yl-2'-[3,5-dimethoxybenzamido]-2'-deoxy-adenosine; tropinone; 2,4,6-trinitrophenol; tnt; 3,5,6,8-tetramethyl-n-methyl phenanthrolinium; o-(2-acetamido-2-deoxy-alpha-d-galactopyranosyl)-l-serine; tolrestat; n-[tosyl-d-prolinyl]amino-ethanethiol; sp-722; sp-876; trans-2-phenylcyclopropylamine; n-(2-thienylmethyl)-2,5-thiophenedisulfonamide; 4-carbamoyl-4-{[6-(difluoro-phosphono-methyl)-naphthalene-2-carbonyl]-amino}-butyric acid; 2-amino-3-(1h-indol-3-yl)-propan-1-ol; phosphonothreonine; thiamine diphosphate; 5-(2-carboxy-2-aminoethyl)-4-hydroxy-1,2-benzoquinone; 2,4,5-trihydroxyphenylalanine quinone; topa quinone; tosyl-d-proline; thiamin phosphate; 2,2':6',2''-terpyridine platinum(ii); tipranavir; 5-phenylsulfanyl-2,4-quinazolinediamine; 5-[(4-methylphenyl)sulfanyl]-2,4-quinazolinediamine; 5-[4-tert-butylphenylsulfanyl]-2,4-quinazolinediamine; 5-(4-morpholin-4-yl-phenylsulfanyl)-2,4-quinazolinediamine; 6-(octahydro-1h-indol-1-ylmethyl)decahydroquinazoline-2,4-diamine; aconitate ion; tricarballylic acid; lipid fragment; 2'-deoxy-thymidine-beta-l-rham nose; 1,2,4-triazole; 1h-benoximidazole-2-carboxylic acid; nz2-tryptophan; 2-hydroxy-tryptophan; 2,4-diamino-5-(3,4,5-trimethoxybenzyl)-pyrimidin-1-ium; 1-{2-[2-(2-methoxyethoxy) ethoxy]ethoxy}-4-(1,1,3,3-tetramethylbutyl)benzene; 4-{2,6,8-trioxo-9-[(2s,3r,4r)-2,3,4,5-tetrahydroxypentyl]-1,2,3,6,8,9-hexahydro-7h-purin-7-yl}butyl dihydrogen phosphate; 4-{2,6,8-trioxo-9-[(2r,3s,4r)-2,3,4,5-tetrahydroxypentyl]-1,2,3,6,8,9-hexahydro-7h-purin-7-yl}butyl dihydrogen phosphate; glutathionylspermidine disulfide; glutathionylspermidine; 5'-o-(n-(1-threonyl)-sulfamoyl)adenosine; (2s,3r)-1-amino-2-methylbutane-2,3-diol; 7-[4-(dimethylamino) phenyl]-n-hydroxy-4,6-dimethyl-7-oxo-2,4-heptadienamide; (3r)-4-(p-toluenesulfonyl)-1,4-thiazane-3-carboxylicacid-l-leucine; para-toluene sulfonate; 1-allyl-3-butyl-8-(n-acetyl-4-aminobenzyl)-xanthine; tetraphenyl-arsonium; ttnpb; tartronate; (3,4-dihydroxy-phenyl)-triphenyl-arsonium; thymidine-5'-triphosphate; tu-514; l-threonohydroxamate 4-phosphate; tyrosinal; l-tyrosinamide; thymidine-5'-diphosphate; 3,5-diiodotyrosine; tryptophanyl-5'amp; (3s,8ar)-3-(4-hydroxybenzyl)hexahydropyrrolo[1,2-a]pyrazine-1,4-dione; 3-amino-6-hydroxy-tyrosine; 2-amino-3-[4-hydroxy-6-oxo-2-(2-phenyl-cyclopropylimino)-cyclohexa-1,4-dienyl]-propionic acid; tyvelose; 3-(4-hydroxy-3-imino-6-oxo-cyclohexa-1,4-dienyl)-alanine; para acetamido benzoic acid; 3,8-diamino-6-phenyl-5-[6-[1-[2-[(1,2,3,4-tetrahydro-9-acridinyl)amino]ethyl]1h-1,2,3-triazol-4-yl]hexyl]-phenanthridinium; 3,8-diamino-6-phenyl-5-[6-[1-[2-[(1,2,3,4-tetrahydro-9-acridinyl)amino]-ethyl]-1h-1,2,3-triazol-5-yl]hexyl]-phenanthridinium; (4s)-2-[(1e)-1-aminoprop-1-enyl]-4,5-dihydro-1,3-thiazole-4-carboxylic acid; 1,2,4-triazole-carboxamidine; 4-methyl-5-hydroxyethylthiazole; 2-(sec-butyl)thiazole; 1,3-thiazole-4-carboxylic acid; 4-methyl-5-hydroxyethylthiazole phosphate; uridine-5'-monophosphate; uridine-5'-diphosphate-2-deoxy-2-fluoro-alpha-d-galactose; phosphoric acid-2'-[2'-deoxy-uridine] ester-5'-guanosine ester; phosphoric acid mono-[2-(2,4-dioxo-3,4-dihydro-2h-pyrimidin-1-yl)-4-hydroxy-5-hydroxymethyl-tetrahydro-furan-3-yl]; 3'-uridinemonophosphate; 4-[(6-amino-4-pyrimidinyl) amino]benzenesulfonamide; 1-(3-o-phosphono-beta-l-arabinofuranosyl)pyrimidine-2,4(1 h,3h)-dione; 6-carboxymethyluracil; uridine-5'-diphosphate-n-acetylmuramoyl-l-alanine-d-glutamate; 1,4-dideoxy-5-dehydro-o2-sulfo-glucuronic acid; 7-hydroxystaurosporine; uridine-diphosphate-n-acetylglucosamine; uridine-diphosphate-n-acetylgalactosamine; 3'-1-carboxy-1-phosphonooxy-ethoxy-uridine-diphosphate-n-acetylglucosamine; 6-aminohexyl-uridine-c1,5'-diphosphate; uridine-5'-diphos-phate; udp-alpha-d-xylopyranose; uridine-5'-diphosphate-4-deoxy-4-fluoro-alpha-d-galactose; uridine-5'-diphosphate-mannose; 5-fluoro-2'-deoxyuridine-5'-monophosphate; udp-glucuronic acid; 6-[(z)-amino(imino)methyl]-n-[4-(aminomethyl)phenyl]-4-(pyrimidin-2-ylamino)-2-naphthamide; 8-(pyrimidin-2-ylamino)naphthalene-2-carboximidamide; 7-methoxy-8-[1-(methylsulfonyl)-1 h-pyrazol-4-yl]naphthalene-2-carboximidamide; [2,4,6-tri-isopropyl-phenylsulfonyl-l-[3-amidino-phenylalanine]]-piperazine-n'-beta-alanine; ulapualide a; 2'-deoxyuridine 3'-monophosphate; uridine-5'-diphosphate-n-acetylmuramoyl-l-alanine; 1-(2-deoxy-2-fluoro-3-o-phosphono-beta-l-ribofuranosyl)pyrimidine-2,4(1h,3h)-dione; methylumbelliferyl chitotriose; dump; undecyl-beta-d-maltopyranoside; 5-{[(2-amino-9h-purin-6-yl)oxy]methyl}-2-pyrrolidinone; undecanal; 5-amino 6-nitro uracil; lipid fragment; (6,7-difluoro-quinazolin-4-yl)-(1-methyl-2,2-diphenyl-ethyl)-amine; p1-(adenosine-5'-p5-(uridine-5)pentaphosphate; 6-aza-ump; uridylyl-2'-5'-phospho-adenosine; uridine-5'-monophosphate 2-deoxy-2-fluoro-galactopyranosyl-mono-phosphate ester; uridine-5'-monophosphate glucopyranosyl-monophosphateester; phenyl-uridine-5'-diphosphate; 4-[3-carboxymethyl-3-(4-phosphonooxy-benzyl)-ureido]-4-[(3-cyclohexyl-propyl)-methyl-carbamoyl]butyric acid; uracil; 7,9-dihydro-1h-purine-2,6,8(3h)-trione; urea; 5-flouroura-cil; uridine; 5,6-diaminouracil; (2e)-3-(1h-imidazol-4-yl) acrylic acid; n-phenylthiourea; sulfoquinovose-uridine-c1, 6-diphosphate; uridine 5'-triphosphate; uridine-2',3'-vanadate; acetylphosphate; cyclo-tetrametavanadate; meta vanadate; trivanadate; vancomycin; 4-epi-vancosaminyl derivative of vancomycin; alpha-d-glucose-1-phosphate-6-vanadate; thiamin, vitamin b1; 4-amino hexanoic acid; n5-(1-imino-3-butenyl)-l-ornithine; virginiamycin ml; (2r)-2,5, 7,8-tetramethyl-2-[(4r,8r)-4,8,12-trimethyltridecyl] chroman-6-ol; 4-hydroxy-3-methoxybenzoate; l-valinol; valpromide; 3-[n-[benzyloxycarbonyl]-phenylalaninyl-amino]-5-phenyl-pentane-1-sulfonylmethylbenzene; 3-[n-[benzyloxycarbonyl]-phenylalaninyl-amino]-5-phenyl-pentane-1-sulfonic acid 4-nitro-phenyl ester; 3-[[4-methyl-piperazinyl]carbonyl]-phenylalaninyl-amino]-5-phenyl-pentane-1-sulfonic acid benzyloxy-amide; wrr-204; vinylsulphonic acid; methylphosphonic acid ester group; n-{3-[(7ar,12as,12bs)-7-oxo-1,3,4,6,7,7a,12a,12b-octahy-droindolo[2,3-a]quinolizin-12(2h)-yl]propyl}propane-2-sulfonamide; 4-{2-[4-(2-aminoethyl)piperazin-1-yl]pyridin-4-yl}-n-(3-chloro-4-methylphenyl)pyrimidin-2-amine; way-151693; 5-amino-1h-pyrimidine-2,4-dione; methyl (6s)-1-thio-l-manno-hexodialdo-6,2-pyranoside; bromo-wr99210; (s)-wiskostatin; n-(6-aminohexyl)-5-chloro-1-naphthalenesulfonamide; (6,7-dihydro-5h-cyclopenta[d] imidazo[2,1-b]thiazol-2-yl]-4,7-dihydro[1,4]thiazepine-3,6-dicarboxylic acid; 5-amino-3-methyl-pyrrolidine-2-carboxylic acid; (1s,2s)-1-amino-1-(1,3-thiazol-2-yl) propan-2-ol; xanthine; violaxanthin; (3s)-2,3,4,5-tetrahydropyridin-3-amine; dextrofloxacine; 3-hydroxy-4-(3,4,5-trihydroxy-tetrahydro-pyran-2-yloxy)-piperidin-2-one; xylose-derived imidazole; 5-monophosphate-9-beta-d-ribofuranosyl xanthine; analogue of indinavir drug; decaethylene glycol; d-xylulose; 9-beta-d-xylofuranosyl-adenine; 2,5-xylidine; 5(r)-5-fluoro-beta-d-xylopyranosyl-enzyme intermediate; xylarohydroxamate; d-xylitol; xylopyranose; cysteine-s-acetamide; 2,5-dimethylpyrimidin-4-amine; 5-{[ethyl(methyl)amino]methyl}-2-methyl-5,6-dihydropyrimidin-4-amine; 7,10,13-tri(carboxymethyl)-5, 15-dioxo-4,7,10,13,16-pentaaza-1,19-dithianonadecane; 3-fluorotyrosine; (s)-3-(4-(2-carbazol-9-yl-ethoxy)-phenyl)-2-ethoxy-propionic acid; tyrosyladenylate; y-700; 7-hydroxy-2-oxo-chromene-3-carboxylic acid ethyl ester; zebularine; p1-(5'-adenosyl)p5-(5'-(3'azido-3'-deoxythymidyl)) pentaphosphate; z-ala prolinal; 3-[(acetyl-methyl-amino)-methyl]-4-amino-n-methyl-n-(1-methyl-1h-indol-2-ylmethyl)-benzamide; 6-(4-difluoromethoxy-3-methoxyphenyl)-2h-pyridazin-3-one; zn(ii)-(20-oxo-protoporphyrin ix); [4-(6-chloro-naphthalene-2-sulfonyl)-piperazin-1-yl]-(3,4,5,6-tetrahydro-2h-[1,4']bipyridinyl-4-yl)-methanone; [3-(4-bromo-2-fluoro-benzyl)-7-chloro-2,4-dioxo-3,4-dihydro-2h-quinazolin-1-yl]-acetic acid; (3r)-3-{[(benzyloxy) carbonyl]amino}-2-oxo-4-phenylbutane-1-diazonium; zinc trihydroxide; 9alpha-fluorocortisol; protoporphyrin ix containing zn; z-pro-prolinal; benzoyl-arginine-alanine-methyl ketone; arecoline; dazoxiben; enalkiren; eniluracil; fotemustine; hexobarbital; hirulog; methoxyamphetamine; nalorphine; peldesine; phenacetin; phencyclidine; piretanide; sorbinil; terlipressin; thiorphan; vanoxerine; Vitamin C; Vitamin B6 (Pyridoxine); Calcitriol; Vitamin B12; Vitamin D2 (Ergocalciferol); Calcidiol; Vitamin A; Vitamin D3 (Cholecalciferol); Vitamin B1 (Thiamine); Vitamin B2 (Riboflavin); Adenosine monophosphate; Adenine; L-Alanine; L-Arginine; L-Asparagine; L-Aspartic Acid; Adenosine triphosphate; Cysteine; Biotin; Choline; Citrulline; Creatine; L-Cystine; Icosapent; Folic Acid; L-Glutamine; L-Glutamic Acid; Glycine; Glutathione; L-Histidine; L-Isoleucine; g-Homolinolenic acid; L-Leucine; a-Linolenic acid; Lipoic Acid; Xanthophyll; L-Lysine; L-Methionine; N-Acetyl-D-glucosamine; NADH; Nicotinic acid; L-Ornithine; L-Phenylalanine; Pyridoxal P; Aspartame; L-Proline; Phosphatidylserine; Pyridoxal; Pyruvic acid; Retinoic acid; S-Adenosylmethionine; L-Serine; Succinic acid; Spermine; Tetrahydrofolic acid; L-Threonine; L-Tryptophan; L-Tyrosine; L-Valine; Vitamin E; and Vitamin K3.

Other chemicals which may be used with the present invention include the following, along with any salts and free bases: abacavir; abarelix; acamprosate; acarbose; acetophenazine; acetylcysteine; acetyldigitoxin; acitretin; acrisorcin; acyclovir; adapalene; adefovir dipivoxil; adenosine\vidarabine; alatrofloxacin; albendazole; alclometasone; alendronate; alfentanil; alfuzosin; almotriptan; alosetron; alpha-tocopherol\vitamin e; alprostadil; ambenonium; amcinonide; amdinocillin; amikacin; aminoglutethimide; aminolevulinic acid; aminosalicylic acid; amiodarone; amlexanox; amlodipine; amoxapine; amoxicillin; amphetamine\dextroamphetamine; ampicillin; amprenavir; amrinone\inamrinone; anagrelide; anastrozole; anidulafungin; anileridine; anisindione; apomorphine; apraclonidine; aprepitant; arbutamine; argatroban; aripiprazole; atazanavir; atomoxetine; atorvastatin; atracurium\cisatracuriurn; auranofin; avobenzone; azatadine; azathioprine; azelastine; azlocillin; aztreonam; bacampicillin; baclofen; balsalazide; beclomethasone; benazepril; benoxinate; bentiromide; benzonatate; benzquinamide; betamethasone benzoate; betaxolol\levobetaxolol; betazole; bethanechol; bethanidine; bexarotene; bicalutamide; bimatoprost; biperiden; bisoprolol; bitolterol; bivalirudin; bortezomib; bosentan; bretylium; brimonidine; brinzolamide; bromfenac; bromocriptine; brompheniramine\dexbrompheniramine; buclizine; budesonide; buprenorphine; bupropion; buspirone; busulfan; butenafine; butoconazole; butorphanol; cabergoline; calcifediol; calcipotriol/calcipotriene; calcitonin human; calcitriol; candesartan cilexetil; candicidin; capecitabine; capreomycin; carbachol; carbenicillin indanyl sodium; carboprost; carmustine; carphenazine; carprofen; carteolol; carvedilol; caspofungin; cefaclor; cefazolin; cefepime; cefotaxime; cefoxitin; ceftazidime; cefuroxime; celecoxib; cephalexin; cephaloglycin; cephalothin; cephapirin; cephradine; cerivastatin; ceruletide; cetirizine; cetrorelix; cevimeline; chenodiol\ursodiol; chlorambucil; chloramphenicol palmitate; chlordiazepoxide; chlorhexidine gluconate; chlorphenesin carbamate; chlorpheniramine\dexchlorpheniramine; chlortetracycline; chlorthalidone; cholecalciferol; ciclopirox; cidofovir; cilastatin; cilostazol; cinacalcet; ciprofloxacin; cisapride; citalopram\escitalopram; cladribine; clavulanate; clemastine; clindamycin palmitate; clobetasol propionate; clocortolone pivalate; clofarabine; clopidogrel; clorazepate; cloxacillin; clozapine; cobalamin\hydroxocobalamin; colfosceril palmitate; colistimethate sodium; colistin; conivaptan; corticorelin ovine triflutate; corticotropin; cosyntropin; cyclacillin; cyclobenzaprine; cyclopentolate; cyclosporine; cycrimine; cytarabine; dacarbazine; dactinomycin; dalfopristin; dantrolene; dapiprazole; daptomycin; darifenacin; deferasirox; delavirdine; demecarium; desirudin; deslanoside; desloratadine; desmopressin; desogestrel; desonide; desoximetasone; desoxycorticosterone pivalate; dexamethasone sodium phosphate; dexmedetomidine; dexmethylphenidate\methylphenidate; dexpanthenol; dexrazoxane; dextromethorphan polistirex; dextrothyroxine\levothyroxine; dezocine; diatrizoate meglumine; dichlorphenamide; dicloxacillin; didanosine; diethylpropion; diethylstilbestrol; difenoxin; diflorasone diacetate; digoxin; dinoprost tromethamine; dinoprostone; diphenmethanil-methylsulfate/diphemanil; diphenoxylate; dipivefrin; docetaxel; dofetilide; dolasetron; donepezil; dopamine; dorzolamide; doxacurium; doxazosin; doxepin; doxercalciferol; doxorubicin\epirubicin; dromostanolone propionate; dronabinol; drospirenone; duloxetine; dutasteride; dyclonine; dydrogesterone; echothiophate; efavirenz; eflornithine; eletriptan; emedastine; emtricitabine; enalaprilat; enflurane; enfuvirtide; enoxacin; entacapone; entecavir; epinastine; eplerenone; epoprostenol; eprosartan; eptifibatide; erlotinib; ertapenem; erythromycin estolate; esmolol; estradiol acetate; estramustine phosphate; estrone; estropipate; eszopiclone; ethchlorvynol; ethopropazine; ethotoin; ethylestrenol; ethynodiol diacetate; etidronate; etodolac; etonogestrel; etoposide phosphate; etretinate; exemestane; exenatide; ezetimibe; famciclovir; famotidine; felodipine; fexofenadine; finasteride; flavoxate; floxuridine; fluconazole; fludeoxyglucose f-18; flumazenil; flumethasone pivalate; flunisolide; fluocinolone acetonide; fluocinonide; fluorometholone acetate; fluoxymesterone; fluphenazine enanthate; fluprednisolone; flurandrenolide; flurbiprofen; flutamide; fluvastatin; fluvoxamine; fondaparinux; formoterol; fosamprenavir; foscarnet; fosinopril; fosphenytoin; frovatriptan; fulvestrant; furazolidone; gabapentin; gadoteridol; gallamine triethiodide; ganciclovir sodium; ganirelix; gatifloxacin; gefitinib; gemcitabine; gemfibrozil; gemifloxacin; gemtuzumab ozogamicin; glimepiride; glucagon; gluconolactone; glutethimide; gonadorelin; goserelin; gramicidin; granisetron; grepafloxacin; guanadrel; guanethidine; guanfacine; halcinonide; halobetasol propionate; haloperidol decanoate; haloperidol lactate; haloprogin; hetacillin; hexafluorenium; hexocyclium; hydrochlorothiazide; hydrocortamate; hydroxyprogesterone caproate; hydroxystilbamidine; hydroxyzine pamoate; ibandronic-acid\ibandronate; ibuprofen lysine; ibutilide; icodextrin; idarubicin; idoxuridine; ifosfamide; iloprost; imatinib; imipenem; imipramine pamoate; imiquimod; indinavir; indocyanine green; iobenguane; iocetamic acid; iodamide meglumine; iodipamide meglumine; iodixanol; iodoxamate meglumine; iofetamine; iohexol; iopamidol; iophendylate; iopromide; iothalamate diagnostic; iotrolan; ioversol; ioxaglate meglumine; ioxilan; ipodate; irbesartan; irinotecan; isocarboxazid; isoetharine; isoflurane; isosorbide dinitrate; isosulfan blue; isradipine; ivermectin; ketotifen; labetalol; lamivudine; lamotrigine; latanoprost; leflunomide; lenalidomide; lepirudin; letrozole; leuprolide; levacetylmethadol hydrochloride\levomethadyl acetate; levallorphan; levamisole; levetiracetam; levobunolol; levocabastine; levocarnitine; levomepromazine; levonorgestrel\norgestrel; liothyronine\liotrix; lisinopril; lithium; lodoxamide; lomustine; lopinavir; loracarbef; losartan; loteprednol etabonate; lovastatin; loxapine; lubiprostone; lypressin\vasopressin tannate; mazindol; mecamylamine; meclocycline sulfosalicylate; medrysone; megestrol acetate; meglumine metrizoate; meloxicam; melphalan; meperidine; mephentermine; mephenytoin; meprednisone; mercaptopurine; meropenem; mesna; mesoridazine; metaxalone; methacycline; methanthelinium\methantheline; methazolamide; methdilazine; methenamine hippurate; methicillin; methimazole; methixene; methohexital; methoxamine; methoxsalen; methsuximide; methyl aminolevulinate; methyldopate; methylergonovine; methylprednisolone acetate; methyprylon; methysergide; metipranolol; metocurine; metolazone; metrizoate\metrizoic acid; metronidazole; metyrapone; metyrosine; mezlocillin; micafungin; midodrine; mifepristone; miglitol; miglustat; milrinone; minoxidil; mirtazapine; misoprostol; mitotane; mitoxantrone; mivacurium; moexipril; molindone; mometasone furoate; montelukast; moricizine; moxalactam; moxifloxacin; mupirocin; nabilone; nafarelin; naftifine; nalbuphine; nalmefene; naloxone; naltrexone; naratriptan; natamycin; nateglinide; nedocromil; nefazodone; nelarabine; nelfinavir; neomycin; nepafenac; nesiritide; netilmicin; nevirapine; nicardipine; niclosamide; nifedipine; nilutamide; nimodipine; nisoldipine; nitazoxanide; nitisinone; nitrofurantoin; nitrofurazone; nitroglycerin; nizatidine; norelgestromin; norethindrone acetate; norethynodrel; norgestimate; nystatin; octinoxate; octreotide; olanzapine; olmesartan medoxomil; olopatadine; omega-3-acid ethyl esters; omeprazole/esomeprazole; ondansetron; orlistat; orphenadrine citrate; oseltamivir; oxacillin; oxamniquine; oxandrolone; oxaprozin; oxcarbazepine; oxiconazole; oxtriphylline; palonosetron; pamidronate; pancuronium; pantoprazole; pantothenic acid; paramethadione; paramethasone acetate; pargyline;

paricalcitol; paroxetine; pegaptanib; pemetrexed; pemirolast; penbutolol; penciclovir; penicillin g procaine; pentagastrin; pentamidine; pentazocine; pentetreotide; pentolinium; pentostatin; pergolide; perindopril; permethrin; perphenazine; phensuximide; phentolamine; phenyl aminosalicylate; phenylbutazone; pimecrolimus; pinacidil; pindolol; pioglitazone; pipecuronium; piperacetazine; piperazine; pipobroman; pirbuterol; piroxicam; plicamycin; polyestradiol phosphate; polymyxin b; porfimer; povidone-iodine; pramipexole; pramlintide; pravastatin; prednicarbate; prednisolone acetate; pregabalin; procarbazine; prochlorperazine edisilate; promethazine; propiolactone; propiomazine; propoxyphene; propoxyphene napsylate; propylthiouracil; protirelin; protriptyline; pseudoephedrine; pyrvinium pamoate; quetiapine; quinapril; quinestrol; quinupristin; rabeprazole; raloxifene; ramelteon; ramipril; ranolazine; rapacuronium; remifentanil; repaglinide; rescinnamine; rifapentine; rifaximin; riluzole; rimantadine; rimexolone; risedronate; risperidone; ritodrine; ritonavir; rivastigmine; rizatriptan; rocuronium; rofecoxib; ropinirole; rosiglitazone; rosuvastatin; salmeterol xinafoate; saquinavir; saralasin; secretin; selegiline; selenomethionine; seractide; sermorelin; sertaconazole; sertraline; sevoflurane; sibutramine; sildenafil citrate; simvastatin; sincalide; sirolimus; solifenacin; sorafenib; sotalol; spirapril; stanozolol; stavudine; streptomycin sulfate; streptozocin; sufentanil; sulbactam; sulfacytine; sulfamerazine; sulfameter; sulfamethazine; sulfisoxazole acetyl; sumatriptan; sunitinib; supprelin/histrelin; suprofen; tacrolimus; tadalafil; tamoxifen; tamsulosin; tannic acid; tazarotene; tazobactam; tegaserod; telmisartan; temozolomide; teniposide; tenofovir disoproxil; terazosin; terbinafine; teriparatide; testolactone; testosterone; tetrahydrozoline; thalidomide; thiethylperazine; thioguanine; thiopental; thiothixene; thonzonium; tiagabine; ticarcillin; tigecycline; tiludronate; timolol; tinidazole; tioconazole; tiotropium; tipranavir; tirofiban; tizanidine; tobramycin; tolcapone; tolterodine; topiramate; toremifene; torsemide; trandolapril; tranylcypromine; travoprost; treprostinil; tretinoin\alitretinoin\isotretinoin; triamcinolone; triclofos; tridihexethyl; trifluopromazine; trifluridine; trilostane; trimethaphan camsylate; trimethobenzamide; trimipramine; trioxsalen; triptorelin pamoate; troglitazone; tropicamide; trospium; trovafloxacin; tubocurarine; tyloxapol; tyropanoate; undecoylium; unoprostone isopropyl; valacyclovir; valdecoxib; valganciclovir; valproate\valproic acid\divalproex; valrubicin; valsartan; vardenafil; vecuronium; venlafaxine; verapamil; verteporfin; vinorelbine; viomycin; vitamin a palmitate; voriconazole; zaleplon; zanamivir; ziconotide; zidovudine; zileuton; ziprasidone; zoledronic acid; zolmitriptan; zolpidem; zonisamide; 1-alpha-24-dihydroxycolecalciferol; 2',3'-dideoxythymidine; 5-hydroxyrofecoxib; acecainide-hydrochloride; aceclidine; aceclofenac; aceglatone; acenocoumarol; acepromazine-maleate; acetaminosalol; acetiamine; acetosulfone sodium; acetoxolone; acetylcarnitine; acetyldigoxin-beta; acetyldihydrocodeine; acetylstrophanthidin; acetylsulfamethoxypyrazine; acipimox; acivicin; aclarubicin; ademetionine-disulfate-ditosilate; adenine hydrochloride; adrafinil; afloqualone; ag-81; ajmalicine; aklomide; alacepril; alafosfalin; alanosine; alaproclate; alclofenac; alcloxa; alcuronium-chloride; aldesulfone; aldioxa; alfacalcidol; alfadolone-acetate; alfaprostil; alfaxalone; algestone-acetophenide; alibendol; alinidine; alizapride; allocamide; alloyohimbine; allylestrenol; alminoprofen; almitrine; aloin; alpha-acetyldigoxin; alpha-prodine-hydrochloride; alprenolol-benzoate; alrestatin-sodium; alsactide; aluminum-clofibrate; alverine-citrate; ambicromil; ambucetamide; ambuside; ambutonium-bromide; amdinocillin-pivoxil; amezinium-metilsulfate; amfenac; amfetaminil; amifloxacin; amineptine; aminorex; aminothiazoline camphorate; amiprilose-hydrochloride; amisulpride; amitriptyline embonate; ammonium peroxydisulfate; amorolfine hydrochloride; amosulalol hydrochloride; amphomycin; amprolium; amylmetacresol; androsterone; anetholtrithion; angiotensin-2; angiotensin-amide; antrafenine; apalcillin; apazone; aprindine-hydrochloride; arabinosyluracil-triphosphate; arbaprostil; argipressin; armodafinil\modafinil; arotinolol; arsphenamine; aspoxicillin; atosiban; atromepine; avoparcin; azamethonium-bromide; azanidazole; azaperone; azapetine-phosphate; azaribine; azauridine; azidamfenicol; azidocillin; azolimine; azosemide; bacitracin; bambermycin; bambuterol-hydrochloride; bamethan; bamifylline-hydrochloride; bamipine; barbetonium iodide; barbexaclone; befunolol; befuraline hydrochloride; bekanamycin; bemetizide; benapryzine; bencyclane; bendazac; benethamine-penicillin; benfluorex; benfotiamine; benfurodil-hemisuccinate; benorilate; benoxaprofen; benperidol; benproperine embonate; benzalamide; benzaldehyde; benzarone; benzilonium-bromide; benziodarone; benznidazole; benzoctamine; benzopiperylone; benzquercin; benzydamine salicylate; benzylhydrochlorothiazide; bergapten; betamipron; bevantolol; bevonium-metilsulfate; bezitramide; bibrocathol; biclotymol; bietaserpine; bifemelane hydrochloride; binifibrate; biphenamine-hydrochloride; bisantrene; bisbentiamine; bisbutitiamine; bisdequalinium diacetate; bisorcic; bisoxatin-acetate; bm-23014; bolasterone; boldenone-undecylenate; bornaprine; brivudine; bromhexine; bromperidol-decanoate; bronopol; broparestrol; brotianide; broxaldine; broxuridine; bucindolol; buclosamide; bucloxic-acid; bucolome; bufetolol; bufotenine; bufrolin; bufuralol; bumadizone; bunamidine; bunazosin hydrochloride; bunitrolol; bupranolol; buquineran; buserelin; buserelin-acetate; butalamine; butamirate; buthiazide; butibufen; butikacin; butofilolol; butopiprine; butriptyline; butropium-bromide; buzepide-methiodide; cadralazine; cafaminol; caffeine sodium benzoate; camostat mesilate; camylofin; canrenoate-potassium; canrenone; canthaxanthin; capobenic-acid; captodiame-hydrochloride; carazolol; carbadox; carbazochrome; carbimazole; carbinoxamine-tannate; carbomer; carboprost-methyl; carboquone; carbutamide; carbuterol-hydrochloride; carglumic-acid; carnidazole; caroverine; carpipramine; carubicin; carumonam-sodium; celiprolol-hydrochloride; cephacetrile-sodium; cephaloridine; cethexonium-chloride; cetiedil; cetiedil citrate; cetostearyl-alcohol; cetotiamine; cetraxate-hydrochloride; cetylpyridinium-chloride; chloral-betaine; chloramine-b; chlorbenzoxamine; chlorcyclizine; chlorhexadol; chlormadinone-acetate; chlormethiazole; chlormethine-n-oxide hydrochloride; chlormidazole; chloroxylenol; chloroxymorphamine; chlorozotocin; chlorphenoxamine embonate; chlorproethazine-hydrochloride; chlorpromazine embonate; chlorpyrifos; chlorquinaldol; chlorthenoxazine; cholesterol; cholinemagnesium trisalicylate; chromocarb; chromonar; chrysarobin; cianidanol; ciclazindol; ciclesonide; cicletanine; ciclonicate; ciclosidomine; cicloxilic-acid; cilastatin, n-acetyl; cilazapril; cilobamine-mesylate; cinametic-acid; cinchophen; cinepazet; cinepazide; cinmetacin; cinoxate; cinpropazide maleate; ciprofibrate; ciprostene-calcium; ciramadol-hydrochloride; citicoline sodium; clebopride; clefamide; clemizole sulfate; clenbuterol; clidanac; clinofibrate; clioxanide; clobazam; clobenzorex; clobetasol; clobetasone-butyrate; clobutinol; clobuzarit; clocanfamide; clocapramine; clocinizine; clodronic acid; clofarabine-triphosphate; clofenamide; clofexamide; clofibrate pyridoxine; clofibride; clofilium-phosphate; clofoctol; cloforex; clometacin; clomethiazole edisilate; clometocillin; clomocycline; clonixin; clopamide; clopenthixol-decanoate; cloperastine fendizoate; clopirac; cloprednol; cloprostenol-sodium; cloranolol; clorexolone; clorgiline; cloridarol; clorindione; clorophene; clorprenaline-hydrochloride; clortermine; clostebol-acetate; clothiapine; clovoxamine; cloxacillin benzathine; cobamamide; cocarboxylase magnesium; colestyramine hydrochloride; colextran; colimycin; colistin sulfate; colistin-b; congo-red; conorphone-hydrochloride; cortivazol; cotarnine-chloride; coumazoline; coumetarol; creatinolfosfate; croconazole hydrochloride; cropropamide; cyamemazine; cyclandelate; cyclazocine; cycloartenol-ferulate; cyclobendazole; cyclofenil; cycloguanil-pamoate; cyclopentamine-hydrochloride; cyclopenthiazide; cycotiamine; cynarine; cyprodenate; cyproterone; cyproterone-acetate; cytochalasine-d; cytosine; danitracen; deanol-aceglumate; deanol-phosphate; debrisoquin; decoquinate; deflazacort; dehydroemetine; delapril hydrochloride; delmadinone-acetate; demegestone; demexiptiline; demoxytocin; denatonium-benzoate; deoxyglucose; deoxydeptropine-citrate; desaspidin; detorubicin; dexecadotril; dexetozoline; dexlofexidine; dextranomer; dextrofemine; dextromoramide; diacerein; diacetolol-hydrochloride; diacetylmorphine-hydrochloride; diamfenetide; dianhydrogalactitol; diaveridine; dibekacin; dibenzepin; dibenzoyl-disulfide; dibrompropamidine; dibromsalan; dibunate-sodium; dichloralphenazone; dichlorisone-acetate; dichlorodifluoromethane; dichlorotetrafluoroethane; diclofenamide sodium; diclofensine; dicolinium-iodide; dieldrin; diethyl-phthalate; diethyltoluamide; difemerine-hydrochloride; difenamizole; difenpiramide; difetarsone; diflucortolone-valerate; difluprednate; diftalone; dihexyverine-hydrochloride; dihydralazine; dihydroergocryptine-beta mesilate; dihydrotachysterol; dihydroxydibutylether; diisopromine; dilazep; diloxanide; dimecrotic-acid; dimefline-hydrochloride; dimemorfan; dimethindene maleate; dimethisterone; dimethylacetamide; dimethyl-phthalate; dimethyltryptamine; dimetofrine; dimetridazole; dimoxyline phosphate; diniprofylline; dioxation; dioxybenzone; dipenine-bromide; diphenadione; diphenan; diphenhydramine acefylline; diphenylthiocarbazone; dipipanone-hydrochloride; diprenorphine; dipyrocetyl; disodium adenosine-triphosphate; disulfamide; ditazole; dithranol-triacetate; dixyrazine; dodicin; domiodol; domperidone; dopexamine; doxantrazole; doxpicomine-hydrochloride; dropropizine; drostanolone\dromostanolone; drotaverine; drotebanol; echothiopate-iodide; edoxudine; efaproxiral; efloxate; elcatonin; eledoisin; elizabethin; elliptinium-acetate; embramine; emepronium-carrageenate; endralazine-mesylate; endrysone; enilconazole; enoximone; enprostil; enviomycin; enviroxime; eperisone-hydrochloride; epicillin; epiestriol; epimestrol; epithiazide; epitiostanol; epomediol; eprazinone; eprozinol; eptazocine; erythrityl-tetranitrate; erythromycin-propionate; erythromycin-succinate; erythrosine; eseridine; etamiphyllin camsilate; etebenecid; eterobarb; etersalate; ethadione; ethaverine; ethiazide; ethopabate; ethyl-biscoumacetate; ethyl-icosapentate; ethylloflazepate; ethyl-orthoformate; ethynodiol; etifelmine; etifoxine; etiroxate; etodroxizine; etofamide; etofenamate; etofibrate; etoglucid; etoperidone-hydrochloride; etoricoxib; etosalamide; exalamide; exifone; exiproben; exisulind; fampridine; famprofazone; fazadinium-bromide; febantel; febuprol; fecloburone; fedrilate; felypressin; fenaftic-acid; fenalamide; fenalcomine; fenbendazole; fenbutrazate; fencamfamin; fencibutirol; fenclofenac; fenclonine; fenclozic-acid; fendosal; fenfluramine hydrochloride; fenitrothion; fenmetozole; fenoterol; fenoverine; fenoxazoline-hydrochloride; fenozolone; fenpentadiol; fenproporex; fenprostalene; fenquizone; fenretinide; fenspiride; fenthion; fentiazac; fenticonazole; fentonium-bromide; feprazone; fezatione; fibracillin; flavodic-acid; floctafenine; florantyrone; flosequinan; fluanisone; fluazacort; flucloronide; fludarabine; fludrocortisone; flufenamate-decanoate; fluindione; flumedroxone-acetate; flumequine; flumeridone; flumethiazide; flunixin-meglumine; flunoxaprofen; fluocortin-butyl; fluocortolone; fluorescein-dilaurate; fluoresone; fluotracen; flupamesone; flupentixol; flupentixol-decanoate; fluperolone-acetate; flupirtine; fluprednidene-acetate; fluprostenol-sodium; flurothyl; fluspirilene; fluticasone propionate; flutroline; fominoben; fonazine-mesylate; formebolone; formestane; formocortal; formosulfathiazole; fosfosal; furapromidium; furonazide; fursultiamine; fusaric-acid; gabexate mesilate; gabob; gallopamil; gamolenic-acid; ganglioside; gefarnate; gemeprost; gepefrine; gepirone-hydrochloride; gestodene; gestrinone; gitaloxin; gitoformate; glaucine phosphate; glibornuride; gliflumide; gliquidone; glisentide; glisolamide; glisoxepide; glucametacin; glucosulfone; glucuronamide; glutathione; glybuzole; glyclopyramide; glyconiazide; glycyclamide; glymidine-sodium; gramicidin-s; guabenxan; guacetisal; guaiacol-phenylacetate; guaiapate; guaietolin; gualenate-sodium; guamecycline; guanacline-sulfate; guanazodine sulfate; guanoclor-sulfate; guanoxabenz; guanoxan; halofenate; halofuginone-sulfate; halometasone; halopredone; halopredone-acetate; haloxon; hematoporphyrin; hepronicate; hetacillin-potassium; hexachloroethane; hexacyprone; hexamethonium-tartrate; hexamidine; hexapropymate; hexestrol-dipropionate; hexetidine; hexobendine; hexoprenaline; histapyrrodine; homidium-bromide; homofenazine; hopantenate calcium; hyaluronate-sodium; hycanthone; hydrastine-hydrochloride; hydrobentizide; hydroxydione-sodium-succinate; hydroxyestrone-diacetate; hydroxyphenamate; hypoglycin-a; ibacitabine; ibopamine; ibudilast; ibufenac; ibuproxam; ibuterol; idebenone; idrocilamide; ifenprodil; imafen-hydrochloride; imazodan; imcarbofos; imidapril; imidocarb; imipraminoxide; imolamine; impromidine-hydrochloride; indeloxazine; indenolol; indobufen; indoramin; inosine-pranobex; iobenzamate; iocarmic acid; iodamide; iodopyracet (i125); iodothiouracil; iodothymol; iodoxamic-acid; iotasul; ipriflavone; iproclozide; ipronidazole; isoaminile; isobromindione; isobutiacilate; isoconazole; isoflupredone-acetate; isoleucine; isolysergide; isomalt; isonixin; isospaglumate magnesium; isosulphan-blue; josamycin-propionate; kainic-acid; kawain; kebuzone; keracyanin; ketanserin; ketobemidone; kitasamycin; lachesine-chloride; lacidipine; lactalfate; lactitol; laetrile; lanatoside-c; lasalocid-sodium; laurolinium acetate; lawsone; lercanidipine; lergotrile-mesylate; letosteine; leucocianidol; levomepromazine embonate; levomoprolol; levopropoxyphene dibudinate; levopropylcillin; levopropylhexedrine; levoprotiline; levosimendan; lidoflazine; lisuride; lobeline; lodoxamide, desethyl; lofentanil oxalate; lofepramine; loflucarban; lonazolac; lonidamine; lorajmine-hydrochloride; lornoxicam; lucanthone; luprostiol; lymecycline; lynestrenol; magaldrate; magnesium gluceptate; malachite-green-oxalate; mandelic acid; mannomustine; mazaticol; mebanazine; mebeverine embonate; mebhydrolin; mebhydrolin napadisilate; mebolazine; mebutizide; mecobalamin; mecrifurone; medifoxamine; medrogestone; medroxalol hydrochloride; medroxyprogesterone; medrylamine; mefenidramium-metilsulfate; mefenorex; mefruside; meglutol; melanostatin; melarsonyl-potassium; melitracen; melperone; memotine-hydrochloride; menatetrenone; mepartricin-lauryl-sulfate sodium; mephenoxalone; mepindolol; mepitiostane; mepixanox;

meproscillarin; meptazinol; mesterolone; mesulergine; mesulfen; metabromsalan; metadoxine; metahexanamide; metallibure zinc; metapramine; meteneprost; metenoloneenanthate; metergoline; metescufylline; metformin embonate; methallenestril; methaniazide; methenolone-acetate; methoprene; methoserpidine; methoxyphenamine; methylergometrine; methylthiouracil; metiazinic-acid; metindizate; metioprim; metopimazine; mevastatin; mianserin; mibefradil dihydrochloride; mibolerone; mikamycin; milnacipran; miloxacin; misonidazole; mizolastine; mocimycin; moclobemide; mofebutazone; molsidomine; moperone; mopidamol; morantel-tartrate; morazone; morclofone; morinamide; morniflumate; motretinide; moxaverine; moxestrol; moxonidine; muzolimine; naboctate-hydrochloride; nadide; nadoxolol; nafarelin; nafronyl; naftalofos; naftazone; nalorphine; nandrolone-cyclohexylpropionate; nebivolol; nequinate; neutral-red; niaprazine; nicametate; nicarbazin; nicergoline; niceritrol; niclofolan; nicoclonate; nicofibrate; nicofuranose; nicofurate; nicorandil; nifenalol; nifuratel; nifurfoline; nifuroxazide; nifursol; nifurtimox; nifurtoinol; nifurzide; nikometamide; nilvadipine; nimesulide; nimorazole; nimustine; niridazole; nisin; nithiamide; nitrefazole; nitrendipine; nitroscanate; nitrovin; nitroxinil; nomegestrolacetate; nomifensine; nonivamide; norbormide; nordefrinhydrochloride; norethandrolone; norethisterone-enanthate; norgestrienone; noscapine; nosiheptide; noxiptiline; octafonium-chloride; octanoic-acid; octotiamine; octoxynol-9; oleandomycin-phosphate; omapatrilat; ondascora; opipramol hydrochloride; ornidazole; ornipressin; oxabolone-cipionate; oxaflozane; oxametacin; oxantel-pamoate; oxapiumiodide; oxatomide; oxendolone; oxetorone; oxfendazole; oxfenicine; oxibendazole; oxidopamine; oxiniacate olamine; oxiperomide; oxiracetam; oxitriptan; oxybromonaftoic-acid; oxychlorosene; oxyclozanide; oxyfedrine; oxymesterone; oxypendyl; oxypertine; padimate-a; padimate-o; palmidrol; pancreozymin; panipenem; papaveroline; parapenzolate-bromide; pararosaniline-pamoate; parathiazine teoclate; parecoxib; pargeverine; parsalmide; pas-hydrazide; pasiniazid; pecilocin; pefloxacin; penfluridol; pengitoxin; penimepicycline; pentaerythritol-tetranitrate; pentagestrone-acetate; pentetate meglumine; penthienate; pentisomicin; pentrinitrol; peplomycin-sulfate; pepstatin; perazine; perhexiline phosphate; periciazine embonate; perlapine; peruvoside; pheneticillin; phenglutarimide; phenprobamate; phenyltoloxamine citrate; phenyramidol; pholcodine; phthalofyne; phytate-persodium; picloxydine; picotamide; pifarnine; pimethixene; pinaverium-bromide; pipamazine; pipamperone; pipazethate; pipebuzone; piperoxan; pipethanate-ethobromide; pipotiazine-palmitate; pipoxolan-hydrochloride; pipratecol; piprinhydrinate; piprozolin; pirarubicin; pirazolac; pirenoxine; pirenperone; pirenzepine; piretanide; piribedil; pirifibrate; piriMiphos-ethyl; pirimiphos-methyl; pirisudanol; piritramide; pirlindole; pirmenol-hydrochloride; piroheptine; piromidic-acid; piroximone; pirozadil; pirprofen; pivampicillin; pivcefalexin hydrochloride; pizotyline; plafibride; plaunotol; poldine; polymyxin; polynoxylin; polyoxyethylene-cetyl-ether; polyphloroglucinol-phosphate; ponalrestat; potassium polystyrene-sulfonate; practolol; prajmalium bitartrate; pramiverine; pranoprofen; pranosal; prednazoline; prednimustine; prednisolamate; prednylidene; prednylidene-diethylaminoacetate; prenalterol-hydrochloride; prenoxdiazine; prenoxdiazine hibenzate; prenylamine; pristinamycin; procaterol; procodazole; profenamine hibenzate; progabide; proglumetacin; proglumide; promazine embonate; promazine-hydrochloride; promegestone; promestriene; propacetamol; propallylonal; propamidine; propanidid; propatyl-nitrate; propiram; propiverine hydrochloride; propizepine; propyleneglycol-monostearate; propyl-gallate; propyphenazone; propyromazine-bromide; proquazone; prorenoate-potassium; proscillaridin; prostalene; prothipendyl; protionamide; protizinic-acid; protoveratrineb; proxazole; proxicromil; prozapine; psilocybine; puromycin; pyrantel; pyrantel-pamoate; pyricarbate; pyritidium; pyritinol; pyrovalerone-hydrochloride; pyrrobutaminephosphate; pyrrolnitrin; quinagolide; quinbolone; quinestradol; quingestanol-acetate; quinidine sulfate; quinocide; quinoline-yellow; quinupramine; quinuronium-sulfate; rafoxanide; raltitrexed; ramoplanin; ranimustine; rasagiline mesilate; reboxetine; remoxipride; reproterol; rifamide; rimazolium-metilsulfate; rimiterol; rioprostil; ritanserin; rociverine; rolipram; ronidazole; rosaprostol; rosaramicin; rosoxacin; roxarsone; roxatidine acetate; roxithromycin; ruscogenin; safrazine; salicylate-ethyl; salmefamol; sapropterin; sc-44463; secnidazole; sefavirenz; semustine; sennoside; sennoside-a; serotonin; sertindole; simfibrate; sizofiran; sobrerol; sodium cefuzonam; sodium estriolsuccinate; sodium flomoxef; sodium picosulfate; sodium polymetaphosphate; sodium prednisolone-meta-sulfobenzoate; sodium warfarin; sodium-bensuldazate; sodium-loxoprofen; sodium-ozagrel; solasulfone; somatostatin; sorbinil; sorbitan-monolaurate; spaglumic-acid; sparteine amp; sparteine theophylline; spiclomazine; spiperone; spiramycin adipate; stallimycin; stepronin; stibocaptate; stibophen; stilbazium iodide; strophanthin-h; succinimide; succinylsulfathiazole bismuth; sulbenicillin; sulbutiamine; sulfadicramide; sulfaguanole; sulfamethoxypyridazine-acetyl; sulfametrole; sulfamonomethoxine; sulfanitran; sulfaperin; sulfaproxyline; sulfaquinoxaline; sulfarsphenamine; sulfazamet; sulfiram; sulisatin; sulmazole; sulpiride adamantanecarboxylate; sulprostone; sulthiame; sultopride; sultroponium; sunset-yellow; suxethonium-chloride; suxibuzone; syrosingopine; talampicillin-hydrochloride; taleranol; tamitinol; tartrazine; taxol; teclothiazide; teclozan; tedelparin; tefazoline; teicoplanin; temafloxacin; temocillin; temoporfin; tenamfetamine; tenidap; tenitramine; tenonitrozole; tenoxicam; teprenone; teprotide; terizidone; terlipressin; terlipressin acetate; terodiline-hydrochloride; tertatolol; tetrabenazine; tetradecylsulfate-sodium; tetrahydrozoline hydrochloride; tetramethrin; tetrydamine; tezosentan; thebacon; theobromine-sodium-acetate; theofibrate; theophyllineacetate-sodium; thiambutosine; thiamine-propyl-disulfide; thiamphenicol-glycinate hydrochloride; thiamphenicolpalmitate; thiamylal-sodium; thiazinamium; thiazolsulfone; thibenzazoline; thiocoichicoside; thiophanate; thiopropazate; thiouracil; thymalfasin; thymopentin; tiamenidine; tiamulin-fumarate; tianeptine; tiapamil-hydrochloride; tiapride; tiaprofenic acid; tiaramide-hydrochloride; tibezonium-iodide; tibolone; ticrynafen; tidiacic; tiemonium-iodide; tigloidine; tilidine-hydrochloride; timepidium bromide; timonacic arginine; tinoridine; tiocarlide; tioclomarol; tioxolone; tipepidine hibenzate; tiquizium-bromide; tiratricol; tirilazad; tiropramide; tixocortol-pivalate; tocamphyl; tocopherol-alpha-nicotinate; tocopheryl-quinone; todralazine; tolciclate; tolmesoxide; tolnaftate; toloconiummetilsulfate; tolonidine; toloxatone; tolperisone; tolpropamine; tolrestat; tonazocine-mesylate; tosactide; tramazoline; tranilast; trenbolone; trenbolone-cyclohexylacetate; trengestone; treosulfan; tretoquinol; triacetin; tribenoside; tribromoethanol; tribuzone; triclobisonium-chloride; triclocarban; triethylenemelamine; trifenmorph; trifluperidol; triflusal; triiodostearate-ethyl; trimazosin; trimebutine; trimetazidine; trimethidinium-methosulfate; trimetrexate; trimoprostil; tripamide; tritiozine; tritoqualine; trofosfamide; trolnitrate-phosphate; tromantadine; tropatepine; tropenziline-bromide; tropisetron hydrochloride; trospectomycin; troxerutin; troxipide; tulobuterol; tybamate; tymazoline; tyrothricin; ubiquinone; udpg; ufenamate; undecenoate calcium; unitiol; urapidil; urazamide; valnoctamide; valproate-pivoxil; valspodar; vasopressin; velnacrine; velapride; vesnarinone; vetrabutine; vigabatrin; viloxazine-hydrochloride; viminol; vinburnine; vincamine; vincamine-teprosilate; vindesine; vinpocetine; vinylbital; vinzolidine sulfate; viprostol; viquidil; virginiamycin; visnadine; xamoterol-fumarate; xanoxic-acid; xantofyl-palmitate; xibornol; xipamide; xylazine; zaprinast; zimeldine; zinostatin; zipeprol; zolimidine; zomepirac; zorubicin; zotepine; zucapsaicin; and zuclopenthixol-acetate.

Chemicals that are especially preferable to be used with the present invention include the following chemicals and their salts and free bases: abarelix, abciximab, acamprosate, acetazolamide, acetohexamide, acetophenazine, acetrizoate, acetylcysteine, adefovir dipivoxil, alatrofloxacin, albendazole, alclometasone, alendronate, almotriptan, alprazolam, ambenonium, amifostine, amiloride, amiodarone, amlodipine, amlodipine, amodiaquine, amoxapine, amoxicillin, ampicillin, amprenavir, anagrelide, anakinra, apraclonidine, aprepitant, ardeparin, argatroban, aripiprazole, articaine, atorvastatin, atovaquone, auranofin, azathioprine, azelastine, azlocillin, aztreonam, bacampicillin, bacitracin, baclofen, beclomethasone, bendroflumethiazide, benzthiazide, betamethasone, bicalutamide, bismuth subsalicylate, bleomycin, bosentan, bretylium, brimonidine, brinzolamide, bromfenac, bromocriptine, bromodiphenhydramine, brompheniramine, buclizine, bumetanide, bupropion, busulfan, butalbital, butoconazole, capecitabine, capreomycin, captopril, carbenicillin, carbenicillin indanyl, carbinoxamine, carboplatin, carmustine, carphenazine, carprofen, cefaclor, cefadroxil, cefamandole, cefazolin, cefdinir, cefditoren, cefepime, cefixime, cefmenoxime, cefmetazole, cefonicid, cefoperazone, cefonanide, cefotaxime, cefotetan, cefotiam, cefoxitin, cefpiramide, cefpodoxime proxetil, cefprozil, ceftazidime, ceftibuten, ceftizoxime, ceftriaxone, cefuroxime, cefuroxime axetil, celecoxib, cephalexin, cephaloglycin, cephalothin, cephapirin, cephradine, cerivastatin, cetirizine, cetrorelix, cevimeline, chlophedianol, chlorambucil, chloramphenicol, chlordiazepoxide, chlorhexidine, chlormezanone, chloroprocaine, chloroquine, chlorothiazide, chlorotrianisene, chloroxine, chlorphenesin, chlorpheniramine, chlorphentermine, chlorpromazine, chlorpropamide, chlorprothixene, chlortetracycline, chlorthalidone, chlorzoxazone, chromium picolinate, chromium salts, cilastatin, cimetidine, cinacalcet, ciprofloxacin, cisapride, cisplatin, citalopram, cladribine, clemastine, clindamycin, clindamycin, clindamycin, clioquinol, clobetasol, clocortolone, clofarabine, clofazimine, clofibrate, clomiphene, clomipramine, clonazepam, clonidine, clopidogrel, clorazepate, clotrimazole, cloxacillin, clozapine, colestipol, cyclophosphamide, cyclothiazide, cysteamine, cysteine, dalfopristin, dapsone, delavirdine, demeclocycline, desflurane, desloratadine, desmopressin, dexamethasone, dexamethasone, dexamethasone, dexbrompheniramine, dexchlorpheniramine, diatrizoate, diazepam, diazoxide, dichlorphenamide, diclofenac, dicloxacillin, diethylstilbestrol, diflorasone, diflunisal, diltiazem, dimenhydrinate, dimercaprol, dimethyl sulfoxide, dimyristoyl, disulfiram, dofetilide, dorzolamide, droperidol, duloxetine, dutasteride, echothiophate, econazole, efavirenz, eflornithine, eletriptan, emtricitabine, enflurane, enoxacin, eprosartan, eptifibatide, ertapenem, escitalopram, esmolol, esomeprazole, estazolam, estramustine, eszopiclone, ethacrynate, ethacrynic acid, ethchlorvynol, ethiodized oil, ethionamide, ethopropazine, ethoxzolamide, etidronate, etoposide, evans blue, ezetimibe, famotidine, felodipine, fenofibrate, fenoldopam, flecainide, floxuridine, fluconazole, flucytosine, fludarabine, fludeoxyglucose, fludrocortisone, flumazenil, flumethasone, flunisolide, fluocinolone acetonide, fluocinonide, fluorometholone, fluorometholone, fluorouracil, fluoxetine, fluoxymesterone, fluphenazine, fluphenazine enanthate, fluphenazine, fluprednisolone, flurandrenolide, flurazepam, flurbiprofen, flutamide, fluticasone, fluvastatin, fluvoxamine, fomivirsen, fondaparinux, fosamprenavir, foscarnet, fosfomycin tromethamine, fosinopril, frovatriptan, fulvestrant, furosemide, gadobenate, gadodiamide, gadopentetate, gadoteridol, gadoversetamide, gallium citrate, gallium salts, ganirelix, gatifloxacin, gefitinib, gemcitabine, gemifloxacin, glimepiride, glipizide, glucagon, glyburide, grepafloxacin, griseofulvin, guanabenz, guanfacine, halazepam, halobetasol, halofantrine, haloperidol, haloprogin, halothane, heparin, hexachlorophene, hydrochlorothiazide, hydrocortisone, hydroflumethiazide, hydroxocobalamin, hydroxychloroquine, hydroxyzine, ibandronate, ibutilide, idoxuridine, ifosfamide, imipenem, indapamide, indium and its salts, indium oxyquinoline, indium pentetate, indium, indocyanine green, indomethacin, iobenguane, iocetamic acid, iodamide, iodipamide, iodixanol, iodohippurate, iofetamine, iohexol, iopamidol, iopanoic acid, iopromide, iothalamate, iothalamate, iotrolan, ioversol, ioxaglate, ioxilan, ipodate, isoflurane, isoflurophate, itraconazole, ketamine, ketoconazole, ketotifen, lamivudine, lamotrigine, lansoprazole, leflunomide, levamisole, levocabastine, levofloxacin, levothyroxine, lincomycin, lindane, linezolid, liothyronine, lodoxamide, lomefloxacin, lomustine, loperamide, loracarbef, loratadine, lorazepam, losartan, loteprednol, loxapine, mafenide, magnesium salts, malathion, mangafodipir, manganese salts, mazindol, mechlorethamine, meclizine, meclocycline, meclofenamate, mefloquine, meloxicam, melphalan, mercaptopurine, meropenem, mersalyl, mesoridazine, methazolamide, methdilazine, methicillin, methimazole, methixene, methotrimeprazine, methoxyflurane, methyclothiazide, metoclopramide, metolazone, metrizamide, mezlocillin, micafungin, miconazole, midazolam, mitotane, modafinil, mometasone, montelukast, moxalactam, moxifloxacin, nafcillin, naratriptan, nefazodone, nelfinavir, niclosamide, nilutamide, nitazoxanide, nizatidine, nofetumomab, norfloxacin, octreotide, ofloxacin, olanzapine, omeprazole, oxacillin, oxaliplatin, oxazepam, oxiconazole, oxytocin, pamidronate, pantoprazole, paramethasone, paroxetine, pegaptanib, penicillamine, penicillin g benzathine, penicillin v, pentetate, pentosan polysulfate, perflexane, perflubron, perfluoropolymethylisopropyl ether, perflutren, pergolide, permethrin, perphenazine, phenoxybenzamine, pimecrolimus, pimozide, pioglitazone, piperacetazine, piperacillin, pipobroman, piroxicam, polythiazide, porfimer, potassium salts, povidone-iodine, pramipexole, pramlintide, prazepam, prednisolone, probenecid, probucol, prochlorperazine, proguanil, promazine, promethazine, propiomazine, propyliodone, propylthiouracil, pyrimethamine, pyrithione zinc, quazepam, quetiapine, quinethazone, quinupristin, rabeprazole, raloxifene, ranitidine, ranitidine bismuth citrate, riluzole, risedronate, risperidone, ritonavir, rofecoxib, rose bengal, rosiglitazone, rosuvastatin, rubidium salts, samarium lexidronam, selenium sulfide; selenite salts, selenate salts, selenomethionine, sertaconazole, sertraline, sevoflurane, sibutramine, sildenafil, silver sulfadiazine, simethicone-cellulose, sodium fluoride, sodium iodide, sotalol, sparfloxacin, spirapril, spironolactone, strontium chloride, succimer, sucralfate, sufentanil, sulconazole, sulfacetamide, sulfacytine, sulfadiazine, sulfadoxine, sulfamerazine, sulfameter, sulfamethizole, sulfamethoxazole, sulfanilamide, sulfaphenazole, sulfasalazine, sulfinpyrazone, sulfisoxazole, sulfisoxazole acetyl, sulfoxone, sulfur, sulindac, sumatriptan, sumatriptan, suprofen, tamsulosin, tazarotene, tazobactam, temazepam, teniposide, tenofovir disoproxil, terconazole, thallous chloride, thiabendazole, thiamine, thiamylal, thiethylperazine, thioguanine, thiopental, thioridazine, thiotepa, thiothixene, tiagabine, ticarcillin, ticlopidine, tiludronate, timolol, tinidazole, tinzaparin, tioconazole, tiopronin, tiotropium, tirofiban, tizanidine, tolazamide, tolbutamide, topiramate, toremifene, torsemide, travoprost, trazodone, triamcinolone, triamcinolone acetonide, triamcinolone diacetate, triamcinolone hexacetonide, triazolam, trichlormethiazide, triclofos, triclosan, trifluoperazine, triflupromazine, trifluridine, trimeprazine, trimethaphan, troglitazone, trovafloxacin, tyropanoate, uracil mustard, valdecoxib, valrubicin, vancomycin, vardenafil, voriconazole, zafirlukast, ziconotide, zileuton, ziprasidone, zoledronic acid. The present invention is especially useful when a solution of at least two chemicals is used, where the first chemical is selected from the above lists of chemicals and the second chemical does not have the same empirical formula as the first chemical.

Protein classes that are especially preferable to use with the present invention consist of the following list: Cytokines; chemokines; G protein-coupled receptors; Glycosidases; glycosyltransferases; Ion channels; Nuclear receptors; Phosphodiesterases; Proteases; Protein kinases; Protein phosphatases; Nucleic acids; Transporter proteins; Serotonin receptors; Dopamine receptors; Adrenergic receptors; Histamine receptors; Muscarinic receptors; Nucleotide receptors; Cannabinoid receptors; Chemokine receptors; Opioid receptors; Tyrosine kinases; Cytoplasmic serine kinases; cytoplasmic threonine kinases; Thyroid hormone-like receptors; HNF3-like receptors; and Estrogen-like receptors. Proteins that are especially preferable to use with the present invention consist of the following list: 1,3,4,6-Tetrachloro-1,4-Cyclohexadiene H; 1,3,6,8-Tetrahydroxynaphthalene Reductase; 1,3-1,4-Beta-Glucanase; 1,4-Alpha Maltotetrahydrolase; 1,4-Alpha-D-Glucan Glucanohydrolase; 1,4-Beta-D-Glucan Cellobiohydrolase Cell; 1,4-Beta-D-Glucan Cellobiohydrolase I; 1,4-dihydropyridine Receptor on alpha1 subunit of L-type voltage sensitive Ca2+ channels; 10 Kda Chaperonin; 10-Formyltetrahydrofolate Dehydrogenase; 11-cis retinol dehydorgenase; 12-Oxophytodienoate Reductase; 12-Oxophytodienoate Reductase 1; 12-Oxophytodienoate-10,11-Reductase; 14-3-3-Like Protein C; 15-hydroxyprostaglandin dehydrogenase [NAD+]; 17-Beta-Hydroxysteroid Dehydrogenase; 17-Beta-Hydroxysteroid Dehydrogenase 4; 17 Kd Fetal Brain Protein; 19-Mer Peptide Fragment Of Rhodopsin; 1-Aminocyclopropane-1-Carboxylate Deaminase; 1-Deoxy-D-Xylulose 5-Phosphate Reductois; 1-Pyrroline-5-Carboxylate Dehydrogenase; 1SY6:H OKT3 Heavy Chain 1; 1SY6:L OKT3 Light Chain 1; 2,2-Dialkylglycine Decarboxylase; 2,3-Bisphosphoglycerate-Independent Phosphog; 2,3-Dihydroxybenzoate-Amp Ligase; 2,3-Dihydroxybiphenyl Dioxygenase; 2,3-Dihydroxybiphenyl-1,2-Dioxygenase; 2,4-Dienoyl-Coa Reductase; 2,5-Diketo-D-Gluconic Acid Reductase; 23-Kda Polypeptide Of Photosystem II Oxygen-; 23S Ribosomal; 23S Ribosomal RNA; 23S rRNA of 50S ribosomal subunit; 25-hydroxyvitamin D-1 alpha hydroxylase, mitochondrial; 2'-5'-Oligoadenylate Synthetase 1; 26S proteasome non-ATPase regulatory subunit 1; 2-amino-3-ketobutyrate coenzyme A ligase; 2-Amino-4-Hydroxy-6-Hydroxymethyldihydropte; 2-amino-4-hydroxy-6-hydroxymethyldihydropteridine pyrophosphokinase; 2-Aminoethylphosphonate-Pyruvate Aminotr; 2-C-Methyl-D-Erythritol 2,4-Cyclodiphosphate; 2-C-Methyl-D-Erythritol 4-Phosphate Cytidyly; 2C-Methyl-D-Erythritol-2,4-Cyclodiphosphate; 2-Dehydro-3-Deoxyphosphooctonate Aldolase; 2-Enoyl-Coa Hydratase; 2-Haloacid Dehalogenase; 2-Isopropylmalate Synthase; 2-Keto-3-Deoxy Gluconate Aldolase; 2-Keto-3-Deoxygluconate Kinase; 2-oxoglutarate dehydrogenase E1 component, mitochondrial precursor; 2-Pyrone Synthase; 3 beta-hydroxysteroid dehydrogenase/delta 5-; 3,2-Trans-Enoyl-Coa Isomerase, Mitochondrial; 3,4-Dihydroxy-2-Butanone 4-Phosphate Synthase; 3',5'-Cyclic Nucleotide Phosphodiesterase 2A; 30S ribosomal protein S12; 30S ribosomal protein S4; 30S Ribosomal Protein S6; 30S ribosomal protein S9; 32.1 Kda Protein In Adh3-Rca1 Intergenic; 33 Kda Chaperonin; 3'-5' Exonuclease Eri1; 36 Kda Soluble Lytic Transglycosylase; 367Aa Long Hypothetical Cytochrome P450; 385Aa Long Conserved Hypothetical Protein; 3-Alpha, 20-Beta-Hydroxysteroid Dehydrogenase; 3-Alpha-Hydroxysteroid Dehydrogenase; 3Alpha-Hydroxysteroid Dehydrogenase Type 3; 3-Alpha-Hydroxysteroid/Dihydrodiol Dehydrogease; 3-Carboxy-Cis, Cis-Muconate Cycloisomerase; 3-Dehydroquinate Dehydratase; 3-Dehydroquinate Dehydratase Arod; 3-Dehydroquinate Synthase; 3-Deoxy-D-Arabino-Heptulosonate-7-Phosphatase; 3-Deoxy-Manno-Octulosonate Cytidylyltransfer; 3-Hydroxy-3-Methylglutaryl-Coa Synthase; 3-Hydroxy-3-Methylglutaryl-Coenzyme A Reductase; 3-Hydroxyacyl-Coa Dehydrogenase; 3-Hydroxyacyl-Coa Dehydrogenase Type II; 3-hydroxyisobutyrate dehydrogenase, mitochondrial precursor; 3-Isopropylmalate Dehydrogenase; 3-Ketoacetyl-Coa Thiolase; 3-Keto-L-Gulonate 6-Phosphate Decarboxylase; 3-keto-steroid reductase; 3-Mercaptopyruvate Sulfurtransferase; 3-Methyl-2-Oxobutanoate Hydroxymethyltra; 3-Methyl-2-Oxobutanoate Hydroxymethyltransfe; 3-Methyladenine DNA Glycosylase; 3-Methylaspartate Ammonia-Lyase; 3-oxo-5-alpha-steroid 4-dehydrogenase 2; 3-Oxoacyl-; 3-Oxoacyl-[Acyl-Carrier Protein] Reductase; 3-Oxoacyl-[Acyl-Carrier Protein] Synthas; 3-Oxoacyl-[Acyl-Carrier-Protein] Synthas; 3-oxoacyl-[acyl-carrier-protein] synthase I; 3-oxoacyl-[acyl-carrier-protein] synthase II; 3-oxoacyl-[acyl-carrier-protein] synthase III; 3-Phosphoglycerate Kinase; 3-Phosphoinositide Dependent Protein Kin; 3-Phosphoinositide Dependent Protein Kinase-; 3-Phosphoshikimate 1-Carboxyvinyltransferase; 3-Phytase A; 47 Kda Membrane Antigen; 4-Alpha-Glucanotransferase; 4-Amino-4-Deoxychorismate Lyase; 4-Aminobutyrate Aminotransferase; 4-Chlorobenzoyl Coa Ligase; 4-Chlorobenzoyl Coenzyme A Dehalogenase; 4-Cresol Dehydrogenase [Hydroxylating] Flavo; 4-Diphosphocytidyl-2-C-Methyl-D-Erythrit; 4-Diphosphocytidyl-2-C-Methylerythritol Synt; 4-Hydroxybenzoyl-Coa Thioesterase; 4-Hydroxyphenylpyruvate Dioxygenase; 4-Hydroxyphenylpyruvic Acid Dioxygenase; 4-Hydroxythreonine-4-Phosphate Dehydrogenase; 4M5.3 Anti-Fluorescein Single Chain Antibody; 4-Oxalocrotonate Tautomerase; 4'-Phosphopantetheinyl Transferase Sfp; 4-trimethylaminobutyraldehyde dehydrogenase; 5,10-Methenyltetrahydrofolate Synthetase; 5,10-Methylenetetrahydrofolate Dehydrogenase; 5,10-Methylenetetrahydrofolate Reductase; 50S Ribosomal Protein LIP; 50S subunit of the 70S ribosome of bacteria; 5-alpha reductase 1; 5-Aminolaevulinic Acid Dehydratase; 5-aminolevulinate synthase; 5-Aminolevulinic Acid Dehydratase; 5'-AMP-activated protein kinase, beta-2 subunit; 5'-AMP-activated protein kinase, catalytic alpha-1 chain; 5'-D; 5'-Deoxy-5'-Methylthioadenosine Phosphorylas; 5-Enolpyruvylshikimate-3-Phosphate Synthase; 5-Epi-Aristolochene Synthase; 5'-Fluoro-5'-Deoxyadenosine Synthase; 5-HT-1A Receptor; 5-HT-1B Receptor; 5-HT-1 D Receptor; 5-HT-2A Receptor; 5-HT-3 Receptor; 5HT4 receptor; 5-hydroxytryptamine 1E receptor; 5-hydroxytryptamine 1F receptor; 5-hydroxytryptamine 2C receptor; 5-hydroxytryptamine 7 receptor; 5-Methyltetrahydrofolate S-Homocysteine; 5-Methyltetrahydrofolate S-Homocysteine Meth; 5-Methyltetrahydropteroyltriglutamate-; 5-Methyltetrahydropteroyltriglutamate-Homo; 5'-Methylthioadenosine Phosphorylase; 5'-Nucleotidase; 5'-R; 6,7-Dimethyl-8-Ribityllumazine Synthase; 6-5 Deoxyerythronolide B Hydroxylase; 6-Hydroxymethyl-7,8-Dihydropterin Pyrophosph; 6-Oxocamphor Hydrolase; 6-Phospho-Beta-D-Galactosidase; 6-Phospho-Beta-Glucosidase 6-Phosphofructo-2-Kinase/Fructose-2,6-Bisp; 6-Phosphofructo-2-Kinase/Fructose-2,6-Bipho; 6-Phosphofructo-2-Kinase/Fructose-2,6-Bisph; 6-Phosphofructokinase; 6-Phosphogluconate Dehydrogenase; 6-Phosphogluconolactonase; 6-Pyruvoyl Tetrahydropterin Synthase; 7 Alpha-Hydroxysteroid Dehydrogenase; 7,8-Diamino-Pelargonic Acid Aminotransferase; 7,8-Dihydro-6-Hydroxymethylpterin-Pyrophosp; 70 Kilodalton Heat Shock Protein; 70-Kda Soluble Lytic Transglycosylase; 7-dehydrocholesterol reductase; 8-Amino-7-Oxononanoate Synthase; 8-Oxoguanine DNA Glycosylase; 92 Kda Type IV Collagenase; A chain; A/G-Specific Adenine Glycosylase; Aac; Aah2: Lqh-Alpha-It; Abc Transporter, ATP Binding Protein; Acetate Kinase; Acetoacetyl-Coa Thiolase; Acetohydroxy-Acid Isomeroreductase; Acetohydroxy-Acid Synthase; Acetoin Reductase; Acetolactate Synthase, Catabolic; Acetolactate Synthase, Mitochondrial; Acetyl Group; Acetyl Transferase; Acetyl Xylan Esterase; Acetylcholine Binding Protein; Acetylcholine-Binding Protein; Acetylcholinesterase; Acetylcholinesterase; Acetylcholinesterase (AChE); Acetylcholinesterase precursor; Acetyl-Coa Acetyltransferase; Acetyl-CoA Acetyltransferase (Mitochondrial); Acetyl-Coa Carboxylase; Acetyl-CoA carboxylase 2; Acetyl-Coa Synthetase; Acetyl-Coenzyme A Acetyltransferase 2; Acetyl-Coenzyme A Carboxylase; Acetyl-Coenzyme A Synthetase 1; Acetyl-coenzyme A synthetase 2-like, mitochondrial; Acetyl-coenzyme A synthetase, cytoplasmic; Acetylglutamate Kinase; Acidic Fibroblast Growth Factor; Acidic Lectin; Acireductone Dioxygenase; Aclacinomycin Methylesterase; Aclacinomycin-10-Hydroxylase; Aconitase; Aconitate Hydratase; Aconitate Hydratase 2; Acriflavine Resistance Protein B; Actagardine; Actin; Actin Alpha 1; Actin Depolymerizing Factor; Actin, Alpha Skeletal Muscle; Actin-Fragmin Kinase; Activated Cdc42 Kinase 1; Activator Of; Activin receptor; Activin Receptor Type II; Actva-Orf6 Monooxygenase; Acutohaemonlysin; Acyl Carrier. Protein; Acyl Carrier Protein Phosphodiesterase; Acyl Carrier Protein Synthase; Acyl carrier protein, mitochondrial precursor; Acyl-[Acyl-Carrier Protein] Desaturase; Acyl-[Acyl-Carrier-Protein]-Udp-N-Acetylgl; Acylamino-Acid-Releasing Enzyme; Acyl-Coa Dehydrogenase; Acyl-CoA dehydrogenase family member 8; Acyl-Coa Dehydrogenase Family Member 8, Mito; Acyl-Coa Dehydrogenase, Medium-Chain Specific; Acyl-CoA dehydrogenase, short-chain specific, mitochondrial precursor; Acyl-Coa Hydrolase; Acyl-Coa Oxidase; Acyl-Coa Thioesterase I; Acyl-Coa Thioesterase II; Acyl-Coenzyme A Binding Protein; acyl-coenzyme A:cholesterol acyltransferase; Acylphosphatase; Adam 33; Adamalysin II; Adenine Glycosylase; Adenine Phosphoribosyltransferase; Adenine-N6-DNA-Methyltransferase Taqi; Adenosine 2B receptor; Adenosine A1 receptor; Adenosine A3 receptor; Adenosine Deaminase; Adenosine Kinase; Adenosylcobinamide Kinase; Adenosylhomocysteinase; Adenosylmethionine-8-Amino-7-Oxononanoat; Adenosylmethionine-8-Amino-7-Oxononanoate Am; Adenylate Cyclase; Adenylate cyclase (cAMP); Adenylate Kinase; Adenylate Kinase 1; Adenylate Kinase Isoenzyme-3; Adenylosuccinate Synthetase; Adenylosuccinate synthetase isozyme 1; Adenylyl Cyclase; Adenylylsulfate Kinase; Adipocyte Lipid Binding Protein; Adipocyte Lipid-Binding Protein; ADP Compounds Hydrolase Nude; ADP, ATP Carrier Protein Heart Isoform T1; ADP, ATP carrier protein, fibroblast isoform; ADP, ATP carrier protein, heart/skeletal muscle isoform T1; ADP, ATP carrier protein, liver isoform T2; ADP-Dependent Glucokinase; ADP-L-Glycero-D-Mannoheptose 6-Epimerase; Adpr Pyrophosphatase; ADP-Ribose Pyrophosphatase; ADP-Ribosyl Cyclase; ADP-Ribosylation Factor 1; ADP-Ribosylation Factor 2; ADP-Ribosylation Factor 4; ADP-Ribosylation Factor 6; ADP-Ribosylation Factor-Like 8; ADP-Ribosylation Factor-Like Protein 1; ADP-Ribosylation Factor-Like Protein 3; ADP-Ribosylation Factor-Like Protein 5; ADP-Ribosyltransferase; Adrenodoxin; Adrenodoxin Reductase; Adsorption Protein P2; Aequorin; Aequorin 2; *Aeromonas caviae*; AFG3-like protein 1; AFG3-like protein 2; Agglutinin; Agglutinin; Agglutinin Isolectin 3; Agglutinin Isolectin I/Agglutinin Isolect; Agglutinin Isolectin Vi; Agglutinin Isolectin Vi/Agglutinin Isolec; Agmatinase; Agmatine Iminohydrolase; *Agrobacterium Tumefaciens* Dps; Ahplaao; Aicar Transformylase-Imp Cyclohydrolase; Alamethicin; Alanine aminotransferase; Alanine Dehydrogenase; Alanine Racemase; Alanine racemase, biosynthetic; Alanine-Glyoxylate Aminotransferase; Alanine-glyoxylate aminotransferase 2; Alanyl-tRNA synthetase; Alcohol Dehydrogenase; Alcohol Dehydrogenase; Alcohol dehydrogenase [NADP+]; Alcohol dehydrogenase 6; Alcohol Dehydrogenase Alpha Chain; Alcohol Dehydrogenase Beta Chain; Alcohol dehydrogenase class II pi chain precursor; Alcohol Dehydrogenase Class III Chi Chain; Alcohol dehydrogenase class IV mu/sigma chain; Alcohol Dehydrogenase Class IV Sigma Chain; Alcohol Dehydrogenase E Chain; Alcohol Dehydrogenase Gamma Chain; Alcohol Dehydrogenase, Class II; Alcohol Dehydrogenase, Class II; Alcohol Dehydrogenase, Iron-Containing; Alcohol Sulfotransferase; Aldehyde Dehydrogenase; Aldehyde Dehydrogenase; Aldehyde dehydrogenase 1A3; Aldehyde dehydrogenase 3B1; Aldehyde dehydrogenase 3B2; Aldehyde dehydrogenase family 7 member A1; Aldehyde dehydrogenase X, mitochondrial precursor; Aldehyde Dehydrogenase, Cytosolic 1; Aldehyde dehydrogenase, dimeric NADP-preferring; Aldehyde Dehydrogenase, Mitochondrial Precur; Aldehyde dehydrogenase, mitochondrial precursor; Aldehyde Ferredoxin Oxidoreductase Protein C; Aldehyde oxidase; Aldehyde Oxidoreductase; Aldehyde Reductase; Aldo-Keto Reductase Family 1 Member C1; Aldo-keto reductase family 1 member C2; Aldo-Keto Reductase Family 1 Member C3; Aldo-keto reductase family 1 member C4; Aldolase; Aldolase Protein; Aldose 1-Epimerase; Aldose Reductase; Alginate Lyase; Algq1; Algq2; ALK tyrosine kinase receptor; Alkaline Phosphatase; Alkaline Phosphatase; Alkyl Hydroperoxide Reductase Subunit F; Allantoate Amidohydrolase; Allene Oxide Synthase-Lipoxygenase Protein; Alliin Lyase; Alpha Amylase; Alpha Glutathione S-Transferase; Alpha, Alpha-Trehalose-Phosphate Synthase; Alpha-1 Catenin; Alpha1,2-Mannosidase; Alpha-1,2-Mannosidase; Alpha-1,3-Mannosyl-Glycoprotein Beta-1,2-N—; Alpha-1,4-Galactosyl Transferase; Alpha-1,4-Glucan-4-Glucanohydrolase; Alpha-1,4-N-Acetylhexosaminyltransferase Ext; Alpha-1A Adrenergic Receptor; Alpha1-Antitrypsin; Alpha-1-Antitrypsin; Alpha-1B adrenergic receptor; Alpha-1D adrenergic receptor;

Alpha-1-Purothionin; Alpha-2,3/8-Sialyltransferase; Alpha-2A Adrenergic Receptor; Alpha-2B adrenergic receptor; Alpha-2C adrenergic receptor; Alpha-2-Macroglobulin; Alpha-2U-Globulin; Alpha-aminoadipic semialdehyde synthase, mitochondrial precursor; Alpha-Amylase; Alpha-Amylase I; Alpha-Amylase II; Alpha-Amylase Isozyme 1; Alpha-Amylase, Pancreatic; Alpha-Amylase, Salivary; AlphaChain (LH); Alpha-Conotoxin Gid; Alpha-D-Glucose 1,6-Bisphosphate Phosphotran; Alpha-D-Glucuronidase; Alpha-Galactosidase; Alpha-Galactosidase A; Alpha-Glucosidase; Alpha-Glucosidase; Alpha-Glucuronidase; Alpha-Ketoglutarate-Dependent Taurine Dioxyg; Alpha-L-Arabinofuranosidase; Alpha-L-Arabinofuranosidase B; Alpha-Lytic Protease; Alpha-Mannosidase II; Alpha-Momorcharin; Alpha-Momorcharin Complexed With Adenine; Alpha-Momorcharin Complexed With Formycin; Alpha-N-Acetylgalactosaminidase; Alpha-N-acetylgalactosaminidase precursor; Alpha-N-acetylglucosaminidase precursor; Alpha-Neurotoxin Tx12; Alpha-Tocopherol Transfer Protein; Alpha-Trehalose-Phosphate Synthase; Alpha-Trichosanthin Complexed With Adenine; Amic; Amicyanin; Amidase Operon; Amidophosphoribosyltransferase; Amidophosphoribosyltransferase [precursor]; Amidophosphoribosyltransferase precursor; Amidotransferase Hish; Amiloride-sensitive amine oxidase [copper-containing] precursor; Amiloride-sensitive cation channel 1, neuronal; Amiloride-sensitive cation channel 2, neuronal; Amiloride-sensitive sodium channel alpha-subunit; Amiloride-sensitive sodium channel beta-subunit; Amiloride-sensitive sodium channel delta-subunit; Amiloride-sensitive sodium channel gamma-subunit; Amine Oxidase; Amine Oxidase [Flavin-Containing] A; Amine Oxidase [Flavin-Containing] B; Amine Oxidase, Copper Containing; Amine Oxidase, Flavin-Containing; Aminoacylase-1; Aminoglycoside 2'-N-acetyltransferase; Aminoglycoside 3'-Phosphotransferase; Aminoglycoside 6'-N-Acetyltransferase; Aminomethyltransferase; Aminopeptidase; Aminopeptidase P; Aminotransferase; Aminotransferase, Putative; Amnionless protein; AMP deaminase 1; Amp Nucleosidase; AMP-activated protein kinase (AMPK); AMT protein; Amyloid Beta-Peptide; Amyloid protein-binding protein 1; Amylomaltase; Amylosucrase; Anabaena Sensory Rhodopsin; Anaerobic Ribonucleotide-Triphosphate Reduct; Androgen Receptor; Angiogenin; Angiostatin; Angiotensin Converting Enzyme; Angiotensin-converting enzyme (ACE); Annexin A1; Annexin III; Annexin V; Anthocyanidin Synthase; Anthranilate Phosphoribosyltransferase; Anthranilate Phosphoribosyltransferase 2; Anthrax Toxin Receptor 2; Anti IgE antibody VH domain chain 1; Anti IgE antibody VL domain chain 1; Antibody Vhh Lama Domain; Antifungal Protein 1; Antigen 85B; Antigen 85-C; Anti-H; Anti-Muellerian hormone type II receptor; Anti-Platelet Protein; Anti-Sigma F Factor Antagonist; Antithrombin III (ATM); Antithrombin-III; Antiviral Protein 3; Antiviral Protein S; Apag Protein; Apc35852; Apc35880; Apical Membrane Antigen 1; Apocarotenoid-Cleaving Oxygenase; Apoferritin Co-Crystallized With Sn-Protopor; Apolipoprotein; Apolipoprotein A-II; Apoptosis regulator Bcl-2; Apoptotic Protease Activating Factor 1; Apyrase; Aquaporin 1; Aquaporin Z; Arabinan Endo-1,5-Alpha-L-Arabinosidase A; Arabinan-Endo 1,5-Alpha-L-Arabinase; Arabinose Operon Regulatory Protein; Arac; Arachidonate 15-lipoxygenase; Arachidonate 5-lipoxygenase; A-Raf proto-oncogene serine/threonine-protein kinase; Arcelin-1; Arcelin-5A; Archaeal Sm-Like Protein Af-Sm2; Archaeosine tRNA-Guanine Transglycosylase; Arginase; Arginase 1; Arginase I; Arginase II; Arginase II, Mitochondrial Precursor; arginine decarboxylase; Arginine Kinase; Arginine N-Succinyltransferase, Alpha Ch; Argininosuccinate Synthase; Argininosuccinate synthase [Fragment]; Argininosuccinate Synthetase; Arginosuccinate lyase; Arginosuccinate synthase; Aristolochene Synthase; Arnb Aminotransferase; Arno; Aromatase; Aromatic Amino Acid Aminotransferase; Arpg836; Arsenate Reductase; Arsenical pump-driving ATPase; Arsenical Resistance Operon Repressor, Pu; Arsenite-Translocating Atpase; Arthropodan Hemocyanin; Artificial Nucleotide Binding Protein; Artocarpin; Aryl Sulfotransferase; Arylamine N-Acetyltransferase; Arylsulfatase; Arylsulfatase A; Arylsulfatase A; Ascorbate Oxidase; Ascorbate Peroxidase; Asparagine synthetase; Asparagine Synthetase B; Asparaginyl-tRNA synthetase; Aspartate 1-Decarboxylase; Aspartate 1-Decarboxylase Precursor; Aspartate Aminotransferase; Aspartate Aminotransferase; Aspartate aminotransferase, cytoplasmic; Aspartate aminotransferase, mitochondrial; Aspartate Dehydrogenase; Aspartate Receptor; Aspartate Transcarbamoylase; Aspartate-Semialdehyde Dehydrogenase; Aspartic Protease Bla G 2; Aspartic Proteinase; Aspartoacylase; Aspartyl aminopeptidase; Aspartyl/asparaginyl beta-hydroxylase; Aspartyl-tRNA Synthetase; Aspergillopepsin; Assemblin; Astacin; At5G11950; ATP Phosphoribosyltransferase; ATP Sulfurylase; ATP Synthase; ATP synthase delta chain, mitochondrial [Precursor]; ATP-binding cassette; ATP-Dependent Clp Protease ATP-Binding Subun; ATP-Dependent DNA Helicase; ATP-Dependent Hsl Protease ATP-Binding S; ATP-Dependent Metalloprotease Ftsh; ATP-Dependent RNA Helicase P54; ATP-Phosphoribosyltransferase; ATP-sensitive inward rectifier potassium channel 1; ATP-sensitive inward rectifier potassium channel 11; Atrial Natriuretic Peptide Clearance Recepto; Atrial natriuretic peptide receptor A; Atrial Natriuretic Peptide Receptor A; Atrolysin C; Augmenter Of Liver Regeneration; Aurora-Related Kinase 1; Autocrine Motility Factor; Autoinducer-2 Production Protein Luxs; Autolysin; Auxin Binding Protein 1; Avermectin-Sensitive Chloride Channel Gl; Avian Sarcoma Virus Integrase; Avidin; Axin; Azurin; B chain; B Lymphocyte Stimulator; B4Dimer; B9340; Bacterial azoreductase (*Bacillus* sp); Bacterial isoleucyl-tRNA synthetase; Bacterial Leucyl Aminopeptidase; Bacterial membranes; Bacterial Sialidase; Bacterial Sulfite Oxidase; Bactericidal/Permeability-Increasing Protein; Bacteriochlorophyll A Protein; Bacterioferritin; Bacteriophage Lambda Lysozyme; Bacteriophage T4 Short Tail Fibre; Bacteriorhodopsin; Baculoviral Iap Repeat-Containing Protein 4; Bap1; Basement Membrane Protein Bm-40; Basic Fibroblast Growth Factor; Basic Phospholipase A2; Bba1; Bba5; B-cell receptor; Benzoate 1,2-Dioxygenase Reductase; Benzodiazepine Receptor; Benzoylformate Decarboxylase; Benzyl Alcohol Dehydrogenase; Beta 1 adrenergic receptor; Beta 1,4 Galactosyltransferase; Beta 2 adrenergic receptor; beta chain (FSH); Beta Crystallin B1; Beta Lactamase; Beta platelet-derived growth factor receptor precursor; Beta Trypsin; Beta-(1,3)-glucan synthase [Fragment]; Beta-1,4-D-Glycanase Cex-Cd; Beta-1,4-Galactanase; Beta-1,4-Galactosyltransferase; Beta-1,4-Galactosyltransferase 1; Beta-1,4-Mannanase; Beta2-Glycoprotein-1; Beta3 Alcohol Dehydrogenase; Beta-adrenergic receptor kinase 1; Beta-adrenergic receptor kinase 2; Beta-Agarase A; Beta-Alanine Synthase; Beta-Amylase; Beta-B2-Crystallin; Beta-Carbonic Anhydrase; Beta-Catenin; BetaChain; BetaChain (LH); Beta-Conglycinin, Beta Chain; Beta-Cryptogein; Beta-D-Glucan Exohydrolase Isoenzyme Exo1; Beta-D-Glucan Glucohydrolase Isoenzyme Exo1; Beta-Elicitin Cryptogein; Beta-Fructosidase; Beta-Galactosidase; Beta-Galactoside-Binding Lectin; Beta-Glucosidase; Beta-Glucosidase A; Beta-Glucosyltransferase; Beta-Glucuronidase; Beta-Hexosaminidase; Beta-Hexosaminidase Beta Chain; Beta-Hordothionin; Beta-Hydroxydecanoyl Thiol Ester Dehydrase; Betaine-Homocysteine Methyltransferase; Betaine-Homocysteine S-Methyltransferase; Beta-Keto Acyl Carrier Protein Reductase; Beta-Ketoacyl [Acyl Carrier Protein] Synthas; Beta-Ketoacyl-[Acyl-Carrier-Protein] Synthas; Beta-Ketoacyl-Acp Synthase III; Beta-Ketoacyl-Acyl Carrier Protein Synth; Beta-Ketoacyl-Acyl Carrier Protein Synthase; Beta-Ketoacylsynthase III; Beta-Lactam Synthetase; Beta-Lactamase; Beta-Lactamase Ctx-M-14; Beta-Lactamase Ctx-M-27; Beta-Lactamase Ctx-M-9; Beta-Lactamase II; Beta-Lactamase Imp-1; Beta-Lactamase Oxa-1; Beta-Lactamase Oxa-10; Beta-Lactamase Oxa-2; Beta-Lactamase Pse-2; Beta-Lactamase Shy-1; Beta-Lactamase Shv-2; Beta-Lactamase Tem; Beta-Lactamase, Type II; Beta-Lactoglobulin; Beta-Mannanase; Beta-Mannosidase; Beta-Methylaspartase; Beta-Momorcharin; Beta-N-Acetylhexosaminidase; Beta-N-Acetylhexosaminidase; Beta-Phosphoglucomutase; Beta-Purothionin; Beta-Secretase 1; Beta-Spectrin; Beta-Trypsin; Beta-Tryptase; Bh0236 Protein; Bifunctional 3'-Phosphoadenosine 5'-Phospho; Bifunctional adenosylcobalamin biosynthesis protein cobU; Bifunctional aminoacyl-tRNA synthetase; Bifunctional Deaminase/Diphosphatase; Bifunctional Dihydrofolate Reductase-Thymidy; Bifunctional dihydrofolate reductase-thymidylate synthase; Bifunctional Histidine Biosynthesis Prot; Bifunctional methylenetetrahydrofolate dehydrogenase/cyclohydrolase; Bifunctional P-450: Nadph-P450 Reductase; Bifunctional PGK/TIM [Includes: Phosphoglycerate kinase, EC 2.7.2.3, Triosephosphate isomerase, EC 5.3.1.1, TIM, Triose-phosphate isomerase]; Bifunctional Purine Biosynthesis Protein Pur; Bifunctional purine biosynthesis protein PURH [Includes: Phosphoribosylaminoimidazolecarboxamide formyltransferase, EC 2.1.2.3, AICAR transformylase, IMP cyclohydrolase, EC 3.5.4.10, Inosinicase, IMP synthetase, ATIC]; Bifunctional Puta Protein; Bifunctional Rela/Spot; Bikunin; Bile Acid Receptor; Bile salt export pump; Bile-Salt Activated Lipase; Biliary Glycoprotein C; Bilin Binding Protein; Bilin-Binding Protein; Biliverdin Ix Beta Reductase; Biliverdin Reductase A; Biliverdin reductase A precursor; Bioh Protein; Biosynthetic Thiolase; Biotin Synthase; biotinidase; biotin-protein ligase; Biphenyl-2,3-Diol 1,2-Dioxygenase; Bleomycin Resistance Determinant; Bleomycin Resistance Protein; Bleomycin-Binding Protein; Blood Coagulation Factor Vii; Blue Fluorescent Protein; B-Luffin; Bm-40; Bone Marrow Stromal Cell Antigen 1; Bone Morphogenetic Protein 2; Bone Morphogenetic Protein 7; Botulinum Neurotoxin Type B; Bovine Beta-Lactoglobulin A; Bowman-Birk Inhibitor Derived Peptide; Bp40; Bradykinin; B-Raf proto-oncogene serine/threonine-protein kinase; Branched-chain alpha-ketoacid dehydrogenase kinase; Branched-Chain Amino Acid Aminotransferase; Branched-Chain Amino Acid Aminotransferase; Branched-chain-amino-acid aminotransferase, cytosolic; Branched-chain-amino-acid aminotransferase, mitochondrial; Brazzein; Bruton'S Tyrosine Kinase; Bse6341 Restriction Endonuclease; Butyryl-Coa Dehydrogenase; C Protein Alpha-Antigen; *C. pasteurianum* Hydrogenase I; C-1027 Apoprotein; C1R Complement Serine Protease; C-1-tetrahydrofolate synthase; C-4 methylsterol oxidase; C4-Dicarboxylate Transport Transcriptional R; Caffeic Acid 3-O-Methyltransferase; Caffeoyl-Coa O-Methyltransferase; Cag-Z; Calcineurin B subunit isoform 1; Calcineurin B-Like Protein 4; Calcitonin; Calcitonin Analogue; Calcitonin receptor; Calcium/Calmodulin-Dependent 3',5'-Cycli; Calcium/Calmodulin-Dependent Protein Kinase; calcium-activated potassium channel; Calcium-binding mitochondrial carrier protein Aralar1; Calcium-binding mitochondrial carrier protein Aralar2; Calcium-Dependent Protease, Small Subunit; Calcium-transporting ATPase type 2C member 1; Calgizzarin; Calmodulin; Calpain 1, Large [Catalytic] Subunit; Camp Dependent Protein Kinase; cAMP Phosphodiesterase; Camp-Dependent Protein Kinase; Camp-Dependent Protein Kinase Regulatory Sub; Camp-Dependent Protein Kinase Type 1; Camp-Dependent Protein Kinase Type I-Alpha R; Camp-Dependent Protein Kinase, Alpha-Cat; Camp-Specific 3',5'-Cyclic Phosphodieste; Camp-Specific 3',5'-Cyclic Phosphodiesterase; cAMP-specific 3',5'-cyclic phosphodiesterase 7B; Camp-Specific Phosphodiesterase Pde4D2; Cannabinoid receptor 2; Cannabinoid Receptors; Capsid Protein C; Capsid Protein P40; Capsid Protein P40: Assemblin Protease; Cara; Carbapenem Synthase; Carbohydrate-Phosphate Isomerase; Carbon Monoxide Oxidation System Transcripti; Carbonic Anhydrase; Carbonic Anhydrase I; Carbonic Anhydrase II; Carbonic Anhydrase III; Carbonic Anhydrase IV; Carbonic Anhydrase Xii; Carbonic Anhydrase Xiv; Carbonyl Reductase; Carbonyl Reductase [Nadph] 1; Carboxy Methyl Transferase For Protein Phosp; Carboxy-Cis, Cis-Muconate Cyclase; Carboxyethylarginine Synthase; Carboxylesterase; Carboxylesterase Est2; Carboxylesterase Precursor; Carboxymethylated Rhodanese; Carboxymuconolactone Decarboxylase Family Pr; Carboxypeptidase A; Carboxypeptidase Gp180 Residues 503-882; Carboxypeptidase M; Carboxy-Terminal Domain RNA Polymerase I; Carminomycin 4-O-Methyltransferase; Carnitine Acetyltransferase; Carnitine Acetyltransferase Isoform 2; Carnitine O-acetyltransferase; Carnitine O-palmitoyltransferase I, mitochondrial liver isoform (CPT-1); Carnitine O-palmitoyltransferase II, mitochondrial (CPT-2); Casein Kinase II, Alpha Chain; Casein Kinase-1; Caspase-1 precursor; Caspase-3; Caspase-7; Catabolic Alanine Racemase Dadx; Catabolite Gene Activator; Catabolite Gene Activator Protein; Catalase; Catalase 1; Catalase A; Catalase Hpii; Catalase-Peroxidase; Catalase-Peroxidase Protein Katg; Catechol 1,2-Dioxygenase; Catechol Oxidase; Catechol-O-Methyltransferase; Catechol-O-methyltransferase (COMT); Cathepsin B; Cathepsin F; Cathepsin G; Cathepsin K; Cathepsin S; Cathepsin V; Cation-Dependent Mannose-6-Phosphate Recepto; Cation-Dependent Mannose-6-Phosphate Recepto; Cationic amino acid transporter-3; Cationic amino acid transporter-4; Cation-Independent Mannose 6-Phosphate Recep; Cbp21; Cd2; CD2 lymphocyte antigen; CD20 B-lymphocyte antigen; CD33 antigen; Cd46; CD52 Antigen; Cd58; Cd59 Complexed With Glcnac-Beta-1,4-Glcnac-Be; Cdc25 B-Type Tyrosine Phosphatase; Cdc42Hs-GDP; Cdp-Glucose 4,6-Dehydratase; Cdp-Glucose-4,6-Dehydratase; Cdp-Tyvelose-2-Epimerase; CEA or carcinoembryonic antigen-multiple sequences; Cell Cycle Arrest Protein Bub3; Cell Division Control Protein 2 Homolog; Cell Division Control Protein 6; Cell Division Inhibitor; Cell Division Protein Ftsy; Cell division protein ftsZ; Cell Division Protein Ftsz Homolog 1; Cell Division Protein Kinase 2; Cell Division Protein Kinase 7; Cell Division Protein Zipa; Cell Wall Pentapeptide Ala-[; Cell Wall Peptide In Complex With Deglucobalhi; Cellobiohydrolase; Cellobiohydrolase Cel6A; Cellobiohydrolase I; Cellobiohydrolase I Catalytic Domain; Cellobiohydrolase II; Cellobiose Dehydrogenase; Cellular retinaldehyde-binding protein; Cellular retinoic acid binding protein 1; Cellular retinoic acid binding protein 2; Cellulase; Cellulase B; Cellulase Cel48F; Cellulase Cel9M; Cellulase Celc; Cellulomonas Fimi Family 10 Beta-1,4-Glycana; Cellulosomal Scaffoldin; Cephaibol B; Cephalosporin C Deacetylase; Cephalosporinase; Ceramide glucosyltransferase; Ceruloplasmin; Cg14704 Protein; cGMP Phosphodiesterase; Cgmp Phosphodiesterase A2; Cgmp-Inhibited 3',5'-Cyclic Phosphodiesteras; Cgmp-Specific 3',5'-Cyclic Phosphodiesterase; Chalcone Synthase; Chalcone Synthase 2; Chalcone-Flavonone Isomerase 1; Chalcone-Flavonone Isomerase 1; Chaperone Protein Htpg; C-Ha-Ras; Charybdotoxin; Chemosensory Protein A6; Chemotactic Peptide; Chemotaxis Protein Chea; Chemotaxis Protein Chey; Chemotaxis Receptor Methyltransferase Cher; Chimera Of Glutathione S-Transferase-Synthet; Chimera Of Maltose-Binding Periplasmic Prote; Chitinase; Chitinase; Chitinase 1; Chitinase A; Chitinase A; Chitinase B; Chitinase B; Chitinase-3 Like Protein 1; Chitobiase; Chitobiose Phosphorylase; Chitosanase; Chitotriosidase; Chitotriosidase 1; Chitotriosidase Synonym: Chitinase; Chloramphenicol Acetyltransferase; Chloramphenicol Phosphotransferase; Chlorella Virus DNA Ligase-Adenylate; Chloride channel protein 2; Chloride Intracellular Channel Protein 1; Chlorocatechol 1,2-Dioxygenase; Chloroperoxidase; Chloroperoxidase F; Chlorophyll A-B Binding Protein Ab80; Chlorophyll A-B Binding Protein, Chloroplast; Chloroplast Ferredoxin-Nadp+ Oxidoreductase; Chloroplast Outer Envelope Protein Oep34; Chloroplast Ascorbate Peroxidase; Cho Reductase; Cholecystokinin type A receptor; Cholera Toxin; Cholera Toxin B Subunit; Cholesterol Esterase; Cholesterol Oxidase; Choline dehydrogenase; Choline kinase alpha; Choline-acetyltransferase; Choline/ethanolamine kinase; Choline-phosphate cytidylyltransferase A; Choline-phosphate cytidylyltransferase B; Cholinesterase; Choloylglycine Hydrolase; Chondroitin Ac Lyase; Chondroitinase Ac; Chondroitinase B; Chorionic Gonadotropin; Chorismate Lyase; Chorismate Mutase; Chorismate Synthase; Chromosomal Replication Initiator Protei; Chymase; Chymase; Chymotrypsin; chymotrypsin B; Chymotrypsinogen A; Circadian Clock Protein Kaib; Cis-Biphenyl-2,3-Dihydrodiol-2,3-Dehydrogena; Cite; Citrate Lyase, Beta Subunit; Citrate Synthase; Citrate Synthase; C-Kit Protein; Claret Segregational Protein; Class B Acid Phosphatase; Class B Carbapenemase Blab-1; Class C Beta-Lactamase; Class I Alpha-1,2-Mannosidase; Class-Mu Glutathione S-Transferase; Clavaminate Synthase 1; Clpb Protein; Cmp-N-Acetylneuraminic Acid Synthetase; Coagulation Factor Ix; Coagulation Factor V; Coagulation Factor VII; Coagulation Factor VIII; Coagulation Factor Viii Precursor; Coagulation Factor X; Coagulation Factor Xiii; Coagulation Factor Xiii A Chain; Coagulation factor XIII A chain precursor; Coat Protein; Coatomer Gamma Subunit; Cob; Cob(I)yrinic acid a,c-diamide adenosyltransferase; Cobalamin-Dependent Methionine Synthase; Cobalt-Precorrin-4 Transmethylase; Cocaine Esterase; Coenzyme A Biosynthesis Bifunctional Protein; Coenzyme F420-Dependent N5, N10-Methylenete; Coenzyme F420H2: Nadp+ Oxidoreductase; Coenzyme Pqq Synthesis Protein C; Cog4826: Serine Protease Inhibitor; Collagen; Collagenase 3; Collagenase-3; Collagen-Like Peptide; Complement C1R Component; Complement C1S Component; Complement C3Dg; Complement Control Protein; Complement Decay-Accelerating Factor; Complement Factor B; Complement Protein C8Gamma; Complement Receptor Type 2; COMT (catecol-O-methyltransferase); Conantokin-T; Conantoxin G; Congerin I; Congerin II; Conjugal Transfer Protein Trwb; Connective Tissue Activating Peptide-III; Conotoxin Gs; Conserved Hypothetical Protein; Conserved Hypothetical Protein Af2008; Conserved Hypothetical Protein Mth1747; Conserved Hypothetical Protein Tm1158; Conserved Hypothetical Protein Tm1464; Conserved Hypothetical Protein Ydce; Conserved Hypothetical Protein Yffb; Conserved Hypothetical Protein Yuaa; Conserved Protein Mth1675; Constitutive Androstane Receptor; Contryphan-R; Contryphan-Sm; Contryphan-Vn, Major Form; Copper Amine Oxidase; Copper Amine Oxidase; Copper Amine Oxidase, Liver Isozyme; Copper Transport Protein Atox1; Copper-Containing Nitrite Reductase; Core Protein; Corticosteroid 11-Beta-Dehydrogenase Isozyme; Corticosteroid 11-Beta-Dehydrogenase, Isozym; Corticosteroid 11-beta-dehydrogenase, isozyme 1; Corticosteroid 11-beta-dehydrogenase, isozyme 2; Corticosteroid Receptor; Corticotropin Releasing Hormone; COX-1; COX-2; Crabp-I; Crca Protein; C-Reactive Protein; Creatine kinase B-type; Creatine kinase M-type; Creatine Kinase, B Chain; Creatine kinase, sarcomeric; Creatine kinase, ubiquitous; Crk-Associated Substrate; Crotonobetainyl-Coa: Carnitine Coa-Trans; Crotonobetainyl-Coa: Carnitine Coa-Transfera; Crustacyanin; Crustacyanin A1 Subunit; Crustacyanin C2 Subunit; Cruzipain; Cryptochrome 1 Apoprotein; Csdb; Csdb Protein; C-Terminal Analogue Of Neuropeptide Y, A; C-Terminal Binding Protein 1; C-Terminal Binding Protein 3; C-Terminal Src Kinase; Ctla-4; Ctp Synthase; Ctp: Phosphocholine Cytidylytransferase; C-Type Lectin Dc-Signr; Cutinase; Cyan Fluorescent Protein Cfp; Cyanate Lyase; Cyanoglobin; Cyanovirin-N; Cyclic Alpha Melanocyte Stimulating Hormo; Cyclic Hexapeptide Rr; Cyclic Parathyroid Hormone; Cyclic Phosphodiesterase; Cyclin Dependent Kinase Subunit, Type 1; Cyclin-Dependent Protein Kinase 2; Cyclo; Cyclodextrin. Glycosyltransferase; Cyclodextrin-Glycosyltransferase; Cyclomaltodextrin Glucanotransferase; Cyclooxygenase-2; Cyclophilin; Cyclopropane-Fatty-Acyl-Phospholipid Syn; Cyclopropane-Fatty-Acyl-Phospholipid Synthas; Cyclopropane-fatty-acyl-phospholipid synthase 1; Cyclosporin A As Bound To Cyclophilin; Cyp175A1; CYP1A2; Cystalysin; Cystathionine Beta-Synthase; Cystathionine gamma-lyase; Cystathionine Gamma-Synthase; Cysteine desulfurase; Cysteine dioxygenase [fragment]; Cysteine dioxygenase type I; Cysteine sulfinic acid decarboxylase; Cysteine-Rich Domain Of Mannose Receptor; Cysteinyl leukotriene Receptor 1; Cysteinyl leukotriene receptor 2; Cysteinyl-tRNA Synthetase; Cystic Fibrosis Transmembrane Conductanc; Cystic Fibrosis Transmembrane Conductance Re; Cystine/glutamate transporter; Cystinosin; Cytidine Deaminase; Cytidine Monophospho-N-Acetylneuraminic Acid; Cytidylate Kinase; Cytochrome B=5=Reductase; Cytochrome B2; Cytochrome B2, Mitochondrial; Cytochrome B5; Cytochrome B5 Outer Mitochondrial Membrane Is; Cytochrome B562; Cytochrome C; Cytochrome C'; Cytochrome C"; Cytochrome C Family Protein; Cytochrome C Nitrite Reductase; Cytochrome c oxidase subunit 1; Cytochrome C Peroxidase; Cytochrome C Peroxidase, Mitochondrial; Cytochrome C, Iso-1; Cytochrome C, Putative; Cytochrome C2; Cytochrome C2, Iso-2; Cytochrome C3; Cytochrome C3, A Dimeric Class III C-Type Cy; Cytochrome C4; Cytochrome C549; Cytochrome C550; Cytochrome C551; Cytochrome C-551; Cytochrome C551 Peroxidase; Cytochrome C552; Cytochrome C-552; Cytochrome C-553; Cytochrome C-554; Cytochrome C-556; Cytochrome C6; Cytochrome C7; Cytochrome Cd1 Nitrite Reductase; Cytochrome Cl; Cytochrome F; Cytochrome Oxidase Subunit II; Cytochrome P450; Cytochrome P450 107A1; Cytochrome P450 119; Cytochrome P450 121; Cytochrome P450 152A1; Cytochrome P450 154C1; Cytochrome P450 17A1; Cytochrome P450 19 (Aromatase); Cytochrome P450 27; Cytochrome P450 2B4; Cytochrome P450 2C5; Cytochrome P450 2C8; Cytochrome P450 2C9;

Cytochrome P450 2R1; Cytochrome P450 3A4; Cytochrome P450 4A11 precursor; Cytochrome P450 51; Cytochrome P450 51 (Yeast); Cytochrome P450 55A1; Cytochrome P450 Bm-3; Cytochrome P450 Cyp119; Cytochrome P450 CYP11B1 (steroid hydroxylase); Cytochrome P450Cam; Cytochrome P450-Cam; Cytochrome P450Epok; Cytochrome P450Eryf; Cytochrome P450Nor; Cytochrome Rc557; Cytoglobin; Cytohesin 2; Cytokine Receptor Common Beta Chain; Cytokinin Dehydrogenase 1; Cytosine Deaminase; cytosolic 5-nucleotidase II; Cytosolic phospholipase A2; Cytotoxic T Lymphocyte Associated Antigen 4; Cytotoxic Tcell Valpha Domain; Cytotoxin 3; D (1B) dopamine receptor; D (2) Dopamine Receptor; D (3) Dopamine Receptor; D (4) dopamine receptor; D1 dopamine receptor-interacting protein calcyon; D199S Mutant Of Bovine 70 Kilodalton Heat Sh; D206S Mutant Of Bovine 70 Kilodalton Heat Sh; D-2-Hydroxyisocaproate Dehydrogenase; D3, D2-Enoyl Coa Isomerase Eci1; D-3-Phosphoglycerate Dehydrogenase; D-3-Phosphoglycerate Dehydrogenase; Dabd; Dahp Synthetase; D-Ala Ligase; D-Alanine Aminotransferase; D-Alanine: D-Lactate Ligase; D-alanine-D-alanine ligase A; D-Alanyl-D-Alanine Carboxypeptidase; D-Amino Acid Aminotransferase; D-Amino Acid Oxidase; D-amino-acid oxidase; D-Aminoacylase; Dape; Daptomycin; D-beta-hydroxybutyrate dehydrogenase, mitochondrial precursor; Dcoh; Ddab; De Novo Designed 21 Residue Peptide; De Novo Designed Cyclic Peptide; Deacetoxycephalosporin C Synthase; Death-Associated Protein Kinase; Death-Associated Protein Kinase 1; Decorin; Dehaloperoxidase; Dehydrogenase/reductase SDR family member 4; Delta 2 Crystallin; Delta Crystallin I; Delta Crystallin II; Delta-1-pyrroline-5-carboxylate dehydrogenase, mitochondrial precursor; Delta-Aminolevulinic Acid Dehydratase; Delta-Conotoxin Evia; Deoxycytidine Kinase; Deoxycytidine Triphosphate Deaminase; Deoxycytidylate Deaminase; Deoxycytidylate Hydroxymethylase; Deoxy-D-Mannose-Octulosonate 8-Phosphate Pho; Deoxyhypusine Synthase; Deoxyhypusine Synthase; Deoxynucleoside Monophosphate Kinase; Deoxyribodipyrimidine Photolyase; Deoxyribonuclease I; Deoxyribonucleoside Kinase; Deoxyribose-Phosphate Aldolase; Deoxyuridine 5'-Triphosphate Nucleoditohydro; Deoxyuridine 5'-Triphosphate Nucleotide Hydr; Deoxyuridine 5'-Triphosphate Nucleotidohydro; Deoxyuridine Triphosphatase; Dephospho-Coa Kinase; Der F II; Des[Glyl]-Contryphan-R; Designed Protein Ctpr2; Designed Protein Ctpr3; Dethiobiotin Synthetase; Devb Protein; Dextranase; D-GalactoseD-GLUCOSE BINDING PROTEIN; D-Glucose 6-Phosphotransferase; D-Glyceraldehyde-3-Phosphate Dehydrogena; D-Glyceraldehyde-3-Phosphate Dehydrogenase; D-Glyceraldehyde-3-Phosphate-Dehydrogena; D-Glyceraldehyde-3-Phosphate-Dehydrogenase; Dhps, Dihydropteroate Synthase; D-Hydantoinase; Diacylglycerol kinase; Diadenosine Tetraphosphate Hydrolase; Diamine acetyltransferase 1; Diamine acetyltransferase 2; Diaminopimelate Decarboxylase; Dianthin 30; Dienelactone Hydrolase; Dienoyl-Coa Isomerase; Diga16; Di-Haem Cytochrome C Peroxidase; Diheme Cytochrome C Napb; Di-Heme Peroxidase; Dihydrodipicolinate Reductase; Dihydrodipicolinate Reductase; Dihydrodipicolinate Synthase; Dihydrofolate Reductase; Dihydrofolate Reductase (malarial); Dihydrolipoamide Dehydrogenase; Dihydrolipoyl dehydrogenase, mitochondrial precursor; Dihydrolipoyl Transacetylase; Dihydrolipoyllysine-residue acetyltransferase component of pyruvate dehydrogenase complex, mitochondrial precursor; Dihydroneopterin Aldolase; Dihydroorotase; Dihydroorotate Dehydrogenase; Dihydroorotate Dehydrogenase A; Dihydroorotate Dehydrogenase, mitochondrial [Precursor]; dihydropterate synthase (bacterial); Dihydropteridine Reductase; Dihydropteridine Reductase; Dihydropteroate synthase; Dihydropteroate Synthase (malarial); Dihydropteroate synthase (*Pneumocystis carinii*); Dihydropteroate Synthase I; Dihydropyridine calcium channel; Dihydropyridine-sensitive L-type, calcium channel alpha-2/delta subunits; Dihydropyrimidine dehydrogenase; Dihydroxyacetone Kinase; Diisopropylfluorophosphatase; Dimeric Hemoglobin; Dimethyl Sulfoxide Reductase; Dipeptidyl Aminopeptidase-Like Protein 6; Dipeptidyl Peptidase I; Dipeptidyl Peptidase IV; Dipeptidyl Peptidase IV; Dipeptidyl Peptidase IV Soluble Form; Diphtheria Toxin; Diphtheria Toxin Repressor; Diphthine Synthase; Dissimilatory Copper-Containing Nitrite; Dissimilatory Copper-Containing Nitrite Redu; D-Iactate dehydrogenase; D-Lactate Dehydrogenase; Dip-1; D-Maltodextrin-Binding Protein; Dmso Reductase; DNA Adenine Methylase; DNA Beta-Glucosyltranferase; DNA Cytosine Methyltransferase Dnmt2; DNA Double-Strand Break Repair Rad50 Atpase; DNA Gyrase B; DNA gyrase subunit A; DNA Gyrase Subunit B; DNA Helicase; DNA Ligase; DNA Ligase I; DNA Ligase III; DNA Ligase, Nad-Dependent; DNA Ligase, Nad-Dependent; DNA Mismatch Repair Protein Mutl; DNA Nucleotide Excision Repair Enzyme Uvrb; DNA Photolyase; DNA Polymerase; DNA Polymerase (human cytomegalovirus); DNA polymerase (human herpes simplex virus 1); DNA Polymerase (human); DNA polymerase (Varicella-zoster virus); DNA Polymerase alpha (human); DNA Polymerase Beta; DNA Polymerase I; DNA Polymerase III Subunit Gamma; DNA Polymerase III, Epsilon Chain; DNA Primase; DNA Primase Small Subunit; DNA Primase/Helicase; DNA Repair and Recombination Protein Rad; DNA Repair and Recombination Protein Rada; DNA Repair Protein Xrcc4; DNA Replication Protein; DNA Topoisomerase I; DNA Topoisomerase II; DNA Topoisomerase II (bacterial); DNA-3-Methyladenine Glycosylase I; DNA-3-Methyladenine Glycosylase II; DNA-Binding Response Regulator; DNA-directed RNA polymerase (*E. coli*); DNA-directed RNA polymerase beta chain; DNA-directed RNA polymerase beta chain; DNA-Directed RNA Polymerase Subunit L; Dodecin; DOPA Decarboxylase; Dopamine beta hydroxylase; Dopamine D1 Receptor; Dopamine reuptake pump; Dp-Tt2; Dr Hemagglutinin Structural Subunit; D-Ribose-5-Phosphate Isomerase; D-Ribose-Binding Protein Complexed With Beta; D-Ribose-Binding Protein Mutant With Gly 134; D-Ribose-Binding Protein Mutant With Ile 132; Drosophila Neuroglian; Dtdp-4-Dehydrorhamnose 3,5-Epimerase; Dtdp-4-Dehydrorhamnose Reductase, Rfbd O; Dtdp-6-Deoxy-D-Xylo-4-Hexulose 3,5-Epimerase; Dtdp-D-Glucose 4,6-Dehydratase; Dtdp-Glucose Oxidoreductase; Dual Adaptor Of Phosphotyrosine and 3-Phosp; Dual Specificity Mitogen-Activated Protein K; Dual Specificity Protein Kinase Clk1; Duck Ovotransferrin; Duodenase; Dutp Pyrophosphatase; D-Xylose Isomerase; *E. coli* citrate synthetase; *E. coli* glutathione reductase; *E. coli* malate dehydrogenase; E. Coli Maltodextrin Phosphorylase; *E. coli* pyruvate dehydrogenase; *E. coli* ribosomal proteins; Eafp 2; Early Endosomal Autoantigen 1; Ecotin; Eh Domain Binding Protein Epsin; Eif2Gamma; Elastase; Elastase 1; Eledoisin; Elongation Factor; Elongation Factor 1-Alpha; Elongation Factor 2; Elongation Factor G; Elongation Factor G Complexed With Guanosine; Elongation Factor Tu; Endo/Exocellulase E4; Endo-1,4-B-D-Mannanase; Endo-1,4-Beta Glucanase Engf; Endo-1,4-Beta-D-Xylanase; Endo-1,4-Beta-Glucanase; Endo-1,4-Beta-Glucanase F; Endo-1,4-Beta-Xylanase; Endo-1,4-beta-xylanase 2 precursor; Endo-1,4-Beta-Xylanase A; Endo-1,4-Beta-Xylanase A Precursor; Endo-1,4-Beta-Xylanase II; Endo-1,4-Beta-Xylanase Y; Endo-Alpha-Sialidase; Endo-Beta-1,4-Glucanase; Endo-Beta-N-Acetylglucosaminidase F3; Endocellulase E1; Endoglucanase; Endoglucanase 5A; Endoglucanase 9G; Endoglucanase A; Endoglucanase B; Endoglucanase C; Endoglucanase I; Endoglucanase I; Endoglucanase V Cellobiose Complex; Endoplasmic Reticulum Mannosyl-Oligosacchari; Endoplasmin; Endopolygalacturonase; Endopolygalacturonase; Endosome-Associated Protein; Endothelial Nitric-Oxide Synthase; Endothelial Protein C Receptor; Endothelin B receptor precursor; Endothelin-1; Endothelin-1 receptor precursor; Endothiapepsin; Endothiapepsin precursor; Endoxylanase; Endoxylanase 11A; Engrailed Homeodomain; Enhancing Lycopene Biosynthesis Protein; Enkephalinase; Enolase; Enolase 1; Enoyl Acp Reductase; Enoyl Acyl Carrier Protein Reductase; Enoyl-[Acyl-Carrier Protein] Reductase; Enoyl-[Acyl-Carrier-Protein] Reductase; Enoyl-[Acyl-Carrier-Protein] Reductase; Enoyl-[Acyl-Carrier-Protein] Reductase [Nadh; Enoyl-[acyl-carrier-protein] reductase [NADH]; Enoyl-Acp Reductase; Enoyl-Acp Reductase; Enoyl-Acyl Carrier Protein; Enoyl-Coa Hydratase; Enoyl-Coa Hydratase, Mitochondrial; Envelope Glycoprotein; Envelope Glycoprotein; Envelope glycoprotein GP340; Envelope glycoprotein GP340/GP220; Eosinophil Cationic Protein; Eosinophil Lysophospholipase Chain: A; Eosinophil-Derived Neurotoxin; Ep-Cadherin; Ephrin Type-A Receptor 2; Ephrin-A5; Ephrin-B2; Epidermal Growth Factor; Epidermal Growth Factor Receptor; Epidermal Growth Factor Receptor 2; Epidermal growth factor receptor precursor; Epidermin Modifying Enzyme Epid; Epididymal Secretory Protein E1; Epilancin 15X; Epoxide Hydrolase; Epoxide Hydrolase 2, Cytoplasmic; Epsin; Epsp Synthase; Ergosterol biosynthetic protein 28; Ermc' Methyltransferase; Erv2 Protein, Mitochondrial; *Erythrina Crista*-Galli Lectin; Erythropoietin receptor; Esa1 Histone Acetyltransferase; Esa1 Protein; E-Selectin; Esta; Esterase; Estradiol 17 Beta-Dehydrogenase 1; Estradiol 17 Beta-Dehydrogenase 4; Estradiol 17-beta-dehydrogenase 1; Estradiol 17-beta-dehydrogenase 2; Estradiol 17-beta-dehydrogenase 3; Estradiol 17-beta-dehydrogenase 8; Estrogen Receptor; Estrogen Receptor (ER); Estrogen Receptor Alpha; Estrogen Receptor Beta; Estrogen Sulfotransferase; Estrogen-Related Receptor Gamma; Eukaryotic Peptide Chain Release Factor GTP-; Eukaryotic Translation Initiation Factor 4E; Evolved beta-galactosidase alpha-subunit; Excinuclease Abc Subunit B; Exo-; Exocellobiohydrolase I; Exoglucanase I; Exo-Inulinase; Exo-Maltotetraohydrolase; Exopolyphosphatase; Exotoxin A; Expressed Protein; Exterior Membrane Glycoprotein Gp120; Extracellular calcium-sensing receptor precursor; Extracellular Regulated Kinase 2; Extracellular Signal-Regulated Kinase 2; Extracellular Subtilisin-Like Serine Protein; Extrahepatic lipoprotein lipase (LL); F17-Ag Lectin; F1-Gramicidin A; F1-Gramicidin C; F420-Dependent Alcohol Dehydrogenase; F65A/Y131C-Mi Carbonic Anhydrase V; Factor D; Factor II|Factor IX|Factor VII|Factor X; Factor Inhibiting Hif1; Farnesyl Diphosphate Synthase; Farnesyl pyrophosphate synthetase; Fasciclin I; Fatty Acid Binding Protein; Fatty Acid Binding Protein Homolog; Fatty Acid Metabolism Regulator Protein; Fatty Acid/Phospholipid Synthesis Protein; Fatty Acid-Binding Protein; Fatty Acid-Binding Protein, Adipocyte; Fatty Acid-Binding Protein, Brain; Fatty acid-binding protein, liver; Fatty aldehyde dehydrogenase; Fatty-Acid Amide Hydrolase; F-Box Only Protein 2; Fc Fragment; Fc Gamma Receptor FCGR1_HUMAN; Feglymycin; Feline Immunodeficiency Virus Protease; Feline Leukemia Virus Receptor-Binding Domain; Ferredoxin; Ferredoxin II; Ferredoxin Reductase; Ferredoxin: Nadp+ Oxidoreductase; Ferredoxin: Nadp+ Reductase; Ferredoxin-Dependent Glutamate Synthase; Ferredoxin-Nadp Reductase; Ferredoxin-Nadp Reductase; Ferredoxin-Nadp+ Reductase; Ferredoxin-Nadp+ Reductase; Ferric Hydroxamate Receptor; Ferric Hydroxamate Uptake Receptor; Ferrichrome-Binding Periplasmic Protein; Ferrichrome-Iron Receptor; Ferrichrome-Iron Receptor Precursor; Ferripyochelin Binding Protein; Ferripyoverdine Receptor; Ferritin heavy chain; Ferritin light chain; Ferrochelatase; Feruloyl Esterase A; Fez-1 Beta-Lactamase; Fgf Receptor 1; Fiber Protein; Fibrin; Fibrinogen-420; Fibroblast Activation Protein, Alpha Subunit; Fibroblast Growth Factor 9; Fibroblast Growth Factor Receptor 2; Fibroblast growth factor-4 precursor; Fibronectin; Fimbrial Lectin; Fk506 Binding Protein; Fk506-Binding Protein; FK506-binding protein 1A; Fk506-Binding Protein 4; Fkbp12.6; FKBP12-rapamycin complex-associated protein; Fkbp25; Fkbp-Type Peptidyl-Prolyl Cis-Trans Isom; Fksg76; FL cytokine receptor precursor; Flavin reductase; Flavocytochrome B2; Flavocytochrome C; Flavocytochrome C Fumarate Reductase; Flavocytochrome C3; Flavocytochrome C3 Fumarate Reductase; Flavodoxin; Flavodoxin Reductase; Flavohemoprotein; Flavoprotein; Fluorescent Protein Fp538; Fmn-Binding Protein; Fms1 Protein; Focal Adhesion Kinase 1; Folate receptor alpha; Folate receptor beta; Folate receptor gamma; Folate transporter 1; Folc Bifunctional Protein; Follicle Stimulating Hormone Receptor; Follistatin; Folylpolyglutamate synthase; Folylpolyglutamate synthase, mitochondrial; Folylpolyglutamate Synthetase; Formaldehyde Dehydrogenase; Formaldehyde Ferredoxin Oxidoreductase; Formaldehyde-Activating Enzyme Fae; Formate Acetyltransferase 1; Formate Dehydrogenase H; Formiminotransferase-Cyclodeaminase; Formyl-Coenzyme A Transferase; Formylmethionine Deformylase; Four-Helix Bundle Model; Fpra; Fr-1 Protein; Fragile Histidine Protein; Fragile Histidine Triad Protein; Fructan 1-Exohydrolase Iia; Fructose 1,6-Bisphosphatase; Fructose 1,6-Bisphosphatase/Inositol Monopho; Fructose 1,6-Bisphosphate Aldolase; Fructose-1,6-Bis; Fructose-1,6-Bisphosphatase; Fructose-2,6-Bisphosphatase; Fructose-Bisphosphate Aldolase; Fructose-Bisphosphate Aldolase A; Fructose-Bisphosphate Aldolase Class I; Fructose-Bisphosphate Aldolase II; Ftsz; Fucose-Specific Lectin; Fumarase C; Fumarate Hydratase Class II; Fumarate reductase flavoprotein subunit; Fumarylacetoacetate Hydrolase; Fusion Protein; Fusion Protein Consisting Of Kinesin-Like Pr; Fusion Protein Consisting Of *Staphylococcus*; Fv Fragment; G Protein Gi Alpha 1; G15-Gramicidin A; G25K GTP-Binding Protein; GABA Transaminase; GABAA Receptor; GABA-B Receptor; Gag Polyprotein; Gal10 Bifunctional Protein; Galactanase; Galactokinase; Galactose Mutarotase; Galactose Oxidase; Galactose Oxidase Precursor; Galactose-1-Phosphate Uridyl Transferase-Lik; Galactose-1-Phosphate Uridylyltransferase; Galactose-Binding Protein Complex With Gluco; Galactose-Specific Lectin; Galactoside O-Acetyltransferase; Galactosylgalactosylxylosylprotein 3-Beta-G; Galectin-1; Galectin-1; Galectin-2; Galectin-3; Galectin-3; Galectin-7; Gamma Chymotrypsin; Gamma-Aminobutyrate Metabolism Dehydratase/I; Gamma-aminobutyric-acid receptor alpha-2 subunit precursor; Gamma-aminobutyric-acid receptor alpha-3 subunit precursor; Gamma-aminobutyric-acid receptor alpha-4 subunit precursor; Gamma-aminobutyric-acid receptor alpha-5 subunit precursor; Gamma-aminobutyric-acid receptor alpha-6 subunit precursor; Gamma-aminobutyric-acid receptor rho-1 subunit [Precursor]; Gamma-Glutamyl Hydrolase; Ganglioside Gm2 Activator; Gastrotropin; GDH/6PGL endoplasmic bifunctional protein precursor [Includes: Glucose 1-dehydrogenase; Gdnf Family Receptor Alpha 1; GDP-D-Mannose-4,6-Dehydratase; GDP-Fucose Synthetase; GDP-L-fucose synthetase; GDP-Mannose 4,6 Dehydratase; GDP-Mannose 4,6-Dehydratase; GDP-Mannose 6-Dehydrogenase; GDP-Mannose Mannosyl Hydrolase; General Control Protein Gcn4; General Secretion Pathway Protein E; General Stress Protein 69; Genome Polyprotein; Gephyrin; Geranyltranstransferase; Gfp-Like Chromoprotein Fp595; Gia1; Giding Protein-Mglb; Glandular Kallikrein-13; Glcnac1P Uridyltransferase Isoform 1: Agx1; Globin; Globin I; Globin Li637; Globin-3; Glpe Protein; Glucagon receptor; Glucan 1,3-Beta-Glucosidase I/II; Glucan 1,4-Alpha-Maltohexaosidase; Glucarate Dehydratase; Glucoamylase; Glucoamylase-471; Glucocorticoid Receptor; Glucokinase; Glucokinase Isoform 2; Gluconate 5-Dehydrogenase; Gluconate Kinase; Glucosamine 6-Phosphate Synthase; Glucosamine-6-Phosphate Deaminase; Glucosamine-6-Phosphate Isomerase; Glucosamine-Fructose-6-Phosphate Aminotrans; Glucosamine-Phosphate N-Acetyltransferase; Glucose 1-Dehydrogenase; Glucose 6-Phosphate 1-Dehydrogenase; Glucose 6-Phosphate 1-Dehydrogenase; Glucose 6-Phosphate Dehydrogenase; Glucose Dehydrogenase; Glucose Oxidase; Glucose-1-Phosphatase; Glucose-1-Phosphate Adenylyltransferase Smal; Glucose-1-Phosphate Cytidylyltransferase; Glucose-1-Phosphate Thymidylyltransferas; Glucose-1-Phosphate Thymidylyltransferase; Glucose-6-Phosphate 1-Dehydrogenase; Glucose-6-Phosphate Isomerase; Glucose-Fructose Oxidoreductase; Glucose-Fructose Oxidoreductase; Glucose-Resistance Amylase Regulator; Glucosylceramidase; Glucuronyltransferase I; Glutaconyl-Coa Decarboxylase A Subunit; Glutamate [NMDA] receptor subunit epsilon 1 precursor; Glutamate [NMDA] receptor subunit epsilon 2 precursor; Glutamate [NMDA] receptor subunit epsilon 3 precursor; Glutamate Carboxypeptidase II; Glutamate decarboxylase 1; Glutamate decarboxylase 2; Glutamate Decarboxylase Alpha; Glutamate Decarboxylase Beta; Glutamate Dehydrogenase; Glutamate Dehydrogenase; Glutamate Dehydrogenase 1; Glutamate dehydrogenase 1, mitochondrial precursor; Glutamate dehydrogenase 2, mitochondrial precursor; Glutamate Racemase; Glutamate receptor 1 [Precursor]; Glutamate Receptor 2; Glutamate Receptor 2 Precursor; Glutamate receptor 3; Glutamate receptor 4; Glutamate Receptor 6; Glutamate Receptor Subunit 2; Glutamate Receptor, Ionotropic Kainate 1; Glutamate receptor, ionotropic kainate 1 precursor; Glutamate Receptor, Ionotropic Kainate 2; Glutamate receptor, ionotropic kainate 3; Glutamate receptor, ionotropic kainate 5; Glutamate Semialdehyde Aminotransferase; Glutamate-Cysteine Ligase; Glutamate-cysteine ligase catalytic subunit; Glutamate-cysteine ligase regulatory subunit; Glutaminase, kidney isoform; Glutaminase, liver isoform; Glutaminase-Asparaginase; Glutamine Aminotransferase; Glutamine Phosphoribosylpyrophosphate; Glutamine Phosphoribosylpyrophosphate Amidot; Glutamine Receptor 2; Glutamine Synthetase; Glutamyl-Endopeptidase; Glutamyl-tRNA Reductase; Glutamyl-tRNA Synthetase; Glutaredoxin 3; Glutaryl-Coa Dehydrogenase; Glutathine Synthetase; Glutathione Reductase; Glutathione reductase (mitochondrial); Glutathione S-Transferase; Glutathione S-Transferase; Glutathione S-Transferase 1-6; Glutathione S-Transferase 2; Glutathione S-Transferase 26 Kda; Glutathione S-Transferase A1; Glutathione S-Transferase A1-1; Glutathione S-Transferase A3-3; Glutathione S-Transferase Class Pi Chimaera; Glutathione S-Transferase Gt41A; Glutathione S-Transferase Mu 1; Glutathione S-Transferase Mu 2; Glutathione S-Transferase P; Glutathione S-transferase pi; Glutathione S-Transferase Tsi-1; Glutathione S-Transferase Ya Chain; Glutathione S-Transferase Yb1; Glutathione S-Transferase Yfyf; Glutathione S-Transferase, Mitochondrial; Glutathione Synthetase; Glutathione Transferase; Glutathione Transferase; Glutathione Transferase Gst1-3; Glutathione Transferase Gst1-6; Glutathione Transferase Zeta; Glutathione-Dependent Formaldehyde Dehydroge; Glutathione-Dependent Formaldehyde-Activatin; Glutathione-Requiring Prostaglandin D Syntha; Glutathione-S-Transferase; Glyceraldehyde 3-Phosphate Dehydrogenase; Glyceraldehyde 3-Phosphate Dehydrogenase; Glyceraldehyde 3-Phosphate Dehydrogenase A; Glyceraldehyde-3-Phosphate Dehydrogenase; Glyceraldehyde-3-Phosphate Dehydrogenase; Glyceraldehyde-3-Phosphate Dehydrogenase A; Glyceraldehyde-3-phosphate dehydrogenase, liver; Glyceraldehyde-3-phosphate dehydrogenase, testis-specific; Glycerol Dehydratase; Glycerol Dehydrogenase; Glycerol Kinase; Glycerol Uptake Facilitator Protein; Glycerol Uptake Operon Antiterminator-Re; Glycerol-3-Phosphate Cytidylyltransferase; Glycerol-3-Phosphate Dehydrogenase; Glycerol-3-phosphate dehydrogenase [NAD+], cytoplasmic; Glycinamide ribonucleotide formyltransferase (fragment); Glycinamide Ribonucleotide Transformylase; GLycine alpha 2 receptor; Glycine amidinotransferase; Glycine Betaine-Binding Periplasmic Protein; Glycine dehydrogenase; Glycine N-Methyltransferase; Glycine Oxidase; Glycine receptor alpha-1 chain [Precursor]; Glycine receptor alpha-3 chain; Glycine receptor beta chain; Glycogen phosphorylase; Glycogen Phosphorylase b; Glycogen Phosphorylase, Liver Form; Glycogen phosphorylase, muscle form; Glycogen Synthase 1; Glycogen Synthase Kinase-3 Beta; Glycogenin-1; Glycolate Oxidase; Glycolipid 2-Alpha-Mannosyltransferase; Glycolipid Transfer Protein; Glycoprotein D; Glycoprotein-Fucosylgalactoside Alpha-Galac; Glycoprotein-Fucosylgalactoside Alpha-N-Ace; Glycosyl Transferase; Glycosylase; Glycosyltransferase A; Glycosyltransferase B; Glycosyltransferase Gtfa; Glycosyltransferase Gtfd; Glyoxalase Family Protein; Glyoxalase II; Glyoxylate reductase/hydroxypyruvate reductase; Gmp Reductase I; GMP synthase [glutamine-hydrolyzing]; Gmp Synthetase; Gomesin; Gonadotropin-releasing hormone II receptor; Gonadotropin-releasing hormone receptor; GP41 envelope protein (first heptad repeat); Gp70; GPIIb Receptor; GPIIIa Receptor; Gramicidin; Gramicidin A; Gramicidin B; Gramicidin C; Gramicidin D; Gramicidin Synthetase 1; Granulocyte colony stimulating factor receptor (CD114 antigen); Granulocyte-macrophage colony stimulating factor receptor (GM-CSF-R-alpha or CSF2R); Granulysin; Granzyme B; Green Fluorescent Protein; Green-Fluorescent Protein; Griffonia Simplicifolia Lectin 4; Group X Secretory Phospholipase A2; Growth Differentiation Factor 5; Growth Factor Receptor-Bound Protein 2; Growth hormone releasing hormone receptor (GRF receptor); Growth-arrest-specific protein 6; Grp1; Gst2 Gene Product; GTP Cyclohydrolase I; Gtpase-Activating Protein 1; GTP-Binding Nuclear Protein Ran; GTP-Binding Protein Ran; GTP-Binding Protein Rheb; GTP-Binding Protein Ypt51; GTP-Binding Protein Ypt7P; GTP-Binding Protein Ysxc; Guanidinoacetate Methyltransferase; Guanidinoacetate N-Methyltransferase; Guanine Deaminase; Guanine Nucleotide Exchange Factor and I; Guanine Nucleotide Exchange Factor and Integ; Guanine Nucleotide-Binding Protein G; Guanine Phosphoribosyltransferase; Guanylate Kinase; Guanyl-Specific Ribonuclease T1; Guanyl-Specific Ribonuclease T1 Precursor; Gurmarin; H–; H. Pylori rdxA; H+/K+ ATPase (Proton pump); Hal; Haematopoetic Cell Kinase; Haloalkane Dehalogenase; Halohydrin Dehalogenase; Halorhodopsin; Halotolerance Protein Hal2; Halotolerance Protein Hal3; Hcv Ns5B Polymerase; Hcys Beta3-Cys Analogue Of Hiv Gp41; Hdlp; Head Decoration Protein; Heat Shock 70 Kda Protein 1; Heat Shock 90Kda Protein 1, Alpha; Heat Shock Cognate Kda70; Heat Shock Locus U; Heat Shock Protein 90; Heat Shock Protein Hslu; Heat Shock Protein Hsp 90-Alpha; Heat Shock Protein Hsp 90-Beta; Heat Shock Protein Hsp33; Heat Shock Transcription Factor; Heat Shock-Like Protein 1; Heat-labile enterotoxin B chain precursor; Heat-Labile Enterotoxin B Subunit; Heat-Shock 70 Kd Protein; Heat-Shock Cognate 70 Kd Protein; Heavy chain; Heavy chain 1 B72.3 (murine); Hemagglutinin Precursor; Hemagglutinin-Neuraminidase; Hemagglutinin-Neuraminidase Glycoprotein; Hematopoetic Cell Kinase Hck; Hematopoietic Prostagladin D Synthase; Heme Oxygenase; Heme Oxygenase 1; Heme Oxygenase 2; Heme Oxygenase-1; Heme Pas Sensor Protein; Heme-Based Aerotactic Transducer Hemat; Heme-Based Methyl-Accepting Chemotaxis P; Heme-Based Methyl-Accepting Chemotaxis Prote; Heme-Binding Protein A; Hemerythrin; Hemk Protein; Hemo; Hemocyanin; Hemocyanin; Hemoglobin; Hemoglobin beta chain; Hemoglobin Gamma Chains; Hemoglobin V; Hemoglobin-Like Protein Hbn; Hemoglobin-Like Protein Hbo; Hemolytic Lectin Cel-III; Hemolytic Lectin Lsla; Hemopexin; Heparan Sulfate; Heparan Sulfate D-Glucosaminyl 3-O-Sulfotra; Heparan Sulfate N-Deacetylase/N-Sulfotransfe; Heparin Binding Protein; Heparin Cofactor II; Heparin cofactor II precursor; Heparin-Binding Growth Factor 1; Heparin-binding growth factor 1 precursor; Heparin-Binding Protein; Hepatitis C Virus Ns5B RNA Polymerase; Hepatitis C Virus Ns5B RNA-Dependent RNA Pol; Hepatocyte Growth Factor; Hepatocyte Growth Factor Activator Precursor; Hepatocyte Growth Factor Receptor; Hepatocyte Growth Factor-Regulated Tyrosine; Hepatocyte Nuclear Factor 1-Alpha; Hepatocyte Nuclear Factor 4-Alpha; Hepatocyte Nuclear Factor 4-Gamma; Her-1 Protein; Heroin Esterase; Herpes Thymidine Kinase; Hevamine; Hevamine A; Hevea brasiliensis; Hevein; Hevein; Hexokinase; Hexokinase Type I; Hexon Protein; Hexose-1-Phosphate Uridylyltransferase; Hi0065; Hi1317; High Affinity Immunoglobulin Epsilon Recepto; High affinity immunoglobulin epsilon receptor alpha-subunit precursor; High affinity immunoglobulin epsilon receptor gamma-subunit precursor; High Affinity Ribose Transport Protein Rbsd; High Mobility Group Protein 1; High-Affinity Branched Chain Amino Acid Tran; High-Affinity Branched-Chain Amino Acid Tran; High-affinity cAMP-specific 3',5'-cyclic phosphodiesterase 7A; High-affinity cationic amino acid transporter-1; High-affinity choline transporter 1; High-Molecular-Weight Cytochrome C; Histamine H1 Receptor; Histamine H2 Receptor; Histamine H4 Receptor; Histamine N-Methyltransferase; Histidine ammonia-lyase; Histidine Containing Protein; Histidine decarboxylase; Histidine Triad Nucleotide-Binding Protein; Histidine triad nucleotide-binding protein 1; Histidinol Dehydrogenase; Histidinol Phosphate Aminotransferase; Histidinol-Phosphate Aminotransferase; Histidyl-tRNA synthetase; Histo-Blood Group Abo System Transferase; Histone Acetyltransferase Gcn5; Histone Deacetylase 8; Histone H3; Histone Methyltransferase Doti L; Histone-Lysine N-Methyltransferase, H3 Lysin; Hiv1 Gp41 Hser Analogue Peptide Ace-Ile-T; Hiv-1 Integrase; Hiv-1 Protease; HIV-1 Reverse Transcriptase; HIV-2 Protease; Hmg-Coa Reductase; Holliday Junction DNA Helicase Ruvb; Holliday-Junction Resolvase; Holo-; Holo-D-Glyceraldehyde-3-Phosphate Dehydrogen; *Homo Sapiens* V-Kit Hardy-Zuckerman 4 Feline; Homoprotocatechuate 2,3-Dioxygenase; Homoserine Dehydrogenase; Homoserine Kinase; Hormone Receptor Alpha 1, Thra1; Horseradish Peroxidase C1A; Host Factor For Q Beta; Hpha; H-Protein; Hpv11 Regulatory Protein E2; Hst2 Protein; HTH-type transcriptional regulator malT; Htlv-1 Gp21 Ectodomain/Maltose-Binding Prote; Human Beta2-Glycoprotein I; Human Cd2; Human Cytochrome P450 CYP2D6; Human Cytochrome P450 CYP3A4; Human Growth Hormone Receptor; Human Immunodeficiency Virus Type 2; Human keratinocyte growth factor receptor; Human Neutrophil Gelatinase; Human Ornithine Decarboxylase; Human Procathepsin L; Human Protective Protein; Human RSV Fusion glycoprotein; Human Sigma Alcohol Dehydrogenase; Human Sorbitol Dehydrogenase; Human Thioltransferase; Human Thioredoxin Peroxidase-B; Hut Operon Positive Regulatory Protein; Hyaluronate Lyase; Hyaluronate lyase precursor; Hyaluronidase; Hyaluronoglucosaminidase; Hybrid; Hybrid Cluster Protein; Hydantoinase; Hydrogen peroxide-inducible genes activator; Hydrolase; Hydrolase Angiogenin; Hydroxyacid Oxidase 3; Hydroxyacylglutathione Hydrolase; Hydroxyethylthiazole Kinase; Hydroxylamine Oxidoreductase; Hydroxylamine Reductase; Hydroxymethylglutaryl-CoA lyase; Hydroxynitrile Lyase; Hydroxyquinol 1,2-Dioxygenase; Hydroxysteroid Sulfotransferase; Hypothetical 22.5 Kda Protein In Tub1-Cp; Hypothetical 22.5 Kda Protein In Tub1-Cpr3 I; Hypothetical 28.8 Kda Protein In Psd1-Sk; Hypothetical 32.1 Kda Protein In Adh3-Rca1 I; Hypothetical 65.0 Kda Protein In Cox14-C; Hypothetical 65.0 Kda Protein In Cox14-Cos 3; Hypothetical Abc Transporter ATP-Binding; Hypothetical Abc Transporter ATP-Binding Pro; Hypothetical Isochorismatase Family Protein; Hypothetical Oxidoreductase Ydhf; Hypothetical Oxidoreductase Yiak; Hypothetical Oxidoreductase Yqhd; Hypothetical Protein; Hypothetical Protein Af0103; Hypothetical Protein Af1403; Hypothetical Protein Af1521; Hypothetical Protein Af1796; Hypothetical Protein Af2198; Hypothetical Protein Agr_L_1239; Hypothetical Protein Alr5027; Hypothetical Protein Apc35924; Hypothetical Protein Apc36103; Hypothetical Protein Aq_328; Hypothetical Protein Bsu33890; Hypothetical Protein Egc068; Hypothetical Protein Flj11149; Hypothetical Protein Hi0828; Hypothetical Protein Hi1388.1; Hypothetical Protein Lecb; Hypothetical Protein Mds018; Hypothetical Protein Mj1247; Hypothetical Protein Pa0094; Hypothetical Protein Pa2260; Hypothetical Protein Pa3270; Hypothetical Protein Pa3967; Hypothetical Protein Pa-Ho; Hypothetical Protein pH0236; Hypothetical Protein pH0642; Hypothetical Protein pH1313; Hypothetical Protein pH1602; Hypothetical Protein pH1897; Hypothetical Protein pH1917; Hypothetical Protein Rbstp0775; Hypothetical Protein Rv0793; Hypothetical Protein Rv0819; Hypothetical Protein Rv1170; Hypothetical Protein Rv1347C/Mt1389; Hypothetical Protein Rv2238C/Mt2298; Hypothetical Protein Rv2991; Hypothetical Protein Slr1257; Hypothetical Protein Smu.260; Hypothetical Protein Sso2532; Hypothetical Protein Ta0175; Hypothetical Protein Ta1320; Hypothetical Protein Tm0021; Hypothetical Protein Tm0449; Hypothetical Protein Tm1070; Hypothetical Protein Tm1380; Hypothetical Protein Tm1457; Hypothetical Protein Tm1553; Hypothetical Protein Tm1643; Hypothetical Protein Tm841; Hypothetical Protein Tt0907; Hypothetical Protein Tt1426; Hypothetical Protein Vc1899; Hypothetical Protein Vca0042; Hypothetical Protein Ycdx; Hypothetical Protein Ycfc; Hypothetical Protein Ydce; Hypothetical Protein Yddu; Hypothetical Protein Yese; Hypothetical Protein Yfdw; Hypothetical Protein Ygbm; Hypothetical Protein Yhai; Hypothetical Protein Yhda; Hypothetical Protein Yhfp; Hypothetical Protein, Similar To Potassium C; Hypothetical Protein, Similar To Strepto; Hypothetical Shikimate 5-Dehydrogenase-L; Hypothetical Transcriptional Regulator I; Hypothetical Transcriptional Regulator In Qa; Hypothetical tRNA/Rrna Methyltransferase Hi0; Hypothetical Upf0124 Protein Yfih; Hypothetical Upf0131 Protein pH0828; Hypothetical Upf0204 Protein Af0625; Hypothetical Zinc-Type Alcohol Dehydrogenase; Hypoxanthine Phosphoribosyltransferase; Hypoxanthine-Guanine Phosphoribosyltransfera; Hypoxanthine-Guanine Phosphoribosyltransfera; hypoxanthine-guanine phosphoribosyltransferase; Hypoxanthine-Guanine-Xanthine Phosphoribosyl; Iag-Nucleoside Hydrolase; IclR Transcriptional Regulator; Ig Gamma-1 Chain C Region; Ig Gamma-2A Chain C Region; Ig kappa chain V-III region GOL; IgA2; Igf-1 Receptor Kinase; IGG1; II Purple Acid Phosphatase; 11-6 Receptor Alpha Chain; Ileal Lipid Binding Protein; Imaginal Disc Growth Factor-2; Imidazole Glycerol Phosphate Dehydratase; Imidazole Glycerol Phosphate Synthase Hishf; Immunoglobulin Alpha Fc Receptor; Immunoglobulin Heavy Chain Epsilon-1; Immunoglobulin Lambda Light Chain; Immunoglobulin Lambda Light Chain Dimer; Immunoglobulin Vh Domain; Immunoglobulin VI Domain; IMP dehydrogenase; Imp-1 Metallo Beta-Lactamase; Indole-3-Glycerol Phosphate Synthase; Indole-3-Glycerol-Phosphate Synthase; Indole-3-Pyruvate Decarboxylase; Indoleamine 2,3-dioxygenase; Inducible Nitric Oxide Synthase; Influenza A Subtype N2 Neuraminidase; Influenza A Subtype N9 Neuraminidase; Influenza Virus B/Lee/40 Neuraminidase; Inorganic Polyphosphate/ATP-Glucomannokinase; Inorganic Polyphosphate/ATP-Nad Kinase; Inorganic Pyrophosphatase; Inosine Monophosphate Dehydrogenase 2; Inosine Monophosphate Dehydrogenase I; Inosine-5'-Monophosphate Dehydrogenase; Inosine-5'-Monophosphate Dehydrogenase 2; Inosine-Adenosine-Guanosine Preferring Nucle; Inosine-Adenosine-Guanosine-Preferring Nucle; Inositol 1,3,4-Trisphosphate 5/6-Kinase; Inositol 1,4,5-Trisphosphate Receptor Type 1; Inositol Monophosphatase; Inositol-3-Phosphate Synthase; Inositol-3-Phosphate Synthase; Inositol-Trisphosphate 3-Kinase A; Insecticyanin A Form; Insulin; Insulin receptor; Insulin-Like Growth Factor I; Insulin-Like Growth Factor Receptor 1; Intact Lactose Operon Repressor With Gratuit; Integrase; Integrin alpha-4; Integrin Alpha-L; Integrin Beta-4 Subunit; Intercellular Adhesion Molecule-1; Intercellular Adhesion Molecule-2; Interferon gamma receptor including IFNGR1 and IFNGR2 (IFN-gamma binds directly to IFNGR1 and indirectly to IFNGR2); Interferon receptor IFNAR1; Interferon receptor IFNAR2c; Interferon Stimulated Gene 20Kda; Interferon-Beta; Interferon-Inducible Gtpase; Interleukin 17F; Interleukin-1 type I receptor (IL-1RI); Interleukin-11 receptor alpha chain (IL-11R-alpha); Interleukin-12 Beta Chain; Interleukin-19; Interleukin-2; Interleukin-2 receptor alpha chain (IL-2-RA); Interleukin-2 receptor beta chain (IL-2-RB); Interleukin-3 precursor; Intermediate conductance Ca(2+)-activated K(+) channel, hIK1; Internalin A; Interphotoreceptor retinoid-binding protein; Intestinal Fatty Acid-Binding Protein; Intramolecular Trans-Sialidase; Intron-Associated Endonuclease 1; Invasin; Invertase Inhibitor; Inward rectifier potassium channel 2; Iols Protein; Ionotropic Glutamate Receptor 5; Iota Toxin Component Ia; Iota-Carrageenase; Iron; Iron Binding Protein Fbpa; Iron-Utilization Periplasmic Protein; Isoaspartyl Dipeptidase; Isocitrate Dehydrogenase; Isocitrate Dehydrogenase; Isocitrate dehydrogenase [NAD] subunit alpha, mitochondrial precursor; Isocitrate dehydrogenase [NAD] subunit beta, mitochondrial precursor; Isocitrate dehydrogenase [NAD] subunit gamma, mitochondrial precursor; Isocitrate Dehydrogenase [Nadp] Cytoplasmic; Isocitrate Lyase; Isoflavone O-Methytransferase; Isolectin B4; Isoleucine-tRNA synthetase; Isoleucyl-tRNA Synthetase; Isoliquiritigenin 2'-O-Methyltransferase; Isomerase; Isopenicillin N Synthase; Isopentenyl Diphosphate Delta-Isomerase; Isopentenyl-Diphosphate Delta-Isomerase; Isovaleryl-Coa Dehydrogenase; Ispd/Ispf Bifunctional Enzyme; Iswi Protein; Kallikrein; Kallikrein 1; Kallikrein 6; Kanamycin nucleotidyltransferase; Kappa-4 Immunoglobulin; Kata Catalase; Kdo-8-Phosphate Synthetase; Kdpg Aldolase; Ketoacyl Reductase; Kex1; Killer Cell Immunoglobulin-Like Receptor 2Ds; Kindling Fluorescent Protein; Kinesin; Kinesin Heavy Chain; Kinesin Heavy Chain-Like Protein; Kinesin Motor Ncd; Kinesin-Like Protein Kar3; Kinesin-Like Protein Kif11; Kinesin-Like Protein Kif1A; Kinesin-Like Protein Kif2C; Kinesin-Related Motor Protein Eg5; Kynureninase; Kynurenine/alpha-aminoadipate aminotransferase mitochondrial; Kynurenine-Oxoglutarate Transaminase I; L; L-2-Haloacid Dehalogenase; L-2-Hydroxyisocaproate Dehydrogenase; L-3-Hydroxyacyl Coa Dehydrogenase; L-3-Hydroxyacyl-Coa Dehydrogenase; L-3-Phosphoserine Phosphatase; Laccase; Laccase; Laccase 1; Laccase 2; Lactadherin; Lactaldehyde Reductase; Lactate Dehydrogenase; Lactate Dehydrogenase; Lactoferrin; Lactoferrin; Lactose Permease; Lactotransferrin; Lactoylglutathione Lyase; L-Alanine Dehydrogenase; L-Allo-Threonine Aldolase; Lambda Exonuclease; Laminarinase 16A; L-Amino Acid Oxidase; Lanosterol Synthase; Lantibiotic Mersacidin; L-Arabinose-Binding Protein; L-Arabinose-Binding Protein Complex With L-A; Large T Antigen; L-Arginine: Glycine Amidinotransferase; L-Arginine\: Glycine Amidinotransferase; L-Asparaginase; L-Asparagine Amidohydrolase; L-Aspartate Ammonia-Lyase; L-Aspartate Oxidase; Lck Kinase; L-Cysteine/L-Cystine C-S Lyase; Lectin; Lectin; Lectin Cel-I, N-Acetyl-D-Galactosamine-Speci; Lectin Complex With Lactose; Lectin Pal; Lectin, Isoform 1; Lectin-D2; Leghemoglobin; Leghemoglobin A; Lens Fiber Major Intrinsic Protein; Lethal; Lethal Factor; Leucine Aminopeptidase; Leucine carboxyl methyltransferase 1; Leucine carboxyl methyltransferase 2; Leucoagglutinating Phytohemagglutinin; Leucoanthocyanidin Dioxygenase; Leucyl-tRNA Synthetase; Leucyl-tRNA synthetase, cytoplasmic; Leukoagglutinin; Leukocidin F Subunit; Leukocyte Elastase; Leukosialin; Leukotriene A-4 Hydrolase; Leukotriene B4 12-Hydroxydehydrogenase/Pros; Levansucrase; Levodione Reductase; L-Fucose Isomerase; L-Fuculose 1-Phosphate Aldolase; L-Fuculose-1-Phosphate Aldolase; L-Histidinol Dehydrogenase; light chain; Light chain 1 B72.3 (murine); Lignin Peroxidase; Limonene-1,2-Epoxide Hydrolase; Lipase; Lipase; Lipase 2; Lipase 3; Lipase, Gastric; Lipid Transfer Protein; Lipj; Lipoate-Protein Ligase, Putative; Lipoprotein Mxim; Lipoprotein Nlpi; Lipoxygenase-3; Lipoyltransferase 1; Lithostathine; Liver Alcohol Dehydrogenase; Liver Carboxylesterase; Liver Carboxylesterase I; Liver Fatty Acid Binding Protein; Liver Glycogen Phosphorylase; L-Lactate Dehydrogenase; L-Lactate Dehydrogenase; L-lactate dehydrogenase A chain; L-Iactate dehydrogenase A-like 6A; L-lactate dehydrogenase A-like 6B; L-lactate dehydrogenase B chain; L-Lactate Dehydrogenase B Chain; L-lactate dehydrogenase C chain; L-Lactate Dehydrogenase H Chain; L-Lactate Dehydrogenase M Chain; L-Lactate/Malate Dehydrogenase; Lmaj004091Aaa; Lmaj004144Aaa Protein; Long-Chain Fatty Acid Transport Protein; Long-chain-fatty-acid-CoA ligase 1; Long-chain-fatty-acid-CoA ligase 3; Long-chain-fatty-acid-CoA ligase 4; Long-Chain-Fatty-Acid-Coa Synthetase; Low density lipoproteins (LDL); Low-affinity cationic amino acid transporter-2; Low-Density Lipoprotein Receptor; Lq2; L-Rhamnose Isomerase; L-serine dehydratase; L-Sulfolactate Dehydrogenase; L-Threonine-O-3-Phosphate Decarboxylase; L-type amino acid transporter 1 (LAT1); L-type amino acid transporter 2; Luciferase; Lumazine Synthase; Luteinizing Hormone Releasing Hormone (LHRH) Receptor; L-Xylulose Reductase; Lymphocyte function-associated antigen 1 (CD11a antigen); Lysine Biosynthesis Enzyme; Lysine hydroxylase; Lysozyme; Lysozyme C; Lysozyme Insertion Mutant With Ala Inserted; Lysozyme; Lysozyme Mutant With Cys 54 Replaced By Thr; Lysyl Oxidase; Lysyl Oxidase; Lysyl-tRNA synthetase; Lytic Murein Transglycosylase B; M=4=Lactate Dehydrogenase; M1 muscarinic acetylcholine receptor; M2 muscarinic acetylcholine receptor; Mac-2 Binding Protein; Macromomycin; Macrophage Metalloelastase; Macrophage Migration Inhibitory Factor; Magnesium-Dependent Phosphatase-1; Major Allergen I Polypeptide, Fused Chain 2; Major Autolysin; Major Capsid Protein; Major Envelope Protein E; Major Nad; Major Pollen Allergen Bet V 1-L; Major Urinary Protein; Major Urinary Protein 2; Major Urinary Protein I; Malate Dehydrogenase; Malate Dehydrogenase; Malate dehydrogenase, cytoplasmic; Malate Dehydrogenase, Glyoxysomal; Malate dehydrogenase, mitochondrial precursor; Malate Synthase G; Male-B363; Malic Enzyme; Malic Enzyme 2; Malonamidase E2; Malonyl Coa: Acyl Carrier Protein Malonyltra; Maltodextrin Glycosyltransferase; Maltodextrin Phosphorylase; Maltodextrin-Binding Protein; Maltodextrin-Binding Protein Male-B133; Maltogenic Amylase; Maltooligosyl Trehalose Synthase; Maltooligosyltrehalose Trehalohydrolase; Maltoporin; Maltose Binding Protein Fused With Designed; Maltose Transport Protein Malk; Maltose-6'-Phosphate Glucosidase; Maltose-Binding Periplasmic Protein; Maltose-Binding Protein; Maltose-Binding Protein Mutant Male31; Maltotetraose-Forming Amylase; Mandelate Racemase; Manganese Peroxidase; Manganese-Dependent Inorganic Pyrophosphatas; Mannan Endo-1,4-Beta-Mannosidase; Mannanase A; Mannitol Dehydrogenase; Mannose Receptor; Mannose-6-Phosphate Isomerase; Mannose-Binding Protein A; Mannose-Binding Protein Associated Serin; Mannose-Binding Protein C; Mannose-Binding Protein-A; Mannose-Binding Protein-C; Mannosyl-Oligosaccharide 1,2-Alpha-Mannosida; Mannosyl-Oligosaccharide Alpha-1,2-Mannosida; Map Kinase P38; Map Kinase-Activated Protein Kinase 2; Maspin Precursor; Mast/stem cell growth factor receptor precursor; Matrix Gla-protein; Matrix metalloprotease 2 (MMP-2); matrix metalloprotease 9 (MMP-9); Matrix Metalloproteinase 3; Matrix Metalloproteinase-16; Matrix Metalloproteinase-2; Matrix Metalloproteinase-8; Matrix Porin; Matrix Porin Outer Membrane Protein F; Matrix protein M2; Mdc-Sign1B Type I Isoform; Mdc-Sign2 Type I Isoform; Medium Chain Acyl-Coa Dehydrogenase; Melatonin Receptor; Melatonin receptor type 1B; Membrane Copper Amine Oxidase; Menb; Merozoite Surface Protein-1; Meso-Diaminopimelate D-Dehydrogenase; Metabotropic glutamate receptor 1; Metabotropic Glutamate Receptor Subtype 1; Meta-Cleavage Product Hydrolase; Metallo Beta-Lactamase II; Metallochaperone Atx1; Methionine adenosyltransferase; Methionine Aminopeptidase; Methionine Aminopeptidase 2; Methionine Gamma-Lyase; Methionine Synthase; Methionine synthase reductase; Methionine-R-sulfoxide reductase; Methionine-R-sulfoxide reductase B2; Methionyl Aminopeptidase; Methionyl-tRNA synthetase; Methoxy Mycolic Acid Synthase 2; Methuselah Ectodomain; Methyl-Accepting Chemotaxis Protein; Methylaspartate Mutase S Chain; Methylated-DNA-protein-cysteine methyltransferase; Methylcrotonoyl-CoA; Methylcrotonoyl-CoA 2; Methylene Tetrahydromethanopterin Dehydrogen; Methylenetetrahydrofolate Dehydrogenase/Cy; Methylenetetrahydrofolate reductase; Methylglyoxal Synthase; Methylmalonate-semialdehyde dehydrogenase; Methylmalonic aciduria protein; Methylmalonyl Coa Decarboxylase; Methylmalonyl-Coa Carboxyltransferase 12S Su; Methylmalonyl-CoA mutase, mitochondrial precursor; Mevalonate Kinase; Mgp-40; Mhc Class I Homolog Mic-A; Microcystin-Lr; microsomal triglyceride transfer protein; Microtubule Motor Protein Ncd; Mimochrome IV, Miniaturized Metalloprotei; Mineralocorticoid Receptor; Minor Core Protein Lambda 3; Mitchondrial carnitine/acylcarnitine carrier protein CACL; Mitochondrial Aconitase; Mitochondrial Aldehyde Dehydrogenase; Mitochondrial aspartate-glutamate carrier protein; Mitochondrial carnitine/acylcarnitine carrier protein; Mitochondrial folate transporter/carrier; Mitochondrial glutamate carrier 1; Mitochondrial glutamate carrier 2; Mitochondrial ornithine transporter 1; Mitochondrial ornithine transporter 2; Mitogen-Activated Protein Kinase 10; Mitogen-Activated Protein Kinase 14; Moad Related Protein; Modification Methylase Hhai; Modification Methylase Rsri; Module-Substituted Chimera Hemoglobin Beta-A; Mol_Id: 1; Molecule: 6-Phospho-Beta-Glucosid; Mol_Id: 1; Molecule: Adenylate Kinase; Chain; Mol_Id: 1; Molecule: Bacteriorhodopsin; Mol_Id: 1; Molecule: Beta-Lactamase II; Syno; Mol_Id: 1; Molecule: Carbamate Kinase-Like C; Mol_Id: 1; Molecule: Cytochrome C2; Chain: A; Mol_Id: 1; Molecule: Endo-1,4-Beta-Xylanase; Mol_Id: 1; Molecule: Glutaredoxin; Engineered; Mol_Id: 1; Molecule: Maltodextrin Phosphoryl; Mol_Id: 1; Molecule: Progesterone Receptor; Molecule: Apomyoglobin; Other_Details: Cryst; Molecule: Cathepsin B; Ec: 3.4.22.1; Mutatio; Molecule: Human ADP-Ribosylation Factor 1; S; Molecule: Protein Kinase C Delta Type; Domain; Molybdenum Cofactor Biosynthesis Protein; Molybdenum Cofactor Biosynthesis Protein A; Molybdopterin Biosynthesis Cnx1; Molybdopterin Converting Factor Subunit 2; Molybdopterin-Guanine Dinucleotide Biosynthe; Momordin; Mono-ADP-Ribosyltransferase C3; Monoamine oxidase A (MAO-A); Monoamine oxidase B (MAO-B); Monocarboxylate transporter 1; Monocarboxylate transporter 2; Monocarboxylate transporter 3; Monocarboxylate transporter 4; Monocarboxylate transporter 5; Monocarboxylate transporter 6; Monocarboxylate transporter 7; Monocarboxylate transporter 8; Monocyte Chemotactic Protein 2; Monocyte Differentiation Antigen Cd14; Mono-Heme C-Type Cytochrome Scya; Monomer Hemoglobin Component III; Monomer Hemoglobin Component IV; Monomeric Sarcosine Oxidase; Monomethylamine Methyltransferase Mtmb1; Morphinone Reductase; Motuporin; M-Phase Inducer Phosphatase 2; Mre11 Nuclease; Mrna Capping Enzyme; Mrna Decapping Enzyme; Mrsd Protein; Mta/Sah Nucleosidase; Mu Class Glutathione S-Transferase Of Isoenz; Mu Class Tetradeca-; Mu-Conotoxin Piiia; Mu-Conotoxin Smiiia; Mucosal Addressin Cell Adhesion Molecule-1; Mu-crystallin homolog; Multidrug Resistance Abc Transporter ATP-Bin; Multidrug Resistance Protein; Multidrug Resistance Protein Mexa; Multidrug-Efflux Transporter 1 Regulator Bmr; Multiple. Antibiotic Resistance Protein Marr; Multiple T-cell antigens (CD1, CD2, CD3, CD5, CD5, CD7, CD8); multivitamin transporter; Muscarinic acetylcholine receptor M3; Muscarinic acetylcholine receptor M4; Muscarinic acetylcholine receptor M5; Mutator Mutt Protein; Muth; Mycotic Acid Synthase; Myoglobin; Myohemerythrin; Myo-Inositol Hexaphosphate Phosphohydrol; Myo-Inositol Hexaphosphate Phosphohydrolase; Myo-Inositol Monophosphatase; Myo-Inositol-1-Phosphate Synthase; Myo-Inositol-1-Phosphate Synthase; Myo-Inositol-1-Phosphate Synthase-Related Pr; Myosin; Myosin Ie Heavy Chain; Myosin II Heavy Chain; Myosin II Heavy Chain Fused To Alpha-Actini; Myosin-3 Isoform; Myristoyl-Coa: Protein N-Myristoyltransferas; Myrosinase; N Utilization Substance Protein B Homolog; N, N-Dimethylglycine Oxidase; N-4 Cytosine-Specific Methyltransferase Pvu; N5-Carboxyaminoimidazole Ribonucleotide Synt; Na+/K+/2Cl-co-transporter; N-Acetylgalactosamine-4-Sulfatase; N-Acetylglucosamine-1-Phosphate Uridyltransf; N-Acetylglucosamine-6-Phosphate Deacetylase; N-Acetyllactosaminide Alpha-1,3-Galactosylt; N-Acetyllactosaminide Alpha-1,3-Galactosyltr; N-Acetyl-L-Ornithine Carbamoyltransferase; N-Acetylneuraminate Lyase; N-Acetylneuraminate Lyase Subunit; N-Acylamino Acid Racemase; N-acylglucosamine 2-epimerase; Nad; NAD(P) transhydrogenase, mitochondrial precursor; Nad-Dependent Alcohol Dehydrogenase; Nad-Dependent Deacetylase 2; Nad-Dependent Formate Dehydrogenase; Nad-Dependent Malic Enzyme; Nad-Dependent Malic Enzyme; Nad-Dependent Malic Enzyme, Mitochondria; NAD-dependent malic enzyme, mitochondrial precursor; Nadh Oxidase; Nadh Oxidase/Nitrite Reductase; Nadh Peroxidase; Nadh Pyrophosphatase; Nadh-Azoreductase, Fmn-Dependent; NADH-cytochrome b5 reductase; Nadh-Dependent Butanol Dehydrogenase; NADH-ubiquinone oxidoreductase 13 kDa-A subunit, mitochondrial precursor; NADH-ubiquinone oxidoreductase 13 kDa-B subunit; NADH-ubiquinone oxidoreductase 15 kDa subunit; NADH-ubiquinone oxidoreductase 18 kDa subunit, mitochondrial precursor; NADH-ubiquinone oxidoreductase 19 kDa subunit; NADH-ubiquinone oxidoreductase 20 kDa subunit, mitochondrial precursor; NADH-ubiquinone oxidoreductase 23 kDa subunit, mitochondrial precursor; NADH-ubiquinone oxidoreductase 24 kDa subunit, mitochondrial precursor; NADH-ubiquinone oxidoreductase 30 kDa subunit, mitochondrial precursor; NADH-ubiquinone oxidoreductase 39 kDa subunit, mitochondrial precursor; NADH-ubiquinone oxidoreductase 42 kDa subunit, mitochondrial precursor; NADH-ubiquinone oxidoreductase 49 kDa subunit, mitochondrial precursor; NADH-ubiquinone oxidoreductase 51 kDa subunit, mitochondrial precursor; NADH-ubiquinone oxidoreductase 75 kDa subunit, mitochondrial precursor; NADH-ubiquinone oxidoreductase 9 kDa subunit, mitochondrial precursor; NADH-ubiquinone oxidoreductase AGGG subunit, mitochondrial precursor; NADH-ubiquinone oxidoreductase ASHI subunit, mitochondrial precursor; NADH-ubiquinone oxidoreductase B12 subunit; NADH-ubiquinone oxidoreductase B14 subunit; NADH-ubiquinone oxidoreductase B15 subunit; NADH-ubiquinone oxidoreductase B16.6 subunit; NADH-ubiquinone oxidoreductase B17 subunit; NADH-ubiquinone oxidoreductase B18 subunit; NADH-ubiquinone oxidoreductase B22 subunit; NADH-ubiquinone oxidoreductase B8 subunit; NADH-ubiquinone oxidoreductase B9 subunit; NADH-ubiquinone oxidoreductase chain 1; NADH-ubiquinone oxidoreductase chain 2; NADH-ubiquinone oxidoreductase chain 3; NADH-ubiquinone oxidoreductase chain 4; NADH-ubiquinone oxidoreductase chain 4L; NADH-ubiquinone oxidoreductase chain 5; NADH-ubiquinone oxidoreductase chain 6; NADH-ubiquinone oxidoreductase KFYI subunit, mitochondrial precursor; NADH-ubiquinone oxidoreductase MLRQ subunit; NADH-ubiquinone oxidoreductase MLRQ subunit homolog; NADH-ubiquinone oxidoreductase MNLL subunit; NADH-ubiquinone oxidoreductase MWFE subunit; NADH-ubiquinone oxidoreductase PDSW subunit; NADH-ubiquinone oxidoreductase SGDH subunit, mitochondrial precursor; NADH-ubiquinone oxidoreductase subunit B14.5a; NADH-ubiquinone oxidoreductase subunit B14.5b; NADH-ubiquinone oxidoreductase subunit B14.7; NADH-ubiquinone oxidoreductase subunit B17.2; Nadp; Nadp Dependent Non Phosphorylating Glycerald; Nadp-Dependent Alcohol Dehydrogenase; NADP-dependent malic enzyme; NADP-dependent malic enzyme, mitochondrial precursor; Nadp-Dependent Mannitol Dehydrogenase; Nadp-Dependent Nonphosphorylating Glyceralde; Nadph Dehydrogenase 1; Nadph Dependent Thioredoxin Reductase; Nadph\: Ferredoxin Oxidoreductase; Nadph-Cytochrome P450 Reductase; Nadph-Flavin Oxidoreductase; Nadp-Malate Dehydrogenase; Nagd Protein, Putative; Naip; Namn Adenylyltransferase; Nbla; N-Carbamyl-D-Amino Acid Amidohydrolase; Ndx1; Nei Endonuclease Viii-Like 1; Neocarzinostatin; Neopullulanase; Neopullulanase 2; Neprilysin; N-Ethylmaleimide Sensitive Fusion Protein; Neural Globin; Neural Hemoglobin; Neural Kinase, Nuk=Eph/Elk/Eck Family Recept; Neuraminidase; Neuraminidase; Neuraminidase N2; Neuraminidase N9; Neuroglobin; Neuronal Calcium Sensor 1; Neuropeptide Y; Neuropsin; Neurotensin receptor type 2; Neurotoxin Bmk M4; Neurotoxin Bmk37; Neutral amino acid transporter A; Neutral amino acid transporter B; m Neutral Protease II; Neutrophil Collagenase; Neutrophil elastase; Neutrophil Gelatinase; Neutrophil Gelatinase-Associated Lipocalin; Neutrophil-Activating Protein A; NG,NG-dimethylarginine dimethylaminohydrolase 1; NG,NG-dimethylarginine dimethylaminohydrolase 2; Nh; Niacin receptor HM74A; Nickel Responsive Regulator; Nicotinamide Mononucleotide Adenylyl Tra; Nicotinamide Mononucleotide Adenylyl Transfe; Nicotinamide Mononucleotide Adenylyltransfer; Nicotinamide Mononucleotide Adenylyltransfer; Nicotinamide Nucleotide Transhydrogenase; Nicotinamide Nucleotide Transhydrogenase; Nicotinamide Nucleotide Transhydrogenase, Su; Nicotinamide-Nucleotide Adenylyltransferase; Nicotinate D-ribonucleotide phyrophsopate phosphoribosyltransferase; Nicotinate Mononucleotide:5,6-Dimethylbenzi; Nicotinate N-methyltransferase; Nicotinate Phosphoribosyltransferase; Nicotinate Phosphoribosyltransferase From Th; Nicotinate-Nucleotide Adenylyltransferase; Nicotinate-Nucleotide-Dimethylbenzimidazole; nicotinic acetylcholine (ganglion) receptor; Nicotinic acetylcholine Receptor alpha2/alpha3; Nima-Related Protein; Nine-Haem Cytochrome C; Nine-Heme Cytochrome C; Nit-Fragile Histidine Triad Fusion Protein; Nitrate Reductase; Nitric Oxide Reductase; Nitric Oxide Synthase; Nitric oxide synthase IIB; Nitric Oxide Synthase, Inducible; Nitric-Oxide Reductase Cytochrome P450 55A1; Nitric-Oxide Synthase; Nitric-oxide synthase brain; Nitric-Oxide Synthase Homolog; Nitric-oxide synthase IIC; Nitric-Oxide Synthase, Brain; Nitric-Oxide Synthase, Endothelial; Nitrite Reductase; Nitrogen Fixation Regulatory Protein Fixl; Nitrogen Regulation Protein; Nitrogen Regulatory Iia Protein; Nitrogen Regulatory Protein Pii; Nitrogenase Iron Protein; Nitrogenase Iron Protein 1; Nitrophorin 1; Nitrophorin 2; Nitrophorin 4; Nitroreductase; Nitroreductase Family Protein; Nitrosocyanin; Nitrous Oxide Reductase; Nitrous-Oxide Reductase; Nk Receptor; NMDA receptor; N-Methyl-D-Aspartate Receptor Subunit 1; Nmra; Nogalonic Acid Methyl Ester Cyclase; Non Catalytic Protein 1; Nonaheme Cytochrome C; Non-ATP Dependent L-Selective Hydantoina; Non-Catalytic Protein 1; Non-heme chloroperoxidase; Nonspecific Lipid Transfer Protein; Nonspecific Lipid-Transfer Protein; Nonstructural Polyprotein Pp1A; Non-Symbiotic Hemoglobin; Not Applicable; NPC1L1 (Niemann-Pick C1 Like 1) Protein transporter; Npqtn Specific Sortase B; Nrdi Protein; NRH dehydrogenase [quinone] 2; Ntpase P4; Nuclear Inclusion Protein A; Nuclear receptor OB1; Nuclear Receptor Ror-Alpha; Nucleoside 2-Deoxyribosyltransferase; Nucleoside Diphosphate Kinase; Nucleoside Diphosphate Kinase A; Nucleoside Diphosphate Kinase II; Nucleoside Diphosphate Kinase, Cytosolic; Nucleoside Diphosphate Transferase; Nucleoside-Specific Channel-Forming Protein; Nudix Homolog; 06-Alkylguanine-DNA Alkyltransferase; Obelin; Odorant Binding Protein; Odorant Binding Protein Lush; Odorant-Binding Protein; Old Yellow Enzyme; Olfactory Marker Protein; Oligopeptide Abc Transporter, Periplasmi; Omegac-Txix; Omp Synthase; Ompk36; Opioid delta Receptor (OP1); Opioid kappa Receptor (OP2); Opioid mu Receptor (OP3); Opioid sigma 1 Receptor; Opioid sigma Receptor (OP4); Orange Carotenoid Protein; Orc2; Orexin-A; Orf, Conserved Hypothetical Protein; Orf3; Organic acid transporter 3 (OAT3); organic anion transporter (MRP1, MRP2 and MRP3, MRP4 and MRP5); Organic cation/carnitine transporter 1; Organic cation/carnitine transporter 2; Organic Hydroperoxide Resistance Protein; Ornithine Aminotransferase; Ornithine aminotransferase, mitochondrial; Ornithine Carbamoyltransferase; Ornithine carbamoyltransferase, mitochondrial; Ornithine Cyclodeaminase; Ornithine Decarboxylase; Ornithine decarboxylase antizyme; Ornithine Transcarbamoylase; Orotidine 5'-Monophosphate Decarboxylase; Orotidine 5'-Phosphate Decarboxylase; Orotidine Monophosphate Decarboxylase; Orphan Nuclear Receptor Pxr; Osmolarity Sensor Protein; Osmoprotection Protein; Osmotically Inducible Protein C; Osteocalcin; O-Succinylbenzoate Synthase; Outer Membrane Lipoprotein Lolb; Outer Membrane Phospholipase A; Outer Membrane Protein A; Outer Membrane Protein F; Outer Membrane Protein Nspa; Outer Membrane Protein Tolc; Outer Membrane Protein X; Outer Protein Yopm; Ovalbumin; Ovocleidin; Ovomucoid; Ovotransferrin; Ovotransferrin; Oxygen-Insensitive Nad; Oxygen-insensitive NAD(P)H nitroreductase; Oxygen-Insensitive Nadph Nitroreductase; Oxysterols Receptor Lxr-Beta; Oxytocin receptor (Neurophysin 1); P protein [Includes: DNA-directed DNA polymerase; P protein [Includes: DNA-directed DNA polymerase, RNA-directed DNA polymerase, Ribonuclease H]; P/neurokinin 1 Receptor; P1 Nuclease; P2 Myelin Protein; P2 Protein; P2Y12 platelet ADP Receptor; P-30 Protein; P300/Cbp Associating Factor; P35; P450 Epoxidase; P450 Monooxygenase; P450Cin; P64K; P97; Palmitoyl Protein Thioesterase 1; Palmitoyl-Protein Thioesterase 2 Precursor; P-Aminobenzoate Synthase Component I; pancreatic alpha amylase; Pancreatic alpha-amylase precursor; Pancreatic Hormone; Pancreatic Lipase Related Protein 1; Pancreatic Lipase Related Protein 2; pancreatic triacylglycerol lipase; Pancreatic triacylglycerol lipase [Precursor]; Pancreatic Trypsin Inhibitor; Pantoate-Beta-Alanine Ligase; Pantoate-Beta-Alanine Ligase; Pantothenate kinase; Pantothenate Synthetase; Papain; Para-aminobenzoate synthase component I; Para-aminobenzoic acid (PABA); Parathion Hydrolase; Parm; Parvalbumin; Parvalbumin Alpha; Pbcv-1 DNA Ligase; Pcza361.16; P'-D-Mannopyranosyl Ester), GDP-Mannose 6-Dehydrogenase; Pea Lectin; Peanut Lectin; Peanut Peroxidase, Major Cationic Isozym; Pectate Lyase; Pectin Methylesterase; Penicillin V Acylase; Penicillin-binding protein 1A; Penicillin-binding protein 1B; Penicillin-binding protein 2; Penicillin-Binding Protein 2A; Penicillin-binding protein 2B; Penicillin-Binding Protein 2X; Penicillin-binding protein 3; Penicillin-binding protein 4 precursor; Penicillin-Binding Protein 5; Penicillin-binding protein 5 precursor; Penicillin-binding proteins 1A/1B; Penicillin-Insensitive Murein Endopeptidase; Penicillopepsin; Pentaerythritol Tetranitrate Reductase; Penton Protein; Pentosyltransferase; Pepp1; Peptaibol; Peptide; Peptide Amidase; Peptide Deformylase; Peptide Deformylase 2; Peptide Deformylase Defb; Peptide Deformylase Pdf1; Peptide Methionine Sulfoxide Reductase; Peptide N-Myristoyltransferase; Peptide Transporter Tap1; Peptide-N; Peptidic Toxin Nodularin; Peptidoglycan Recognition Protein I-Alph; Peptidoglycan Recognition Protein Sa Cg11709; Peptidoglycan synthetase ftsl; Peptidyl-Glycine Alpha-Amidating Monooxygena; Peptidylglycine Alpha-Hydroxylating Monooxyg; Peptidyl-Lys Metalloendopeptidase; Peptidyl-Prolyl Cis-Trans Isomerase; Peptidyl-Prolyl Cis-Trans Isomerase 5; Peptidyl-Prolyl Cis-Trans Isomerase A; Pepv; Peridinin-Chlorophyll Protein; Peripheral nerve Sodium channel 3; Peripheral nerve sodium channel 5; Peripheral Plasma Membrane Cask; Periplasmic Divalent Cation Tolerance Pr; Periplasmic Divalent Cation Tolerance Protein; Periplasmic Molybdate-Binding Protein; Peroxidase; Peroxidase C1A; Peroxidase N; Peroxidase/Catalase T; Peroxiredoxin; Peroxiredoxin 5 Residues 54-214; Peroxiredoxin 5, mitochondrial precursor; Peroxisomal bifunctional enzyme; Peroxisomal Carnitine O-Octanoyltransfer; Peroxisomal Carnitine O-Octanoyltransferase; Peroxisomal Hydratase-Dehydrogenase-Epim; Peroxisomal Hydratase-Dehydrogenase-Epimeras; Peroxisomal multifunctional enzyme type 2; Peroxisomal Trans 2-Enoyl Coa Reductase; Peroxisome Proliferator Activated Receptor A; Peroxisome Proliferator Activated Receptor D; Peroxisome Proliferator Activated Receptor G; pH 2.5 Acid Phosphatase; Phage T4 Lysozyme Insertion Mutant With Ser; Phaseolin; Phenazine Biosynthesis Protein Phzd; Phenazine Biosynthesis Protein Phzf; Phenazine Biosynthesis Protein Phzg; Phenol 2-Hydroxylase Component B; Phenol 2-Monooxygenase; Phenol Hydroxylase; Phenylacetone Monooxygenase; Phenylalanine Ammonia-Lyase; Phenylalanine Ammonia-Lyase 1; Phenylalanine Hydroxylase; Phenylalanine-4-Hydroxylase; Phenylalanine-Regulated 3-Deoxy-D-Arabino-H; Phenylalanyl-tRNA synthetase; Phenylalanyl-tRNA synthetase alpha chain; Phenylalanyl-tRNA synthetase beta chain; Phenylethanolamine N-Methyltransferase; Phenylethylamine Oxidase; Pheromone Binding Protein; Pheromone-Binding Protein; Pheromone-Binding Protein Asp1; Phoq Histidine Kinase; Phosphatase; Phosphatase; Phosphate Acetyltransferase; Phosphate-Binding Protein; Phosphatidylcholine Transfer Protein; Phosphatidylethanolamine Binding Protein; Phosphatidylethanolamine-Binding Protein; Phosphatidylinositol 3-Kinase Catalytic Subu; Phosphatidylinositol Phosphate Phosphatase; Phosphatidylinositol Transfer Protein A1; Phosphatidylinositol Transfer Protein Alpha; Phosphatidylinositol Transfer Protein Sec14P; Phosphatidylinositol-Specific Phospholipase; Phosphatidylserine decarboxylase proenzyme; Phosphatidylserine receptor; Phospho-2-Dehydro-3-Deoxyheptonate Aldolase; Phospho-2-Dehydro-3-Deoxyheptonate Aldolase; Phosphocarrier Protein Hpr; Phosphodiesterase 4D; Phosphoenolpyruvate Carboxykinase; Phosphoenolpyruvate Carboxykinase, Cytos; Phosphoenolpyruvate Carboxykinase, Cytosolic; Phosphoenolpyruvate Carboxylase; Phosphoenolpyruvate Mutase; Phosphoenolpyruvate Phosphomutase; Phosphonzyme Intermediate Of Fru-2,6-Bi; Phosphofructokinase; Phosphoglucose Isomerase; Phosphoglycerate kinase; Phosphoglycerate kinase 1; Phosphoglycerate kinase, glycosomal; Phosphoglycerate Mutase; Phosphoglycerate Mutase 1; Phosphoglycolate Phosphatase; Phosphoheptose Isomerase; Phosphoinositide-Specific Phospholipase C, I; Phospholipase A=2=; Phospholipase A2; Phospholipase A2 Homolog; Phospholipase A2 Homolog 2; Phospholipase A2 inhibitory protein; Phospholipase A2 Isoform 2; Phospholipase A2 Isoform 3; Phospholipase A2, Major Isoenzyme; Phospholipase C; Phospholipase C Delta-1; Phosphomannomutase; Phosphomethylpyrimidine Kinase; Phosphonoacetaldehyde Hydrolase; Phosphonoacetate Hydrolase; Phosphopantetheine Adenylyltransferase; Phosphoribosyl Anthranilate Isomerase; Phosphoribosyl Pyrophosphate Synthetase; Phosphoribosylamidoimidazole-Succinocar; Phosphoribosylamine-Glycine Ligase; Phosphoribosylformylglycinamidine Synth; Phosphoribosyiglycinamide Formyltransferase; Phosphoribosyltransferase-Related Protein; Phosphorylated Map Kinase P38-Gamma; Phosphoserine Aminotransferase; Phosphoserine Phosphatase; Phosphotriesterase; Phosphotriesterase Homology Protein; Photoactive Yellow Protein; Photolyase; Phy3 Protein; P-Hydroxybenzoate Hydroxylase; P-Hydroxybenzoate Hydroxylase Complexed With; P-Hydroxybenzoate Hydroxylase Mutant With Ty; Phytase; Phytochrome Response Regulator Rcpa; Phytochrome Response Regulator Rcpb; Phytohemagglutinin-L; Pi Glutathione Transferase; Pigment Epithelium-Derived Factor; Pituitary Adenylate Cyclase Activating Po; Placenta Growth Factor; Plasma retinol-binding protein; Plasmepsin 2; Plasmepsin II; Plasminogen; Plasminogen Activator; Plasminogen Activator Inhibitor-1; Plasminogen precursor; Plasmodium proton pump; Platelet Glycoprotein Ib Alpha Chain Precurs; Platelet-Activating Factor Acetylhydrolas; Platelet-Activating Factor Acetylhydrolase; PML-RAR Alpha Protein; Pms1 Protein Homolog 2; Pnp Oxidase; Pokeweed Antiviral Protein; Pol Polyprotein; Pollen Allergen Phl P 1; Poly; Poly [ADP-Ribose] Polymerase-1; Polyamine Oxidase; Polyandrocarpa Lectin; Polygalacturonase; Polygalacturonase I; Polygalacturonase II; Polygalacturonase Inhibiting Protein; Polynucleotide Kinase; Polyomavirus Coat Protein Vp1; Polyomavirus Vp1 Pentamer; Polypeptide Deformylase; Polypeptide N-Acetylgalactosaminyltransferas; Polyprotein; Polysialic Acid Capsule Biosynthesis Protein; Porcine Alpha-Amylase; Porcine Pancreatic Spasmolytic Polypepti; Porin; Porphobilinogen Deaminase; Porphobilinogen Synthase; Possible 3-Mercaptopyruvate Sulfurtransf; Possible G-T Mismatches Repair Enzyme; Postsynaptic Density Protein; Postsynaptic Density Protein 95; Potassium Channel; Potassium Channel Blocking Toxin 1; Potassium Channel Protein Rck4; Potassium channel subfamily K member 1; Potassium channel subfamily K member 2; Potassium channel subfamily K member 6; Potassium large conductance calcium-activated channel, subfamily M, alpha member 1; Potassium transporter (bacterial); Potassium voltage-gated channel subfamily A member 1; Potassium voltage-gated channel subfamily E member 1; Potassium voltage-gated channel subfamily H member 2; Potassium voltage-gated channel subfamily H member 6; Potassium voltage-gated channel subfamily H member 7; Potassium voltage-gated channel subfamily KQT member 1; Potassium/Sodium Hyperpolarization-Activ; Potassium/Sodium Hyperpolarization-Activated; Potassium-Transporting Atpase B Chain; Potassium-transporting ATPase beta chain; Pp60 V-Src Tyrosine Kinase Transforming Prot; PPAR-alpha; Ppc Decarboxylase Athal3A; Ppca; Ppr; Pr3; Precorrin-6Y Methyltransferase/Putative; Precorrin-8X Methylmutase; Precursor Form Of Glucose-Fructose Oxiredu; Precursor Of Periplasmic Sugar Receptor; Predicted Amidotransferase; Predicted Cobalamin Binding Protein; Preprotein Translocase Seca; Preprotein Translocase Seca 1 Subunit; Preprotein Translocase Seca Subunit; Prfa; Prion Protein; Probable 2-Phosphosulfolactate Phosphata; Probable Ammonium Transporter; Probable arabinosyltransferase A; Probable arabinosyltransferase B; Probable arabinosyltransferase C; Probable Aromatic Acid Decarboxylase; Probable ATP-Dependent RNA Helicase P47; Probable Butyrate Kinase 2; Probable Cell Division Inhibitor Mind; Probable Cysteine Desulfurase; Probable Fosfomycin Resistance Protein; Probable Glutaminase Ybas; Probable Glutaminase Ybgj; Probable Gtpase Engc; Probable GTP-Binding Protein Enga; Probable Inorganic Polyphosphate/ATP-Nad Kin; Probable Inorganic Polyphosphate/ATP-Nad Kin; Probable leucyl-tRNA synthetase, mitochondrial; Probable low molecular weight protein-tyrosine-phosphatase epsP; Probable Malate Synthase G; Probable Methylisocitrate Lyase; Probable Polysaccharide Deacetylase Pdaa; Probable Pyridoxamine 5'-Phosphate Oxidase; Probable S-Adenosylmethionine:2-Demethylmen; Probable Serine/Threonine-Protein Kinase; Probable Serine/Threonine-Protein Kinase Pel; Probable Serine/Threonine-Protein Kinase Pkn; Probable tautomerase ydcE; Probable tyrosyl-tRNA synthetase, mitochondrial; Probable Uracil Phosphoribosyltransferase; Procarboxypeptidase B; Proclavaminate Amidino Hydrolase; Profilin II; Progesterone Receptor; Progesterone Receptor (PR); Programmed Cell Death Protein 8; Programmed Cell Death Protein 8; Prolactin receptor precursor; Proline Dehydrogenase; Proline Iminopeptidase; Proline oxidase; Proline-tRNA Synthetase; Prolyl Endopeptidase; Prolyl hydroxylase; Prolyl Oligopeptidase; Prophospholipase A=2=; Propionyl-CoA carboxylase alpha chain; Propionyl-CoA carboxylase beta chain; Propionyl-Coa Carboxylase Complex B Subunit; Prostacyclin synthase; Prostaglandin D2 receptor; Prostaglandin E2 receptor, EP1 subtype; Prostaglandin E2 receptor, EP2 subtype; Prostaglandin Endoperoxide H Synthase-1; Prostaglandin F Synthase; Prostaglandin F2-alpha receptor; Prostaglandin G/H Synthase 1 Precursor; Prostaglandin G/H Synthase 2; Prostaglandin H2 Synthase; Prostaglandin H2 Synthase-1; Prostaglandin H2 Synthase-2; Prostaglandin Receptor; Prostaglandin-E2 9-Reductase; Prostate-specific membrane antigen (7E11-05.3 antigen/FOLH1-human/glutamate carboxypeptidase II); Prostatic Acid Phosphatase; Protease; Protease II; Protease Retropepsin; Protease Synthase and Sporulation Negati; Protease Vii; Protegrin 3; Protein: Ketosteroid Isomerase; Protein 1 D10; Protein Arginine Methyltransferase Prmt3; Protein Arginine N-Methyltransferase 1; Protein C; Protein Fkbi; Protein Kinase C; Protein Kinase C Interacting Protein; Protein Kinase C, Theta Type; Protein Kinase Ck2; Protein Mat Protein Methyltransferase Hemk; Protein Ninb; Protein Rdmb; Protein With Similarity To Flavin-Contai; Protein Ybgc; Protein Ybhh; Protein Ycei; Protein Yebr; Protein Yesu; Protein Yfbg; Protein Yojf; Protein Ytnj; Protein: Igfbp-1 Antagonist; Proteinase; Proteinase K; Protein-Glutamine Gamma-Glutamyltransferase; Protein-Glutamine Glutamyltransferase E; Protein-glutamine glutamyltransferase E [precursor]; Protein-Glutamine Glutamyltransferase E3; Protein-L-Isoaspartate; Protein-L-Isoaspartate O-Methyltransferase; Protein-Tyrosine Phosphatase 1B; Protein-Tyrosine Phosphatase Yoph; Protein-Tyrosine Phosphatase, Non-Recept; Protein-Tyrosine Phosphatase, Non-Receptor T; Protein-Tyrosine-Phosphatase; Prothrombin; Prothrombin; Prothrombin Fragment 1; Protoheme Ferrolyase; Proton-coupled amino acid transporter 1; Proto-Oncogene Serine/Threonine-Protein; Proto- Oncogene Serine/Threonine-Protein Kina; Proto-Oncogene Tyrosine-Protein Kinase Abl1; Proto-Oncogene Tyrosine-Protein Kinase Lck; Proto-Oncogene Tyrosine-Protein Kinase S; Proto-Oncogene Tyrosine-Protein Kinase Src; Protooncoprotein; Protoporphyrinogen Oxidase, Mitochondria; P-Selectin; Pseudoazurin; Pseudocatalase; Pseudomonas Aeruginosa Lectin II; Psychrophilic Phosphatase I; Pteridine Reductase; Pteridine Reductase 1; Pteridine Reductase 2; Pts System, Chitobiose-Specific Iib Comp; Pulmonary Surfactant-Associated Protein A; Pulmonary Surfactant-Associated Protein D; Pumilio 1; Pur Operon Repressor; Pure; Purine Nucleoside Phosphorylase; Purine Regulatory Protein Yabj; Purine Trans Deoxyribosylase; Purine-Nucleoside Phosphorylase; Purple Acid Phosphatase; Purple Acid Phosphatase; Putative Acyl-Coa Thioester Hydrolase Hi0827; Putative Alkylsulfatase Atsk; Putative Alpha-L-Fucosidase; Putative Aspartate Aminotransferase; Putative ATP-Dependent Clp Protease Proteoly; Putative Betaine Aldehyde Dehydrogenase; Putative Blue Light Receptor; Putative Cellulase; Putative Cellulase Cel6; Putative Clc Family, Chlorine Transport Prot; Putative Cytochrome P450; Putative Cytochrome P450 154A1; Putative Family 31 Glucosidase Yici; Putative Flavin Oxidoreducatase; Putative Glur0 Ligand Binding Core; Putative Glur0 Ligand Binding Core; Putative G-protein coupled receptor 40; Putative Ketoacyl Reductase; Putative Lipase From The G-D-S-L Family; Putative Mannosyl-3-Phosphoglycerate Phospha; Putative Modulator Of DNA Gyrase; Putative Nadph Dependent Oxidoreductases; Putative Oxalate Decarboxylase; Putative Oxidoreductase Rv2002; Putative Oxidoreductase Rv2002; Putative Phosphatase; Putative Polyprotein/Phosphatase; Putative Protease La Homolog; Putative Riboflavin Kinase; Putative Snrnp Sm-Like Protein; Putative Sugar Kinase; Putative Transcriptional Regulator; Putative Xylanase; Putidaredoxin Reductase; Putrescine-Binding Protein; Pyelonephritic Adhesin; Pyranose Oxidase; Pyridoxal kinase; Pyridoxal Phosphate Biosynthetic Protein Pdx; Pyridoxal phosphate phosphatase; Pyridoxamine Kinase; Pyridoxine 5'-Phosphate Oxidase; Pyridoxine 5'-Phosphate Oxidase; Pyridoxine 5'-Phosphate Synthase; Pyridoxine-5'-phosphate oxidase; Pyrimidine Nucleoside Phosphorylase; Pyrogenic Exotoxin B; Pyrophosphatase; Pyrr Bifunctional Protein; Pyrroline-5-carboxylate reductase 1; Pyrroline-5-carboxylate reductase 2; Pyrroline-5-carboxylate synthetase; Pyruvate carboxylase; Pyruvate Decarboxylase; Pyruvate dehydrogenase; Pyruvate Dehydrogenase E1 Component; Pyruvate dehydrogenase E1 component alpha subunit, somatic form, mitochondrial precursor; Pyruvate dehydrogenase E1 component alpha subunit, testis-specific form, mitochondrial precursor; Pyruvate Dehydrogenase Kinase, Isozyme 2; Pyruvate dehydrogenase protein X component, mitochondrial precursor; Pyruvate Kinase; Pyruvate kinase, isozymes Ml/M2; Pyruvate Kinase, Isozymes R/L; Pyruvate Oxidase; Pyruvate Phosphate Dikinase; Pyruvate, Orthophosphate Dikinase; Pyruvate:ferredoxin oxidoreductase (PFOR) in anaerobes; Pyruvate-Ferredoxin Oxidoreductase; Pyruvoyl-Dependent Arginine Decarboxylase; Pyst1; Quercetin 2,3-Dioxygenase; Queuine tRNA-Ribosyltransferase; Quinohemoprotein Alcohol Dehydrogenase; Quinolinate Phosphoribosyl Transferase; Quinolinic Acid Phosphoribosyltransferase; Quinone Oxidoreductase; Quinone Reductase; Quinone Reductase Type 2; Quinone-Reductase; Quinoprotein Ethanol Dehydrogenase; Rab GDP Disossociation Inhibitor Alpha; Rab6 Gtpase; RAC serine/threonine-protein kinase; Rac-Alpha Serine/Threonine Kinase; Radixin; RAF proto-oncogene serine/threonine-protein kinase; Ramoplanin; Ran; Rap2A; Ras-Related C3 Botulinum Toxin Substrate 1 I; Ras-Related Protein Rab-11A; Ras-Related Protein Rab-5A; Ras-Related Protein Rab-7; Ras-Related Protein Rab-9A; Ras-Related Protein Ral-A; Ras-Related Protein Sec4; Rat ADP-Ribosylation Factor-1; Rat Synapsin I; Rc-Rnase6 Ribonuclease; Reca; Reca Protein; Receptor Protein-Tyrosine Kinase Erbb-3; Receptor-Type Adenylate Cyclase Gresag 4.1; Recombinant Lignin Peroxidase H8; Recombination Protein Recr; Red Fluorescent Protein Fp611; Redox-Sensing Transcriptional Repressor; Regulatory Protein Blarl; Regulatory Protein Teni; Renal Dipeptidase; Renin; Renin; Replicase, Hydrolase Domain; Replication Protein; Resistin; Response regulator pleb; Restriction Endonuclease Bglii; Reticulon 4 Receptor; Reticulon 4 Receptor; Retinal dehydrogenase 1; Retinal dehydrogenase 2; Retinal Dehydrogenase Type II; Retinoic acid induced 3 protein; Retinoic acid receptor alpha; Retinoic Acid Receptor Beta; Retinoic Acid Receptor Gamma-1; Retinoic Acid Receptor Gamma-2; Retinoic acid receptor responder protein 1; Retinoic acid receptor RXR-alpha; Retinoic acid receptor RXR-beta; Retinoic acid receptor RXR-gamma; Retinoid X Receptor, Beta; Retinol Binding Protein Complexed With Axero; Retinol Dehydratase; retinol dehydrogenase 12; retinol dehydrogenase 13; Retinol-binding protein I; Retinol-binding protein II; Retinol-binding protein III; Retinol-binding protein IV; Retropepsin; Reverse Gyrase; Rfbc; Rfcs; Rhamnogalacturonan Acetylesterase; Rhamnogalacturonase A; Rhamnulose-1-Phosphate Aldolase; Rhizome Secoisolariciresinol Dehydrogenase; Rhoa; Rhodanese; Rhodopsin; Rho-Related GTP-Binding Protein Rhoe; Riboflavin kinase; Riboflavin Kinase/Fmn Adenylyltransferase; Riboflavin Synthase; Riboflavin Synthase Alpha Chain; Ribokinase; Ribonuclease; Ribonuclease 1; Ribonuclease 4; Ribonuclease A; Ribonuclease Hii; Ribonuclease Mc; Ribonuclease Mc1; Ribonuclease Pancreatic; Ribonuclease pH; Ribonuclease Sa; Ribonuclease T1; Ribonuclease U2; Ribonuclease UK114; Ribonuclease Z; Ribonuclease, Seminal; Ribonucleoside-Diphosphate Reductase 2 Alpha; Ribonucleoside-Diphosphate Reductase M2 Chai; Ribonucleotide reductase; Ribonucleotide Reductase R2; Ribonucleotide Reductase R2-2 Small Subunit; Ribonucleotide Reductase Subunit R2F; Ribose 5-Phosphate Isomerase; Ribose-5-Phosphate Isomerase A; Ribose-5-Phosphate Isomerase Rpib; Ribosomal Protein L1; Ribosomal Protein L4; Ribosomal Protein S6 Kinase Alpha 5; Ribosomal Small Subunit Pseudouridine Sy; Ribosomal Small Subunit Pseudouridine Syntha; Ribosome Recycling Factor; Ribosome-Inactivating Protein Alpha-Trichos; Ribulose-1,5 Bisphosphate Carboxylase/Oxygen; Ricin; Ricin A Chain; Right-Handed Coiled Coil Tetramer; Right-Handed Coiled Coil Trimer; RNA 3'-Terminal Phosphate Cyclase; RNA Dependent RNA Polymerase; RNA Ligase 2; RNA Polymerase Alpha Subunit; RNA-Binding Protein Regulatory Subunit; RNA-Dependent RNA Polymerase; RNA-Directed RNA Polymerase; Rnase L Inhibitor; Rnase Ngr3; Rnd3/Rhoe Small GTP-Binding Protein; Rod Shape-Determining Protein Mreb; Rop Ala2Ile2-6; Rubredoxin; Rubredoxin: Oxygen Oxidoreductase; Ruvb; Rv3303C-Lpda; Ryanodine receptor 1; S-Gamma86-Beta-Mercaptoethanol-Lysozyme; S-Gamma97-Beta-Mercaptoethanol Lysozyme; S100A6; S3-Rnase; Saccharopepsin; Saccharopepsin precursor; Saccharopine Reductase; S-Adenosylhomocysteine Hydrolase; S-Adenosyl-L-Homocysteine Hydrolase; S-Adenosyl-L-Methionnine: Salicylic Acid Car; S-Adenosylmethionine Decarboxylase Proen; S-Adenosylmethionine Decarboxylase Proenzyme; S-Adenosylmethionine Synthetase; S-Adenosyl-Methyltransferase Mraw; Salicylic Acid-Binding Protein 2; Salivary Lipocalin; Salivary Nitrophorin; *Salvia officinalis*; Sandostatin; Saposin B; Sar1; Sarcoplasmic/Endoplasmic Reticulum Calcium A; Sarcosine Oxidase; Sarcosine Oxide; Scaffolding Dockerin Binding Protein A; Scavenger receptor class B member 1; Scorpion Neurotoxin; Scytalone Dehydratase; SDHA protein; Sec14-Like Protein 2; SEC14-like protein 3; SEC14-like protein 4; Sec18P; Secretin receptor; Sedolisin; Seed Coat Peroxidase; Seed Lipoxygenase-3; Segmentation Polarity Homeobox Protein Engrai; Segregation Protein; Selenocysteine Lyase; Selenosubtilisin Bpn; Semaphorin 3A; Seminal Plasma Protein Pdc-109; Sensor Kinase Cita; Sensor Protein Fixl; Sensory Rhodopsin II; Sepiapterin Reductase; Serine Acetyltransferase; Serine Carboxypeptidase; Serine Hydroxymethyltransferase; Serine hydroxymethyltransferase (mitochondrial); Serine Hydroxymethyltransferase, Cytosolic; Serine palmitoyltransferase 1; Serine palmitoyltransferase 2; Serine Protease; Serine racemase; Serine/Threonine Kinase 6; Serine/Threonine Protein Kinase Tao2; Serine/Threonine Protein Phosphatase 5; Serine/Threonine Protein Phosphatase Pp1-Gam; Serine/threonine-protein kinase ALS2CR7; Serine/threonine-protein kinase receptor R2; Serine/threonine-protein kinase receptor R3; Serine/Threonine-Protein Kinase Ymr216C; Serine-Carboxyl Proteinase; Serine-pyruvate aminotransferase; Serotonin N-Acetyltransferase; Serotransferrin; Serotransferrin precursor; Serratia Marcescens Aminoglycoside-3-N-Acet; Serum Albumin; Serum albumin precursor; Serum Amyloid P Component; Serum Transferrin; Seryl-tRNA synthetase; Set9; Sex Comb On Midleg Cg9495-Pa; Sex Hormone-Binding Globulin; Sex hormone-binding globulin precursor; Sf11-Rnase; Sfua; Sh3 Domain-Binding Glutamic Acid-Rich Protein; Shiga Toxin B-Chain; Shiga-Like Toxin I B Subunit; Shiga-Like Toxin I Subunit B; Shiga-Like Toxin lie B Subunit; Shikimate 5'-Dehydrogenase; Shikimate 5-Dehydrogenase; Shikimate 5-Dehydrogenase 2; Shikimate Kinase; Short Chain 3-Hydroxyacyl-Coa Dehydrogenase; Short chain 3-hydroxyacyl-CoA dehydrogenase, mitochondrial precursor; Short Chain Acyl-Coa Dehydrogenase; Short-Chain Dehydrogenase/ReduCtase Family M; Shp-2; Siah-1A Protein; Sialic Acid Binding Ig-Like Lectin 7; Sialidase; Sialidase 2; Sialoadhesin; Sigf1-Gfp Fusion Protein; Sigma Factor Sigb Regulation Protein Rsbq; Signal Peptidase I; Signal Processing Protein; Signal Processing Protein; Signal Recognition Particle 9/14 Fusion Prot; Signal Recognition Particle Protein; Signal Sequence Recognition Protein Ffh; Signalling Protein Spb; Silent Information Regulator 2; Simian Immunodeficiency Virus; Similar To Synaptotagmini/P65; Similar To Thymidylate Kinase; Sindbis Virus Capsid Protein; Single Stranded DNA Binding Protein; Siroheme Biosynthesis Protein Met8; Siroheme Synthase; Skeletal Dihydropydrine Receptor; Smad2; Small Inducible Cytokine A20; Small inducible cytokine A23 precursor; Small Inducible Cytokine A5; Small Inducible Cytokine B10; Small Nuclear Ribonucleoprotein Homolog; Small Tetraheme Cytochrome C; Sm-Like Archaeal Protein 1; SNAP-25; Sniffer Cg10964-Pa; Sodium- and chloride-dependent creatine transporter 1; Sodium- and chloride-dependent creatine transporter 2; Sodium- and chloride-dependent GABA transporter 1; Sodium- and chloride-dependent neutral and basic amino acid transporter B(0+); Sodium/Hydrogen Exchanger 1; Sodium/potassium-transporting ATPase alpha-1 chain; Sodium/potassium-transporting ATPase gamma chain; Sodium-dependent norepinephrine re-uptake pump; Sodium-dependent proline transporter; Sodium-dependent serotonin re-uptake pump; Soluble Cytochrome B562; Soluble Lytic Transglycosylase Slt70; Soluble Quinoprotein Glucose Dehydrogenase; Soluble Tumor Necrosis Factor Receptor 1; Solute carrier family 12, member 2; Solute carrier family 12, member 4; Solute carrier family 12, member 5; Solute carrier family 12, member 6; Solute carrier family 12, member 7; Solute carrier family 13, member 1; Solute carrier family 13, member 2; Solute carrier family 13, member 3; Solute carrier family 23 member 1; Solute carrier family 23 member 2; Somatostatin receptor type 1; Somatostatin receptor type 2; Sorbitol Dehydrogenase; Sorting Nexin Grd19; sp|O43272|PROD_HUMAN Proline oxidase, mitochondrial precursor (EC 1.5.3.-) (Proline dehydrogenase); sp|P04746|AMYP_HUMAN Pancreatic alpha-amylase precursor; sp|P04798|CP1A1_HUMAN Cytochrome P450 1A1 (EC 1.14.14.1); sp|P05108|C11A_HUMAN Cytochrome P450 11A1; sp|P05177|CP12_HUMAN Cytochrome P450 1A2; sp|P05177|CP1A2_HUMAN Cytochrome P450 1A2 (EC 1.14.14.1); sp|P05181|CP2E1_HUMAN Cytochrome P450 2E1 (EC 1.14.14.1); sp|P05186|PPBT_HUMAN Alkaline phosphatase, tissue-nonspecific isozyme precursor; sp|P08263|GSTA1_HUMAN Glutathione S-transferase A1; sp|P08684|CP3A4_HUMAN Cytochrome P450 3A4 (EC 1.14.13.67); sp|P09210|GSTA2_HUMAN Glutathione S-transferase A2; sp|P10632|CP2C8_HUMAN Cytochrome P450 2C8 (EC 1.14.14.1); sp|P10635|CP2D6_HUMAN Cytochrome P450 2D6 (EC 1.14.14.1); sp|P11509|CP2A6_HUMAN Cytochrome P450 2A6 (EC 1.14.14.1); sp|P11712|CP2C9_HUMAN Cytochrome P450 2C9 (EC 1.14.13.80); sp|P15104|GLNA_HUMAN Glutamine synthetase (EC 6.3.1.2) (Glutamate-ammonia ligase) (GS); sp|P15289|ARSA_HUMAN Arylsulfatase A precursor (EC 3.1.6.8) (ASA) (Cerebroside-sulfatase) [Contains: Arylsulfatase A component B; Arylsulfatase A component C]; sp|P15531|NDKA_HUMAN Nucleoside diphosphate kinase A (EC 2.7.4.6); sp|P16152|DHCA_HUMAN Carbonyl reductase [NADPH] 1; sp|P16435|NCPR_HUMAN NADPH-cytochrome P450 reductase; sp|P19099|C11B2_HUMAN Cytochrome P450 11B2; sp|P19971|TYPH_HUMAN Thymidine phosphorylase; sp|P20711|DDC_HUMAN Aromatic-L-amino-acid decarboxylase; sp|P20813|CP2B6_HUMAN Cytochrome P450 2B6 (EC 1.14.14.1); sp|P21397|AOFA_HUMAN Amine oxidase [flavin-containing]; sp|P22309|UD11_HUMAN UDP-glucuronosyltransferase 1-1 precursor; sp|P22310|UD14_HUMAN UDP-glucuronosyltransferase; sp|P23141|EST1_HUMAN Liver carboxylesterase 1 precursor (EC 3.1.1.1); sp|P27338|AOFB_HUMAN Amine oxidase B; sp|P27707|DCK_HUMAN Deoxycytidine kinase (EC 2.7.1.74) (dCK); sp|P28332|ADH6_HUMAN Alcohol dehydrogenase 6 (EC 1.1.1.1); sp|P32320|CDD_HUMAN Cytidine deaminase (EC 3.5.4.5); sp|P33261|CP2CJ_HUMAN Cytochrome P450 2C19 (EC 1.14.13.80); sp|P42898|MTHR_HUMAN Methylenetetrahydrofolate reductase; sp|P47989|XDH_HUMAN Xanthine dehydrogenase/oxidase; sp|P48775|T23O_HUMAN Tryptophan 2,3-dioxygenase (EC 1.13.11.11) (Tryptophan pyrrolase) (Tryptophanase) (Tryptophan oxygenase) (Tryptamin 2,3-dioxygenase) (TRPO); sp|P50135|HNMT_HUMAN Histamine N-methyltransferase to; sp|Q06278|ADO_HUMAN Aldehyde oxidase (EC 1.2.3.1); sp|Q07973|CP24A_HUMAN Cytochrome P450 24A1; sp|Q16696|CP2AD_HUMAN Cytochrome P450 2A13 (EC 1.14.14.1); sp|Q6GRK0|Q6GRK0_HUMAN Cytochrome P450, subfamily IIIA, polypeptide 4; sp|Q9NTN3|S35D1_HUMAN UDP-glucuronic acid; Sperm Whale Metaquomyoglobin Variant H93G; Spermidine Synthase; Spermidine/Putrescine-Binding Protein; Spermine oxidase; Sphingosine-1-phosphate lyase 1; Split-Soret Cytochrome C; SpoOA; SpoOB-Associated GTP-Binding Protein; Spore Coat Polysaccharide Biosynthesis Prote; Spp-40; Squalene Epoxidase; Squalene-Hopene Cyclase; Squalene-Hopene Cyclase; Sr Protein Kinase; S-Ribosylhomocysteinase; Sst1-Selective Somatostatin; Sst1-Selective Somatostatin Analog; Staphopain; Staphylococcal Enterotoxin B; Stat Protein; Stem/Leaf Lectin Db58; Steroid Delta-Isomerase; Steroid Sulphotransferase; Sterol 14-alpha demethylase; Sterol Carrier Protein 2; Sterol-4-alpha-carboxylate 3-dehydrogenase, decarboxylating; Steryl-Sulfatase; Sticholysin II; Streptavidin; Streptavidin precursor; Streptogramin A Acetyltransferase; Stringent Starvation Protein A; Stromelysin 3; Stromelysin-1; Structural Polyprotein; Subtilisin 8321; Subtilisin 8324; Subtilisin Bpn'; Subtilisin BPN' 8350; Subtilisin Carlsberg; Subtilisin Carlsberg, Type Viii; Subtilisin Pb92; Subtilisin-Carlsberg; Subunit C; Succinate dehydrogenase; Succinate semialdehyde dehydrogenase, mitochondrial precursor; Succinylarginine Dihydrolase; Succinyl-CoA ligase [GDP-forming] beta-chain; Sucrose Phosphorylase; Sucrose-Specific Porin; Sugar Transport Protein; Sulfatase Modifying Factor 2; Sulfate Adenylyltransferase; Sulfide Dehydrogenase; Sulfite Oxidase; Sulfite Reductase; Sulfite Reductase Hemoprotein; Sulfolipid Biosynthesis; Sulfolipid Biosynthesis Protein Sqd1; sulfonyl urea receptor (SUR1); Sulfonylurea receptor 1; Sulfonylurea receptor 2; Sulfotransferase; Sulfotransferase Family, Cytosolic, 2B, Memb; Sulfurtransferase; Superoxide Dismutase; Superoxide Dismutase [Cu—Zn]; Superoxide Dismutase [Fe]; Superoxide Dismutase [Mn], Mitochondrial; Superoxide Dismutase [Ni]; Suppressor Of Tumorigenicity 14; Surface Layer Protein; Surface Protein; Survival Protein E; Synapsin Ia; Synthetic Designed Peptide "Alpha-1"; Synthetic Peptide Analogue Of Shk Toxin; System N amino acid transporter 1; T Lymphocyte Activation Antigen; T3-785; T4 Lysozyme; Tachylectin-2; Tagatose-Bisphosphate Aldolase Agay; Tailspike Protein; Taka Amylase; Tandem pH Domain Containing Protein-1; Taq DNA Polymerase; Taste receptor type 1 member 1; Taste receptor type 1 member 2; Taste receptor type 1 member 3; Tatd-Related Deoxyribonuclease; Tat-Interacting Protein Tip30; T-Cell Ecto-ADP-Ribosyltransferase 2; T-Cell Ecto-ADP-Ribosyltransferase 2; T-cell surface glycoprotein CD3 epsilon chain (CD3E); Tdp-Glucose-4,6-Dehydratase; Tdp-Glucose-4,6-Dehydratase; Techylectin-5A; Tem-1 Beta Lactamase; Tem-1 Beta-Lactamase; Terminal Deoxynucleotidyltransferase Short I; Tetanus Toxin; Tetanus Toxin Hc; Tetanus Toxin Heavy Chain; Tetra-; Tetracycline Repressor; Tetrahydrodipicolinate N-Succinyltransferase; Tetrameric Beta-Beta-Alpha Mini-Protein; Tgf-Beta Receptor Type I; Tgf-Beta Receptor Type II; Th10Aox; Th10Box; Th1Ox; Thaumatin I; The GTP-Binding Protein Obg; The Hypothetical Protein; The Major Capsid Protein Of Pbcv-1, Vp54; Thermal Hysteresis Protein; Thermolysin; Thermonuclease; Thermonuclease precursor; Thermosome Alpha Subunit; Thiamin Phosphate Synthase; Thiamin Pyrophosphokinase; Thiamine pyrophosphokinase; Thiamine transporter 1; Thiamine triphosphatase; Thiazide-sensitive sodium-chloride cotransporter; Thiazole Biosynthetic Enzyme; Thioesterase; Thioesterase I; Thiol Peroxidase; Thiol: Disulfide Interchange Protein; Thiol-Disulfide Oxidoreductase Resa; Thioredoxin; Thioredoxin reductase; Thiostrepton; Threonine Synthase; Threonine synthase-like 1; Threonyl-tRNA Synthetase; Threonyl-tRNA Synthetase 1; Thrombomodulin; Thrombospondin 1; Thromboxane A2 receptor; Thromboxane A2 synthase; Thromboxane synthase; Thymidine Kinase; Thymidine Kinase, Cytosolic; Thymidine Phosphorylase; Thymidylate Kinase; Thymidylate Synthase; Thymidylate Synthase Thyx; Thyroid hormone receptor alpha; Thyroid Hormone Receptor Beta-1; Thyroid hormone receptor beta-2; Thyroid peroxidase; Thyrotropin receptor (Thyroid stimulating hormone receptor); Thyroxine-binding globulin precursor; Tick-Borne Encephalitis Virus Glycoprotein; Tissue-Type Plasminogen Activator; Toho-1 Beta-Lactamase; Toll-Like Receptor 2; Toll-like receptor 7 precursor; Toluene-4-Monooxygenase System Protein C; Topoisomerase IV subunit A; Topoisomerase IV Subunit B; Tora Specific Chaperone; Toxin Bmkk4; tr|Q17328|Q17328_CAEEL Avermectin-sensitive glutamate-gated chloride channel GluC1 beta; tr|Q46759|Q46759_ECOLI Beta-lactamase; tr|Q5VUYO|Q5VUYO_HUMAN Novel protein similar to esterases; tr|Q75NA5|Q75NA5_MUSDO GABA-gated chloride channel subunit; tr|Q8ITG2|Q8ITG2_CAEEL GABA-A receptor subunit; Trafficking Protein Particle Complex Subunit; Trai Protein; Transaldolase; Transcarboxylase 5S Subunit; Transcobalamin I; Transcobalamin II; Transcription Antitermination Protein Nusg; Transcription Antiterminator Lict; Transcription factor PPAR gamma; Transcriptional Activator Tena; Transcriptional Regulator; Transcriptional Regulator Nadr; Transcriptional Regulator, Hth_3 Family; Transcriptional Regulator, Rok Family; Transcriptional Regulatory Protein Fixj; Transcriptional Regulatory Protein, Sir2 Fam; Transcriptional Repressor Ethr; Transducin-Alpha; Transferrin Receptor Protein; Transforming Growth Factor-Beta 3; Transforming Protein P21/H-Ras-1; Transforming Protein Rhoa; Transhydrogenase Diii; Transient Receptor Potential-Related Protein; Transitional Endoplasmic Reticulum Atpas; Transitional Endoplasmic Reticulum Atpase; Transketolase; Transketolase-like 1; Translation Elongation Factor Selb; Translation Initiation Factor Eif4E; Translation Initiation Factor If2/Eif5B; Transpeptidase (bacterial); Transposase Inhibitor Protein From Tn5; Trans-Sialidase; Transthyretin; Transthyretin precursor; Transthyretin Thr119Met Variant; Trehalose Operon Repressor; Triacylglycerol Lipase, Gastric; Triacyl-Glycerol-Hydrolase; Trichodiene Synthase; Trichotoxin_A50E; Tricorn Protease; Trifunctional enzyme alpha subunit, mitochondrial precursor; Trigger Factor; Triggering Receptor Expressed On Myeloid Cel; Trihydroxynaphthalene Reductase; Trimethylamine Dehydrogenase; Triose Phosphate Isomerase; Triosephosphate Isomerase; Triosephosphate Isomerase, Glycosomal; Trk System Potassium Uptake Protein Trka Horn; tRNA; tRNA Cca-Adding Enzyme; tRNA Nucleotidyltransferase; tRNA-Guanine Transglycosylase; Tropinone Reductase-I; Tropinone Reductase-II; Troponin C, Slow Skeletal and Cardiac Muscles; Troponin I, cardiac muscle; Troponin T, cardiac muscle; Trp Operon Repressor; Trp Repressor Binding Protein Wrba; Trp RNA-Binding Attenuation Protein Complexed; Trypanothione Oxidoreductase; Trypanothione Reductase; Tryparedoxin II; Trypsin; Trypsin I; Trypsin II, Anionic; Trypsin Inhibitor Bgit; Trypsin Inhibitor I; Trypsin Iva; Trypsinogen; Tryptamine D receptors (5HT2B); Tryptophan 2,3-dioxygenase; Tryptophan 5-hydroxylase 1; Tryptophan 5-hydroxylase 2; Tryptophan 5-Monooxygenase; Tryptophan Synthase Alpha Chain; Tryptophan Synthase Alpha Chain, Chloroplast; Tryptophan-tRNA Ligase; Tryptophanyl-tRNA Synthetase; Tt0826; Ttk003001606; Tubby Protein; Tubulin; Tubulin alpha chain; Tubulin alpha-1 chain; Tubulin alpha-2 chain; Tubulin alpha-3 chain; Tubulin alpha-6 chain; Tubulin alpha-8 chain; Tubulin alpha-ubiquitous chain; Tubulin beta chain; Tubulin beta-1 chain; Tubulin beta-2C chain; Tubulin beta-3 chain; Tubulin beta-4 chain; Tubulin beta-4q chain; Tubulin-Specific Chaperone A; Tumor Necrosis Factor Alpha; Tumor necrosis factor precursor; Type 2 Malate/Lactate Dehydrogenase; Type 2 Rhinovirus 3C Protease; Type 4 Pilin; Type II DNA Topoisomerase Vi Subunit B; Type II Quinohemoprotein Alcohol Dehydrogena; Type III Chloramphenicol Acetyltransferase; Type III phosphodiesterase; Type III Secretion Chaperone Syce; Type T voltage gated calcium channel; Type-1 angiotensin II Receptor (AT1); Tyrosinase precursor; Tyrosine 3-Monooxygenase; Tyrosine Aminotransferase; Tyrosine Phenol-Lyase; Tyrosine Phosphatase; Tyrosine-protein kinase ABL2; Tyrosine-Protein Kinase Btk; Tyrosine-Protein Kinase Itk/Tsk; Tyrosine-Protein Kinase Receptor Tyro3; Tyrosine-Protein Kinase Syk; Tyrosine-Protein Kinase Zap-70; Tyrosine-protein phosphatase, non-receptor type 1; Tyrosyl-tRNA Synthetase; Tyrosyl-tRNA synthetase, cytoplasmic; U1A RNA Binding Domain; Ubiquinol-cytochrome-c reductase complex core protein I, mitochondrial precursor; Ubiquitin; Ubiquitin-Activating Enzyme E1 1; Ubiquitin-Conjugating Enzyme E2 2; Ubiquitin-Conjugating Enzyme E2-25 Kda; Ubiquitin-Like Protein 7, Rub1; Ubiquitin-Protein Ligase E3 Mdm2; Udp-3-O[3-Hydroxymyristoyl] N-Acetylglucosa; Udp-Galactopyranose Mutase; Udp-Galactose 4-Epimerase; Udp-Galactose 4-Epimerase; Udp-Galactose-4-Epimerase; Udpglcnac Pyrophosphorylase; Udp-Glucose 4-Epimerase; Udp-Glucose 4-Epimerase; UDP-glucose 6-dehydrogenase; Udp-Glucose Dehydrogenase; UDP-glucuronosyltransferase 1-9 precursor, microsomal; Udp-N-Acetylenolpyruvoylglucosamine Reductas; Udp-N-Acetylglucosamine 1-Carboxyvinylt; Udp-N-Acetylglucosamine 1-Carboxyvinyl-Trans; UDP-N-acetylglucosamine 1-carboxyvinyltransferase; Udp-N-Acetylglucosamine 2-Epimerase; Udp-N-Acetylglucosamine Enolpyruvyl Tran; Udp-N-Acetylglucosamine Enolpyruvyl Transfer; Udp-N-Acetylglucosamine Pyrophosphorylase; Udp-N-Acetylglucosamine-1-Phosphate Uridyltr; Udp-N-Acetylglucosamine-N-Acetylmuramyl-; Udp-N-Acetylmuramate-Alanine Ligase; Udp-N-Acetylmuramate-L-Alanine Ligase; Udp-N-Acetylmuramoylalanyl-D-Glutamate-; Udp-N-Acetylmuramoyl-L-Alanine: D-Glutam; Udp-N-Acetylmuramoyl-L-Alanine: D-Glutamate; Udp-N-Acteylglucosamine Pyrophosphorylas; Ulex Europaeus Lectin II; Ultraspiracle Protein; UMP-CMP kinase; Uncoordinated protein 63; Unknown Protein; Unknown Protein From 2D-Page; Unlocked Metal-Free Concanavalin A; Unsaturated Glucuronyl Hydrolase; Upf0230 Protein Tm1468; Upper Collar Protein; Uracil Phosphoribosyltransferase; Uracil-DNA Glycosylase; Uracil-DNA Glycosylase Inhibitor; Ure2 Protein; Urease alpha subunit; Uricase; Uridine Diphospho-N-Acetylenolpyruvylglucosa; Uridine Phosphorylase; Uridine Phosphorylase, Putative; Uridine-Cytidine Kinase 2; Uridylate Kinase; Uridylmonophosphate/Cytidylmonophosphate Kin; Urocanase Protein; Urocanate Hydratase; Urokinase; Urokinase-Type Plasminogen Activator; Uroporphyrin-III C-Methyltransferase; Uroporphyrinogen Decarboxylase; Vacuolar ATP Synthase Subunit C; Valyl-tRNA synthetase; Vanadium Bromoperoxidase; Vanillyl-Alcohol Oxidase; Variant Surface Glycoprotein; Vascular endothelial growth factor; Vascular endothelial growth factor receptor 2 precursor; Vascular endothelial growth factor receptor 3 precursor; Vascular Endothelial Growth Factor Toxin; Vasopressin V1a receptor; Vasopressin V1b receptor; Vasopressin V2 receptor; Vasopressin V2 receptor, Neurophysin 2; Venom Serine Proteinase; Venom Serine Proteinase; Vesicular Monoamine Transporter; Vhh-R2 Anti-Rr6 Antibody; Vim-2 Metallo-Beta-Lactamase; Vimentin; Viral guanylyltransfearse; Viral RNA polymerase; Virb11 Homolog; Vitamin B12 Receptor; Vitamin B12 Transport Protein Btuf; Vitamin D Binding Protein; Vitamin D Receptor; Vitamin D3 Receptor; Vitamin D-Dependent Calcium-Binding Prote; Vitamin K Reductase; Vitamin K-dependent protein Z; Voltage gated sodium channel; Voltage-dependent L-type calcium channel alpha-1C subunit; Voltage-dependent L-type calcium channel beta-1 subunit; Voltage-dependent P/Q-type calcium channel alpha-1A subunit; Voltage-dependent T-type calcium channel; Voltage-Gated Potassium Channel; Voltage-gated sodium channel; Volvatoxin A2; Vp1 Protein; Vp39; Vsv Matrix Protein; V-Type Sodium ATP Synthase Subunit K; W224H Variant Of *S. Enterica* Rmla Bound To U; Wbpp; Wheat Germ Agglutinin; Winged Bean Lectin; Wiskott-Aldrich Syndrome Protein; Wunen-Nonfunctional Gfp Fusion Protein; Xaa-Pro Aminopeptidase; Xaa-Pro Dipeptidase; Xanthan Lyase; Xanthine Dehydrogenase; Xanthine oxidase; Xanthine Phosphoribosyltransferase; Xanthine-Guanine Phosphoribosyltransferase; Xanthosine Phosphorylase; Xenobiotic Acetyltransferase; Xylanase; Xylanase 10C; Xylanase Inhibitor Protein I; Xylanase Y; Xyloglucan Endotransglycosylase; Xylose Isomerase; Xylose Reductase; Xylose Reductase; Y177F Variant Of *S. Enterica* Rmla Bound To U; Yajq Protein; Ydr533C Protein; Yeast Cytochrome C Peroxidase; Yeast Iso-1-Ferrocytochrome C; Yeco; Yfua; Yjbi Protein; Yjgf Protein; Ykof; Ylmd Protein Sequence Homologue; Ylr011Wp; Ynk-Contryphan; Yvrk Protein; Zervamicin Iib; Zinc Finger Y-Chromosomal Protein; and Zinc-Alpha-2-Glycoprotein.

Complete System for Analysis

In order to determine binding constants using X-Ray fluorescence, a system must be created that is capable of measuring the X-Ray fluorescence of the bound small molecule or drug. A process must exist for equilibrating the chemical with the protein, this process requires the combination of the chemical and the protein in solution, and incubation of the chemical and protein solution for sufficient time to ensure that chemical equilibrium is obtained; separating the unbound/excess small molecule in a manner that does not unacceptably perturb the binding, and assaying the protein for the bound molecule, which requires that the separation be obtained in less than 5 minutes at 37 degrees Celsius, and more preferably in less than one minute at 4 degrees Celsius, and most preferably in less than 30 seconds at 4 degrees Celsius. In the case of XRF, one or more atoms in the chemical fluoresces when irradiated with X-Rays. This x-ray fluorescence signal can be used to determine the concentration of the bound small molecule when proper calibration is used. Calibration is especially important for X-ray fluorescence, and is more important for x-ray fluorescence than for optical fluorescence, because the x-ray penetration depths of different chemical elements vary greatly. In contrast to optical fluorescence where the optical clarity of the sample and the sample holder is easy to assess; in x-ray fluorescence, the x-ray attenuation in the sample and the effect of secondary excitation from the substrate and secondary excitation within the sample can be large and unpredictable.

The intensity of the XRF fluorescence of the small molecule can be compared in a ratio against the intensity of atoms in the protein, or the concentration of the bound molecule can be compared to known values from the set up of the binding experiments to calculate binding constants. For example, a protein can be incubated with an inhibitor under a range of conditions from very low binding to very high binding (close to 100% of the protein). The unbound ligand is separated via gel filtration or another size exclusion technique, and an aliquot from each sample is spotted onto a substrate for XRF measurement. From the intensity of the fluorescence, a concentration of bound small molecule can be determined. A preferred method for assessing binding constants consists of measuring the intensity of the x-ray fluorescence signal that is due to an atom in the bound chemical; converting the measured intensity into a concentration value, preferably using a computer; plotting the concentration as a saturation isotherm; and extracting the binding constant via fitting of this isotherm through non-linear regression.

The system preferably has security systems for electronic records, electronic signatures, and handwritten signatures executed to electronic records to be trustworthy, reliable, and generally equivalent to paper records and handwritten signatures executed on paper for any records in electronic form that are created, modified, maintained, archived, retrieved, or transmitted. The security system can be conveniently provided by a biometric analysis, i.e. a method of verifying an individual's identity based on measurement of the individual's physical feature(s) or repeatable action(s) where those features and/or actions are both unique to that individual and measurable. The security system may be conveniently provided by means of maintaining a closed system, i.e. an environment in which system access is controlled by persons who are responsible for the content of electronic records that are on the system. The security system may be conveniently provided by means of digital signatures, i.e. an electronic signature based upon cryptographic methods of originator authentication, computed by using a set of rules and a set of parameters such that the identity of the signer and the integrity of the data can be verified. It is preferable that digital signatures that do not use biometric analysis should employ at least two distinct identification components such as an identification code and password. It is preferable that the system be configured such that when an individual executes a series of signings during a single, continuous period of controlled system access, the first signing shall be executed using all electronic signature components; subsequent signings shall be executed using at least one electronic signature component that is only executable by, and designed to be used only by, the individual; and when an individual executes one or more signings not performed during a single, continuous period of controlled system access, each signing shall be executed using all of the electronic signature components. It is especially preferable that the system be configured so that no two individuals have the same combination of identification code and password. It is also preferable that the identification code and password issuances are periodically checked, recalled, or revised (e.g., to cover such events as password aging). It is important that the system be configured so that following loss management procedures to electronically deauthorize lost, stolen, missing, or otherwise potentially compromised tokens, cards, and other devices that bear or generate identification code or password information, and to issue temporary or permanent replacements using suitable, rigorous controls; and that transaction safeguards to prevent unauthorized use of passwords and/or identification codes, and to detect and report in an immediate and urgent manner any attempts at their unauthorized use to the system security unit, and, as appropriate, to organizational management are used.

Method for Using XRF to Monitor Protein Quality

Many proteins such as insulin, vaccines, antibodies, human growth hormone (hGH), and clotting factor VIII are produced by pharmaceutical companies. These proteins must have high purity to be able to be used safely in humans. Quality is very difficult and expensive to monitor for proteins. These methods often require days to complete and significant labor. Thus, improved method of monitoring quality in proteins is needed.

The present invention includes a method for the simple, inexpensive, and rapid method of determining protein purity. Many proteins have atoms detectable by XRF, and properly functional proteins are coordinated by other atoms such as metals that also are detectable by XRF. There are two ways these facts may be exploited: First, a known pure sample may be measured and the elemental composition determined to establish a baseline for metal ratios in pure samples; this baseline may be compared with test samples to see if the purity and functionality match. Second, the correct stoichiometry between coordinating metals and the proteins may be known, and the composition of the protein may be known, so a ratio between the coordinating metal and the protein may be used to provide a purity and functionality measurement. For example, there are 24 sulfur atoms for every two zinc atoms in functional insulin, there are four sulfur atoms for every two zinc atoms in functional hGH, and there are 23 sulfur atoms for every one copper atom.

Method of Determining a Thermodynamic Binding Constant

A thermodynamic binding constant between two binders may be measured by contacting a known amount of each binder, removing unbound material, and measuring the amount of bound material using XRF. This is according the chemical equilibrium equation $k=[B1][B2]/[B1B2]$, where $[B1]$ is the concentration of the first binder, $[B2]$ is the concentration of the second binder, $[B1B2]$ is the concentration of the two binders bound to each other. This can be done more easily if the second binder (B2) has a unique, XRF-measurable atom (i.e., one that is larger than oxygen and that is not contained within the first binder).

EXAMPLE

An embodiment of the present invention is described in the following example. A 1 microliter sample of protein or protein-chemical complex is diluted and re-suspended by adding 10 microliters of a buffer compatible with protein of interest, and vortexed using a Thermolyne MAXI MIX PLUS™ and centrifuged using a revolutionary Science Microcentrifuge at between 6,000 RPM and 10,000 RPM. Matrix modifiers, such as acetic acid and an internal standard are added at this point. Acetic acid is used in amounts to be equivalent to 2% of the total volume of protein sample. If an internal standard is used, the internal standard reagent is mixed with acetic acid to obtain an 8% solution of acetic acid with internal standard. Typically, a 3:1 solution of protein to internal standard in acetic acid is mixed to end up with protein in 2% acetic acid solution. The volumes required for increasing amounts of protein to create standard curve are determined, and the amounts are mixed accordingly. One then aliquots desired amounts into 1.5 ml tubes (EPPENDORF Safe-Lock tubes rated up to 30,000 g) for each individual protein:reagent ratio. The aliquots are then vortexed and centrifuged. A slide is prepared with the desired substrate (i.e. polypropylene, ultralene, mylar, kapton, aluminum, gold) by mounting film on a cardboard or plastic slide mount. Using a pipette or syringe, protein solution is dispensed onto the substrate. For a larger spot, a pipette (EPPENDORF Series 2000 adjustable pipettes) is used to dispense 1 microliter of protein solution onto film, while the operator is careful not to fully evacuate the pipette tip. The sample is preferably deposited by stopping at the first stop on pipette and touching the solution bead on end of tip to film to release the sample without blowing air into sample. For a smaller spot, use a syringe (Hamilton 7000.5 KH 0.5 ul 25/2.76"/3 REV T) and draw from 0.1 to 0.5 microliters of sample into syringe. Dispense sample onto film by depressing syringe completely and then touching film to release bead onto film. The spot is dried under a heat lamp (GE Halogen SP 10.degree. Beam 100W 120V) for 5 minutes. The sample is then measured using x-ray fluorescence on an EDAX Eagle III micro X-ray fluorescence system equipped with a rhodium target excitation source (40 kV, 1000 uA) and a SiLi detector. Initial screening measurements are collected with an excitation beam dwell time of 100 milliseconds. Detailed analyses of individual samples are collected with an excitation beam dwell time of 100 to 600 seconds. Measurements will be standardized by normalizing the RPM intensity in control samples to the RPM signal in the experimental sample.

Briefly, the present invention relates to using x-ray fluorescence (XRF) as a probe to determine binding selectivities of chemicals for receptors. The invention can also be used to estimate therapeutic index of a chemical. Another aspect of the invention relates to providing an estimate of the relative therapeutic indices of two chemicals.

An aspect of this invention is related to estimating the binding selectivity of a chemical to two or more receptors. The receptors are preferably proteins or other biological ligands. The receptors may be arrayed on a substrate. Arrays that include from about 2 to about 100,000,000 receptors, preferably from about 2 to about 1,000,000, and more preferably from about 2 to about 100,000 are especially useful with this invention.

Chemicals used with this invention generally include at least one element with an atomic number of nine or higher; these elements are referred to herein as "heavy elements".

Generally, a baseline XRF signal is established for a heavy element in each portion or aliquot of each receptor used with the invention. The baseline x-ray fluorescence signal may be calculated or measured.

After establishing the baseline XRF signal, the receptor(s) are exposed to one or more chemicals, preferably in solution, that are being tested for binding to the receptor(s). Exposure of the receptor(s) to the chemical(s) may or may not result in the formation of one or more complexes that are referred to herein as "chemical-receptor complexes". If an analog of the chemical is used, then the corresponding complex is referred to herein as an "analog-receptor complex". If the chemical is a drug, then the corresponding complex is referred to herein as "drug-receptor complex". Exposure of the receptor to the chemical/analog/drug allows such a complex to form, if it forms at all, under the conditions of temperature, elapsed time, presence of other chemicals or receptors, receptor concentration, chemical concentration, and other parameters.

After sufficient time has elapsed for one of the aforementioned complexes to form, the x-ray fluorescence signal due to the "heavy" element (e.g. phosphorus, chlorine, fluorine, sulfur, to name a few) in each chemical-receptor complex is measured.

After measuring the XRF signal due to the heavy element, the baseline X-ray fluorescence signal is subtracted from this measured x-ray fluorescence signal; the difference is referred to herein as the "net x-ray fluorescence signal". The net x-ray fluorescence signal is proportional to the amount of the chemical that is bound to the receptor in a chemical-receptor complex. Each net-x-ray fluorescence signal may be standardized by dividing by the amount of the receptor in the portion-used for binding to the chemical. The amount of receptor typically may have units such as molecules, moles, moles per liter, grams, grams per liter, units of activity, and the like. If the same amount of receptor is used for each experiment, then each net x-ray fluorescence signal may be directly compared.

In addition, the net XRF signal should be standardized for the concentration of chemical if receptors are exposed to solutions having different concentrations of the chemical.

The standardized XRF signals obtained using this invention may then be compared in a variety of ways. One standardized x-ray fluorescence signal may be subtracted from another signal, for example. One standardized XRF signal may be divided by another signal. Preferably, when making comparisons among more than two signals, the signals are plotted on a graph so that comparisons among them may be easily visualized.

Another aspect of this invention is related to estimating the binding selectivity of at least two chemicals to two or more receptors and comparing their selectivities. For this aspect of the invention, each chemical must include at least one heavy element. The two or more chemicals may include the same heavy element or different heavy elements. The receptors, preferably proteins or other biological ligands, may be arrayed on a substrate. Arrays may include from about 2 to about 100,000,000 receptors, preferably from about 2 to about 1,000,000, and more preferably from about 2 to about 100,000. A measured or calculated baseline X-ray fluorescence signal would be obtained for the heavy element (s) in each portion or aliquot of each receptor used with the invention. After establishing the baseline X-ray fluorescence signal, the receptors are exposed to a plurality of chemicals, preferably in solution, which are being tested for binding to the receptors. Exposure of the receptors to the chemicals may or may not result in the formation of one or more complexes that are referred to herein as "chemical-receptor complexes". Exposure of the receptor to the chemicals allows such complexes to form, if they form at all, under the conditions of temperature, elapsed time, presence of other chemicals or receptors, receptor concentration, chemical concentration, and other parameters. After sufficient time has elapsed for one of the aforementioned complexes to form, the x-ray fluorescence signal due to the "heavy" element (e.g. phosphorus, chlorine, fluorine, sulfur, to name a few) in each chemical-receptor complex is measured. After measuring the x-ray fluorescence signal due to the heavy element(s), the baseline X-ray fluorescence signal is subtracted from this measured x-ray fluorescence signal; the difference is referred to herein as the "net x-ray fluorescence signal". The net x-ray fluorescence signal is proportional to the amount of the chemical that is bound to the receptor in a chemical-receptor complex. Next, each net x-ray fluorescence signal is standardized by dividing by the amount of the receptor in the portion used for binding to the chemical. The amount of receptor typically may have units such as molecules, moles, moles per liter, grams, grams per liter, units of activity, and the like. If the same amount of receptor is used for each experiment, then each net x-ray fluorescence signal may be directly compared. The standardized x-ray fluorescence signals may be compared in a variety of ways. One standardized x-ray fluorescence signal may be subtracted from another signal, for example. One standardized x-ray fluorescence signal may be divided by another signal. Preferably, when making comparisons among more than two signals, the signals are plotted on a graph so that comparisons among them may be easily visualized.

The invention also relates to drug manufacturing. The drug manufacturing process includes the determination of which chemical or chemicals bind to a type of receptor referred to in the art as a "druggable target," how strongly they bind, whether or not they bind selectively (i.e. whether or not they also bind undesirably to other receptors), and for those that bind selectively to what degree the selectivity is. After identifying a drug that binds strongly and selectively to a desired druggable target, the drug is synthesized in large quantities.

The invention can be used to estimate the binding selectivity of a chemical to one or more receptors under different conditions. For example, the binding affinity of a chemical in one solution can be compared to its binding affinity in a different solution. The chemical would include one or more heavy elements. The effect that other components that do not have a heavy element in either solution have on the binding affinity of the chemical could be inferred by observing any observed differences in binding affinity of the chemical.

Some aspects of the invention are related to personalized medicine, and involve estimating the relative effectiveness of two or more drugs. This may involve, for example, estimating the binding selectivities of two (or more) drugs to two (or more) receptors. The receptors may be proteins or other biological ligands, typically derived from a medical patient or a participant in a clinical drug trial. For medical patients, there may be a question about which drug to use to treat the patient, and the invention can be used to guide the doctor toward prescribing a specific drug for treatment. For applications related to personalized medicine, these types of drugs would include at least one heavy element. For drugs that are being compared, the drugs might include the same heavy element, or different heavy elements. Each drug may be a single chemical, or may be a mixture of chemicals. If the drug is a mixture of chemicals, then one of the active ingredients of the drug must have a heavy element.

An aspect of this invention is related to estimating the binding affinity of a chemical to one or more receptors, preferably proteins or other biological ligands that are arrayed on a substrate. The chemical would include at least one heavy element. First, a baseline XRF signal for the heavy element in each portion or aliquot of each receptor would be obtained, either by measuring or calculating the baseline signal. Afterward, the receptor(s) would be exposed to one or more chemicals. Chemicals that bind to the receptors result in the formation of chemical-receptor complexes that are detectable by measuring the XRF signal due to the heavy element in each chemical-receptor complex. This measured x-ray fluorescence signal is obtained by using x-ray excitation photons with an energy of at least 300 eV, which generate emission photons having a fluorescence lifetime that is less than the dead time of the x-ray detector. After measuring the x-ray fluorescence signal due to the heavy element, the baseline XRF signal is subtracted from this measured x-ray fluorescence signal, yielding the net XRF signal, which is proportional to the amount of the chemical that is bound to the receptor in a chemical-receptor complex. The net XRF signal would then be standardized. The standardized XRF signals may then be compared.

The invention can also be used to detect modifications in proteins. Examples of such detectable protein modification include, but are not limited to, post-translational modification of proteins, phosphorylation of proteins, and dephosphorylation of proteins. Detecting these modifications would typically begin by first establishing a baseline XRF signal for a heavy element in each portion or aliquot of each protein, and then exposing the protein to conditions that may result in protein modification. Afterward, the XRF signal due to the heavy element would be measured. The baseline X-ray fluorescence signal is then subtracted from this measured XRF signal, and the difference is the "net XRF signal". The net XRF signal would be standardized by dividing by the amount of the receptor in the portion being tested. The standardized XRF signals may then be compared.

This invention may be used to estimate the therapeutic index of a chemical/drug/analog. The therapeutic index is a measure of drug selectivity that is ordinarily calculated from data obtained from experiments with animals. The therapeutic index of the drug is typically defined as the ratio of two numbers, LD50/ED50, where LD50 is the dose of a drug that is found to be lethal (i.e. toxic) for 50 percent of the population of animals used for testing the drug, and ED50 is the dose of the drug that is found to have a therapeutic effect for 50 percent of that population. More broadly, it is a measure of the how much of the drug is needed to produce a harmful effect relative to the amount needed to produce a beneficial effect. The ratio LD50/ED50 is therefore, a measure of the approximate "safety factor" for a drug; a drug with a high therapeutic index can presumably be administered with greater safety than one with a low index. The invention may be used to provide an estimate of the therapeutic index by, for example, measuring the binding affinity of a chemical to a receptor associated with side effects and to a receptor associated with efficacy. The ratio of the measured binding affinities (efficacy divided by side effects) provides an estimate of the "therapeutic index". For an example of using DNA arrays with optical fluorescence high-throughput screening to estimate a therapeutic index, see R. Ulrich and S. H. Friend, "Toxicogenomics And Drug Discovery: Will New Technologies Help Us Produce Better Drugs?," *Nature Reviews Drug Discovery*, vol. 1, pp. 84-88 (2002), incorporated herein by reference.

An example relating to the use of the invention to obtain a simple estimate of a therapeutic index may involve exposing an array of the proteins 5HT2A and NAa1 to a solution of olanzapine. Assuming that the 5HT2A and NAa1 of the array are present in equal amounts, the net sulfur XRF signal due to the olanzapine should be between 1.6 and 20 times higher for olanzapine bound to 5HT2A than for olanzapine bound to NAa1.

Another example relating to the use of the invention to obtain an estimate of a therapeutic index is now described. A therapeutic index for a non-steroidal anti-inflammatory drug (commonly referred to as an "NSAID") may be obtained by exposing an array that includes the proteins COX-1 and COX-2 to a solution of meloxicam. Assuming the COX-1 and COX-2 are present in equal amounts, the net XRF signal due to sulfur in the meloxicam should be about 10 times higher for meloxicam bound to COX-2 than for meloxicam bound to COX-1.

Yet another example relating to the use of the invention to obtain an estimate of a therapeutic index may involve exposing an array that includes COX-1, COX-2, and proteins derived from hepatocytes, to a solution of meloxicam. Assuming the COX-1 and COX-2 are present in equal amounts, the net XRF signal due to the sulfur in the meloxicam should be about 10 times higher for meloxicam bound to COX-2 than for meloxicam bound to COX-1. Any XRF signal due to sulfur in meloxicam bound to hepatocyte-derived proteins may suggest that the meloxicam may concentrate in the liver and may be cause for further analysis of the toxicity of meloxicam.

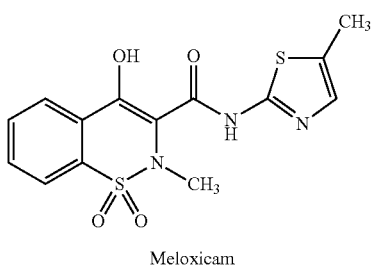 [SMILES: Cc1cnc(NC(=O)C2=C(O)c3ccccc3S(=O)(=O)N2C)s1]

Meloxicam

Binding selectivity information provided by the invention is important for understanding the properties of drugs. It is also important for other applications such as for medical diagnostics. For medical diagnostics, the ratio of the binding affinity of probe molecules (i.e. molecules that selectively bind to proteins associated with a particular disease) for a disease marker (i.e. a protein in a biological sample, such as a blood or sputum sample, from a patient having that disease, which indicates that a disease is present) vs. the binding affinity of probe molecules for other proteins not associated with that disease, is related to the accuracy of a medical test. If the probe molecules bind to the disease marker, then the medical diagnostic test provides a true positive result. However, when the probe molecules bind to other proteins besides the disease marker, then the medical diagnostic test provides a false positive result. The above ratio provides a measure of the true positive relative to the false positive, which is related to the accuracy of the medical test.

Diagnostic tests that use standard immunoassay methods require fluorescently-tagged chemicals. It has been previously pointed out that it is generally assumed that the attachment of a fluorescent tag to a chemical only serves to make visible the otherwise invisible chemical, and does not alter its binding properties. However, small changes to the structure of a chemical could affect its function, so this assumption that tagged chemicals have the same binding affinity and selectivity as their untagged counterparts may not be a valid one. The tagged chemicals are structurally different from their untagged counterparts, and these structural differences could affect their binding affinities and selectivities. Since binding affinities and selectivities derived using tagged chemicals are suspect, the binding properties of receptors and chemicals should be evaluated using the untagged chemical or receptor and not with a tagged chemicals. This is not possible with standard immunoassay methods, which require fluorescently-tagged chemicals. By contrast, the present invention allows an existing, untagged chemical (or analog or drug) to be used as the probe molecule.

An example of using the invention for a diagnostic test for inflammation, for example, may include exposing spatially separated proteins to a drug. Spatially separated proteins, for example COX-1 and COX-2 derived from a blood sample from a patient, may be exposed to the drug meloxicam. The binding affinities of meloxicam to COX-1 and COX-2 are known. Therefore, the net XRF signal due to sulfur in the meloxicam that is bound to COX-1 versus that for COX-2 may indicate the relative amounts of COX-1 and COX-2 in the blood sample.

The invention may also be used to develop optically fluorescent immunoassay diagnostics by comparing the selectivity of a non-fluorescently tagged chemical to a fluorescently-tagged chemical. XRF would be used to determine the binding selectivity of the non-tagged chemical, and either XRF or optical fluorescence would be used to determine the binding selectivity of the tagged chemical. If the selectivities of the tagged and untagged chemicals are proven to be similar, then the tagged-chemical may be used as the diagnostic with the expectation that its binding properties are acceptably similar to those of its untagged counterpart.

Binding selectivity information provided by the present invention is also important for uses related to Materials Science. Binding selectivity information can be used, for example, in designing high performance water filters, such as water filters that remove contaminants such as lead, arsenic, arsenate anions, or pesticides, from contaminated water. Water filters can be manufactured with receptors that have a high affinity for a particular contaminant (lead, for example) and a low affinity for other contaminants (iron, for example) in the contaminated water. By passing the contaminated water through this filter, the lead is removed while the iron isn't. The beneficial effect of not removing the iron is that the iron, which is present in much larger amounts than the lead is, does not overload the filter as the contaminated water is being treated. Overloading would mean that the filter would have to be replaced often.

The binding selectivity, i.e. the ratio of binding affinity of a chemical to one receptor versus the binding affinity to a different receptor, may be performed as follows. First, a baseline x-ray fluorescence is obtained. This baseline may be obtained by, for example, measuring the x-ray fluorescence (XRF) signal due to a particular element from each receptor in the absence of any added chemical. This is an empirical measurement that establishes the baseline XRF signal for that element for each receptor. Alternatively, the baseline XRF can be calculated for each receptor. This calculation requires knowledge of the amount of that element that is present in the receptor and a calibration factor to convert an amount of that element into an XRF intensity signal; the amount of the element believed to be present may then be multiplied by the calibration factor to provide a calculated XRF signal. The calibration factor may be obtained by measuring a set of standards containing that element, and calculating the signal as a function of the amount of the element. Preferably, the XRF baseline is a measured baseline.

For cases where there is a low probability that there is an element in common between the receptor and the chemical and where that element is used for the XRF measurement, a foreknowledge of the composition of the receptor(s) may be sufficient. For obtaining the XRF baseline for a set of organic receptors that are being screened for their binding affinities for a metal (e.g. lead) or for a chemical that has XRF-measurable chemical elements (e.g. phosphorus, chlorine) that are known not to be present in the set of organic receptors, for example, the baseline XRF signal of the receptors may be calculated or assumed to be negligible. For a sulfur-containing receptor (e.g. avidin) and a phosphorus-containing chemical (e.g. biotin-DHPE, or N-(Biotinoyl)-1, 2-dihexadecanoyl-sn-glycero-3-phosphoethanolamine triethylammonium salt), for example, the XRF signal of phosphorus from the avidin may be assumed to be negligible, and any phosphorus XRF signal measured may be assumed to be due to the biotin-DHPE.

A receptor is preferably localized and separated from other receptors. Localization concentrates the receptor and any chemical bound to the receptor, therefore improving the sensitivity of the XRF technique. This sensitivity improvement due to localization for XRF contrasts with other techniques, such as optical fluorescence. Optical fluorescence may be affected by fluorescence quenching, fluorescent resonance energy transfer, photobleaching, and the like. Fluorescence quenching diminishes the optical signal and therefore decreases sensitivity. Fluorescence resonance energy transfer alters the wavelength of the fluorescence signal. Photobleaching degrades the fluorescence signal over time and exposure to light. By contrast, XRF is not subject to fluorescence quenching because the energy differences between the ground state and the excited states are much greater for XRF than for optical fluorescence. Energy loss via optical fluorescence may occur through non-radiative pathways that do not produce an optical signal. XRF sometimes is subject to fluorescence resonance energy transfer (see, for example, J. Sherman, *Spectrochimica Acta*, vol. 7, pp. 283-306 (1955)), incorporated by reference herein). Optical fluorescence usually requires an unsaturated functional group (a carbonyl group, a dienyl group, an aromatic group, etc.) with an electron that can be excited from the ground electronic state to an excited state with non-ionizing radiation (ultraviolet, visible, and near-infrared radiation). This excitation forms a reactive electron-hole pair that can chemically react with neighboring molecules, or within the same molecule. This chemical reaction degrades the optically fluorescent chemical functional groups, which diminishes the optical fluorescence during degradation. In contrast, XRF employs ionizing radiation for exciting inner core electrons of atoms. The chemical environment of the excited atoms does not have a significant effect on the XRF signal. Atoms are not degraded like chemical functional groups, so photobleaching does not occur in XRF.

When the chemical binds to a localized receptor, the chemical also becomes localized. In order to maximize the XRF efficiency, it is preferable that the dimensions of the receptor match those of the spot generated by the excitation beam.

For expensive receptors, it is preferable that the sample of receptor be as small as possible. It is therefore preferable that the receptor sample be localized within an area about 1 mm$^2$ or less, and within a volume of 1 mm$^3$ or less.

When multiple receptors are being tested, they are each deposited in separated portions on a substrate. The portions are spatially separated from each other so that the XRF excitation beam excites only one portion, and any chemical bound to the portion of receptor, at a time.

Receptor arrays such as analytical protein arrays, functional protein arrays, analytical DNA arrays, functional DNA arrays, analytical RNA arrays, functional RNA arrays, arrays derived from clinical patients, arrays derived from participants in clinical trials, tissue samples, tissue arrays, cellular arrays, and cellular samples may be used with the present invention. These and other types of arrays have been described in detail in the following papers: H. Zhu and M. Snyder, "Protein Chip Technology (Review)," *Current Opinion in Chemical Biology*, vol. 7, pp. 55-63, (2003); G. MacBeath and S. L. Schreiber, "Printing proteins as microarrays for high-throughput function determination," *Science*, vol. 289, pp. 1760-1763, (2000); E. T. Fung et al., "Protein biochips for differential profiling," *Current Opinion in Biotechnology*, Vol. 12, pp. 65-69, (2001); T. Kukar et al., "Protein Microarrays to Detect Protein-Protein Interactions Using Red and Green Fluorescent Proteins," *Analytical Biochemistry*, vol. 306, pp. 50-54, (2002); G. Y. J. Chen et al., "Developing a Strategy for Activity-Based Detection of Enzymes in a Protein Microarray," *ChemBioChem*, pp. 336-339, (2003); K. Martin et al., "Quantitative analysis of protein phosphorylation status and protein kinase activity on microarrays using a novel fluorescent phosphorylation sensor dye," *Proteomics*, Vol. 3, pp. 1244-1255, (2003); J. Burbaum and G. M. Tobal, "Proteomics in drug discovery," *Current Opinion in Chemical Biology*, Vol. 6, pp. 427-433, (2002); I. A. Hemmilä and P. Hurskainen, "Novel detection strategies for drug discovery," *Drug Discovery Today*, Vol. 7, pp. S150-S156, (2002). The arrays described in these papers may be used with the present invention.

In order to allow mass transport of a chemical to all parts of a receptor deposited on an area of the substrate, it is preferable that there be some inhomogeneity of the receptor in that deposited area. Regarding the inhomogeneity of the deposition, the amount of receptor on a 1 square micron portion of the deposited area should be different from the amount of receptor on another 1 square micron portion by at least 10 percent. An alternative way of comparing the amount of inhomogeneity of deposited receptor on an area involves measuring the amount of chemical in each 1 square micron pixel within the deposited area, finding the average amount of the chemical per square micron over the entire deposited area, and calculating the standard deviation of the amount of the chemical per square micron pixel. The standard deviation of the amount of the chemical per pixel divided by the average amount of the chemical per square micron of area should be greater than about 0.1% and preferably greater than about 1%.

Receptors may be inhomogeneously deposited by attaching the receptors to polystyrene beads, for example. The points of attachment on polystyrene beads are random and non-uniform. The attachment of receptors to beads is described in U. S. Patent Application 20030027129 entitled "Method for Detecting Binding Events Using Micro-X-ray Fluorescence Spectrometry," which was published on Feb. 6, 2003, which describes the use of beads that were about 80-120 micrometers in diameter, with an average diameter of about 100 micrometers.

The measured binding affinity of a chemical to a receptor depends on the chemical environment and temperature. More specifically, the binding affinity of a chemical to a receptor does not change when the chemical environment does not change. External factors, however, may have an effect on the measured binding affinity.

The free energy of binding of a chemical to a receptor may be represented by the following equation:

$$\Delta G = \Delta H - T \Delta S$$

where $\Delta G$ is the change in the Gibbs free energy of the binding reaction, $\Delta H$ is the change in enthalpy of the binding reaction, T is the temperature, and $\Delta S$ is the change in entropy of the binding reaction (see, for example: Gordon M. Barrow, Physical Chemistry, 5th Ed., McGraw-Hill, NY, 1988, Chapter 7). The temperature should be constant to avoid changing the T$\Delta$S term, because changes to the T$\Delta$S term would introduce temperature derived artifacts into the measurements. $\Delta G$ will also be affected by, for example, the presence of materials that coordinate to the receptor and/or chemical. Bonds that form between these materials and the receptor and/or chemical must be broken before the chemical can bind to the receptor. Energy is required to break these bonds, and this energy will be factored into $\Delta G$ of the equation, and will make $\Delta G$ of binding between the chemical and receptor appear smaller than it actually is. Therefore, in order to obtain binding affinities for a chemical with multiple receptors, the chemical environment for the receptors and chemicals should not change. In addition, the temperature should not vary between measurements and all measurements should be taken at substantially the same temperature, i.e. within ±3° C., and more preferably within ±1° C.

For drug development, the chemical environment preferably approximates that of the physiological environment. Useful drugs should perform optimally at, or near, physiological temperatures. One aspect of this invention is related to determining binding selectivities at or near the temperature of the body, which is about 37 degrees Celsius. Preferably, the exposure of receptors to chemicals/analogs/drugs according to this invention is typically performed at a temperature of from about 15 degrees Celsius and about 45 degrees Celsius, and more preferably is between 32 degrees Celsius and 42 degrees Celsius, and most preferably at a temperature of about 37 degrees Celsius.

Useful drugs should also perform optimally in the presence of other, potentially interfering chemicals that are also present in a physiological environment. The therapeutic index provides an estimate of the performance of a drug. Simple estimates of a therapeutic index may be obtained for a chemical in a solution that does not contain potentially interfering chemicals. More realistic estimates of the therapeutic index are obtained when the chemical is in an environment that more closely approximates biological conditions. An example of such an environment is a buffered solution that contains chemicals that are typically found in biological organisms (e.g. blood-borne ligands).

For medical purposes, such as the development of new therapeutic chemicals (i.e. drugs), the ratio of the binding affinity of a chemical to the target receptor versus the binding affinity of that chemical to one or more other receptors (which is an estimate of the therapeutic index according to the present invention) is important to know. It is also important to know the binding affinity and the therapeutic index estimate of the chemical for these receptors in typical chemical environments and in the presence of common biological ligands. The binding affinity may be measured in the presence of, for example, blood-borne proteins, ligands, fats, triglycerides, and fatty acids. These proteins and ligands may function as a proxy for distribution of the chemical between the circulatory system and cells. Fats, triglycerides, and fatty acids may function as a proxy for the distribution of the chemical between fat cells (or cell membranes) and the target receptor, as well as for passive transcellular transport.

Another aspect of the present invention is related to determining whether or not a first chemical and a second chemical have similar selectivity for binding to each of a plurality of receptors. For example, if a baseline is obtained for receptor 1 and receptor 2, and then if chemical A and chemical B and chemical C are exposed to receptor 1 and receptor 2, and the baseline is subtracted from the XRF signals after exposure, the similarity of the binding selectivities can be assessed. For this example, chemical A and chemical B are both are selective for Receptor 1 versus Receptor 2 by about an order of magnitude, while chemical C is not selective for Receptor 1 versus Receptor 2, as shown in TABLE 2 below.

TABLE 2

|  | Receptor 1 | Receptor 2 |
| --- | --- | --- |
| Chemical A | 10 | 1 |
| Chemical B | 11 | 1 |
| Chemical C | 1 | 1 |

This aspect of the invention may be exemplified with specific receptors having known properties. For example, Receptor 1 may be exemplified by COX-1 (inhibition of which is associated with intestinal ulcers) and Receptor 2 may be exemplified by COX-2 (inhibition of which is associated with anti-inflammation).

TABLE 3 below includes selectivity data for sample canine COX-1 and COX-2 (see, for example: Christopher Jones, Practical COX-1 and COX-2 Pharmacology: What's it All About?," which can be found at the website www.vetmedpub.com/cp/pdf/symposium/nov 1.pdf).

TABLE 3

|  | COX-1 | COX-2 |
| --- | --- | --- |
| Celecoxib | 1 | 9 |
| Meloxicam | 1 | 10 |
| Ketoprofen | 1 | .6 |
| New Drug (goal) | 1 | >10 |

TABLE 3 compares the selectivity of CELECOXIB, MELOXICAM, and KETOPROFEN for the receptors COX-1 and COX-2. According to TABLE 3, CELECOXIB has a selectivity of 9 to 1 in favor of COX-2 versus COX-1, and MELOXICAM has a selectivity of 10 to 1 also in favor of COX-2 versus COX-1, while KETOPROFEN has a selectivity in favor of COX-1 versus COX-2 of only 1 to 0.6. Drug development involves finding/developing new drugs that have superior selectivities (i.e. superior therapeutic indices) versus existing drugs. The discovery/development of more selective drugs than those shown in TABLE 3 may involve measuring the selectivity of a new drug and comparing its selectivity to that of the more effective drugs e.g. CELECOXIB. The goal would be to develop a new drug with superior selectivity for COX-2 over COX-1 as compared to CELECOXIB.

A new drug should be at least one percent more selective, and more preferably more than 5 percent more selective than an existing, effective drug.

An example that demonstrates how the present invention may be used to provide information related to the selectivity of a plurality of receptors to a chemical is now described. The chemical is the lead ion. For this example, a library consisting of 400 tripeptide receptors was prepared by split-pool synthesis. Each receptor of the library was covalently attached to a spherical polystyrene resin particle. The particles had an average size of about 100 microns. The library of receptors was exposed to an aqueous solution, having a pH of 7, of lead nitrate (7 mM). A portion of the library of receptors was then analyzed by XRF. The XRF intensity and relative binding affinity of three of the receptors for lead ion are shown in TABLE 4 below.

TABLE 4

| Receptor | Pb XRF Signal | Relative Binding Affinity |
| --- | --- | --- |
| Receptor 4.1 | 991.93 | 1.11919349 |
| Receptor 4.2 | 924.94 | 1.04360875 |
| Receptor 4.3 | 886.29 | 1 |

Another example that demonstrates how the present invention may be used provide information related to the selectivity of a plurality of receptors to two chemicals is now described. The two chemicals are the lead ion and the iron ion. For this example, a library consisting of 400 tripeptide receptors was prepared by split-pool synthesis. Each receptor of the library was covalently attached to a spherical polystyrene resin particle. The particles had an average size of about 100 microns. The library of receptors was exposed to an aqueous solution (pH 7) of lead nitrate (7 mM) and iron nitrate (7 mM). A portion of the receptors was then analyzed by XRF. The XRF intensity and relative binding affinity of two of the receptors for lead ion and iron ion are shown in TABLE 5 below.

TABLE 5

|  | Pb XRF Intensity | Fe XRF Intensity | Pb XRF Intensity/ Fe XRF Intensity |
|---|---|---|---|
| Receptor 5.1 | 2295 | 505 | 4.54 |
| Receptor 5.2 | 13092 | 252 | 51.95 |

The first entry of TABLE 5 relates to data obtained for the receptor labeled receptor 5.1, and the second entry relates to XRF data obtained for the receptor labeled receptor 5.2. The Pb XRF intensity of receptor 5.1 is 2295, the Fe XRF intensity, is 505, and the ratio of Pb XRF intensity to the Fe XRF intensity, which indicates the selectivity of receptor 5.1 for binding to lead versus binding to iron, is 4.54. Similarly, the Pb XRF intensity for receptor 5.2 is 13092, the Fe XRF intensity is 252, and the ratio of the Pb XRF intensity to the Fe XRF intensity is 51.95. The ratio of 51.95 to 4.54, which equals 11.4, indicates that receptor 5.2 is 11.4 times as selective for lead than receptor 5.1 is.

For drug development, it is desirable to understand how the drug will bind to a receptor. Drug development may involve systematically varying the chemicals being tested for their affinities to one or more receptors, in order to optimize the binding affinity of one of these chemical analogs to a desired receptor and to optimize the therapeutic index, i.e. the ratio of the affinity of the chemical to a desired receptor to the affinities of that chemical to undesired receptors. This systematic variation of chemicals for drug development is sometimes referred to as a drug development analog program. The development of a potential new drug using analogs and XRF according to the present invention involves determining the binding affinity of a potential drug to multiple receptors, and comparing these binding affinities to provide selectivity information. This process is completed for a first chemical, and then completed for a second chemical that is an analog of the first chemical. Then the binding affinities and selectivities for the first chemical and for its analog are compared to determine which of the two is the more selective. This may involve mixing the first chemical with one or more receptors, allowing a receptor-chemical complex to form, and then measuring the amount of receptor-chemical complex formed using XRF, then repeating these steps with the analog. Any complexes that form with the analog would also be measured by XRF. This may be repeated with additional analogs of the first chemical.

There are several criteria that may be used to determine whether chemicals are analogs of the first chemical. One criterion is whether the first chemical and another chemical have one or more properties in common. The similarity may be determined by computational modeling, such as a "Quantitative Structure Activity Relationship" (QSAR, see, for example: R. Perkins et al., "Quantitative Structure-Activity Relationship Methods: Perspectives on Drug Discovery and Toxicology," *Environmental Toxicology And Chemistry*, vol. 22, pp. 1666-1679 (2003); and T. W. Schultz et al., "Quantitative Structure-Activity Relationships (QSARs) in Toxicology: a Historical Perspective" *THEOCHEM*, vol. 622, pp. 1-22 (2003), both incorporated by reference herein).

QSAR models compare the charge, polarity, hydrogen-bonding donor/acceptor pattern, lipophilicity, volume, and other properties of chemicals to determine whether two or more chemicals are likely to have similar binding properties for a receptor.

Another criterion for determining whether two chemicals are analogs of each other relates to whether the two chemicals have a common functional group and where that functional group is attached. The following clarifies what is meant by the term analog. Benzene, methylbenzene, ethylbenzene, isopropylbenzene, and n-propylbenzene, for example, are analogs of each other. Olanzapine and trifluoromethylolanzapine are analogs of each other. Methyl salicylate, ethyl salycylate, phenyl salicylate, N-methyl salicylamide, N,N-dimethylsalicylamide, and salicylic acid are analogs of each other. The aromatic compounds 4-chlorotoluene, and 3-chlorotoluene are analogs of each other. Cyclopentane, cyclohexane, and cycloheptane are analogs of each other. Benzene, pyridine, and thiophene are analogs. Ethyl benzene and methoxybenzene are analogs of each other. Ethyl benzene, ethenyl benzene (i.e. styrene), and ethynyl benzene (i.e. phenyl acetylene) are analogs of each other. More generally, enantiomers of a chemical are analogs of each other; diastereomers are also analogs of each other.

A third criterion for determining whether two chemicals are analogs is related to whether the two chemicals share atoms having the same connectivity, where the term connectivity is meant to describe the shortest path of atoms that connect two functional groups. For example, 1,2-diclorobenzene and 1,2-dinitrobenzene have the same connectivity between the two functional groups; the connectivity between the chlorine groups in the chemical 1,3-diclorobenzene is the same as the connectivity between the two nitro groups in the chemical 1,3-dinitrobenzene.

Preferably, a chemical being tested for binding with a receptor according to the present invention includes at least one chemical element having an atomic number of nine or higher. Excitation photons used with the present invention should have energies of at least 300 eV. The excited atoms should have a fluorescence half-life of 10 ns or less. The importance of having such a short fluorescence lifetime is related to the "dead time", which is a period of time after the x-ray fluorescence is measured. No additional x-ray fluorescence can be measured during the dead time. Preferably, the fluorescence lifetime of the type of atom being measured should be less than the dead time of the detector. More preferably, the fluorescence being measured should have a fluorescence half-life of 10 nanoseconds (ns) or less, and most preferably the fluorescence being measured should have a half-life of 100 picoseconds (ps) or less.

If a mixture of chemicals, as opposed to a single chemical, is used, only one of the chemicals is required to have a heavy element. If more than one has a heavy element, and the heavy element is the same element, then a baseline XRF measurement of the binding affinity of each of the chemicals with that element to one or more receptors should be obtained. The measurements may be obtained sequentially, e.g. by measuring the XRF spectrum of each receptor of an array, then exposing the receptors of the array to a chemical, then measuring the XRF spectrum of the array after exposure to the chemical, then adding another chemical, then measuring the XRF spectrum of the array after exposure to the other chemical. This process may be repeated for as many chemicals as desired.

After measuring binding affinities between receptors and chemicals, the receptors may be analyzed in terms of any of their particular structural of functional features than may promote binding or inhibit binding. A variety of analytical techniques useful for performing this type of analysis include spectroscopy (e.g. infrared spectroscopy, fluorescence spectroscopy), spectrometry (e.g. mass spectrometry, nuclear magnetic resonance spectrometry, surface plasmon resonance), functional assays, and the like.

The binding properties of a receptor to a chemical may be correlated with a positive, or with an adverse, response of an animal, clinical trial participant, or medical patient. For the case of clinical trial participants, for example, those participants who respond adversely to the drug candidate may have a different receptor affinity or selectivity than participants that respond positively to the drug candidate.

One aspect of the invention may be demonstrated using an array prepared as described in Kukar et al., "Protein Microarrays to Detect Protein-Protein Interactions Using Red and Green Fluorescent Proteins," *Analytical Biochemistry*, vol. 306, pp. 50-54 (2002). The baseline sulfur content of the receptors of the array would be measured using x-ray fluorescence spectroscopy. Afterward, the receptors of the array would be exposed to a solution of olanzapine, which has the structural formula

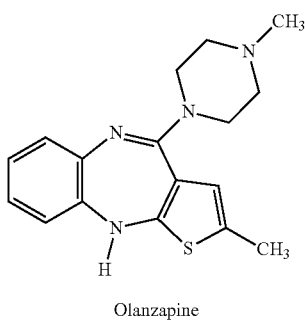 [SMILES: Cc1cc2c(s1)Nc1ccccc1N=C2N1CCN(C)CC1]

Olanzapine and the chemical formula $C_{17}H_{20}N_4S$ (olanzapine is the active ingredient in ZYPREXA®). Afterward, the sulfur content of each receptor would be measured again using x-ray fluorescence microscopy. The difference in sulfur content between the two measurements is related to the binding of olanzapine to receptors the array.

It is believed that the therapeutic effects of olanzapine are a result of olanzapine binding to several receptors, including the human serotonin 5HT2A receptor (see, for example: www.gpcr.org). Toxic effects are believed to occur as a result of olanzapine binding to alpha-1-adrenergic (NAa1) receptors (see, for example: "Olanzapine (ZYPREXA®)" in Clinical Toxicology Review, vol. 18, no. 2, March 1997. The pKi (where pKi=−log Ki, where Ki is the inhibition equilibrium constant) of olanzapine for 5HT2A is reported to be 7.8-8.9, while the pKi of olanzapine for NAa1 is reported to be 6.3-7.6. If the binding of the chemical to a receptor also inhibits that receptor, then the pKa and the pKi of the chemical have the same value.

The selectivity of binding of olanzapine to NAa1 versus 5HT2A may be measured by first preparing an array of NAa1 and 5HT2A on a substrate, then measuring the baseline sulfur content of each enzyme using XRF, then contacting the arrayed enzymes with a solution of olanzapine, and then measuring the total amount of sulfur using XRF, and then subtracting the baseline amount of sulfur from the total amount of sulfur, which indicates the amount of olanzapine that binds to each enzyme.

From the binding data obtained for olanzapine, it appears that chemicals useful as drugs form a complex with at least one receptor that has a pKi of greater than 5.

According to the invention, the x-ray excitation beam is used to excite one receptor at a time. The temperature of the array should be kept constant so that each x-ray measurement is performed at the same temperature, or at nearly the same temperature (±3 degrees Celsius). For the case of measuring the binding of olanzapine to each receptor, for example, each measurement should be performed at the same temperature or at nearly the same temperature because the binding affinity changes as the temperature changes.

After the selectivity of the olanzapine for binding to 5HT2A and to NAa1 is measured, additional chemicals can be similarly measured in order to determine whether any other chemical has a better selectivity for 5HT2A versus NAa1. A chemical such as the trifluoromethylolanzapine, which has the structural formula

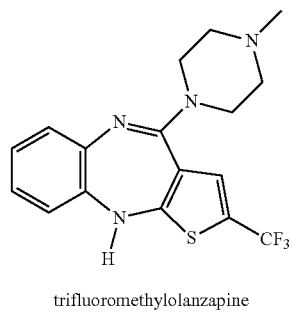 [SMILES: CN1CCN(C2=Nc3ccccc3Nc3sc(C(F)(F)F)cc32)CC1]

trifluoromethylolanzapine for example, may be screened against the same receptor array, or screened against another receptor array having the same proteins, and the binding selectivity for trifluoromethylolanzapine can be measured. If the selectivity of trifluoroolanzapine for 5HT2A versus NAa1 is greater than the selectivity of olanzapine is, then trifluoromethylolanzapine would be expected to be a superior drug.

Another aspect of the present invention relates to the determination of the kinetic parameters of an interaction between a chemical and a receptor.

After the baseline is measured or calculated for a receptor, as previously described, the receptor is exposed to a chemical at a particular temperature. The temperature is preferably a fixed temperature, preferably between about 27 degrees Celsius and about 47 degrees Celsius and more preferably is a fixed temperature between about 32 degrees Celsius and about 42 degrees Celsius. The XRF signal of any receptor-chemical complex formed is then measured. After taking this measurement at a first fixed temperature, the temperature is adjusted so that it is different from the first temperature by at least 2 degrees Celsius. The XRF signal should then be measured for the sample at this new temperature.

Alternatively, the first measurement and second measurement can be performed as follows. The receptor and chemical can be mixed first at one temperature, and next at a different temperature. Then, the chemical-receptor complexes that form are isolated (e.g. by spatially separation) so that any chemical that was bound to the receptor remains spatially associated with the receptor. The XRF measurements may then be obtained at any temperature desired.

The kinetic parameters for the formation of a receptor-chemical complex may similarly be determined by obtaining the baseline XRF signal for at least one receptor as described above, followed by exposing the receptor to a first solution of a chemical where the chemical is present in a fixed concentration. The XRF signal of any chemical-receptor complex is then measured. These steps are then repeated with a second solution having a different concentration of the chemical. The contact times between the first solution and the receptor and the second solution and the receptor are measured in order to determine the rate of the binding reaction, which is related to the amount of complex formed per unit time. Preferably the contact times between the first solution and the receptor and the second solution and the receptor are the same.

The method may also be practiced using a solution having a concentration gradient; using a concentration gradient is similar to using two solutions at two different times. The reaction kinetics may then be determined, as described in Gordon M. Barrow, Physical Chemistry, 5th Ed., McGraw-Hill, NY, 1988, chapter 18. The activation parameters $\Delta G^\neq$, $\Delta H^\neq$, $\Delta S^\neq$ may be determined using the Arrhenius equation (see, for example: Gordon M. Barrow, Physical Chemistry, 5th Ed., McGraw-Hill, NY, 1988, pp. 710-712.) and the Eyring equation (see, for example: Gordon M. Barrow, Physical Chemistry, $5^{th}$ Ed., McGraw-Hill, NY, 1988, pp. 756-757.)

This aspect of the invention may be demonstrated by preparing a protein array that includes at least one protein receptor (see, for example: Kukar et al., "Protein Microarrays to Detect Protein-Protein Interactions Using Red and Green Fluorescent Proteins," Analytical Biochemistry, vol. 306, pp. 50-54 (2002), incorporated herein by reference). The baseline sulfur content of the protein spots of the array is determined using x-ray fluorescence spectroscopy. After determining the baseline sulfur content, the protein array is contacted with a solution of olanzapine. Afterward, the sulfur content of each protein spot is determined again using x-ray fluorescence microscopy. The difference in sulfur content between the two measurements for each protein spot is then quantified. This difference is related to the binding of olanzapine to proteins in the array.

In order to measure the rate of binding of olanzapine to 5HT2A, a solution of olanzapine may be contacted with a 5HT2A. The кHT2A may be in solution, or as part of an array of proteins, or associated with a substrate. If the 5HT2A is in solution, it should be immobilized in some manner, such as in the manner described in U.S. patent application Ser. No. 10/621,825 entitled "Method and Apparatus for Detecting Chemical Binding". Any increase in the sulfur XRF signal, which is presumably due to an increase in the amount of olanzapine that is bound to 5HT2A, may be measured periodically over time to determine the rate at which olanzapine binds to 5HT2A. This may be repeated using solutions having various concentrations of olanzapine, and at different temperatures in order to determine the rate of binding at different temperatures; this is important for determining the activation parameters $\Delta G^\neq$, $\Delta H^\neq$, $\Delta S^\neq$, as well as for determining the binding kinetics that would be expected for a healthy patient (37° C.) versus a patient with a mild (38° C.) or severe (>38° C.) fever.

For examining a chemical that is a candidate for drug discovery according to the present invention, it is preferable that the chemical has one or more features that have come to be known as "Lipinski" features, described in C. A. Lipinski et al., "Experimental And Computational Approaches To Estimate Solubility And Permeability In Drug Discovery And Development Settings," Advanced Drug Delivery Reviews, vol. 23, pp. 3-25, (1997). These features include the following: a molecular weight equal to or less than about 500 daltons; a number of hydrogen bond acceptors that is equal to five or less; a number of hydrogen bond donors that is equal to ten or less; and a log P of five or less where P is the ratio of the solubility of the chemical in octanol to the solubility of the chemical in water. Elaborating on the hydrogen bond acceptor properties of drug candidates, it is preferable that the chemical has the property that the sum of nitrogen, oxygen, sulfur, fluorine, chlorine, bromine, and iodine groups available for hydrogen bonding in the chemical is five or less. For the purposes of counting hydrogen bond acceptors, each of the following is counted as a single hydrogen bonding acceptor: difluoromethyl groups, trifluoromethyl groups, dichloromethyl groups, trichloromethyl groups, dibromethyl groups, tribromethyl groups, ester groups, amide groups, carboxylic acid groups, urea groups, and carbamate groups. Also for the purposes of counting hydrogen bond acceptor groups, the following are not counted as a hydrogen bond acceptor: nitro groups, nitroso groups, and cyano groups.

While the Lipinski features suggest that a molecular weight of less than about 500 is preferable, Hemmilä (vide infra) reported that chemicals having a molecular weight of 5000 daltons or less cannot be tagged with an optical tag without overly perturbing their binding properties, such as binding affinities (see I. A. Hemmilä and P. Hurskainen, "Novel detection strategies for drug discovery,". Drug Discovery Today, Vol. 7, pp. S150-S156, (2002)). The present invention does not employ tags and thus can be used for studying the binding of chemicals that have a molecular weight of 5000 daltons or less.

For a chemical having hydrogen bond donor groups, it is preferable that the chemical has the property that the sum of hydrogen atoms bound to sulfur, nitrogen, and oxygen in the chemical is ten or less.

For drug candidates, it is preferable that chemical is soluble in water. The chemical should be dissolved in a fluid that includes water, preferably with a pH of from about pH 6 to about pH 8.

The chemical may have zero, one, or more than one chiral center. A chemical sample that contains equal amounts of each enantiomer may be used. Once it has been determined using the invention that the chemical binds to a receptor, the chemical may be analyzed to determine which particular enantiomer, if any, is bound to the receptor. For the case of more than one enantiomer binding to the receptor, it may be determined which is bound more strongly to the receptor. It is important to determine which receptor(s) bind to each enantiomer of the chemical in order to identify any potential side effects of a toxic enantiomer. Thalidomide, for example, is a chemical that was used to treat morning sickness until it was discovered that a toxic enantiomer of the chemical was responsible for birth defects.

In order to optimize the balance between the speed of analysis versus the sensitivity of the XRF technique, it is preferable that a sample of receptor, or chemical-receptor complex, be exposed to the X-ray excitation beam for a period of time from about 100 milliseconds to about 600 seconds. To further optimize speed versus sensitivity, it is preferable that the x-ray excitation beam spends more time focused on a pixel that contains receptor and/or receptor-chemical complex than on a pixel that is substantially devoid of receptor or receptor-chemical complex. This way, less time is wasted analyzing parts of a sample that have little useful information.

An x-ray translucent barrier may be used with a receptor or receptor array in order to minimize evaporation and evaporative cooling of receptors and/or chemicals.

Another aspect of the present invention relates to use for personalized medicine. Personalized medicine is described in "Personalized Prescribing," The Scientist, 15[12]:10, Jun. 11, 2001, incorporated herein by reference. Personalized medicine is important because it is expected to decrease the number of adverse drug reactions, which currently result in the deaths of about 100,000 hospitalized patients per year, and cause serious side effects in another 2.2 million people. Personalized medicine currently relies on genotyping a patient in order to guide the physician in administering drugs to the patient. This genotyping focuses on single nucleotide polymorphism (SNP) analysis. The cost per SNP analysis currently is about 1 dollar per SNP, but with the current poor understanding of pharmacogenomics and the large number of possible SNP's (thousands), it is believed that costs related to SNP analysis must decrease to pennies per SNP before SNP analysis becomes more widely used. The analysis provided using the present invention, by contrast, allows phenotyping and direct analysis of drug interactions with protein profiles, thus providing higher quality information about the particular patient and disease Thus, the present invention may be used in personalized medicine to assist physicians in prescribing drugs for their patients. A protein array, such as an array on a commercially available protein chip manufactured by CIPHERGEN™ or ZYOMYX™ for example, may be exposed to protein extracts from a cancer patient. In this case, as in others where there is a clear difference between diseased tissue and healthy tissue, extracts from the tumor and from healthy tissue would be taken from the patient. After exposing the chip to the extracts, a baseline XRF baseline spectrum would be obtained. Solutions of each drug that the doctor is considering for treating the tumor would then be contacted with the protein chip. The binding affinity of each drug would then be measured according to the invention, which involves measuring the XRF signals for heavy elements present in the drug-receptor complex, subtracting out the baseline from this measurement, and then comparing the signals to see which drug exhibits a more selective binding to the tumor versus the healthy tissue and/or which drug binds more strongly to the tumor.

The efficacy of a drug may be correlated with the binding affinity of the drug for diseased tissue; more efficacious drugs tend to bind more strongly to proteins associated with a disease than less efficacious drugs do. Side effects of a drug may be correlated with the ability of the drug to bind to healthy tissue. The choice of which drug to prescribe may be based on the ability of the drug to bind strongly to the diseased tissue (or to proteins associated with the diseased tissue) and to bind weakly, or not at all, to healthy tissue (or to proteins associated with health tissue). A cancer biopsy sample (i.e. from a tumor), for example, may be lysed and arrayed on an analytical protein chip. The chip would then be exposed to a variety of chemotherapy drugs (or even cold radiopharmaceutical surrogates) and the relative binding affinities of the different drugs to the arrayed biopsy sample would guide the course of treatment. Side effects could be quantified and minimized by performing a similar assay using non-cancerous tissue, and selecting the drug based on minimized drug-enzyme interactions. This method may also be used with drug mixtures, which are sometimes referred to as "cocktails".

The invention may be used for participant stratification in clinical trials of proposed drugs. Currently, participant stratification methods are based on DNA chips, where genomic profiles are correlated with the variation in participant response to chemicals (e.g. drug candidates). The correlation of genomic profiles with patient response is sometimes referred to as "pharmacogenomics". Genomic profiles are several steps removed from the proteomic profile of a participant in a clinical trial of a drug; genetics and environmental factors affect which proteins are expressed. Drugs regulate protein behavior, and so the protein make-up of a particular participant and how those proteins interact with the drug(s) in a course of clinical trials will provide the best information for participant stratification. Protein chips have become inexpensive and commercially available.

Regarding the use of the invention for participant stratification in a clinical trial of a drug such as an anti-cancer drug, a protein array on a protein chip may be exposed to protein extracts from a cancer patient, as described above. Protein extracts of the tumor and of healthy tissue would be taken from the patient. After exposing the chip to the extracts, a baseline XRF baseline spectrum would be obtained. Solutions of each drug being tested in the trial would then be contacted with the protein chip having the bound proteins. The binding affinity of each drug would then be measured according to the invention, which involves measuring the XRF signals of heavy elements present in the drug-receptor complex, subtracting out the baseline from this measurement, and then comparing the signals to see which drug exhibits a more selective binding to the tumor versus the healthy tissue and/or which drug binds more strongly to the tumor. This information may then be correlated to the efficacy, toxicity, and side effects of the drugs as measured in the clinical trials. The importance of clinical trial stratification is that if a drug can be shown to only have unacceptable side effects for people with specific genomic and/or proteomic profiles (i.e. a strata), the drug may be approved for other strata for which the drug has acceptable side effects. This process may allow drugs that would otherwise be rejected by the Food and Drug Administration or other regulatory agencies to be accepted for a more limited use, thereby allowing drug candidates to be used that would otherwise be rejected.

Another aspect of the invention relates to drug manufacturing. The drug manufacturing process is lengthy, typically including a period of time where a new drug is discovered, another period of time where the drug is developed, more time where the drug is tested with animals and then humans, and more time where the drug is synthesized on a larger and larger scale. Discovery involves determining which chemicals are likely to be effective drugs, and is often conducted by measuring the interaction between a chemical and a receptor (sometimes referred to in the art as a "druggable target"). Development involves in vitro testing to estimate the likely side effects and pharmacokinetics of a chemical. Animal testing is used to determine whether the drug is safe in animals, and are sometimes used to determine whether a drug is effective in animals. If the drug is deemed sufficiently safe in animals, it may be administered to human volunteers in clinical trials to determine human safety and efficacy. If a drug is deemed safe and effective in human volunteers, it may be mass-produced for use by physicians and patients. All of these steps are necessary.

The invention may be used to estimate the efficacy of a chemical (analog, drug). Measuring the affinity of one or more chemicals for a druggable target fulfills the discovery step.

The invention may be used to estimate side effects and/or pharmacokinetics by measuring the binding selectivity of one or more chemicals for a druggable target versus other proteins that may be associated with side effects or pharmacokinetics. Animal studies and human studies may then be performed, followed by mass production of the drug using chemical synthesis or biological synthesis.

Another aspect of the invention relates to its use in measuring post-translational modification of proteins, such as the phosphorylation or dephosphorylation of one or more proteins. Phosphorylation and desphosphorylation reactions are described by K. Martin et al. in "Quantitative Analysis Of Protein Phosphorylation Status And Protein Kinase Activity On Microarrays Using A Novel Fluorescent Phosphorylation Sensor Dye," *Proteomics*, vol. 3, pp. 1244-1255 (2003). This paper describes the need for radioactive labeling and fluorescent tagging; however, both radioactive labeling and fluorescent tagging are unnecessary in view of the present invention, which can measure the amount of phosphorus directly in an untagged protein using XRF.

An example of the use of the invention for measuring post-translational modifications may include establishing a baseline X-ray fluorescence signal for a heavy element (i.e. an element having an atomic number of nine or greater), such as phosphorus, in a portion of a protein. The portion of protein is then exposed to reaction conditions such as those described by K. Martin et al. in "Quantitative Analysis Of Protein Phosphorylation Status And Protein Kinase Activity On Microarrays Using A Novel Fluorescent Phosphorylation Sensor Dye," *Proteomics*, Vol. 3, pp. 1244-1255, (2003), which alter the amount of phosphorus in the protein. The x-ray fluorescence signal due to the element would then be remeasured using XRF. Subtracting the baseline x-ray fluorescence signal from the remeasured x-ray fluorescence signal provides a net X-ray fluorescence signal that may be correlated with the amount of the element in the protein, which provides an estimate of the extent of phosphorylation of the protein.

The following EXAMPLES provide an illustration of various aspects of this invention.

Example 1

Binding of Ziprasidone to Protein Receptors

A protein array may be prepared as described in G. MacBeath and S. L. Schreiber, "Printing Proteins As Microarrays For High-Throughput Function Determination," Science, vol. 289, pp. 1760-1763, (2000). This protein array may be exposed to a solution of ziprasidone, which is the active ingredient in the drug GEODON™. Ziprasidone has a molecular formula of $C_{21}H_{20}ClN_4OS$ and the structure shown below.

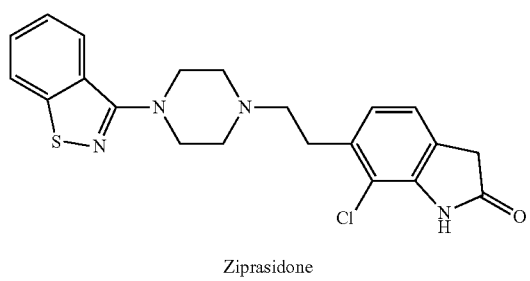 [SMILES: O=C1Cc2ccc(CCN3CCN(c4nsc5ccccc45)CC3)c(Cl)c2N1]

Ziprasidone

The elements chlorine and sulfur may each be detected by x-ray fluorescence. After the array is exposed to the ziprasidone-containing solution, an EDAX Eagle Microprobe x-ray fluorescence microscope, for example, could be used to determine the receptor proteins that bind to the ziprasidone. The amount of ziprasidone that is associated with each receptor may be quantified by x-ray fluorescence.

None of the proteins of the array are expected to contain the element chlorine, so the chlorine x-ray fluorescence baseline may be assumed to be zero (although the chlorine x-ray fluorescence baseline could be measured). At least some of the proteins are expected to contain the element sulfur (from sulfur containing amino acids such as cysteine and methionine). Before exposing the array proteins to ziprasidone, a baseline X-ray fluorescence signal for sulfur may be obtained, and after exposure to the ziprasidone, the X-ray fluorescence signal due to sulfur would be measured again. The difference in the sulfur signals would be used to determine whether any receptor-ziprasidone complex formed, and measuring the amount of any such complex that formed.

Example 2

Binding of Ziprasidone to DNA Receptors

A DNA array such as an AFFYMETRIX GENECHIP™ may be exposed to a solution that contains ziprasidone, as described in EXAMPLE 1. After the array is exposed to the ziprasidone-containing solution, an EDAX Eagle Microprobe x-ray fluorescence microscope, for example, could be used to determine the locations of those receptor DNA that bind to the ziprasidone. The amount of ziprasidone that is associated with each receptor may be quantified by x-ray fluorescence.

None of the DNA receptors of the array are expected to contain the elements chlorine or sulfur, so the chlorine X-ray fluorescence baseline and the sulfur X-ray fluorescence baseline may be assumed to be zero. After exposure to the ziprasidone-containing solution, the X-ray fluorescence signal due to sulfur and/or chlorine would be measured. The measured X-ray fluorescence signal(s) may be used to determine whether any DNA-ziprasidone complex formed, and measuring the amount of any such complex that formed.

The DNA receptors of the array may then be analyzed to identify which of the DNA receptor(s) bind to the ziprasidone and which fail to bind. With this information, which is provided by this EXAMPLE, factors that affect binding may be determined.

Example 3

Binding of DNA Receptors to DNA Probe Molecules

A DNA array such as an AFFYMETRIX GENECHIP™ may be exposed to a solution of DNA molecules that may or may not be complementary to the DNA on the array. If the DNA in solution is not complementary to any of the DNA on the array, then no binding is expected to occur. If the DNA in solution were complementary to any of the DNA on the array, then some binding would be expected to occur. DNA molecules include the element phosphorus that is detectable using x-ray fluorescence of the phosphorus atoms. After the array is exposed to the solution of DNA, the array may be analyzed using an EDAX Eagle Microprobe x-ray fluorescence microscope. The DNA receptors of the array that bind to the added DNA from the DNA-containing solution may be identified by the phosphorus x-rays, and the amount of added DNA that is associated with each receptor may be quantified by the x-ray fluorescence signal.

Preferably, a baseline x-ray fluorescence signal for each portion of DNA receptor would be obtained before exposing the receptor array to the DNA containing solution to determine the phosphorus content of the DNA receptors of the array. After exposing the array to the DNA solution, the difference in the phosphorus x-ray fluorescence signals after contact and before contact with the DNA solution may be quantified and related to the binding of DNA from the solution to various receptors of the array.

This DNA receptor array used with the EXAMPLE may be replaced with an array that includes other molecules, such as RNA and peptides, to examine the binding of DNA from a solution to these other receptors. RNA may also be used as a probe molecule.

Example 4

Binding of Drugs to Protein Receptors

A protein array may be prepared as described in Kukar et al., "Protein Microarrays to Detect Protein-Protein Interactions Using Red and Green Fluorescent Proteins," Analytical Biochemistry, vol. 306, pp. 50-54 (2002). This protein array may be exposed to a solution of olanzapine (the active ingredient in ZYPREXA®) and aripiprazole (the active ingredient in ABILIFY™). Olanzapine has the chemical formula $C_{17}H_{20}N_4S$, and aripiprazole has the chemical formula $C_{23}H_{27}Cl_2N_3O_2$. These molecules have the chemical structures shown below.

Olanzapine:

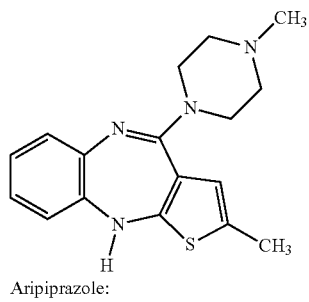

Aripiprazole:

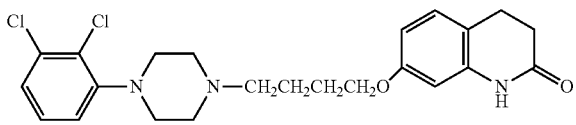

Olanzapine may be detected and quantified by the x-ray fluorescence of its sulfur atom and aripiprazole may be detected and quantified by the x-ray fluorescence of its chlorine atoms.

After the array is exposed to the solution that contains a mixture of aripiprazole and olanzapine, the array may be analyzed using an EDAX Eagle Microprobe x-ray fluorescence microscope. The protein receptors that bind to olanzapine may be identified by the sulfur x-rays. The amount of olanzapine that is associated with each receptor may be quantified by x-ray fluorescence. The protein receptors that bind to aripiprazole may be identified by the chlorine x-rays. The amount of aripiprazole that is associated with each receptor may be quantified by x-ray fluorescence.

Preferably, a baseline x-ray fluorescence signal for chlorine and one for sulfur are measured for each receptor before exposing the receptors to the solution. After contacting the array with the solution, the sulfur and chlorine content of each receptor would be measured again. The difference in the measured sulfur and chlorine x-ray fluorescence signal after contact and before contact with the solution of aripiprazole and olanzapine solution may be quantified and related to the binding of aripiprazole and olanzapine to receptors in the array.

Example 5

Binding of Drugs to Protein Receptors

A protein array may be prepared as described in Kukar et al., "Protein Microarrays to Detect Protein-Protein Interactions Using Red and Green Fluorescent Proteins," Analytical Biochemistry, vol. 306, pp. 50-54 (2002). This protein array may be exposed to a solution that contains a mixture olanzapine (the active ingredient in ZYPREXA®) and acetylsalicylic acid (the active ingredient in aspirin). Olanzapine has the chemical formula $C_{17}H_{20}N_4S$, and acetylsalicylic acid has the chemical formula $C_9H_8O_4$. Olanzapine may be detected and quantified by the x-ray fluorescence of its sulfur atom. Acetylsalicylic acid, however is more difficult to both to detect and differentiate using x-ray fluorescence because it only contains carbon, oxygen and hydrogen, the x-ray fluorescence signals of which are overwhelmed by the corresponding signals in the protein receptors.

After the array is exposed to the solution, the array may be analyzed using an EDAX Eagle Microprobe x-ray fluorescence microscope. The protein receptors that bind to olanzapine in the presence of acetylsalicylic acid may be identified by the net X-ray fluorescence signal from sulfur. The amount of olanzapine that is associated with each receptor may be quantified by x-ray fluorescence.

Preferably, a baseline X-ray fluorescence measurement for the protein receptors of the array would be obtained before exposure to the solution containing acetylsalicylic acid and olanzapine. This analysis may be used to determine the sulfur content of the protein spots on the array. After contacting the array with the solution, the sulfur content of each protein spot may be measured again. The difference in the sulfur after contact and before contact with acetylsalicylic acid and olanzapine solution may be quantified and related to the binding of olanzapine to various protein receptors in the array when acetylsalicylic acid is present.

For comparison, the procedure described above for this EXAMPLE may be repeated using a solution that includes olanzapine without acetylsalicylic acid in order to determine whether the presence of acetylsalicylic acid has any effect on the binding affinity and binding selectivity of olanzapine to the protein receptors. After contacting the array with the solution containing olanzapine (without acetylsalicylic acid), the sulfur content of each protein spot may be measured again. The difference in the sulfur after contact and before contact with olanzapine solution may be quantified and related to the binding of olanzapine to various spots in the array when acetylsalicylic acid is not present. The binding information may be compared to the binding of olanzapine to various spots in the array when acetylsalicylic acid is present.

This EXAMPLE illustrates a particularly important aspect of the present invention, which relates to estimating the therapeutic index of a chemical (in this case, olanzapine)

and comparing it to an estimated therapeutic index of a "cocktail" i.e. a mixture of two or more chemicals.

Example 6

Personalized Medicine

A question arises relating to which antipsychotic drug, olanzapine or aripiprazole, should be prescribed for a patient. A protein array would be prepared as described, for example, in Kukar et al., "Protein Microarrays to Detect Protein-Protein Interactions Using Red and Green Fluorescent Proteins," *Analytical Biochemistry*, vol. 306, pp. 50-54 (2002).

This protein array would be exposed to a solution of a mixture of olanzapine ($C_{17}H_{20}N_4S$) and aripiprazole ($C_{23}H_{27}Cl_2N_3O_2$). Olanzapine may be detected and quantified by the x-ray fluorescence of its sulfur atom, and aripiprazole may be detected and quantified by the x-ray fluorescence of its chlorine atoms.

After the array is exposed to the solution, the array would be analyzed using an, EDAX Eagle Microprobe x-ray fluorescence microscope. The receptor proteins that bind to olanzapine may be identified by their sulfur x-rays. The amount of olanzapine that is associated with each receptor spot may be quantified by x-ray fluorescence. The receptor proteins that bind to aripiprazole may be identified by the chlorine x-rays. The amount of aripiprazole that is associated with each spot may be quantified by x-ray fluorescence.

Preferably, the a baseline x-ray fluorescence signal for each receptor protein of the array is obtained before exposure to the solution. After contacting the array with the solution, the sulfur and chlorine content of each protein receptor spot may be measured again. The difference in the sulfur and chlorine after contact and before contact with the solution may be quantified and related to the binding of aripiprazole and olanzapine to the receptors in the array.

An therapeutic index for this patient for olanzapine and one for aripiprazole may be estimated using the x-ray fluorescence data. These estimated indices may be used to guide the choice of drug to be administered.

Example 7

Patient Stratification

A series of protein arrays may be prepared as described in Kukar et al., "Protein Microarrays to Detect Protein-Protein Interactions Using Red and Green Fluorescent Proteins," *Analytical Biochemistry*, vol. 306, pp. 50-54 (2002). The protein arrays would be prepared using samples from participants in clinical trials of pharmaceutical compounds and/or formulations. This is an EXAMPLE for a study for determining the safety and/or efficacy of olanzapine.

The protein arrays described above would be exposed to a solution that includes olanzapine ($C_{17}H_{20}N_4S$). Olanzapine may be detected and quantified by the x-ray fluorescence of its sulfur atom.

After the array is exposed to the solution, the array may be analyzed using an EDAX Eagle Microprobe x-ray fluorescence microscope. The protein receptors that bind to olanzapine may be identified by the x-ray fluorescence signal due to sulfur. The amount of olanzapine that is associated with each protein receptor spot may be quantified by x-ray fluorescence.

Preferably, a baseline x-ray fluorescence signal would be obtained for each receptor before exposure to the solution. This analysis may be used to determine the sulfur content of the protein spots on the array. After contacting the array with the solution, the sulfur content of each protein spot may be measured again. The difference in the sulfur content after contact and before contact with olanzapine solution may be quantified and related to the binding of olanzapine to various protein receptors in the array.

The binding of olanzapine to various proteins or classes of proteins may be then correlated with the results of the clinical trial, in order to correlate protein-olanzapine binding characteristics with safety and/or efficacy of various formulations of olanzapine-based drugs.

It is preferable to use protein arrays rather than DNA arrays for patient stratification, because proteins are believed to control cell functions. However, this method may also be used with DNA arrays, tissue arrays, cellular arrays, and the like.

In summary, the present invention provides a method for measuring binding selectivities between chemicals and receptors. The invention provides significant advantages over known methods for measuring binding selectivity. Known methods often require either radioactive chemicals, or chemicals that include a covalently attached label that fluoresces upon exposure to ultraviolet excitation radiation. Since the invention does not require radioactive or chemically tagged materials, the problems dealing with the handling of radioactive materials and the disposal of radioactively contaminated waste are avoided. Importantly, since the use of artificially tagged materials is not required, there can be no interference from the tag in the evaluation of the binding affinity of the corresponding desired untagged material. Further, in contrast to methods that require tags, the method of the present invention can be used to evaluate the binding affinity of materials that do not fluoresce while exposed to ultraviolet radiation. It should be understood that although tagged materials are not required, they could also be used and this aspect of the invention offers a distinct advantage in that the invention can provide a direct comparison of binding affinity of the untagged chemical with that of the corresponding tagged surrogate. This comparison could validate or invalidate the assumption that a particular untagged chemical and its tagged surrogate have the same binding affinity to a particular substrate.

The foregoing description of the invention has been presented for purposes of illustration and description and is not intended to be exhaustive or to limit the invention to the precise form disclosed, and obviously many modifications and variations are possible in light of the above teaching.

The embodiment(s) were chosen and described in order to best explain the principles of the invention and its practical application to thereby enable others skilled in the art to best utilize the invention in various embodiments and with various modifications as are suited to the particular use contemplated. It is intended that the scope of the invention be defined by the claims appended hereto.

What is claimed is:

1. A method for estimating, in a sample, binding of a chemical having at least one heavy element of atomic number nine or higher to a biological receptor, comprising:
depositing the biological receptor on a focusing chip, wherein the focusing chip has an amount of the at least one heavy element that produces less than 25% of an X-ray fluorescence signal produced by the sample when both the focusing chip and the sample are measured for the at least one heavy element, the focusing chip being disposed on a solid metal substrate that has a thickness of less than 50 microns, wherein the focusing chip has a thickness of less than 50 microns;

acquiring a first X-ray fluorescence signal due to any presence of the at least one heavy element in the receptor disposed on the focusing chip, as a result of exposing the receptor to a first excitation X-ray beam, prior to exposing the receptor to the chemical;

exposing the receptor to the chemical by depositing the chemical onto the focusing chip, and allowing the chemical to bind to the receptor to form a chemical-receptor complex;

measuring, with an X-ray source, a second X-ray fluorescence signal due to any presence of the at least one heavy element by exposing the chemical-receptor complex to a second excitation X-ray beam, Wherein a cross section of the second excitation X-ray beam transmitted by the X-ray source is between 25% and 250% of an area of the focusing chip occupied by the receptor-chemical complex; and subtracting the first X-ray fluorescence signal from the second X-ray fluorescence signal to quantify the binding of the chemical to the receptor, thereby estimating binding of the chemical to the receptor.

2. The method of claim 1, further comprising standardizing result of the quantification of the binding of the chemical to the receptor by dividing the result of the quantification of the binding of the chemical to the receptor by the amount of the receptor to obtain a standardized result of the quantification of the binding of the chemical to the receptor.

3. The method of claim 1, wherein the first or second X-ray fluorescence signal is provided using a polychromatic X-ray source.

4. The method of claim 1, wherein the focusing chip comprises beryllium, carbon, silicon, aluminum, iron, cobalt or gold.

5. The method of claim 1, wherein the biological receptor is selected from the group consisting of a protein, a DNA, an RNA, a human cell, a plant cell, an animal cell, and a microorganism.

6. The method of claim 1, wherein the chemical to be measured comprises at least one of fluorine, phosphorous, sulfur, chlorine, bromine, iodine, platinum, copper, zinc, gallium, or gadolinium.

7. The method of claim 1, wherein, in order to reduce noise, the focusing chip is substantially free of the at least one heavy element to be measured, and wherein the focusing chip is substantially free of technetium, thorium, and uranium.

8. The method of claim 1, wherein the focusing chip is substantially free of at least one of the heavy elements selected from the group consisting of sulfur, fluorine, phosphorous, chlorine, bromine, iron, zinc, magnesium, calcium, titanium, scandium, and platinum.

9. The method of claim 1, further comprising exposing the chemical and chemical-receptor complex to a buffer that is selected to be substantially free of the at least one heavy element present in the chemical to be measured; and wherein the buffer comprises one or more of chemicals or functional groups selected from the group consisting of amine, imine, nitrate anion nitrite anion, ammonium cation, and iminium cation.

10. The method of claim 1, wherein the chemical-receptor complex is exposed to a solution prior to measurement of the second X-ray fluorescence the solution comprising a matrix modifier.

11. The method of claim 1, wherein the second X-ray fluorescence signal is measured using a chromium, palladium or silver X-ray source.

12. The method of claim 1, wherein the second X-ray fluorescence signal is measured using a rhodium source or a molybdenum source.

13. The method of claim 1, wherein the second X-ray fluorescence signal is measured using an X-ray source having a K-alpha L-alpha line at or above 2.838 KeV and less than 9.441 KeV.

14. The method of claim 1, wherein the receptor is deposited on the focusing chip in volumes between 1 nanoliter and 50 microliters.

15. The method of claim 1, wherein the chemical receptor complex is concentrated on the focusing chip prior to measurement of the second X-ray fluorescence signal.

16. The method of claim 1, wherein the sample contains between ten nanograms and one microgram of the at least one heavy element.

17. The method of claim 1, wherein the focusing chip has a pattern of at least one hydrophobic region and at least one hydrophilic region.

18. The method of claim 1, further comprising selecting the focusing chip based on the at least heavy element to be measured in the chemical-receptor complex by:

for measurement of the heavy element phosphorus, selecting a focusing chip that is substantially free of zirconium, platinum, gold, niobium, mercury, and thallium;

for measurement of the heavy element sulfur, selecting a focusing chip that is substantially free of thallium, molybdenum, sulfur, lead, bismuth, technetium, and ruthenium; and for measurement of the heavy element chlorine, selecting a focusing chip that is substantially free of technetium, ruthenium, rhodium and palladium.

* * * * *

UNITED STATES PATENT AND TRADEMARK OFFICE
CERTIFICATE OF CORRECTION

PATENT NO. : 10,877,035 B2
APPLICATION NO. : 14/693094
DATED : December 29, 2020
INVENTOR(S) : Eva R. Birnbaum It is certified that error appears in the above-identified patent and that said Letters Patent is hereby corrected as shown below:

On the Title Page

On page 2, in Column 1, item (56), OTHER PUBLICATIONS, Line 13, delete "Spectrochemica" and insert --Spectrochimica--.

On page 2, in Column 1, item (56), OTHER PUBLICATIONS, Line 15, delete "Synchroton" and insert --Synchrotron--.

On page 2, in Column 1, item (56), OTHER PUBLICATIONS, Line 33, delete "Eurpean" and insert --European--.

On page 2, in Column 1, item (56), OTHER PUBLICATIONS, Line 41, delete "e" and insert --et--.

On page 2, in Column 1, item (56), OTHER PUBLICATIONS, Line 41, delete "Abstact" and insert --Abstract--.

On page 2, in Column 2, item (56), OTHER PUBLICATIONS, Line 28, delete ""Oianzapine (Zyprexa."" and insert --"Olanzapine (Zyprexa)"--.

On page 2, in Column 2, item (56), OTHER PUBLICATIONS, Line 36, delete "Isue" and insert --Issue--.

In the Specification

In Column 1, Line 6, delete "Continuation" and insert --Division--.

In Column 4, Line 44 approx., delete "Phospoimager" and insert --Phosphorimager--.

In Column 6, Line 18, delete "is provides" and insert --provides--.

Signed and Sealed this
First Day of June, 2021

Drew Hirshfeld
*Performing the Functions and Duties of the*
*Under Secretary of Commerce for Intellectual Property and*
*Director of the United States Patent and Trademark Office*

CERTIFICATE OF CORRECTION (continued)
U.S. Pat. No. 10,877,035 B2

In Column 6, Line 28, delete "manufacturing," and insert --manufacturing.--.

In Column 6, Line 67, delete "of the of the" and insert --of the--.

In Column 7, Line 4, delete "of the of the" and insert --of the--.

In Column 7, Line 43, delete "of the of the" and insert --of the--.

In Column 7, Line 53, delete "of the of the" and insert --of the--.

In Column 8, Line 22, delete "of the of the" and insert --of the--.

In Column 8, Line 26, delete "of the of the" and insert --of the--.

In Column 8, Line 65, delete "of the of the" and insert --of the--.

In Column 9, Line 8, delete "of the of the" and insert --of the--.

In Column 10, Line 37, delete "of the of the" and insert --of the--.

In Column 10, Lines 47-48, delete "of the of the" and insert --of the--.

In Column 14, Line 33, delete "Fims" and insert --Films--.

In Column 15, Line 5, delete "a the" and insert --the--.

In Column 15, Line 39, delete "Cytochrom" and insert --Cytochrome--.

In Column 15, Line 49, delete "phopshopeptide" and insert --phosphopeptide--.

In Column 15, Line 63, delete "steptavidin/" and insert --streptavidin/--.

In Column 16, Line 31, delete ""Electrosprayed" and insert --Electrosprayed--.

In Column 16, Line 55, delete "Electrospary" and insert --Electrospray--.

In Column 17, Line 2, delete "MSI score" and insert --MSE score--.

In Column 19, Line 25, delete "coumassie" and insert --coomassie--.

In Column 21, Line 49, delete "particulary" and insert --particularly--.

In Column 23, Line 40, delete "andrenergic" and insert --adrenergic--.

In Column 23, Line 41, delete "metaprolol" and insert --metoprolol--.

CERTIFICATE OF CORRECTION (continued)
U.S. Pat. No. 10,877,035 B2

In Column 23, Line 54, delete "andrenergic" and insert --adrenergic--.

In Column 27, Line 11 approx., delete "a the" and insert --the--.

In Column 27, Line 20, delete "ZIPPLATE®." and insert --ZipPlate®--.

In Column 27, Line 59, delete "when m" and insert --when--.

In Column 29, Line 8, delete "-.pdf;" and insert --.pdf;--.

In Column 29, Lines 12-13, delete "208.sub.-19.sub.-041." and insert --208_19_041--.

In Column 34, Line 30, delete "Lyspro" and insert --Lispro--.

In Column 34, Line 37, delete "iodonated;" and insert --iodinated;--.

In Column 34, Line 46, delete "-1-" and insert -- -l- --.

In Column 34, Line 46, delete "-1-" and insert -- -l- --.

In Column 34, Line 49, delete "chloroindol" and insert --chloroindole--.

In Column 34, Line 62, delete "triphosphate;" and insert --triphosphate);--.

In Column 36, Line 3, delete "dihydrogenphosphate" and insert --dihydrogen phosphate--.

In Column 36, Line 16, delete "1 h" and insert --1h--.

In Column 37, Line 36, delete "1 h" and insert --1h--.

In Column 37, Line 45, delete "1 h" and insert --1h--.

In Column 37, Lines 63-64, delete "benzoicacid;" and insert --benzoic acid;--.

In Column 38, Line 46, delete "(I-alanyl)" and insert --(l-alanyl)--.

In Column 38, Line 57, delete "(2s,4(r)" and insert --(2s,4r)--.

In Column 39, Line 1, delete "3-trioq-" and insert --3-triol]- --.

In Column 41, Line 57, delete "({5" and insert --(5--.

In Column 42, Line 2, delete "1 h" and insert --1h--.

In Column 42, Line 2, delete "1 h" and insert --1h--.

CERTIFICATE OF CORRECTION (continued)
U.S. Pat. No. 10,877,035 B2

In Column 42, Lines 2-3, delete "1 h" and insert --1h--.

In Column 42, Lines 17-18, delete "1 h" and insert --1h--.

In Column 42, Line 39, delete "diminazine" and insert --diminazene--.

In Column 42, Line 43, delete "(1 h," and insert --(1h,--.

In Column 42, Line 56, delete "(3-" and insert --3- --.

In Column 43, Line 1, delete "(3-" and insert --3- --.

In Column 43, Line 28, delete "amino}0" and insert --amino}--.

In Column 43, Line 30, delete "[1-" and insert --1- --.

In Column 43, Line 40, delete "}4)" and insert --}-(r)--.

In Column 44, Line 9, delete "yl]" and insert --yl--.

In Column 44, Line 40, delete "[2,3-d]" and insert --[2,3d]--.

In Column 44, Line 67, delete "1 h" and insert --1h--.

In Column 45, Line 43, delete "dichlorophenoxyl)" and insert --dichlorophenoxy)--.

In Column 45, Line 54, delete "d-alanine;" and insert --coa; d-alanine;--.

In Column 45, Line 56, delete "2deoxy" and insert --2'deoxy--.

In Column 46, Lines 15-16, delete "1 h" and insert --1h--.

In Column 46, Line 24, delete "1 h" and insert --1h--.

In Column 46, Line 46, delete "yl)" and insert --yl--.

In Column 49, Line 33, delete "1 h" and insert --1h--.

In Column 50, Line 8, delete "guanidinoethylthio)" and insert --guanidinoethylthio--.

In Column 50, Line 28, delete "(8," and insert --8,--.

In Column 51, Lines 33-34, delete "ixcontaining" and insert --ix containing--.

In Column 52, Line 1, delete "1-" and insert --l- --.

In Column 52, Lines 2-3, delete "propyl-]" and insert --propyl]--.

In Column 52, Line 3, delete "1-" and insert --l- --.

In Column 52, Line 18, delete "methylvaleryl)]" and insert --methylvaleryl]--.

In Column 52, Line 21, delete "1 h" and insert --1h--.

In Column 52, Line 22, delete "yl)" and insert --yl--.

In Column 52, Line 48, delete "-[(4-" and insert -- -(4- --.

In Column 52, Line 56, delete "1 h" and insert --1h--.

In Column 53, Line 11, delete "(1 h," and insert --(1h,--.

In Column 54, Line 9, delete "(2-[2-" and insert --2-[2- --.

In Column 54, Line 36, delete "1-" and insert --l- --.

In Column 54, Line 43, delete "3a-" and insert --3- --.

In Column 55, Line 9, delete "methoxyethoxyl)" and insert --methoxyethoxy)--.

In Column 55, Line 44, delete "methoxyethoxyl)" and insert --methoxyethoxy)--.

In Column 55, Line 62, delete "dichlorophenoxyl)" and insert --dichlorophenoxy)--.

In Column 56, Line 43, delete "5)" and insert --5')--.

In Column 56, Line 44, delete "1 h" and insert --1h--.

In Column 56, Lines 50-51, delete "flourouracil;" and insert --fluorouracil;--.

In Column 56, Line 53, delete "6-" and insert --5'- --.

In Column 56, Line 58, delete "1-" and insert --1'- --.

In Column 56, Line 64, delete "3-[[" and insert --3-[[n- --.

In Column 57, Line 41, delete "-1-" and insert -- -l- --.

In Column 59, Line 14, delete "-1-" and insert -- -l- --.

In Column 59, Line 34, delete "(2-" and insert --2- --.

CERTIFICATE OF CORRECTION (continued)
U.S. Pat. No. 10,877,035 B2

In Column 59, Line 35, delete "(2-" and insert --2- --.

In Column 60, Line 15, delete "propyithiocysteine;" and insert --propylthiocysteine;--.

In Column 60, Line 24, delete "[2-(2-" and insert --[2-2- --.

In Column 60, Line 67, delete "1 h" and insert --1h--.

In Column 60, Line 67, delete "hexyl)" and insert --hexyl--.

In Column 61, Lines 26-27, delete "phosphonate," and insert --phosphonate;--.

In Column 61, Line 62, delete "ethyl)" and insert --ethyl--.

In Column 61, Line 62, delete "{-[" and insert --{2-[--.

In Column 63, Line 13, delete "(1-" and insert --(l- --.

In Column 64, Line 43, delete "rham nose;" and insert --rhamnose;--.

In Column 64, Line 46, delete "methoxyethoxyl)" and insert --methoxyethoxy)--.

In Column 64, Line 53, delete "(1-" and insert --(l- --.

In Column 65, Line 18, delete "(1 h," and insert --(1h,--.

In Column 65, Lines 32-33, delete "1 h" and insert --1h--.

In Column 65, Line 43, delete "(adenosine" and insert --adenosine--.

In Column 65, Line 65, delete "amino]" and insert --amino--.

In Column 66, Line 9, delete "-yl]" and insert -- -yl)--.

In Column 73, Line 53, delete "piriMiphos" and insert --pirimiphos--.

In Column 77, Line 42, delete "Cell;" and insert --Cel7;--.

In Column 78, Line 61, delete "LIP;" and insert --L1P;--.

In Column 79, Line 11, delete "6-5" and insert --6- --.

In Column 79, Lines 33-34, delete "Acetylcholinesterase; Acetylcholinesterase; Acetylcholinesterase" and insert --Acetylcholinesterase--.

CERTIFICATE OF CORRECTION (continued)
U.S. Pat. No. 10,877,035 B2

In Column 79, Line 50, delete "Carrier." and insert --Carrier--.

In Column 83, Line 30, delete "[Includes:" and insert --Includes:--.

In Column 83, Line 34, delete "[Includes:" and insert --Includes:--.

In Column 84, Lines 58-59, delete "Cell Wall Pentapeptide Ala-[;" and insert --Cell Wall Pentapeptide--.

In Column 85, Line 28, delete "-acetyltransferase;" and insert --O-acetyltransferase;--.

In Column 87, Line 46, delete "[Glyl]" and insert --[Gly1]--.

In Column 89, Line 21, delete "[Nadh;" and insert --[NADH];--.

In Column 90, Line 52, delete "Ga110" and insert --Gal10--.

In Column 91, Line 3, delete "[Includes:" and insert --Includes:--.

In Column 93, Line 4, delete "Ha13;" and insert --Hal3;--.

In Column 94, Line 31, delete "Cos 3;" and insert --Cos3;--.

In Column 95, Lines 11-14, delete "Hypoxanthine-Guanine Phosphoribosyltransfera; Hypoxanthine-Guanine Phosphoribosyltransfera;".

In Column 96, Line 5, delete "Methytransferase;" and insert --Methyltransferase;--.

In Column 96, Line 61, delete "-Iactate" and insert -- -lactate--.

In Column 99, Line 1, delete "Mycotic" and insert --Mycolic--.

In Column 100, Line 29, delete "m Neutral" and insert --Neutral--.

In Column 101, Line 45, delete "[Includes:" and insert --Includes:--.

In Column 101, Line 46, delete "[Includes:" and insert --Includes:--.

In Column 101, Line 59, delete "kinase;" and insert --Kinase;--.

In Column 101, Line 63, delete "Ester)," and insert --Ester,--.

In Column 104, Line 48, delete "1 D10;" and insert --1D10;--.

In Column 104, Line 52, delete "Mat" and insert --Maf;--.

In Column 106, Line 14, delete "pleb;" and insert --pleD;--.

In Column 107, Line 40-41, delete "/ReduCtase" and insert --/Reductase--.

In Column 107, Line 49, delete "Synaptotagmini/" and insert --Synaptotagmin/--.

In Column 107, Lines 52-53, delete "Dihydropydrine" and insert --Dihydropyridine--.

In Column 108, Line 62, delete "to;" and insert --;--.

In Column 109, Line 9, delete "Somatosatin;" and insert --Somatostatin;--.

In Column 109, Line 9, delete "Somatosatin" and insert --Somatostatin--.

In Column 110, Line 15, delete "GluC1" and insert --Glucl--.

In Column 110, Line 49, delete "Horn;" and insert --Hom;--.

In Column 114, Line 46, delete "revolutionary" and insert --Revolutionary--.

In Column 115, Line 45, delete "mayor" and insert --may or--.

In Column 121, Line 16, delete "herein)." and insert --herein.--.

In Column 124, Line 63, delete "used" and insert --used to--.

In Column 126, Lines 32-33, delete "diclorobenzene" and insert --dichlorobenzene--.

In Column 126, Lines 35-36, delete "diclorobenzene" and insert --dichlorobenzene--.

In Column 127, Line 54, delete "1997." and insert --1997).--.

In Column 129, Line 18, delete "5th" and insert --5$^{th}$--.

In Column 129, Line 43, delete "κHT2A" and insert --5HT2A--.

In Column 131, Line 24, delete "disease" and insert --disease.--.

In Column 133, Line 9, delete "desphosphorylation" and insert --dephosphorylation--.

In Column 137, Line 30, delete "the a" and insert --the--.

In the Claims

In Column 139, Lines 24-25, Claim 2, delete "standardizing" and insert --standardizing a--.

In Column 140, Line 7, Claim 9, delete "measured;" and insert --measured,--.

In Column 140, Line 10, Claim 9, delete "anion" and insert --anion,--.

In Column 140, Line 14, Claim 10, delete "fluorescence" and insert --fluorescence signal,--.

In Column 140, Line 24, Claim 13, delete "K-alpha" and insert --K-alpha or--.